(12) United States Patent
Davie et al.

(10) Patent No.: US 9,533,987 B2
(45) Date of Patent: Jan. 3, 2017

(54) HETEROCYCLIC DERIVATES

(71) Applicant: KALVISTA PHARMACEUTICALS LIMITED, Salisbury (GB)

(72) Inventors: Rebecca Louise Davie, Salisbury (GB); Hannah Joy Edwards, Salisbury (GB); David Michael Evans, Salisbury (GB); Simon Teanby Hodgson, Salisbury (GB); Iain Miller, Nottingham (GB); Andrew Richard Novak, Nottingham (GB); Alun John Smith, Nottingham (GB); Michael John Stocks, Nottingham (GB)

(73) Assignee: Kalvista Pharmaceuticals Limited, Salisbury (GB)

( * ) Notice: Subject to any disclaimer, the term of this patent is extended or adjusted under 35 U.S.C. 154(b) by 0 days.

(21) Appl. No.: 14/892,055

(22) PCT Filed: May 23, 2014

(86) PCT No.: PCT/GB2014/051592
§ 371 (c)(1),
(2) Date: Nov. 18, 2015

(87) PCT Pub. No.: WO2014/188211
PCT Pub. Date: Nov. 27, 2014

(65) Prior Publication Data
US 2016/0108036 A1    Apr. 21, 2016

Related U.S. Application Data

(60) Provisional application No. 61/826,596, filed on May 23, 2013, provisional application No. 61/865,756, filed on Aug. 14, 2013.

(51) Int. Cl.
| | | |
|---|---|---|
| C07D 401/14 | (2006.01) | |
| C07D 403/14 | (2006.01) | |
| C07D 417/14 | (2006.01) | |
| C07D 471/14 | (2006.01) | |
| A61K 31/4725 | (2006.01) | |
| C07D 471/04 | (2006.01) | |
| C07D 413/14 | (2006.01) | |
| C07D 417/06 | (2006.01) | |

(52) U.S. Cl.
CPC ........... *C07D 471/04* (2013.01); *C07D 401/14* (2013.01); *C07D 403/14* (2013.01); *C07D 413/14* (2013.01); *C07D 417/06* (2013.01); *C07D 417/14* (2013.01)

(58) Field of Classification Search
None
See application file for complete search history.

(56) References Cited

U.S. PATENT DOCUMENTS
5,187,157 A    2/1993    Kettner et al.

FOREIGN PATENT DOCUMENTS

| EP | 2281885 | 2/2011 |
|---|---|---|
| WO | WO 92/04371 | 3/1992 |
| WO | WO 94/29335 | 12/1994 |
| WO | WO 95/07921 | 3/1995 |
| WO | WO 03/076458 | 9/2003 |
| WO | WO 2005/123680 | 12/2005 |
| WO | WO 2008/016883 | 2/2008 |
| WO | WO 2008/049595 | 5/2008 |
| WO | WO 2010/142801 | 12/2010 |
| WO | WO 2011/118672 | 9/2011 |
| WO | WO 2012/004678 | 1/2012 |
| WO | WO 2012/017020 | 2/2012 |
| WO | WO 2013/111107 | 8/2013 |
| WO | WO 2013/111108 | 8/2013 |
| WO | WO 2013/130603 | 9/2013 |

OTHER PUBLICATIONS

Chemical Abstract Service, CHEMCATS, RN 1424383-07-2, Mar. 15, 2013.*
International Search Report for PCT/GB2014/051592 completed Jul. 23, 2014.*
Babu et al., "A Simple, Sensitive and Selective Fluorogenic Assay to Monitor Plasma Kallikrein Inhibitory Activity of BCX4161 in Activated Plasma", Journal of Allergy and Clinical Immunology, Feb. 2014, 133(2), 1 page.
Bhoola et al., "Bioregulation of Kinins: Kallikreins, Kininogens and Kininases", Pharmacological Rev., 1992, 44(1), 80 pages.
Campbell, "Towards Understanding the Kallikrein-Kinin System: Insights from the Measurement of Kinin Peptides", Brazilian Journal of Medical and Biological Research, 2000, 33(6), 665-677.
Chilcote et al., "ASP-634: An Oral Drug Candidate for Diabetic Macular Edema", ARVO, Mar. 2012, Presentation 2240, Abstract, 1 page.
Clermont et al., "Plasma Kallikrein Mediates Retinal Vascular Dysfunction and Induces Retinal Thickening in Diabetic Rats", Diabetes, May 2011, 60(5), 1590-1598.

(Continued)

*Primary Examiner* — Zinna Northington Davis
(74) *Attorney, Agent, or Firm* — Baker & Hostetler LLP

(57) ABSTRACT

The present invention provides compounds of formula (I): compositions comprising such compounds; the use of such compounds in therapy (for example in the treatment or prevention of a disease or condition in which plasma kallikrein activity is implicated); and methods of treating patients with such compounds; wherein R5, R6, R7, A, B, W, X, Y and Z are as defined herein.

(I)

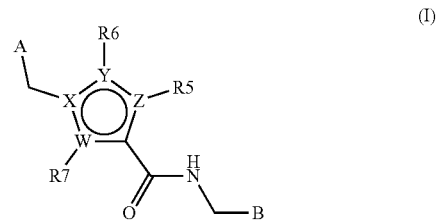

27 Claims, No Drawings

(56) References Cited

OTHER PUBLICATIONS

Collis et al., "BCX4161, An Oral Kallikrein Inhibitor: Safety and Pharmacokinetic Results of a Phase 1 Study in Healthy Volunteers", Journal of Allergy and Clinical Immunology, Feb. 2014, 133(2), 1 page.
Elman et al., "Randomized Trial Evaluating Ranibizumab Plus Prompt or Deferred Laser or Triamcinolone Plus Prompt Laser for Diabetic Macular Edema", Ophthalmology, Jun. 2010, 117(6), e35, 1064-1077.
Evans et al., "Selective Inhibitors of Plasma Kallikrein", Immunopharmacology, May 1996, 32(1-3), 115-116.
Garrett et al. "Peptide Aldehyde Inhibitors of the Kallikreins: an Investigation of Subsite Interactions with Tripeptides Containing Structural Variations at the Amino Terminus", J. Peptide Research, Jul. 1998, 52(1), 60-71.
Griesbacher et al., "Involvement of Tissue Kallikrein But Not Plasma Kallikrein in the Development of Symptoms Mediated by Endogenous Kinins in Acute Pancreatitis in Rats", British Journal of Pharmacology, 2002, 137, 692-700.
Johansen et al., "Assay of Kallikrein Inhibitors and Levels of Acetone-Activated Kallikrein in Plasma Specimens from Reactors to Dextran or to Contrast Media", International Journal Tissue Reactions, 1986, 8, 185-192.
Kolte et al., "Biochemical Characterization of a Novel High-Affinity and Specific Kallikrein Inhibitor", British Journal of Pharmacology, 2011, 162, 1639-1649.
Lehmann, "Ecallantide (DX-88), A Plasma Kallikrein Inhibitor for the Treatment of Hereditary Angioedema and the Prevention of Blood Loss in On-Pump Cardiothoracic Surgery", Expert Opinion on Biological Therapy, Jul. 2008, 8(8), 1187-1199.
Leinweber et al, "Possible Physiological Roles of Carboxylic Ester Hydrolases", Drug Metabolism Reviews, 1987, 18(4), 379-439.
Liang et al. "Fast-Dissolving Intraoral Drug Delivery Systems", Expert Opinion in Therapeutic Patents, 2001, 11(6), 981-986.
Lieberman et al., "Pharmaceutical Dosage Forms: Tablets, vol. 1", Marcel Dekker, 1980, 2, 15 pages.
Marceau et al., "Bradykinin Receptor Ligands: Therapeutic Perspectives", Nature Reviews Drug Discovery, Oct. 2004, 3, 845-852.
Okada et al.; "Development of Potent and Selective Plasmin and Plasma Kallikrein Inhibitors and Studies on the Structure-Activity Relationship", Chem. Pharm. Bull., Sep. 2000, 48(12), 1964-1972.
Remington's Pharmaceutical Sciences, 19th Edition, Gennaro, Mack Publishing Company, 1995, 5 pages.
Shori et al., "New Specific Assays for Tonin and Tissue Kallikrein Activities in Rat Submandibular Glands: Assays Reveal Differences in the Effects of Sympathetic and Parasympathetic Stimulation on Proteinases in Saliva", Biochemical Pharmacology, Mar. 17, 1992, 43(6), 1209-1217.
Sturzebecher et al., "Inhibition of Human Mast Cell Tryptase by Benzamidine Derivatives", Biological Chemistry Hoppe-Seyler, Oct. 1992, 373(2), 1025-1030.
Sturzebecher et al., "Novel Plasma Kallikrein Inhibitors of the Benzamidine Type", Brazilian J. Med. Biol. Res, 1994, 27, 1929-1934.
Teno et al., "Development of Active Center-Directed Plasmin and Plasma Kallikrein Inhibitors and Studies on the Structure-Inhibitory Activity Relationship", Chemical and Pharmaceutical Bulletin, 1993, 41(6), 1079-1090.
Wermuth, "The Practice of Medicinal Chemistry", 2003, 2nd Ed., 561-585.
Young et al., "Small Molecule Inhibitors of Plasma Kallikrein", Bioorganic & Medicinal Chemistry Letters, Apr. 2006, 16(7), 2034-2036.
Zhang et al., "Discovery of Highly Potent Small Molecule Kallikrein Inhibitors"; Medicinal Chemistry, Nov. 2006, 2(6), 545-553.
PubChem Compound ID 22830339 Dec. 5, 2007.
PubChem Compound ID 24488625 Feb. 29, 2008.
PubChem Compound ID 38284485 May 29, 2009.
PubChem Compound ID 38284487 May 29, 2009.
PubChem Compound ID 46438580 Jul. 23, 2010.
PubChem Compound 51143945 May 3, 2011.
PubChem Compound 52011740 May 20, 2011.
PubChem Compound 52011741 May 20, 2001.
PubChem Compound 52011742 May 20, 2011.
PubChem Compound 52011935 May 20, 2011.
PubChem Compound 52011936 May 20, 2011.
PubChem Compound 52011937 May 20, 2011.
PubChem Compound 52011938 May 20, 2011.
PubChem Compound 55389827 Jan. 25, 2012.
PubChem Compound 55408484 Jan. 25, 2012.
PubChem Compound 55408530 Jan. 25, 2012.
PubChem Compound 55408677 Jan. 25, 2012.
PubChem Compound 55408742 Jan. 25, 2012.
PubChem Compound 55408894 Jan. 25, 2012.
PubChem Compound 55438190 Jan. 25, 2012.
PubChem Compound 55494217 Jan. 25, 2012.
PubChem Compound 55650494 Jan. 25, 2012.
PubChem Compound 60376550 Oct. 18, 2012.
PubChem Compound 40150888 May 30, 2009.
CAS extract for Compound 1424383-07-2; Mar. 15, 2013.
CAS extract for Compound 1180236-10-5; Sep. 4, 2009.
CAS extract for Compound 1288488-40-3; May 1, 2011.
CAS extract for Compound 1288531-53-2; May 1, 2011.
CAS extract for Compound 1288265-35-9; May 1, 2011.
CAS extract for Compound 1297493-36-7; May 19, 2011.
CAS extract for Compound 1180808-34-7; Sep. 6, 2009.
CAS extract for Compound 1293757-54-6; May 12, 2011.

* cited by examiner

HETEROCYCLIC DERIVATES

CROSS-REFERENCE TO RELATED APPLICATIONS

This application is the National Stage of International Patent Application No. PCT/GB2014/051592 filed May 23, 2014, which claims the benefit of U.S. provisional application No. 61/826,596, filed May 23, 2013 and U.S. provisional application No. 61/865,756, filed Aug. 14, 2013, the disclosures of which are incorporated herein by reference in their entireties.

This invention relates to heterocyclic derivatives that are inhibitors of plasma kallikrein and to pharmaceutical compositions containing and the uses of, such derivatives.

BACKGROUND TO THE INVENTION

The heterocyclic derivatives of the present invention are inhibitors of plasma kallikrein and have a number of therapeutic applications, particularly in the treatment of retinal vascular permeability associated with diabetic retinopathy and diabetic macular edema.

Plasma kallikrein is a trypsin-like serine protease that can liberate kinins from kininogens (see K. D. Bhoola et al., "Kallikrein-Kinin Cascade", *Encyclopedia of Respiratory Medicine*, p 483-493; J. W. Bryant et al., "Human plasma kallikrein-kinin system: physiological and biochemical parameters" *Cardiovascular and haematological agents in medicinal chemistry*, 7, p 234-250, 2009; K. D. Bhoola et al., *Pharmacological Rev.*, 1992, 44, 1; and D. J. Campbell, "Towards understanding the kallikrein-kinin system: insights from the measurement of kinin peptides", *Brazilian Journal of Medical and Biological Research* 2000, 33, 665-677). It is an essential member of the intrinsic blood coagulation cascade although its role in this cascade does not involve the release of bradykinin or enzymatic cleavage. Plasma prekallikrein is encoded by a single gene and synthesized in the liver. It is secreted by hepatocytes as an inactive plasma prekallikrein that circulates in plasma as a heterodimer complex bound to high molecular weight kininogen which is activated to give the active plasma kallikrein. Kinins are potent mediators of inflammation that act through G protein-coupled receptors and antagonists of kinins (such as bradykinin antagonists) have previously been investigated as potential therapeutic agents for the treatment of a number of disorders (F. Marceau and D. Regoli, Nature Rev., Drug Discovery, 2004, 3, 845-852).

Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastro-intestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (A. Lehmann "Ecallantide (DX-88), a plasma kallikrein inhibitor for the treatment of hereditary angioedema and the prevention of blood loss in on-pump cardiothoracic surgery" *Expert Opin. Biol. Ther.* 8, p 1187-99).

The plasma kallikrein-kinin system is abnormally abundant in patients with advanced diabetic macular edema. It has been recently published that plasma kallikrein contributes to retinal vascular dysfunctions in diabetic rats (A. Clermont et al. "Plasma kallikrein mediates retinal vascular dysfunction and induces retinal thickening in diabetic rats" *Diabetes*, 2011, 60, p 1590-98). Furthermore, administration of the plasma kallikrein inhibitor ASP-440 ameliorated both retinal vascular permeability and retinal blood flow abnormalities in diabetic rats. Therefore a plasma kallikrein inhibitor should have utility as a treatment to reduce retinal vascular permeability associated with diabetic retinopathy and diabetic macular edema.

Other complications of diabetes such as cerebral haemorrhage, nephropathy, cardiomyopathy and neuropathy, all of which have associations with plasma kallikrein may also be considered as targets for a plasma kallikrein inhibitor.

Synthetic and small molecule plasma kallikrein inhibitors have been described previously, for example by Garrett et al. ("Peptide aldehyde . . . " *J. Peptide Res.* 52, p 62-71 (1998)), T. Griesbacher et al. ("Involvement of tissue kallikrein but not plasma kallikrein in the development of symptoms mediated by endogenous kinins in acute pancreatitis in rats" *British Journal of Pharmacology* 137, p 692-700 (2002)), Evans ("Selective dipeptide inhibitors of kallikrein" WO03/076458), Szelke et al. ("Kininogenase inhibitors" WO92/04371), D. M. Evans et al. (*Immunolpharmacology*, 32, p 115-116 (1996)), Szelke et al. ("Kininogen inhibitors" WO95/07921), Antonsson et al. ("New peptides derivatives" WO94/29335), J. Corte et al. ("Six membered heterocycles useful as serine protease inhibitors" WO2005/123680), J. Sturzbecher et al. (*Brazilian J. Med. Biol. Res* 27, p 1929-34 (1994)), Kettner et al. (U.S. Pat. No. 5,187,157), N. Teno et al. (*Chem. Pharm. Bull.* 41, p 1079-1090 (1993)), W. B. Young et al. ("Small molecule inhibitors of plasma kallikrein" Bioorg. Med. Chem. Letts. 16, p 2034-2036 (2006)), Okada et al. ("Development of potent and selective plasmin and plasma kallikrein inhibitors and studies on the structure-activity relationship" *Chem. Pharm. Bull.* 48, p 1964-72 (2000)), Steinmetzer et al. ("Trypsin-like serine protease inhibitors and their preparation and use" WO08/049595), Zhang et al. ("Discovery of highly potent small molecule kallikrein inhibitors" *Medicinal Chemistry* 2, p 545-553 (2006)), Sinha et al. ("IInhibitors of plasma kallikrein" WO08/016883), Shigenaga et al. ("Plasma Kallikrein Inhibitors" WO2011/118672), and Kolte et al. ("Biochemical characterization of a novel high-affinity and specific kallikrein inhibitor", British Journal of Pharmacology (2011), 162(7), 1639-1649). Also, Steinmetzer et al. ("Serine protease inhibitors" WO2012/004678) describes cyclized peptide analogs which are inhibitors of human plasmin and plasma kallikrein.

To date, no small molecule synthetic plasma kallikrein inhibitor has been approved for medical use. The molecules described in the known art suffer from limitations such as poor selectivity over related enzymes such as KLK1, thrombin and other serine proteases, and poor oral availability. The large protein plasma kallikrein inhibitors present risks of anaphylactic reactions, as has been reported for Ecallantide. Thus there remains a need for compounds that selectively inhibit plasma kallikrein, that do not induce anaphylaxis and that are orally available. Furthermore, the vast majority of molecules in the known art feature a highly polar and ionisable guanidine or amidine functionality. It is well known that such functionalities may be limiting to gut permeability and therefore to oral availability. For example, it has been reported by Tamie J. Chilcote and Sukanto Sinha ("ASP-634: An Oral Drug Candidate for Diabetic MacularEdema", ARVO 2012 May 6-May 9, 2012, Fort Lauderdale, Fla., Presentation 2240) that ASP-440, a benzamidine, suffers from poor oral availability. It is further reported that absorption may be improved by creating a prodrug such as ASP-634. However, it is well known that prodrugs can suffer from several drawbacks, for example, poor chemical stability and potential toxicity from the inert carrier or from unexpected metabolites. In another report, indole amides are claimed as compounds that might overcome problems associated with drugs possessing poor or inadequate ADME-tox and physicochemical properties although no inhibition against plasma kallikrein is presented or claimed (Griffioen et al, "Indole amide derivatives and related compounds for use in the treatment of neurodegenerative diseases", WO2010, 142801).

BioCryst Pharmaceuticals Inc. have reported the discovery of the orally available plasma kallikrein inhibitor BCX4161 ("BCX4161, An Oral Kallikrein Inhibitor: Safety and Pharmacokinetic Results Of a Phase 1 Study In Healthy Volunteers", Journal of Allergy and Clinical Immunology, Volume 133, Issue 2, Supplement, February 2014, page AB39 and "A Simple, Sensitive and Selective Fluorogenic Assay to Monitor Plasma Kallikrein Inhibitory Activity of BCX4161 in Activated Plasma", Journal of Allergy and Clinical Immunology, Volume 133, Issue 2, Supplement February 2014, page AB40). However, human doses are relatively large, currently being tested in proof of concept studies at doses of 400 mg three times daily.

There are only few reports of plasma kallikrein inhibitors that do not feature guanidine or amidine functionalities. One example is Brandl et al. ("N-((6-amino-pyridin-3-yl) methyl)-heteroaryl-carboxamides as inhibitors of plasma kallikrein" WO2012/017020), which describes compounds that feature an aminopyridine functionality. Oral efficacy in a rat model is demonstrated at relatively high doses of 30 mg/kg and 100 mg/kg but the pharmacokinetic profile is not reported. Thus it is not yet known whether such compounds will provide sufficient oral availability or efficacy for progression to the clinic. Other examples are Brandl et al. ("Aminopyridine derivatives as plasma kallikrein inhibitors" WO2013/111107) and Flohr et al. ("5-membered heteroarylcarboxamide derivatives as plasma kallikrein inhibitors" WO2013/111108). However, neither of these documents report any in vivo data and therefore it is not yet known whether such compounds will provide sufficient oral availability or efficacy for progression to the clinic.

Therefore there remains a need to develop new plasma kallikrein inhibitors that will have utility to treat a wide range of disorders, in particular to reduce retinal vascular permeability associated with diabetic retinopathy and diabetic macular edema. Preferred compounds will possess a good pharmacokinetic profile and in particular will be suitable as drugs for oral delivery.

SUMMARY OF THE INVENTION

The present invention relates to a series of heterocyclic derivatives that are inhibitors of plasma kallikrein. These compounds demonstrate good selectivity for plasma kallikrein and are potentially useful in the treatment of impaired visual acuity, diabetic retinopathy, macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post operative surgery. The invention further relates to pharmaceutical compositions of the inhibitors, to the use of the compositions as therapeutic agents, and to methods of treatment using these compositions.

In a first aspect, the present invention provides compounds of formula I

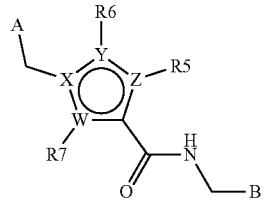

Formula (I)

wherein
B is a fused 6,5- or 6,6-heteroaromatic bicyclic ring, containing N and, optionally, one or two additional heteroatoms independently selected from N, O and S, which is optionally mono-, di or tri-substituted with a substituent selected from alkyl, alkoxy, OH, halo, CN, COOR8, CONR8R9, $CF_3$ and NR8R9;
W, X, Y and Z are independently selected from C, N, O and S, such that the ring containing W, X, Y and Z is a five membered aromatic heterocycle;
wherein,
R5, R6 and R7 are independently absent or independently selected from H, alkyl, halo, OH, aryl, heteroaryl, —NR8R9, CN, COOR8, CONR8R9, —NR8COR9, $CF_3$, and R16;
A is selected from aryl and heteroaryl;
R8 and R9 are independently selected from H and alkyl;
R16 is a carbon-containing 3-, 4-, 5- or 6-membered monocyclic ring system which may be aromatic, saturated or unsaturated non-aromatic and which may optionally contain 1, 2, 3 or 4 heteroatoms selected from N, O and S, wherein the ring system R16 is in turn optionally substituted with substituents selected from alkyl and oxo;
alkyl is a linear saturated hydrocarbon having up to 10 carbon atoms ($C_1$-$C_{10}$) or a branched saturated hydrocarbon of between 3 and 10 carbon atoms ($C_3$-$C_{10}$); alkyl may optionally be substituted with 1 or 2 substituents independently selected from ($C_1$-$C_6$)alkoxy, OH, CN, $CF_3$, COOR10, CONR10R11, fluoro and NR10R11;
alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$); alkoxy may optionally be substituted with 1 or 2 substituents independently selected from OH, CN, $CF_3$, COOR10, CONR10R11, fluoro and NR10R11;
aryl is phenyl, biphenyl or naphthyl; aryl may be optionally substituted with 1, 2 or 3 substituents independently selected from alkyl, alkoxy, methylenedioxy, ethylenedioxy, OH, halo, CN, morpholinyl, piperidinyl, heteroaryl, —($CH_2$)$_{0-3}$—O-heteroaryl, aryl$^b$, —O-aryl$^b$, —($CH_2$)$_{1-3}$-aryl$^b$, —($CH_2$)$_{1-3}$-heteroaryl, —COOR10, —CONR10R11, —($CH_2$)$_{1-3}$—NR14R15, $CF_3$ and —NR10R11;
aryl$^b$ is phenyl, biphenyl or naphthyl, which may be optionally substituted with 1, 2 or 3 substituents independently selected from alkyl, alkoxy, OH, halo, CN, morpholinyl, piperidinyl, —COOR10, —CONR10R11, $CF_3$ and NR10R11;
heteroaryl is a 5, 6, 9 or 10 membered mono- or bi-cyclic aromatic ring, containing, where possible, 1, 2 or 3 ring members independently selected from N, NR8, S and O;

heteroaryl may be optionally substituted with 1, 2 or 3 substituents independently selected from alkyl, alkoxy, OH, OCF$_3$, halo, CN, aryl, morpholinyl, piperidinyl, —(CH$_2$)$_{1-3}$-aryl, heteroaryl$^b$, —COOR10, —CONR10R11, CF$_3$ and —NR10R11;

heteroaryl$^b$ is a 5, 6, 9 or 10 membered mono- or bi-cyclic aromatic ring, containing, where possible, 1, 2 or 3 ring members independently selected from N, NR8, S and O; wherein heteroaryl$^b$ may be optionally substituted with 1, 2 or 3 substituents independently selected from alkyl, alkoxy, OH, halo, CN, morpholinyl, piperidinyl, aryl, —(CH$_2$)$_{1-3}$-aryl, —COOR10, —CONR10R11, CF$_3$ and NR10R11;

R10 and R11 are independently selected from H and alkyl or R10 and R11 together with the nitrogen atom to which they are attached form a carbon-containing 4-, 5-, 6- or 7-membered heterocylic ring which may be saturated or unsaturated with 1 or 2 double bonds and which may be optionally mono- or di-substituted with substituents selected from oxo, alkyl, alkoxy, OH, F and CF$_3$;

R14 and R15 are independently selected from alkyl, aryl$^b$ and heteroaryl$^b$; or R14 and R15 together with the nitrogen atom to which they are attached form a carbon-containing 4-, 5-, 6- or 7-membered heterocylic ring which may be saturated or unsaturated with 1 or 2 double bonds, and optionally may be oxo substituted;

wherein, when R5 is absent or H and R6 is absent or H and R7 is absent or H, then:
either
A is aryl and aryl is phenyl, biphenyl or naphthyl substituted with 1, 2 or 3 substituents independently selected from OH, methylenedioxy, ethylenedioxy, heteroaryl, —(CH$_2$)$_{0-3}$—O-heteroarylaryl$^b$, —O-aryl$^b$, —(CH$_2$)$_{1-3}$-aryl$^b$, —(CH$_2$)$_{1-3}$-heteroaryl, —COOR10, —CONR10R11 and —(CH$_2$)$_3$—NR14R15; wherein,
aryl$^b$ is phenyl, biphenyl or naphthyl, wherein aryl$^b$ is substituted with 1, 2 or 3 substituents independently selected from alkyl, alkoxy, OH, halo, CN, morpholinyl, piperidinyl, —COOR10, —CONR10R11, CF$_3$ and NR10R11; and
heteroaryl is a 5, 6, 9 or 10 membered mono- or bi-cyclic aromatic ring, containing, where possible, 1, 2 or 3 ring members independently selected from N, NR8, S and O, wherein heteroaryl is substituted with 1, 2 or 3 substituents independently selected from alkyl, alkoxy, halo, CN, aryl, morpholinyl, piperidinyl, —(CH$_2$)$_{1-3}$-aryl, heteroaryl$^b$, —COOR10, —CONR10R11, CF$_3$ and —NR10R11;
or
A is heteroaryl and heteroaryl is a 5, 6, 9 or 10 membered mono- or bi-cyclic aromatic ring, containing, where possible, 1, 2 or 3 ring members independently selected from N, NR8, S and O, wherein heteroaryl is substituted with 1, 2 or 3 substituents independently selected from aryl, —(CH$_2$)$_{1-3}$-aryl, heteroaryl$^b$, —COOR10, and —CONR10R11; wherein,
aryl is phenyl, biphenyl or naphthyl, wherein aryl is substituted with 1, 2 or 3 substituents independently selected from alkyl, alkoxy, OH, halo, CN, morpholinyl, piperidinyl, heteroaryl, aryl$^b$, —O-aryl$^b$, —(CH$_2$)$_{1-3}$-aryl$^b$, —(CH$_2$)$_{1-3}$-heteroaryl, —COOR10, —CONR10R11, —(CH$_2$)$_{1-3}$—NR14R15, CF$_3$ and —NR10R11; and
heteroaryl$^b$ is a 5, 6, 9 or 10 membered mono- or bi-cyclic aromatic ring, containing, where possible, 1, 2 or 3 ring members independently selected from N, NR8, S and O, wherein heteroaryl$^b$ is substituted with 1, 2 or 3 substituents independently selected from alkyl, alkoxy, halo, CN, morpholinyl, piperidinyl, aryl, —(CH$_2$)$_{1-3}$-aryl, —COOR10, —CONR10R11, CF$_3$ and NR10R11;

and when B is a fused 6,5-heteroaromatic bicyclic ring, it is linked to —CONH—CH$_2$— via its 6-membered ring component;

and tautomers, isomers, stereoisomers (including enantiomers, diastereoisomers and racemic and scalemic mixtures thereof), pharmaceutically acceptable salts and solvates thereof.

In another aspect the present invention provides a prodrug of a compound of formula (I) as herein defined, or a pharmaceutically acceptable salt thereof.

In yet another aspect the present invention provides an N-oxide of a compound of formula (I) as herein defined, or a prodrug or pharmaceutically acceptable salt thereof.

It will be understood that certain compounds of the present invention may exist in solvated, for example hydrated, as well as unsolvated forms. It is to be understood that the present invention encompasses all such solvated forms.

In a second aspect, the invention comprises a subset of the compounds of formula I,

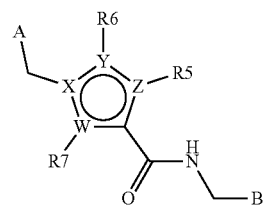

Formula (I)

wherein:
A, W, X, Y and Z are as defined in the first aspect above;
B is a fused 6,5- or 6,6-heteroaromatic bicyclic ring, containing N and, optionally, one or two additional heteroatoms independently selected from N, O and S, which is optionally mono-, di or tri-substituted with a substituent selected from alkyl, alkoxy, OH, halo, CN, COOR8, CONR8R9, CF$_3$ and NR8R9; wherein when B is a fused 6,5-heteroaromatic bicyclic ring, it is linked to —CONH—CH$_2$— via its 6-membered ring component;
R5, R6 and R7 are independently absent or independently selected from H, alkyl, halo, OH, aryl, heteroaryl and CF$_3$; with the proviso that at least one of R5, R6 and R7 must be present and when so present be independently selected from alkyl, halo, aryl, heteroaryl and CF$_3$;
heteroaryl is a 5, 6, 9 or 10 membered mono- or bi-cyclic aromatic ring, containing, where possible, 1, 2 or 3 ring members independently selected from N, NR8, S and O; heteroaryl may be optionally substituted with 1, 2 or 3 substituents independently selected from alkyl, alkoxy, OH, halo, CN, aryl, morpholinyl, piperidinyl, —(CH$_2$)$_{1-3}$-aryl, heteroaryl$^b$, —COOR10, —CONR10R11, CF$_3$ and —NR10R11; alkyl, alkoxy, aryl, heteroaryl$^b$, R8, R9, R10 and R11 are as defined in the first aspect above;

and tautomers, isomers, stereoisomers (including enantiomers, diastereoisomers and racemic and scalemic mixtures thereof), pharmaceutically acceptable salts and solvates thereof.

In another aspect, the invention comprises a compound according to the first aspect above, wherein B is a fused 6,6-heteroaromatic bicyclic ring, containing N and, optionally, one or two additional heteroatoms independently selected from N, O and S, which is optionally mono-, di or tri-substituted with a substituent selected from alkyl, alkoxy, OH, halo, CN, COOR8, CONR8R9, $CF_3$ and NR8R9; wherein alkyl, alkoxy, R8 and R9 are as defined in the first aspect above.

In another aspect, the invention comprises a compound according to the second aspect above, wherein B is a fused 6,6-heteroaromatic bicyclic ring, containing N and, optionally, one or two additional heteroatoms independently selected from N, O and S, which is optionally mono-, di or tri-substituted with a substituent selected from alkyl, alkoxy, OH, halo, CN, COOR8, CONR8R9, $CF_3$ and NR8R9; wherein alkyl, alkoxy, R8 and R9 are as defined in the first aspect above.

In another aspect, the invention comprises a compound according to the first aspect above, wherein B is selected from optionally mono-, di or tri-substituted isoquinolinyl wherein said optional substituent(s) are selected from alkyl, alkoxy, OH, F, Cl, CN, COOR8, CONR8R9, $CF_3$ and NR8R9; and wherein alkyl, alkoxy, R8 and R9 are as defined in the first aspect above.

In another aspect, the invention comprises a compound according to the second aspect above, wherein B is selected from optionally mono-, di or tri-substituted isoquinolinyl wherein said optional substituent(s) are selected from alkyl, alkoxy, OH, F, Cl, CN, COOR8, CONR8R9, $CF_3$ and NR8R9; and wherein alkyl, alkoxy, R8 and R9 are as defined in the first aspect above.

In another aspect, the invention comprises a subset of the compounds of formula (I), as defined by formula (II),

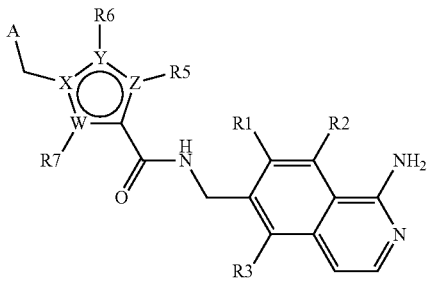

Formula (II)

wherein R1, R2 and R3 are independently selected from H, alkyl, COOR8, CONR8R9, OH, alkoxy, NR8R9, F and Cl; and wherein A, W, X, Y, Z, R5, R6, R7, alkyl, alkoxy, R8 and R9 are as defined in the first or second aspect above; and tautomers, isomers, stereoisomers (including enantiomers, diastereoisomers and racemic and scalemic mixtures thereof), pharmaceutically acceptable salts and solvates thereof.

In another aspect, the invention comprises a subset of the compounds of formula (I), as defined by formula (II),

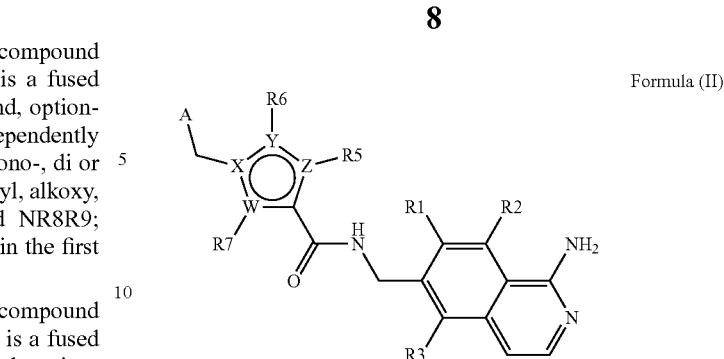

Formula (II)

wherein
W, X, Y and Z are independently selected from C and N, such that the ring containing W, X, Y and Z is a five-membered heterocycle selected from pyrrole, pyrazole, imidazole, 1,2,3-triazole and 1,2,4-triazole;
R5, R6 and R7 are independently absent or independently selected from H, alkyl, halo, OH, aryl, heteroaryl, —NR8R9, CN, COOR8, CONR8R9, —NR8COR9 and $CF_3$; wherein at least one of R5, R6 and R7 is present and is independently selected from alkyl, halo, OH, aryl, heteroaryl, —NR8R9 CN, COOR8, CONR8R9, —NR8COR9, R16 and $CF_3$;
R1, R2 and R3 are independently selected from H, alkyl, COOR8, CONR8R9, OH, alkoxy, NR8R9, F and Cl;
and wherein A, R8, R9, alkyl, alkoxy, aryl and heteroaryl are as defined in the first aspect above; and tautomers, isomers, stereoisomers (including enantiomers, diastereoisomers and racemic and scalemic mixtures thereof), pharmaceutically acceptable salts and solvates thereof.

In another aspect, the invention comprises a subset of the compounds of formula (I), as defined by formula (II),

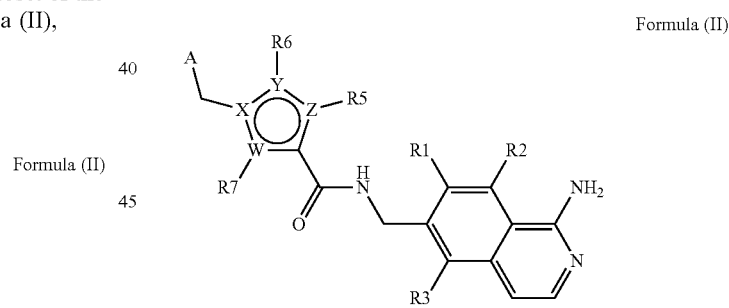

Formula (II)

wherein
W, X, Y and Z are independently selected from C and N, such that the ring containing W, X, Y and Z is a five-membered heterocycle selected from pyrrole, pyrazole, imidazole, 1,2,3-triazole and 1,2,4-triazole;
R5, R6 and R7 are independently absent or independently selected from H, alkyl, halo, aryl, heteroaryl and $CF_3$; wherein at least one of R5, R6 and R7 is present and is independently selected from alkyl, halo, aryl, heteroaryl, and $CF_3$;
R1, R2 and R3 are independently selected from H, alkyl, COOR8, CONR8R9, OH, alkoxy, NR8R9, F and Cl;
and wherein A, R8, R9, alkyl, alkoxy, aryl and heteroaryl are as defined in the first aspect above; and tautomers, isomers, stereoisomers (including enantiomers, diastereoisomers and racemic and scalemic mixtures thereof), pharmaceutically acceptable salts and solvates thereof.

In another aspect, the invention comprises a subset of the compounds of formula (I), as defined by formula (IIa),

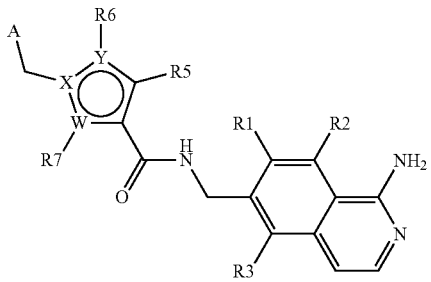

Formula (IIa)

wherein R1, R2 and R3 are independently selected from H, alkyl, COOR8, CONR8R9, OH, alkoxy, NR8R9, F and Cl; and wherein A, W, X, Y, R5, R6, R7, alkyl, alkoxy, R8 and R9 are as defined in the first or second aspect above; and tautomers, isomers, stereoisomers (including enantiomers, diastereoisomers and racemic and scalemic mixtures thereof), pharmaceutically acceptable salts and solvates thereof.

In another aspect, the invention comprises a subset of the compounds of formula (I), as defined by

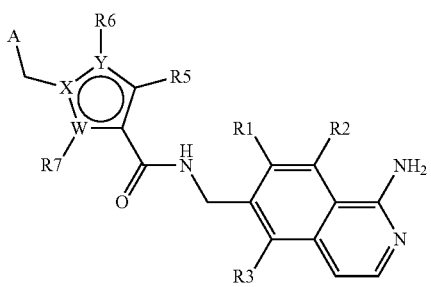

Formula (IIa)

wherein R1, R2 and R3 are independently selected from H, alkyl, COOR8, CONR8R9, OH, alkoxy, NR8R9, F and Cl; W, X and Y are independently selected from C, N, O and S, such that the ring containing W, X and Y is a five-membered membered aromatic heterocycle; and wherein A, R5, R6, R7, alkyl, alkoxy, R8 and R9 are as defined in the first or second aspect above; and tautomers, isomers, stereoisomers (including enantiomers, diastereoisomers and racemic and scalemic mixtures thereof), pharmaceutically acceptable salts and solvates thereof.

In another aspect, the invention comprises a compound according to the first aspect above, wherein B is a fused 6,5-heteroaromatic bicyclic ring, containing N and, optionally, one or two additional heteroatoms independently selected from N, O and S, which is optionally mono-, di or tri-substituted with a substituent selected from alkyl, alkoxy, OH, halo, CN, COOR8, CONR8R9, $CF_3$ and NR8R9; wherein alkyl, alkoxy, R8 and R9 are as defined in the first aspect above.

In another aspect, the invention comprises a compound according to the second aspect above, wherein B is a fused 6,5-heteroaromatic bicyclic ring, containing N and, optionally, one or two additional heteroatoms independently selected from N, O and S, which is optionally mono-, di or tri-substituted with a substituent selected from alkyl, alkoxy, OH, halo, CN, COOR8, CONR8R9, $CF_3$ and NR8R9; wherein B is linked to —CONH—$CH_2$— via its 6-membered ring component; and wherein alkyl, alkoxy, R8 and R9 are as defined in the first aspect above.

In another aspect, the invention comprises a compound according to the first or second aspect above, wherein B is a fused 6,5-heteroaromatic bicyclic ring, containing N and, optionally, one or two additional heteroatoms independently selected from N, O and S, which is optionally mono-, di or tri-substituted with a substituent selected from alkyl, F, Cl and —CN; and wherein alkyl is as defined in the first aspect above.

In another aspect, the invention comprises a compound according to the first aspect above, wherein B is selected from optionally substituted indole, optionally substituted indazole and optionally substituted 1H-pyrrolo[2,3-b]pyridine; wherein said optional substituents are selected from alkyl, alkoxy, OH, F, Cl, CN, COOR8, CONR8R9, $CF_3$ and NR8R9; and wherein alkyl, alkoxy, R8 and R9 are as defined in the first aspect above.

In another aspect, the invention comprises a compound according to the second aspect above, wherein B is selected from optionally substituted indole, optionally substituted indazole and optionally substituted 1H-pyrrolo[2,3-b]pyridine; wherein said optional substituents are selected from alkyl, alkoxy, OH, F, Cl, CN, COOR8, CONR8R9, $CF_3$ and NR8R9; wherein said indole, indazole or 1H-pyrrolo[2,3-b]pyridine ring is linked to —CONH—$CH_2$— via its 6-membered ring component; and wherein alkyl, alkoxy, R8 and R9 are as defined in the first aspect above.

In another aspect, the invention comprises a compound according to the first or second aspect above, wherein B is selected from optionally substituted indole, optionally substituted indazole and optionally substituted 1H-pyrrolo[2,3-b]pyridine; wherein said optional substituents are selected from alkyl, F, Cl and —CN; and wherein alkyl is as defined in the first aspect above.

In another aspect, the invention comprises a compound according to the first aspect above, wherein B is selected from optionally mono-, di or tri-substituted 1H-pyrrolo[2,3-b]pyridine, wherein said optional substituent(s) are selected from alkyl, alkoxy, OH, F, Cl, CN, COOR8, CONR8R9, $CF_3$ and NR8R9; and wherein alkyl, alkoxy, R8 and R9 are as defined in the first aspect above.

In another aspect, the invention comprises a compound according to the second aspect above, wherein B is selected from optionally mono-, di or tri-substituted 1H-pyrrolo[2, 3-b]pyridine, wherein said optional substituent(s) are selected from alkyl, alkoxy, OH, F, Cl, CN, COOR8, CONR8R9, $CF_3$ and NR8R9; wherein said 1H-pyrrolo[2,3-b]pyridine ring is linked to —CONH—$CH_2$— via its 6-membered ring component; and wherein alkyl, alkoxy, R8 and R9 are as defined in the first aspect above.

In another aspect, the invention comprises a compound according to the first or second aspect above, wherein B is selected from optionally mono-, di or tri-substituted 1H-pyrrolo[2,3-b]pyridine; wherein said optional substituents are selected from alkyl, F, Cl and —CN; and wherein alkyl is as defined in the first aspect above.

In another aspect, the invention comprises a subset of the compounds of formula (I), as defined by formula (III),

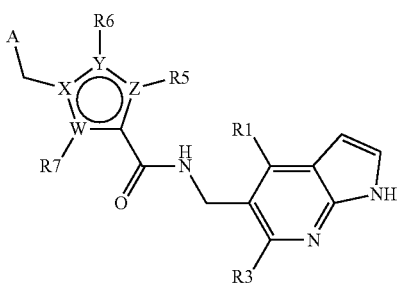

Formula (III)

wherein R1 and R3 are independently selected from H, alkyl, COOR8, CONR8R9, OH, alkoxy, NR8R9, F and Cl; and wherein A, W, X, Y, Z, R5, R6, R7, alkyl, alkoxy, R8 and R9 are as defined in the first aspect above;

and tautomers, isomers, stereoisomers (including enantiomers, diastereoisomers and racemic and scalemic mixtures thereof), pharmaceutically acceptable salts and solvates thereof.

In another aspect, the invention comprises a subset of the compounds of formula (I), as defined by formula (III),

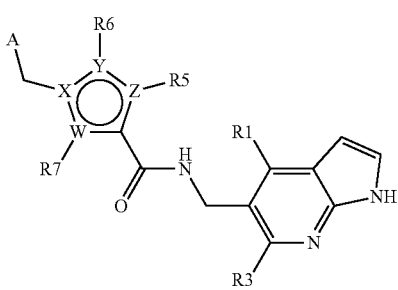

Formula (III)

wherein
W, X, Y and Z are independently selected from C and N, such that the ring containing W, X, Y and Z is a five-membered heterocycle selected from pyrrole, pyrazole, imidazole, 1,2,3-triazole and 1,2,4-triazole;
R5, R6 and R7 are independently absent or independently selected from H, alkyl, halo, aryl, heteroaryl and CF$_3$; wherein at least one of R5, R6 and R7 is present and is independently selected from alkyl, halo, aryl, heteroaryl, and CF$_3$;
R1 and R3 are independently selected from H, alkyl, COOR8, CONR8R9, OH, alkoxy, NR8R9, F and Cl;

and wherein A, R8, R9, alkyl, alkoxy, aryl and heteroaryl are as defined in the first aspect above; and tautomers, isomers, stereoisomers (including enantiomers, diastereoisomers and racemic and scalemic mixtures thereof), pharmaceutically acceptable salts and solvates thereof.

In another aspect, the invention comprises a subset of the compounds of formula (I), as defined by formula (III),

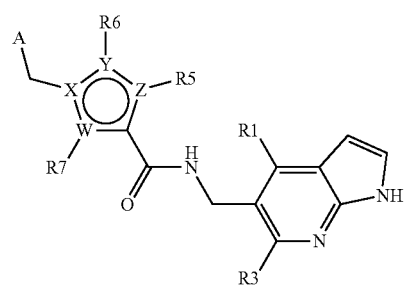

Formula (III)

wherein
W, X, Y and Z are independently selected from C and N, such that the ring containing W, X, Y and Z is a five-membered heterocycle selected from pyrrole, pyrazole, imidazole, 1,2,3-triazole and 1,2,4-triazole;
R5, R6 and R7 are independently absent or independently selected from H, alkyl, halo, aryl, heteroaryl and CF$_3$; wherein at least one of R5, R6 and R7 is present and is independently selected from alkyl, halo, aryl, heteroaryl, and CF$_3$;
R1 and R3 are independently selected from H and alkyl; and wherein A, alkyl, aryl, heteroaryl are as defined in the first aspect above; and tautomers, isomers, stereoisomers (including enantiomers, diastereoisomers and racemic and scalemic mixtures thereof), pharmaceutically acceptable salts and solvates thereof.

In another aspect, the invention comprises a subset of the compounds of formula (I), as defined by formula (IV),

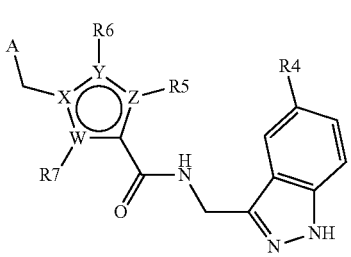

Formula (IV)

wherein R4 is independently selected from H, alkyl, COOR8, CONR8R9, OH, alkoxy, NR8R9, F and Cl; and wherein A, W, X, Y, Z, R5, R6, R7, alkyl, alkoxy, R8 and R9 are as defined in the first aspect above; and tautomers, isomers, stereoisomers (including enantiomers, diastereoisomers and racemic and scalemic mixtures thereof), pharmaceutically acceptable salts and solvates thereof.

In another aspect, the invention comprises a subset of the compounds of formula (I), as defined by formula (IV),

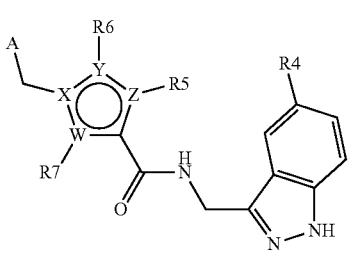

Formula (IV)

wherein
W, X, Y and Z are independently selected from C and N, such that the ring containing W, X, Y and Z is a five-membered heterocycle selected from pyrrole, pyrazole, imidazole, 1,2,3-triazole and 1,2,4-triazole;
R5, R6 and R7 are independently absent or independently selected from H, alkyl, halo, aryl, heteroaryl, —NR8R9, —CN, cyclopropyl and CF$_3$ and at least one of R5, R6 and R7 is not absent and is independently selected from alkyl, halo, aryl, heteroaryl, —NR8R9, —CN, cyclopropyl and CF$_3$;
R4 is selected from H, alkyl, COOR8, CONR8R9, OH, alkoxy, NR8R9, F and Cl;
and wherein A, R8, R9, alkyl, alkoxy are as defined in the first aspect above; and tautomers, isomers, stereoisomers (including enantiomers, diastereoisomers and racemic and scalemic mixtures thereof), pharmaceutically acceptable salts and solvates thereof.

In another aspect, the invention comprises a subset of the compounds of formula (I), as defined by formula (IV),

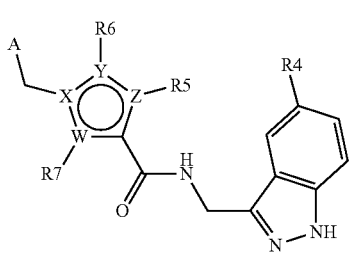

Formula (IV)

wherein
W, X, Y and Z are independently selected from C and N, such that the ring containing W, X, Y and Z is a five-membered heterocycle selected from pyrrole, pyrazole, imidazole, 1,2,3-triazole and 1,2,4-triazole;
R5, R6 and R7 are independently absent or independently selected from H, alkyl, halo, aryl, heteroaryl and CF$_3$ and at least one of R5, R6 and R7 is not absent and is independently selected from alkyl, halo, aryl, heteroaryl, and CF$_3$;
R4 is selected from H, alkyl, COOR8, CONR8R9, OH, alkoxy, NR8R9, F and Cl;
and wherein A, R8, R9, alkyl, alkoxy are as defined in the first aspect above; and tautomers, isomers, stereoisomers (including enantiomers, diastereoisomers and racemic and scalemic mixtures thereof), pharmaceutically acceptable salts and solvates thereof.

The present invention also comprises the following limitations, which may be applied to any of the aspects of the invention described above:
B is a fused 6,5 or 6,6-heteroaromatic bicyclic ring, containing N and, optionally, one or two additional heteroatoms independently selected from N, O and S, which is optionally mono-, di or tri-substituted with a substituent selected from alkyl, alkoxy, OH, halo, CN, COOR8, CONR8R9, CF$_3$ and NR8R9; wherein R8 and R9 are independently selected from H and alkyl; wherein when B is a fused 6,5-heteroaromatic bicyclic ring, it is linked to —(CH$_2$)$_n$— via its 6-membered ring component.
B is a fused 6,5 or 6,6-heteroaromatic bicyclic ring, containing one, two or three N atoms, and no other heteroatoms, which is optionally mono-substituted with a substituent selected from alkyl, alkoxy, OH, halo, CN, COOR8, CONR8R9, CF$_3$ and NR8R9; wherein R8 and R9 are independently selected from H and alkyl.
B is a fused 6,6-heteroaromatic bicyclic ring containing one N atom, and no other heteroatoms, which is optionally mono-substituted with a substituent selected from alkyl, alkoxy, OH, halo, CN, COOR8, CONR8R9, CF$_3$ and NR8R9; wherein R8 and R9 are independently selected from H and alkyl.
B is a fused 6,6-heteroaromatic bicyclic ring, containing one N atom and, optionally, one or two additional heteroatoms independently selected from N and O, which is optionally mono-substituted with a substituent selected from alkyl, alkoxy, OH, halo, CN, COOR8, CONR8R9, CF$_3$ and NR8R9; wherein R8 and R9 are independently selected from H and alkyl.
B is a fused 6,6-heteroaromatic bicyclic ring, containing one N atom, and no other heteroatoms, which is optionally mono-substituted with a substituent selected from alkyl, alkoxy, OH, and NR8R9; wherein R8 and R9 are independently selected from H and alkyl.
B is a fused 6,6-heteroaromatic bicyclic ring, containing one N atom, and no other heteroatoms, which is optionally mono-substituted with NR8R9; wherein R8 and R9 are independently selected from H and alkyl.
B is a fused 6,5-heteroaromatic bicyclic ring, containing N and, optionally, one or two additional heteroatoms independently selected from N, O and S, which is optionally mono-, di or tri-substituted with a substituent selected from alkyl, F, Cl and —CN.
B is a fused 6,5-heteroaromatic bicyclic ring, containing N and, optionally, one or two additional heteroatoms independently selected from N, O and S, which is optionally mono-, di or tri-substituted with a substituent selected from alkyl, F, Cl and —CN; wherein B is linked to —CONH—CH$_2$— via its 6-membered ring component.
B is selected from optionally substituted indole, optionally substituted indazole and optionally substituted 1H-pyrrolo[2,3-b]pyridine; wherein said optional substituents are selected from alkyl, F, Cl and —CN.
B is selected from optionally substituted indole, optionally substituted indazole and optionally substituted 1H-pyrrolo[2,3-b]pyridine; wherein said optional substituents are selected from alkyl, F, Cl and —CN; and wherein said indole, indazole or 1H-pyrrolo[2,3-b]pyridine ring is linked to —CONH—CH$_2$— via its 6-membered ring component.
B is optionally mono-, di or tri-substituted isoquinolinyl, wherein said optional substituent(s) are selected from alkyl, alkoxy, OH, F, Cl, CN, COOR8, CONR8R9, CF$_3$ and NR8R9; wherein R8 and R9 are independently selected from H and alkyl.
B is optionally mono-substituted isoquinolinyl; wherein said optional substituent is selected from alkyl, alkoxy, OH, and NR8R9; wherein R8 and R9 are independently selected from H and alkyl.
B is optionally substituted 1H-pyrrolo[2,3-b]pyridine wherein said optional substituent(s) are selected from alkyl, alkoxy, OH, F, Cl, CN, COOR8, CONR8R9, CF$_3$ and NR8R9 and wherein R8 and R9 are independently selected from H and alkyl.
B is selected from optionally mono-, di or tri-substituted 1H-pyrrolo[2,3-b]pyridine; wherein said optional substituents are selected from alkyl, F, Cl and —CN; and wherein said 1H-pyrrolo[2,3-b]pyridine ring is linked to —CONH—CH$_2$— via its 6-membered ring component.

Preferably, B is optionally mono-substituted isoquinolinyl, wherein said optional substituent is NR8R9; wherein R8 and R9 are independently selected from H and alkyl.

Preferably, B is optionally di- or tri-substituted isoquinolinyl, wherein one of said optional substituent is NR8R9 and the other said optional substituents are alkyl; wherein R8 and R9 are independently selected from H and alkyl.

More preferably, B is optionally di- or tri-substituted isoquinolinyl, wherein one of said optional substituent is NR8R9 and the other said optional substituents are alkyl; wherein R8 and R9 are H.

More preferably, B is optionally mono-substituted isoquinolinyl, wherein said optional substituent is NR8R9; and wherein R8 and R9 are H.

More preferably, B is optionally di- or tri-substituted isoquinolinyl, wherein one of said optional substituent is NR8R9 and the other one or two said optional substituents are alkyl; wherein R8 and R9 are H.

R1, R2, R3 and R4 are independently selected from H, alkyl, COOR8, CONR8R9, OH, alkoxy, NR8R9, F and Cl.

Preferably, R1, R2, R3 and R4 are independently selected from H, alkyl, Cl and F.

Preferably, R1, R2, R3 and R4 are independently selected from H, alkyl and Cl.

More preferably, R1, R2 and R3 are independently selected from H and alkyl.

More preferably, R1, R2 and R3 are independently selected from H and methyl.

More preferably R4 is selected from H and Cl.

W, X, Y and Z are independently selected from C, N, O and S, such that the ring containing W, X, Y and Z is a five-membered aromatic heterocycle.

W, X, Y and Z are independently selected from C and N, such that the ring containing W, X, Y and Z is a five-membered aromatic heterocycle.

W, X, Y and Z are independently selected from C and N, such that the ring containing W, X, Y and Z is selected from pyrrole, pyrazole, imidazole, 1,2,3-triazole and 1,2,4-triazole.

Preferably, X is N.

W is C, X and Y are N and Z is C or N.

X and Y are N and W and Z are C.

X, Y and Z are N and W is C.

X and Z are N and W and Y are C.

W is N and X, Y and Z are C.

X is N and W, Y and Z are C.

R5, R6 and R7 are independently absent or independently selected from H, alkyl, halo, OH, aryl, heteroaryl, —NR8R9, CN, COOR8, CONR8R9, —NR8COR9, CF$_3$, and —R16.

R5, R6 and R7 are independently absent, or are independently selected from H, alkyl, halo, OH, aryl, heteroaryl and CF$_3$.

R5, R6 and R7 are independently absent or independently selected from H, alkyl, halo, OH, aryl, heteroaryl, —NR8R9, CN, COOR8, CONR8R9, —NR8COR9, CF$_3$, and —R16, wherein at least one of R5, R6 and R7 is present and is independently selected from alkyl, halo, OH, aryl, heteroaryl, —NR8R9, CN, COOR8, CONR8R9, —NR8COR9, R16 and CF$_3$.

R5, R6 and R7 are independently absent, or are independently selected from H, alkyl, halo, OH, aryl, heteroaryl and CF$_3$, wherein at least one of R5, R6 and R7 is present and is independently selected from alkyl, halo, OH, aryl, heteroaryl and CF$_3$.

R5 is absent or is selected from H, alkyl, —NR8R9, —CN, R16, CF$_3$ and aryl.

R5 is absent or is selected from H, alkyl, —NR8R9, —CN, cyclopropyl, CF$_3$ and aryl.

R5 is absent or is selected from H, methyl, —NH$_2$, —CN, cyclopropyl, CF$_3$ and aryl.

R5 is absent or is selected from H, methyl, —NH$_2$, cyclopropyl, CF$_3$ and aryl.

R5 is absent or is selected from H, alkyl, CF$_3$ and aryl.

R5 is absent or is selected from H, methyl, CF$_3$ and phenyl.

R6 and R7 are independently absent, or are independently selected from H, alkyl, aryl and CF$_3$.

R6 and R7 are independently absent, or are independently selected from H, methyl, ethyl, n-propyl, phenyl and CF$_3$.

Preferably, R5 is H and R6 and R7 are methyl.

R14 and R15 are independently selected from alkyl, aryl$^b$ and heteroaryl$^b$; or R14 and R15 together with the nitrogen atom to which they are attached form a carbon containing 4-, 5-, 6- or 7-membered heterocylic ring which may be saturated or unsaturated with 1 or 2 double bonds, and optionally may be oxo substituted.

R14 and R15 are independently selected from alkyl and heteroaryl$^b$; or R14 and R15 together with the nitrogen atom to which they are attached form a 4-, 5-, 6- or 7-membered carbon containing heterocylic ring which may be saturated or unsaturated with 1 or 2 double bonds, and optionally may be oxo substituted.

R14 and R15 together with the nitrogen atom to which they are attached form a 4-, 5-, 6- or 7-membered carbon containing heterocylic ring which may be saturated or unsaturated with 1 or 2 double bonds, and optionally may be oxo substituted.

R16 is a carbon-containing 3-, 4-, 5- or 6-membered monocyclic ring system which may be aromatic, saturated or unsaturated non-aromatic and which may optionally contain 1, 2, 3 or 4 heteroatoms selected from N, O and S, wherein the ring system R16 is in turn optionally substituted with substituents selected from alkyl and oxo.

R16 is a carbon-containing 3-, 4-, 5- or 6-membered monocyclic ring system which may be aromatic, saturated or unsaturated non-aromatic and which may optionally contain 1 or 2 heteroatoms selected from N, O and S, wherein the ring system R16 is in turn optionally substituted with substituents selected from methyl, ethyl and oxo.

R16 is selected from oxazole, thiophene, cyclopropyl, cyclobutyl, pyrrolidinyl and morpholinyl, each optionally substituted with substituents selected from methyl and oxo.

X and Y are N, W and Z are C, and R5 and R7 are H.

X, Y and Z are N, W is C, and R7 is H.

W is N, X, Y and Z are C, R7 is ethyl, R6 is methyl and R5 is H.

X is N, W, Y and Z are C, R5 is H and R6 and R7 are methyl.

X and Y are N, W and Z are C, and R5 is selected from alkyl, halo, OH, aryl, heteroaryl, —NR8R9, CN, COOR8, CONR8R9, —NR8COR9, R16 and CF$_3$, and R7 is H.

X and Y are N, W and Z are C, and R5 is selected from alkyl, —NR8R9, —CN, cyclopropyl, CF$_3$ and aryl, and R7 is H.

X and Y are N, W and Z are C, and R5 is selected from methyl, —NH$_2$, —CN, cyclopropyl, CF$_3$ and R7 is H.

X and Y are N, W and Z are C, and R5 is R16 and R16 is as previously defined in the first aspect above.

X and Y are N, W and Z are C, and R5 selected from alkyl, halo, OH, aryl, heteroaryl and CF$_3$, and R7 is H.

A is selected from aryl and heteroaryl, each optionally substituted as specified in the first aspect above.

A is heteroaryl optionally substituted with 1, 2 or 3 substituents independently selected from alkyl, alkoxy, OH, halo, CN, aryl, morpholinyl, piperidinyl, —COOR10, —CONR10R11, CF$_3$ and —NR10R11; wherein R10 and R11 are selected from H and alkyl or R10 and R11 together with the nitrogen atom to which they are attached form a carbon-containing 4-, 5-, 6- or 7-membered heterocylic ring which may be saturated or unsaturated with 1 or 2 double bonds and which may be optionally mono- or di-substituted with substituents selected from oxo, alkyl, alkoxy, OH, F and CF$_3$.

A is heteroaryl optionally substituted with a substituent selected from alkyl, alkoxy, OH, halo, CN, aryl, morpholinyl and piperidinyl.

Preferably, A is heteroaryl substituted by phenyl.

Preferably, A is heteroaryl substituted by NR10R11; wherein R10 and R11 are selected from H and alkyl or R10 and R11 together with the nitrogen atom to which they are attached form a carbon-containing 4-, 5-, 6- or 7-membered heterocylic ring which may be saturated or unsaturated with 1 or 2 double bonds and which may be optionally mono- or di-substituted with substituents selected from oxo, alkyl, alkoxy, OH, F and CF$_3$.

Preferably, A is thiazolyl substituted by phenyl.

Preferably, A is phenyl substituted by heteroaryl, —(CH$_2$)$_{1-3}$-heteroaryl and —(CH$_2$)$_{1-3}$—NR14R15.

Preferably, A is selected from:

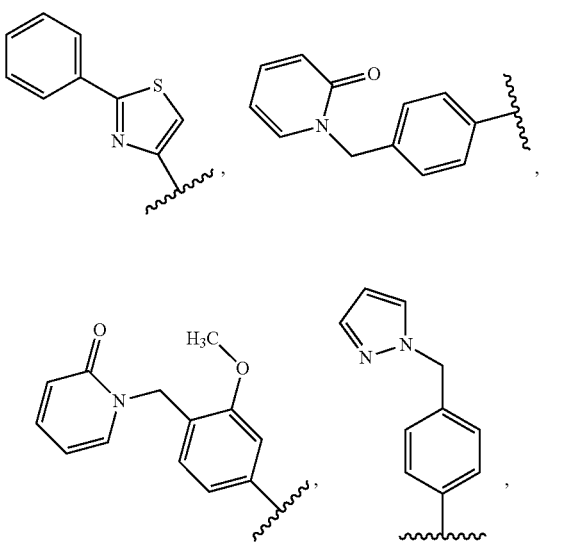

Preferably, A is selected from:

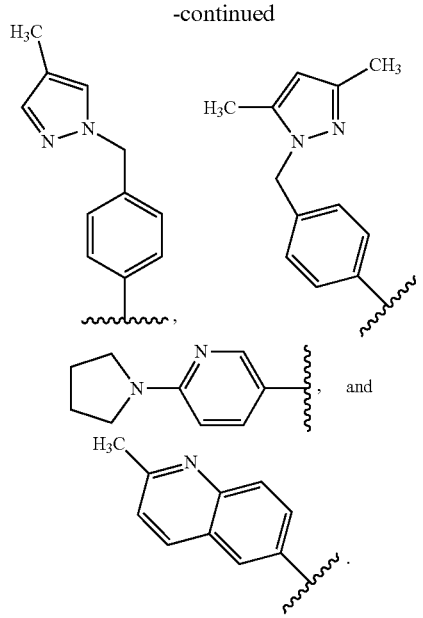

Preferably, A is selected from:

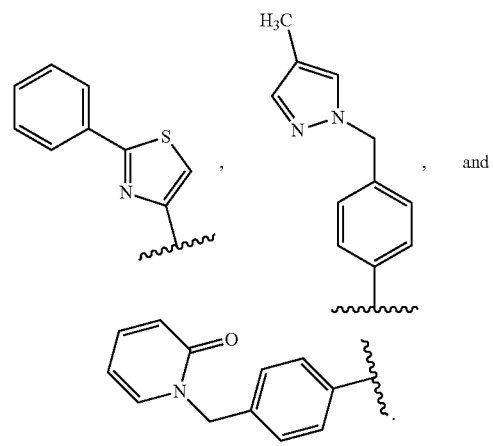

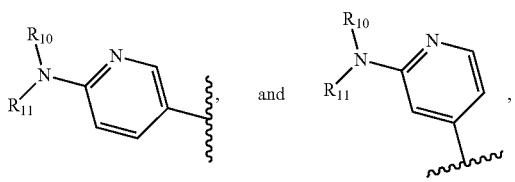

and R10 and R11 are as defined in the first aspect above.

The present invention also encompasses, but is not limited to, the compounds listed in the aspects below.

In an aspect, the invention comprises a compound selected from:

2,5-Dimethyl-1-(2-phenyl-thiazol-4-ylmethyl)-1H-pyrrole-3-carboxylic acid (1-amino-isoquinolin-6-ylmethyl)-amide;

1-[4-(4-Methyl-pyrazol-1-ylmethyl)-benzyl]-1H-imidazole-4-carboxylic acid (1-amino-isoquinolin-6-ylmethyl)-amide;

2,5-Dimethyl-1-[4-(2-oxo-2H-pyridin-1-ylmethyl)-benzyl]-1H-pyrrole-3-carboxylic acid (1-amino-isoquinolin-6-ylmethyl)-amide;

2,5-Dimethyl-1-[4-(4-methyl-pyrazol-1-ylmethyl)-benzyl]-1H-pyrrole-3-carboxylic acid (1-amino-isoquinolin-6-ylmethyl)-amide;

1-Ethyl-4-methyl-5-[4-(4-methyl-pyrazol-1-ylmethyl)-benzyl]-1H-pyrrole-2-carboxylic acid (1-amino-isoquinolin-6-ylmethyl)-amide;

1-Ethyl-4-methyl-5-[4-(2-oxo-2H-pyridin-1-ylmethyl)-benzyl]-1H-pyrrole-2-carboxylic acid (1-amino-isoquinolin-6-ylmethyl)-amide;

1-[4-(4-Methyl-pyrazol-1-ylmethyl)-benzyl]-1H-pyrazole-4-carboxylic acid (1-amino-isoquinolin-6-ylmethyl)-amide;

1-[4-(4-Methyl-pyrazol-1-ylmethyl)-benzyl]-1H-[1,2,3]triazole-4-carboxylic acid (1-amino-isoquinolin-6-ylmethyl)-amide;

1-[4-(Pyridin-2-yloxy)-benzyl]-1H-pyrazole-4-carboxylic acid (1-amino-isoquinolin-6-ylmethyl)-amide;

3-Methyl-1-[4-(4-methyl-pyrazol-1-ylmethyl)-benzyl]-1H-pyrazole-4-carboxylic acid (1-amino-isoquinolin-6-ylmethyl)-amide;

3-Cyclopropyl-1-[4-(4-methyl-pyrazol-1-ylmethyl)-benzyl]-1H-pyrazole-4-carboxylic acid (1-amino-isoquinolin-6-ylmethyl)-amide;

3-Isopropyl-1-[4-(4-methyl-pyrazol-1-ylmethyl)-benzyl]-1H-pyrazole-4-carboxylic acid (1-amino-isoquinolin-6-ylmethyl)-amide;

3-Cyclobutyl-1-[4-(4-methyl-pyrazol-1-ylmethyl)-benzyl]-1H-pyrazole-4-carboxylic acid (1-amino-isoquinolin-6-ylmethyl)-amide;

3-Hydroxymethyl-1-[4-(4-methyl-pyrazol-1-ylmethyl)-benzyl]-1H-pyrazole-4-carboxylic acid (1-amino-isoquinolin-6-ylmethyl)-amide;

3-Cyano-1-[4-(4-methyl-pyrazol-1-ylmethyl)-benzyl]-1H-pyrazole-4-carboxylic acid (1-amino-isoquinolin-6-ylmethyl)-amide;

4-Methyl-2-[4-(4-methyl-pyrazol-1-ylmethyl)-benzyl]-thiazole-5-carboxylic acid (1-amino-isoquinolin-6-ylmethyl)-amide;

3-(3,5-Dimethyl-isoxazol-4-yl)-1-[4-(4-methyl-pyrazol-1-ylmethyl)-benzyl]-1H-pyrazole-4-carboxylic acid (1-amino-isoquinolin-6-ylmethyl)-amide;

1-[4-(4-Methyl-pyrazol-1-ylmethyl)-benzyl]-3-morpholin-4-yl-1H-pyrazole-4-carboxylic acid (1-amino-isoquinolin-6-ylmethyl)-amide;

5-Amino-1-(4-pyrazol-1-ylmethyl-benzyl)-1H-pyrazole-4-carboxylic acid (1-amino-isoquinolin-6-ylmethyl)-amide;

1-(6-Pyrrolidin-1-yl-pyridin-3-ylmethyl)-3-trifluoromethyl-1H-pyrazole-4-carboxylic acid (1-amino-isoquinolin-6-ylmethyl)-amide;

3-Cyclopropyl-1-(5-methoxy-6-pyrrolidin-1-yl-pyridin-3-ylmethyl)-1H-pyrazole-4-carboxylic acid (1-amino-isoquinolin-6-ylmethyl)-amide;

1-[4-(4-Methylpyrazol-1-ylmethyl)-benzyl]-1H-pyrazole-4-carboxylic acid (1-amino-isoquinolin-6-ylmethyl)-amide;

1-[4-(4-Methyl-pyrazol-1-ylmethyl)-benzyl]-1H-imidazole-4-carboxylic acid (1-amino-isoquinolin-6-ylmethyl)-amide;

1-[4-(4-Methyl-pyrazol-1-ylmethyl)-benzyl]-3-phenyl-1H-pyrazole-4-carboxylic acid (1-amino-isoquinolin-6-ylmethyl)-amide;

1-[4-(4-Methyl-pyrazol-1-ylmethyl)-benzyl]-3-trifluoromethyl-1H-pyrazole-4-carboxylic acid (1-amino-isoquinolin-6-ylmethyl)-amide;

3-Amino-1-[4-(4-methyl-pyrazol-1-ylmethyl)-benzyl]-1H-pyrazole-4-carboxylic acid (1-amino-isoquinolin-6-ylmethyl)-amide;

3-Methoxymethyl-1-[4-(4-methyl-pyrazol-1-ylmethyl)-benzyl]-1H-pyrazole-4-carboxylic acid (1-amino-isoquinolin-6-ylmethyl)-amide;

3-Difluoromethyl-1-[4-(4-methyl-pyrazol-1-ylmethyl)-benzyl]-1H-pyrazole-4-carboxylic acid (1-amino-isoquinolin-6-ylmethyl)-amide;

1-[4-(4-Methyl-pyrazol-1-ylmethyl)-benzyl]-3-thiophen-3-yl-1H-pyrazole-4-carboxylic acid (1-amino-isoquinolin-6-ylmethyl)-amide;

5-Amino-1-(4-pyrazol-1-ylmethyl-benzyl)-1H-pyrazole-4-carboxylic acid (1-amino-isoquinolin-6-ylmethyl)-amide;

1-(2-Pyrrolidin-1-yl-pyridin-4-ylmethyl)-3-trifluoromethyl-1H-pyrazole-4-carboxylic acid (1-amino-isoquinolin-6-ylmethyl)-amide;

1-(6-Ethoxy-pyridin-3-ylmethyl)-3-trifluoromethyl-1H-pyrazole-4-carboxylic acid (1-amino-isoquinolin-6-ylmethyl)-amide;

1-[2-(3,3-Difluoro-pyrrolidin-1-yl)-pyridin-4-ylmethyl]-3-trifluoromethyl-1H-pyrazole-4-carboxylic acid (1-amino-isoquinolin-6-ylmethyl)-amide;

1-[6-(3,3-Difluoro-pyrrolidin-1-yl)-pyridin-3-ylmethyl]-3-trifluoromethyl-1H-pyrazole-4-carboxylic acid (1-amino-isoquinolin-6-ylmethyl)-amide;

1-[6-((R)-3-Methyl-pyrrolidin-1-yl)-pyridin-3-ylmethyl]-3-trifluoromethyl-1H-pyrazole-4-carboxylic acid (1-amino-isoquinolin-6-ylmethyl)-amide;

1-[6-((S)-3-Methyl-pyrrolidin-1-yl)-pyridin-3-ylmethyl]-3-trifluoromethyl-1H-pyrazole-4-carboxylic acid (1-amino-isoquinolin-6-ylmethyl)-amide;

1-[6-((S)-3-Fluoro-pyrrolidin-1-yl)-pyridin-3-ylmethyl]-3-trifluoromethyl-1H-pyrazole-4-carboxylic acid (1-amino-isoquinolin-6-ylmethyl)-amide;

1-[6-((R)-3-Fluoro-pyrrolidin-1-yl)-pyridin-3-ylmethyl]-3-trifluoromethyl-1H-pyrazole-4-carboxylic acid (1-amino-isoquinolin-6-ylmethyl)-amide;

1-[6-((S)-2-Methyl-pyrrolidin-1-yl)-pyridin-3-ylmethyl]-3-trifluoromethyl-1H-pyrazole-4-carboxylic acid (1-amino-isoquinolin-6-ylmethyl)-amide;

1-[6-((R)-2-Methyl-pyrrolidin-1-yl)-pyridin-3-ylmethyl]-3-trifluoromethyl-1H-pyrazole-4-carboxylic acid (1-amino-isoquinolin-6-ylmethyl)-amide;

1-(2-Pyrrolidin-1-yl-pyrimidin-5-ylmethyl)-3-trifluoromethyl-1H-pyrazole-4-carboxylic acid (1-amino-isoquinolin-6-ylmethyl)-amide;

1-(5-Pyrrolidin-1-yl-pyrazin-2-ylmethyl)-3-trifluoromethyl-1H-pyrazole-4-carboxylic acid (1-amino-isoquinolin-6-ylmethyl)-amide;

1-[2-((S)-3-Methyl-pyrrolidin-1-yl)-pyridin-4-ylmethyl]-3-trifluoromethyl-1H-pyrazole-4-carboxylic acid (1-amino-isoquinolin-6-ylmethyl)-amide;

1-[6-(3-Hydroxymethyl-pyrrolidin-1-yl)-pyridin-3-ylmethyl]-3-trifluoromethyl-1H-pyrazole-4-carboxylic acid (1-amino-isoquinolin-6-ylmethyl)-amide;

1-[6-((R)-3-Hydroxymethyl-pyrrolidin-1-yl)-pyridin-3-ylmethyl]-3-trifluoromethyl-1H-pyrazole-4-carboxylic acid (1-amino-isoquinolin-6-ylmethyl)-amide;

1-(6-Propoxy-pyridin-3-ylmethyl)-3-trifluoromethyl-1H-pyrazole-4-carboxylic acid (1-amino-isoquinolin-6-ylmethyl)-amide;

1-(5-Fluoro-6-pyrrolidin-1-yl-pyridin-3-ylmethyl)-3-trifluoromethyl-1H-pyrazole-4-carboxylic acid (1-amino-isoquinolin-6-ylmethyl)-amide;
1-(6-Ethoxy-5-fluoro-pyridin-3-yl methyl)-3-trifluoromethyl-1H-pyrazole-4-carboxylic acid (1-amino-isoquinolin-6-ylmethyl)-amide;
1-(4-Pyrazol-1-ylmethyl-benzyl)-3-trifluoromethyl-1H-pyrazole-4-carboxylic acid (1-amino-isoquinolin-6-ylmethyl)-amide;
1-[4-(4-Cyano-pyrazol-1-ylmethyl)-benzyl]-3-trifluoromethyl-1H-pyrazole-4-carboxylic acid (1-amino-isoquinolin-6-ylmethyl)-amide;
1-[4-(4-Carbamoyl-pyrazol-1-ylmethyl)-benzyl]-3-trifluoromethyl-1H-pyrazole-4-carboxylic acid (1-amino-isoquinolin-6-ylmethyl)-amide;
1-(6-Pyrazol-1-ylmethyl-pyridin-3-ylmethyl)-3-trifluoromethyl-1H-pyrazole-4-carboxylic acid (1-amino-isoquinolin-6-ylmethyl)-amide;
1-(2-Pyrazol-1-ylmethyl-thiazol-4-ylmethyl)-3-trifluoromethyl-1H-pyrazole-4-carboxylic acid (1-amino-isoquinolin-6-ylmethyl)-amide;
1-[2-(4-Methyl-pyrazol-1-ylmethyl)-thiazol-4-ylmethyl]-3-trifluoromethyl-1H-pyrazole-4-carboxylic acid (1-amino-isoquinolin-6-ylmethyl)-amide;
3-Cyclopropyl-1-{6-[(2-methoxy-ethyl)-methyl-amino]-pyridin-3-ylmethyl}-1H-pyrazole-4-carboxylic acid (1-amino-isoquinolin-6-ylmethyl)-amide;
3-Cyclopropyl-1-[6-(3,3-difluoro-pyrrolidin-1-yl)-pyridin-3-ylmethyl]-1H-pyrazole-4-carboxylic acid (1-amino-isoquinolin-6-ylmethyl)-amide;
3-Cyclopropyl-1-(4-methoxy-6-pyrrolidin-1-yl-pyridin-3-ylmethyl)-1H-pyrazole-4-carboxylic acid (1-amino-isoquinolin-6-ylmethyl)-amide;
3-Cyclopropyl-1-(6-pyrrolidin-1-yl-pyridin-3-ylmethyl)-1H-pyrazole-4-carboxylic acid (1-amino-isoquinolin-6-ylmethyl)-amide;
3-Cyclopropyl-1-(4-[1,2,3]triazol-1-ylmethyl-benzyl)-1H-pyrazole-4-carboxylic acid (1-amino-isoquinolin-6-ylmethyl)-amide;
3-Cyclopropyl-1-(6-phenoxy-pyridin-3-ylmethyl)-1H-pyrazole-4-carboxylic acid (1-amino-isoquinolin-6-ylmethyl)-amide;
1-(5-Chloro-6-ethoxy-pyridin-3-ylmethyl)-3-cyclopropyl-1H-pyrazole-4-carboxylic acid (1-amino-isoquinolin-6-ylmethyl)-amide;
3-Cyclopropyl-1-(6-diethylamino-5-fluoro-pyridin-3-ylmethyl)-1H-pyrazole-4-carboxylic acid (1-amino-isoquinolin-6-ylmethyl)-amide;
1-(5-Chloro-6-pyrrolidin-1-yl-pyridin-3-ylmethyl)-3-cyclopropyl-1H-pyrazole-4-carboxylic acid (1-amino-isoquinolin-6-ylmethyl)-amide;
3-Amino-1-(6-ethoxy-pyridin-3-ylmethyl)-1H-pyrazole-4-carboxylic acid (1-amino-isoquinolin-6-ylmethyl)-amide;
3-Amino-1-(6-pyrrolidin-1-yl-pyridin-3-ylmethyl)-1H-pyrazole-4-carboxylic acid (1-amino-isoquinolin-6-ylmethyl)-amide;
and pharmaceutically acceptable salts and solvates thereof.

In an aspect, the invention comprises a compound selected from:
2,5-Dimethyl-1-(2-phenyl-thiazol-4-ylmethyl)-1H-pyrrole-3-carboxylic acid (1-amino-isoquinolin-6-ylmethyl)-amide;
1-[4-(4-Methyl-pyrazol-1-ylmethyl)-benzyl]-1H-imidazole-4-carboxylic acid (1-amino-isoquinolin-6-ylmethyl)-amide;
1-[4-(4-Methyl-pyrazol-1-ylmethyl)-benzyl]-1H-pyrazole-4-carboxylic acid (6-methyl-1H-pyrrolo[2,3-b]pyridin-5-ylmethyl)-amide;
2,5-Dimethyl-1-[4-(2-oxo-2H-pyridin-1-ylmethyl)-benzyl]-1H-pyrrole-3-carboxylic acid (1-amino-isoquinolin-6-ylmethyl)-amide;
2,5-Dimethyl-1-[4-(4-methyl-pyrazol-1-ylmethyl)-benzyl]-1H-pyrrole-3-carboxylic acid (1-amino-isoquinolin-6-ylmethyl)-amide;
1-Ethyl-4-methyl-5-[4-(4-methyl-pyrazol-1-ylmethyl)-benzyl]-1H-pyrrole-2-carboxylic acid (1-amino-isoquinolin-6-ylmethyl)-amide;
1-Ethyl-4-methyl-5-[4-(2-oxo-2H-pyridin-1-ylmethyl)-benzyl]-1H-pyrrole-2-carboxylic acid (1-amino-isoquinolin-6-ylmethyl)-amide;
1-[4-(4-Methyl-pyrazol-1-ylmethyl)-benzyl]-1H-pyrazole-4-carboxylic acid (1-amino-isoquinolin-6-ylmethyl)-amide;
1-[4-(4-Methyl-pyrazol-1-ylmethyl)-benzyl]-1H-[1,2,3]triazole-4-carboxylic acid (1-amino-isoquinolin-6-ylmethyl)-amide;
1-[4-(Pyridin-2-yloxy)-benzyl]-1H-pyrazole-4-carboxylic acid (1-amino-isoquinolin-6-ylmethyl)-amide;
1-[4-(4-Methylpyrazol-1-ylmethyl)-benzyl]-1H-pyrazole-4-carboxylic acid (1-amino-isoquinolin-6-ylmethyl)-amide;
1-[4-(4-Methyl-pyrazol-1-ylmethyl)-benzyl]-1H-imidazole-4-carboxylic acid (1-amino-isoquinolin-6-ylmethyl)-amide;
2,5-Dimethyl-1-[4-(2-oxo-2H-pyridin-1-ylmethyl)-benzyl]-1H-pyrrole-3-carboxylic acid (1-amino-isoquinolin-6-ylmethyl)-amide;
2,5-Dimethyl-1-[4-(4-methyl-pyrazol-1-ylmethyl)-benzyl]-1H-pyrrole-3-carboxylic acid (1-amino-isoquinolin-6-ylmethyl)-amide;
1-[4-(4-Methyl-pyrazol-1-ylmethyl)-benzyl]-1H-[1,2,3]triazole-4-carboxylic acid (1H-pyrrolo[2,3-b]pyridin-5-ylmethyl)-amide;
1-[4-(4-Methyl-pyrazol-1-ylmethyl)-benzyl]-1H-pyrazole-4-carboxylic acid (1H-pyrrolo[2,3-b]pyridin-5-ylmethyl)-amide;
and pharmaceutically acceptable salts and solvates thereof.

In an aspect, the invention comprises a compound selected from:
2,5-Dimethyl-1-(2-phenyl-thiazol-4-ylmethyl)-1H-pyrrole-3-carboxylic acid (1-amino-isoquinolin-6-ylmethyl)-amide;
2,5-Dimethyl-1-(2-phenyl-thiazol-4-ylmethyl)-1H-pyrrole-3-carboxylic acid (1-amino-isoquinolin-7-ylmethyl)-amide;
1-[4-(4-Methyl-pyrazol-1-ylmethyl)-benzyl]-1H-imidazole-4-carboxylic acid (1-amino-isoquinolin-6-ylmethyl)-amide;
2,5-Dimethyl-1-[4-(4-methyl-pyrazol-1-ylmethyl)-benzyl]-1H-pyrrole-3-carboxylic acid (1-aminoisoquinolin-6-ylmethyl)-amide;
1-Ethyl-4-methyl-5-[4-(4-methyl-pyrazol-1-ylmethyl)-benzyl]-1H-pyrrole-2-carboxylic acid (1-amino-isoquinolin-6-ylmethyl)-amide;
1-Ethyl-4-methyl-5-(2-phenyl-thiazol-4-ylmethyl)-1H-pyrrole-2-carboxylic acid (1-aminoisoquinolin-6-ylmethyl)-amide;
1-[4-(4-Methyl-pyrazol-1-ylmethyl)-benzyl]-1H-pyrazole-4-carboxylic acid (1-amino-isoquinolin-6-ylmethyl)-amide;
1-(2-Phenyl-thiazol-4-ylmethyl)-1H-imidazole-4-carboxylic acid (1-amino-isoquinolin-6-ylmethyl)-amide;
1-(2-Phenyl-thiazol-4-ylmethyl)-1H-pyrazole-4-carboxylic acid (1-amino-isoquinolin-6-ylmethyl)-amide;

1-[4-(4-Methyl-pyrazol-1-ylmethyl)-benzyl]-1H-[1,2,3]triazole-4-carboxylic acid (1-aminoisoquinolin-6-ylmethyl)-amide;

and pharmaceutically acceptable salts and solvates thereof.

In an aspect, the invention comprises a compound selected from:

1-[4-(4-Methyl-pyrazol-1-ylmethyl)-benzyl]-1H-pyrazole-4-carboxylic acid (6-methyl-1H-pyrrolo[2,3-b]pyridin-5-ylmethyl)-amide;

1-[4-(4-Methyl-pyrazol-1-ylmethyl)-benzyl]-1H-[1,2,3]triazole-4-carboxylic acid (1H-pyrrolo[2,3-b]pyridin-5-ylmethyl)-amide;

1-[4-(4-Methyl-pyrazol-1-ylmethyl)-benzyl]-1H-pyrazole-4-carboxylic acid (1H-pyrrolo[2,3-b]pyridin-5-ylmethyl)-amide;

1-[4-(2-Oxo-2H-pyridin-1-ylmethyl)-benzyl]-3-trifluoromethyl-1H-pyrazole-4-carboxylic acid (1H-pyrrolo[2,3-b]pyridin-5-ylmethyl)-amide;

1-[4-(2-Oxo-2H-pyridin-1-ylmethyl)-benzyl]-3-trifluoromethyl-1H-pyrazole-4-carboxylic acid (4,6-dimethyl-1H-pyrrolo[2,3-b]pyridin-5-ylmethyl)-amide;

1-[4-(4-Methyl-pyrazol-1-ylmethyl)-benzyl]-1H-pyrazole-4-carboxylic acid (1H-pyrrolo[2,3-b]pyridin-5-ylmethyl)-amide;

1-[4-(4-Methyl-pyrazol-1-ylmethyl)-benzyl]-1H-pyrazole-4-carboxylic acid (4,6-dimethyl-1H-pyrrolo[2,3-b]pyridin-5-ylmethyl)-amide;

1-[4-(4-Methyl-pyrazol-1-ylmethyl)-benzyl]-3-trifluoromethyl-1H-pyrazole-4-carboxylic acid (4,6-dimethyl-1H-pyrrolo[2,3-b]pyridin-5-ylmethyl)-amide;

1-[4-(4-Methyl-pyrazol-1-ylmethyl)-benzyl]-3-trifluoromethyl-1H-pyrazole-4-carboxylic acid (1H-pyrrolo[2,3-b]pyridin-5-ylmethyl)-amide;

1-[4-(4-Methyl-pyrazol-1-ylmethyl)-benzyl]-3-trifluoromethyl-1H-pyrazole-4-carboxylic acid (1H-indol-5-ylmethyl)-amide;

3-Amino-1-[4-(2-oxo-2H-pyridin-1-ylmethyl)-benzyl]-1H-pyrazole-4-carboxylic acid (1H-indazol-4-ylmethyl)-amide;

1-[4-(2-Oxo-2H-pyridin-1-ylmethyl)-benzyl]-3-trifluoromethyl-1H-pyrazole-4-carboxylic acid (1H-indazol-4-ylmethyl)-amide;

1-(6-Pyrrolidin-1-yl-pyridin-3-ylmethyl)-3-trifluoromethyl-1H-pyrazole-4-carboxylic acid (5-chloro-1H-indazol-3-ylmethyl)-amide;

1-[4-(2-Oxo-2H-pyridin-1-ylmethyl)-benzyl]-3-trifluoromethyl-1H-pyrazole-4-carboxylic acid (5-chloro-1H-indazol-3-ylmethyl)-amide;

and pharmaceutically acceptable salts and solvates thereof.

Therapeutic Applications

As previously mentioned, the compounds of the present invention are potent and selective inhibitors of plasma kallikrein. They are therefore useful in the treatment of disease conditions for which over-activity of plasma kallikrein is a causative factor.

Accordingly, the present invention provides a compound of formula (I) for use in medicine.

The present invention also provides for the use of a compound of formula (I) in the manufacture of a medicament for the treatment or prevention of a disease or condition in which plasma kallikrein activity is implicated.

The present invention also provides a compound of formula (I) for use in the treatment or prevention of a disease or condition in which plasma kallikrein activity is implicated.

The present invention also provides a method of treatment of a disease or condition in which plasma kallikrein activity is implicated comprising administration to a subject in need thereof a therapeutically effective amount of a compound of formula (I).

In one aspect, the disease or condition in which plasma kallikrein activity is implicated is selected from impaired visual acuity, diabetic retinopathy, diabetic macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post operative surgery.

In a preferred aspect, the disease or condition in which plasma kallikrein activity is implicated is retinal vascular permeability associated with diabetic retinopathy and diabetic macular edema.

Combination Therapy

The compounds of the present invention may be administered in combination with other therapeutic agents. Suitable combination therapies include a compound of formula (I) combined with one or more agents selected from agents that inhibit platelet-derived growth factor (PDGF), endothelial growth factor (VEGF), integrin alpha5beta1, steroids, other agents that inhibit plasma kallikrein and other inhibitors of inflammation. Specific examples of therapeutic agents that may be combined with the compounds of the present invention include those disclosed in EP2281885A and by S. Patel in *Retina*, 2009 June; 29(6 Suppl):S45-8.

When combination therapy is employed, the compounds of the present invention and said combination agents may exist in the same or different pharmaceutical compositions, and may be administered separately, sequentially or simultaneously.

In another aspect, the compounds of the present invention may be administered in combination with laser treatment of the retina. The combination of laser therapy with intravitreal injection of an inhibitor of VEGF for the treatment of diabetic macular edema is known (Elman M, Aiello L, Beck R, et al. "Randomized trial evaluating ranibizumab plus prompt or deferred laser or triamcinolone plus prompt laser for diabetic macular edema". Ophthalmology. 27 Apr. 2010).

DEFINITIONS

The term "alkyl" includes saturated hydrocarbon residues including:

linear groups up to 10 carbon atoms ($C_1$-$C_{10}$), or of up to 6 carbon atoms ($C_1$-$C_6$), or of up to 4 carbon atoms ($C_1$-$C_4$). Examples of such alkyl groups include, but are not limited to, $C_1$—methyl, $C_2$—ethyl, $C_3$—propyl and $C_4$—n-butyl.

branched groups of between 3 and 10 carbon atoms ($C_3$-$C_{10}$), or of up to 7 carbon atoms ($C_3$-$C_7$), or of up to 4 carbon atoms ($C_3$-$C_4$). Examples of such alkyl groups include, but are not limited to, $C_3$—iso-propyl, $C_4$—sec-butyl, $C_4$—iso-butyl, $C_4$—tert-butyl and $C_5$—neo-pentyl.

each optionally substituted as stated above.

Cycloalkyl is a monocyclic saturated hydrocarbon of between 3 and 7 carbon atoms; wherein cycloalkyl may be optionally substituted with a substituent selected from alkyl, alkoxy and NR10R11; wherein R10 and R11 are independently selected from H and alkyl or R10 and R11 together with the nitrogen to which they are attached form a 4-, 5-, 6- or 7-membered heterocyclic ring which may be saturated or unsaturated with 1 or 2 double bonds and which may be optionally mono- or di-substituted with substituents selected from oxo, alkyl, alkoxy, OH, F and $CF_3$. Cycloalkyl groups may contain from 3 to 7 carbon atoms, or from 3 to 6 carbon atoms, or from 3 to 5 carbon atoms, or from 3 to 4 carbon atoms. Examples of suitable monocyclic cycloalkyl groups include cyclopropyl, cyclobutyl, cyclopentyl, cyclohexyl and cycloheptyl.

The term "alkoxy" includes O-linked hydrocarbon residues including:
- linear groups of between 1 and 6 carbon atoms ($C_1$-$C_6$), or of between 1 and 4 carbon atoms ($C_1$-$C_4$). Examples of such alkoxy groups include, but are not limited to, $C_1$—methoxy, $C_2$—ethoxy, $C_3$—n-propoxy and $C_4$—n-butoxy.
- branched groups of between 3 and 6 carbon atoms ($C_3$-$C_6$) or of between 3 and 4 carbon atoms ($C_3$-$C_4$). Examples of such alkoxy groups include, but are not limited to, $C_3$—iso-propoxy, and $C_4$—sec-butoxy and tert-butoxy.

each optionally substituted as stated above.

Unless otherwise stated, halo is selected from Cl, F, Br and I.

Aryl is as defined above. Typically, aryl will be optionally substituted with 1, 2 or 3 substituents. Optional substituents are selected from those stated above. Examples of suitable aryl groups include phenyl and naphthyl (each optionally substituted as stated above). Preferably aryl is selected from phenyl, substituted phenyl (substituted as stated above) and naphthyl.

Heteroaryl is as defined above. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl and isoquinolinyl (optionally substituted as stated above). Preferably heteroaryl is selected from pyridyl, benzothiazole, indole, N-methylindole, thiazole, substituted thiazole, thiophenyl, furyl, pyrazine, pyrazole and substituted pyrazole; wherein substituents are as stated above.

The term "N-linked", such as in "N-linked heterocycloalkyl", means that the heterocycloalkyl group is joined to the remainder of the molecule via a ring nitrogen atom.

The term "O-linked", such as in "O-linked hydrocarbon residue", means that the hydrocarbon residue is joined to the remainder of the molecule via an oxygen atom.

In groups such as —COOR* and —$(CH_2)_{1-3}$-aryl, "-" denotes the point of attachment of the substituent group to the remainder of the molecule.

"Pharmaceutically acceptable salt" means a physiologically or toxicologically tolerable salt and includes, when appropriate, pharmaceutically acceptable base addition salts and pharmaceutically acceptable acid addition salts. For example (i) where a compound of the invention contains one or more acidic groups, for example carboxy groups, pharmaceutically acceptable base addition salts that can be formed include sodium, potassium, calcium, magnesium and ammonium salts, or salts with organic amines, such as, diethylamine, N-methyl-glucamine, diethanolamine or amino acids (e.g. lysine) and the like; (ii) where a compound of the invention contains a basic group, such as an amino group, pharmaceutically acceptable acid addition salts that can be formed include hydrochlorides, hydrobromides, sulfates, phosphates, acetates, citrates, lactates, tartrates, mesylates, succinates, oxalates, phosphates, esylates, tosylates, benzenesulfonates, naphthalenedisulphonates, maleates, adipates, fumarates, hippurates, camphorates, xinafoates, p-acetamidobenzoates, dihydroxybenzoates, hydroxynaphthoates, succinates, ascorbates, oleates, bisulfates and the like.

Hemisalts of acids and bases can also be formed, for example, hemisulfate and hemicalcium salts.

For a review of suitable salts, see "Handbook of Pharmaceutical Salts: Properties, Selection and Use" by Stahl and Wermuth (Wiley-VCH, Weinheim, Germany, 2002).

"Prodrug" refers to a compound which is convertible in vivo by metabolic means (e.g. by hydrolysis, reduction or oxidation) to a compound of the invention. Suitable groups for forming prodrugs are described in 'The Practice of Medicinal Chemistry, $2^{nd}$ Ed. pp 561-585 (2003) and in F. J. Leinweber, *Drug Metab. Res.*, 1987, 18, 379.

The compounds of the invention can exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Where compounds of the invention exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application or adaptation of known methods (e.g. asymmetric synthesis).

In the context of the present invention, references herein to "treatment" include references to curative, palliative and prophylactic treatment.

General Methods

The compounds of formula (I) should be assessed for their biopharmaceutical properties, such as solubility and solution stability (across pH), permeability, etc., in order to select the most appropriate dosage form and route of administration for treatment of the proposed indication. They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

Compounds of the invention intended for pharmaceutical use may be administered as a solid or liquid, such as a tablet, capsule or solution. Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Accordingly, the present invention provides a pharmaceutical composition comprising a compound of formula (I) and a pharmaceutically acceptable carrier, diluent or excipient.

For the treatment of conditions such as retinal vascular permeability associated with diabetic retinopathy and diabetic macular edema, the compounds of the invention may be administered in a form suitable for injection into the ocular region of a patient, in particular, in a form suitable for intravitreal injection. It is envisaged that formulations suitable for such use will take the form of sterile solutions of a compound of the invention in a suitable aqueous vehicle. The compositions may be administered to the patient under the supervision of the attending physician.

The compounds of the invention may also be administered directly into the blood stream, into subcutaneous tissue, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous or oily solutions. Where the solution is aqueous, excipients such as sugars (including but not restricted to glucose, manitol, sorbitol, etc.), salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

Parenteral formulations may include implants derived from degradable polymers such as polyesters (i.e., polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of co-solvents and/or solubility-enhancing agents such as surfactants, micelle structures and cyclodextrins.

In one embodiment, the compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Formulations suitable for oral administration may also be designed to deliver the compounds of the invention in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, Expert Opinion in Therapeutic Patents, 2001, 11 (6), 981-986.

The formulation of tablets is discussed in Pharmaceutical Dosage Forms: Tablets, Vol. 1, by H. Lieberman and L. Lachman (Marcel Dekker, New York, 1980).

For administration to human patients, the total daily dose of the compounds of the invention is typically in the range 0.01 mg and 1000 mg, or between 0.1 mg and 250 mg, or between 1 mg and 50 mg depending, of course, on the mode of administration.

The total dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Synthetic Methods

The compounds of the present invention can be prepared according to the procedures of the following schemes and examples, using appropriate materials, and are further exemplified by the specific examples provided herein below. Moreover, by utilising the procedures described herein, one of ordinary skill in the art can readily prepare additional compounds that fall within the scope of the present invention claimed herein. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The compounds of the invention may be isolated in the form of their pharmaceutically acceptable salts, such as those described previously herein above.

It may be necessary to protect reactive functional groups (e.g. hydroxy, amino, thio or carboxy) in intermediates used in the preparation of compounds of the invention to avoid their unwanted participation in a reaction leading to the formation of the compounds. Conventional protecting groups, for example those described by T. W. Greene and P. G. M. Wuts in "Protective groups in organic chemistry" John Wiley and Sons, 4th Edition, 2006, may be used. For example, a common amino protecting group suitable for use herein is tert-butoxy carbonyl (Boc), which is readily removed by treatment with an acid such as trifluoroacetic acid or hydrogen chloride in an organic solvent such as dichloromethane. Alternatively the amino protecting group may be a benzyloxycarbonyl (Z) group which can be removed by hydrogenation with a palladium catalyst under a hydrogen atmosphere or 9-fluorenylmethyloxycarbonyl (Fmoc) group which can be removed by solutions of secondary organic amines such as diethylamine or piperidine in an organic solvents. Carboxyl groups are typically protected as esters such as methyl, ethyl, benzyl or tert-butyl which can all be removed by hydrolysis in the presence of bases such as lithium or sodium hydroxide. Benzyl protecting groups can also be removed by hydrogenation with a palladium catalyst under a hydrogen atmosphere whilst tert-butyl groups can also be removed by trifluoroacetic acid. Alternatively a trichloroethyl ester protecting group is removed with zinc in acetic acid. A common hydroxy protecting group suitable for use herein is a methyl ether, deprotection conditions comprise refluxing in 48% aqueous HBr for 1-24 hours, or by stirring with borane tribromide in dichloromethane for 1-24 hours. Alternatively where a hydroxy group is protected as a benzyl ether, deprotection conditions comprise hydrogenation with a palladium catalyst under a hydrogen atmosphere.

The compounds according to general formula I can be prepared using conventional synthetic methods for example, but not limited to, the route outlined in Scheme 1. The amine 2 is coupled to an acid 1 to give the compound 3 This coupling is typically carried out using standard coupling condition such as hydroxybenzotriazole and carbodiimide such as water soluble carbodiimide in the presence of an organic base. Other standard coupling methods include the reaction of acids with amines in the presence of 2-(1H-benzotriazole-1-yl)-1,1,3,3-tetramethylaminium hexafluorophosphate or benzotriazole-1-yl-oxy-tris-pyrrolidino-phosphoium hexafluorophosphate or bromo-trispyrolidino-phosphoium hexafluorophosphate in the presence of organic bases such as triethylamine, diisopropylethylamine or N-methylmorpholine. Alternatively the amide formation can take place via an acid chloride in the presence of an organic base. Such acid chlorides can be formed by methods well known in the literature, for example reaction of the acid with oxalyl chloride or thionyl chloride.

Scheme 1

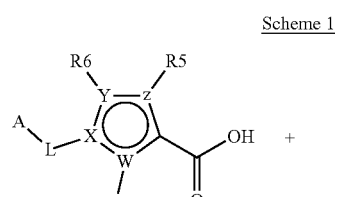

1

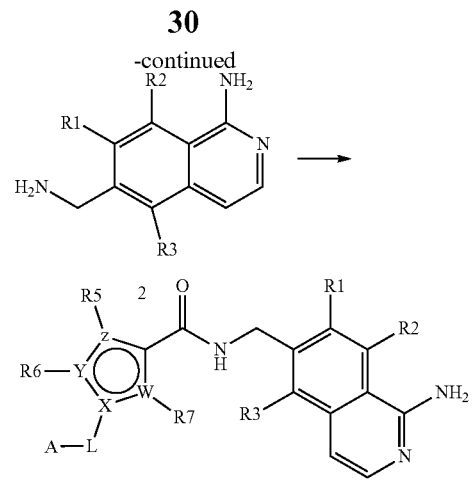

Alternatively compounds according to general formula I can be prepared using the route exemplified in Scheme 2. The acid 1 can be coupled to an amine 4 using suitable coupling methods as previously described to give compound 5 in which the second amino group is amino-protected with a standard protecting group such as tert-butyloxycarbonyl (Boc), benzyloxycarbonyl (Z) or 9-fluorenylmethyloxycarbonyl (Fmoc). In a typical second step the protecting group is removed to give compound 3 using standard methods as previously described.

Scheme 2

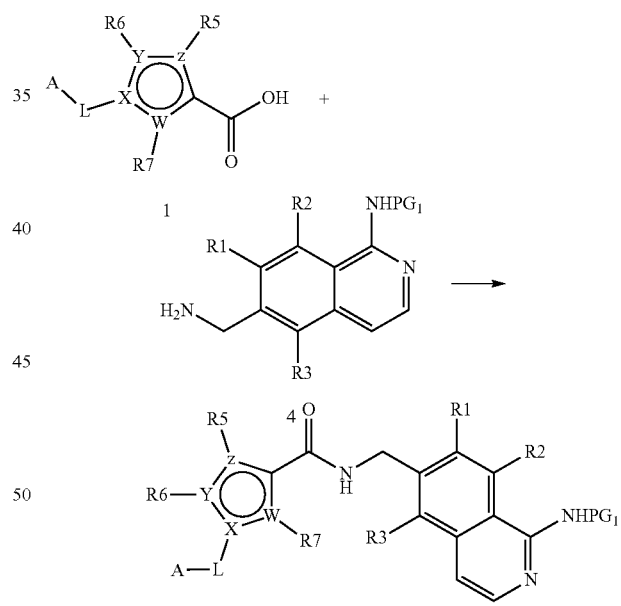

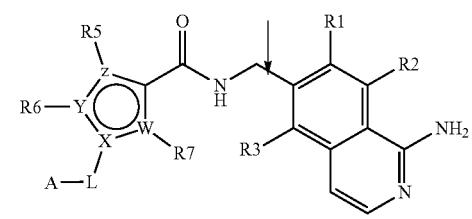

3

Alternatively compounds according to general formula I can be prepared using the route outlined in Scheme 3. The acid 6 can be coupled to an amine 4 using suitable coupling methods as previously described to give compound 7 in which the second amino group is amino-protected with a standard protecting group such as tert-butyloxycarbonyl (Boc), benzyloxycarbonyl (Z) or 9-fluorenylmethyloxycarbonyl (Fmoc). In a typical second step the nitrogen of the heterocyclic ring is alkylated with compound 8 to give compound 9. The alkylation can be carried out in the presence of a base such as potassium carbonate, cesium carbonate, sodium carbonate or sodium hydride in which case the leaving group is a halide or sulphonate. Alternatively the alkylation may be carried out using an alcohol under Mitsunobu conditions in the presence of triphenylphosphine. In a third step the protecting group is removed to give compound 10 using standard methods as previously described.

Alternatively compounds according to general formula I can be prepared using the route outlined in Scheme 4. The pyrrole 15 can be formed in two steps the first of which involves reaction of the sodium salt of an alkyl ketoacetate 11 with a chloroketone 12 in the presence of a base such as potassium carbonate to give compound 13 which in a typical second step is reacted with the amine 14 in the presence of an acid such as but not limited to sulphonic acid derivatives e.g. p-toluenesulphonic acid to yield compound 15 which in a typical third step is subsequently hydrolysed to the corresponding acid 16 using standard methods as described previously. In a typical fourth step the acid 16 can be coupled to an amine 2 using suitable coupling methods as previously described to give compound 17. The second amino group may be amino-protected with a standard protecting group such as tert-butyloxycarbonyl (Boc), benzyloxycarbonyl (Z) or 9-fluorenylmethyloxycarbonyl (Fmoc), if such protection is used the final step will involve removal of the protecting group using standard methods as previously described.

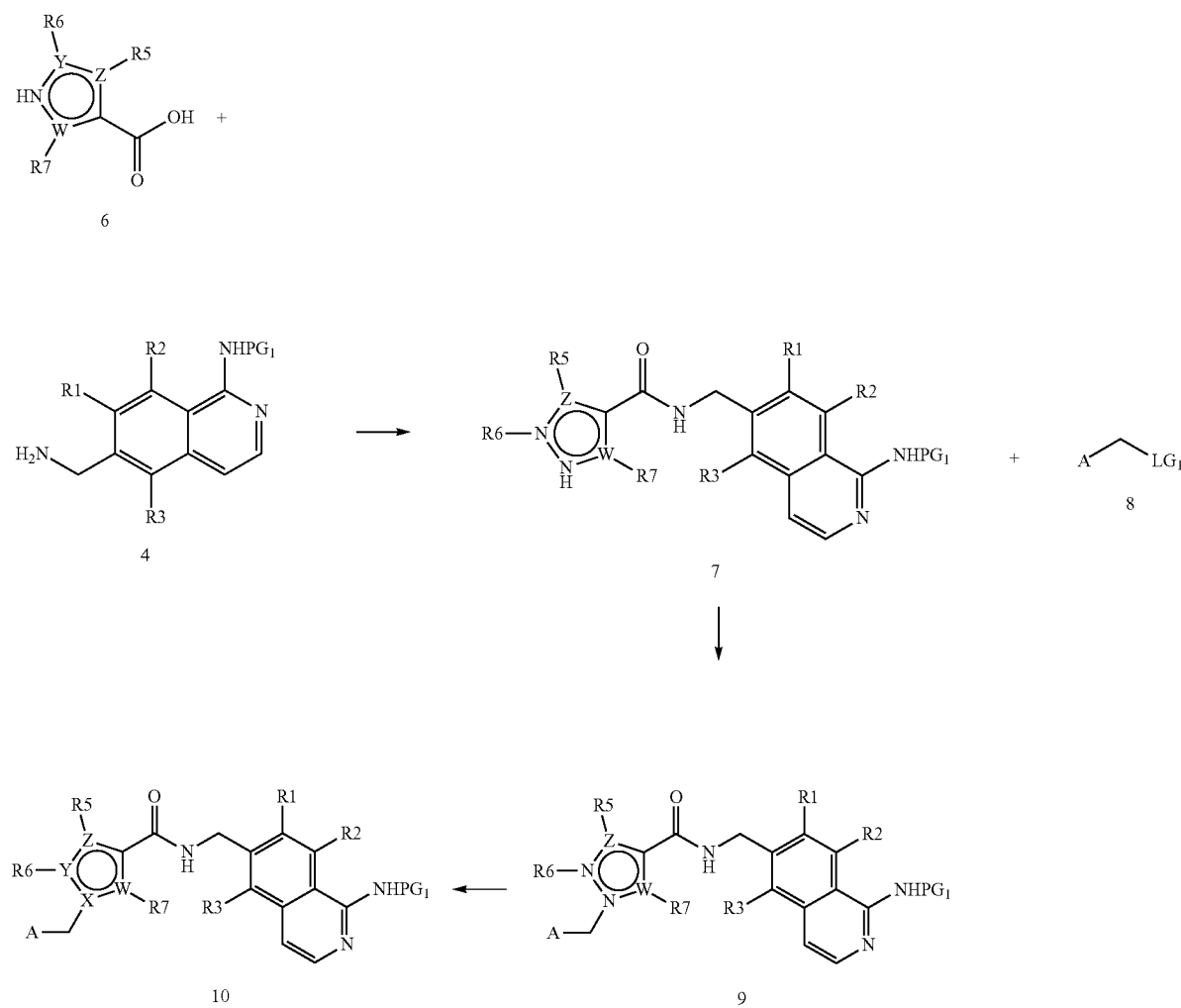

Scheme 3

Scheme 4

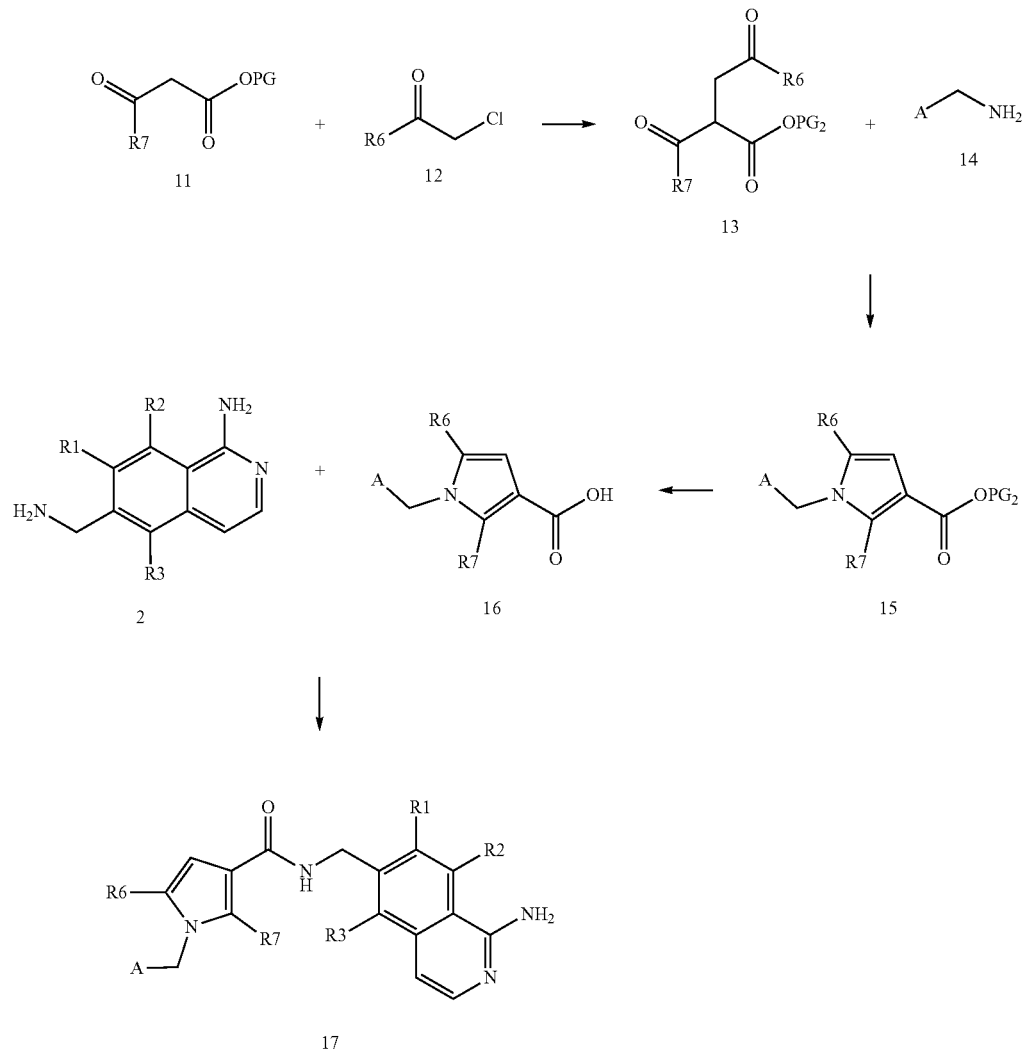

Alternatively compounds according to general formula I can be prepared using the route outlined in Scheme 5. The triazole 19 can be formed by reaction of an alkyl propiolate with the azide 18 under azide alkyne Huisgen cycloaddition conditions employing a catalyst such as copper salts with abscorbic acid derivatives. In a typical second step the ester is hydrolysed to the corresponding acid 20 using standard methods as described previously. In a typical third step the acid 20 can be coupled to an amine 2 using suitable coupling methods as previously described to give compound 21. The second amino group may be amino-protected with a standard protecting group such as tert-butyloxycarbonyl (Boc), benzyloxycarbonyl (Z) or 9-fluorenylmethyloxycarbonyl (Fmoc), if such protection is used the final step will involve removal of the protecting group using standard methods as previously described.

Scheme 5

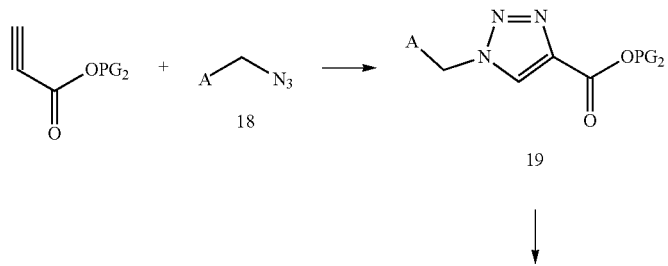

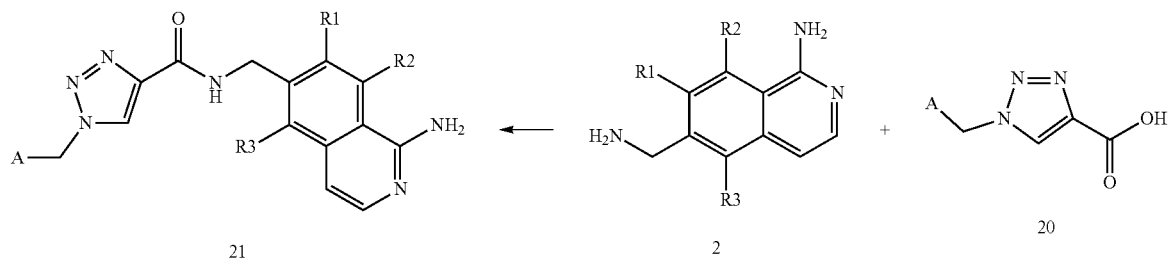

Alternatively compounds according to general formula I can be prepared using the route outlined in Scheme 6. The imidazole 23 can be formed by reaction of the acrylate derivative 22 with the amine 14 in the presence of organic bases such as diisopropylethylamine or triethylamine. In a typical second step the ester is hydrolysed to the corresponding acid 24 using standard methods as described previously. In a typical third step the acid 24 can be coupled to an amine 2 using suitable coupling methods as previously described to give compound 25. The second amino group may be amino-protected with a standard protecting group such as tert-butyloxycarbonyl (Boc), benzyloxycarbonyl (Z) or 9-fluorenylmethyloxycarbonyl (Fmoc), if such protection is used the final step will involve removal of the protecting group using standard methods as previously described.

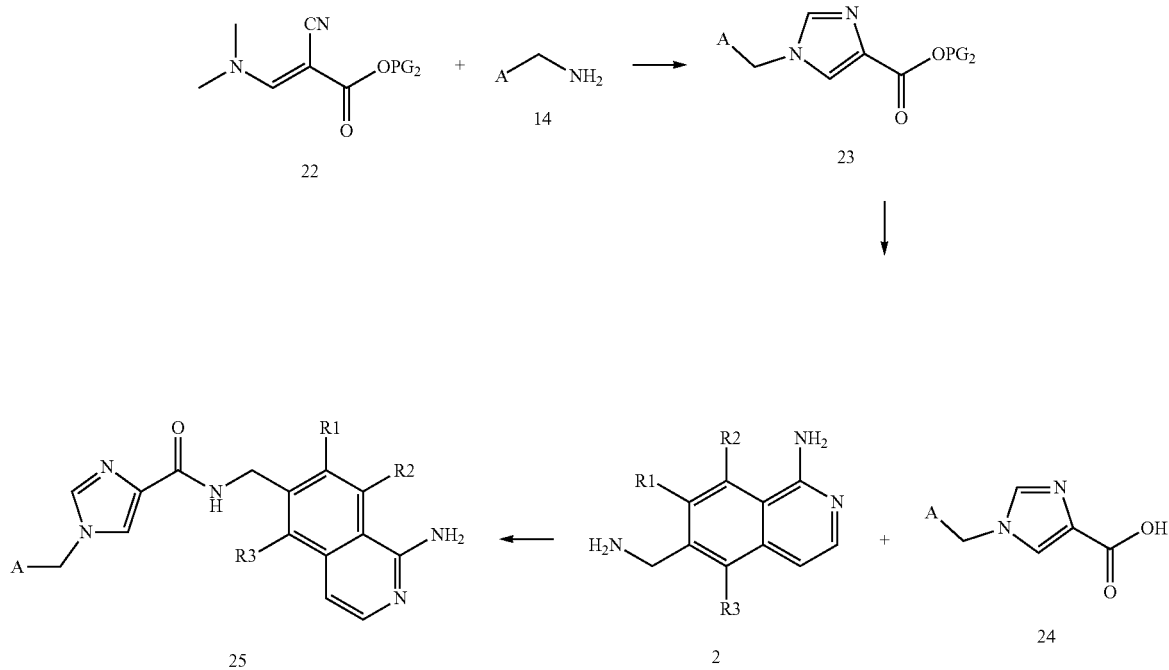

Alternatively compounds according to general formula I can be prepared using the route outlined in Scheme 7. In a typical first step the nitrogen of the heterocyclic ring is derivatised by reaction of compound 7 with the sulphonyl chloride 26 in the presence of organic bases such as diisopropylethylamine or triethylamine to give compound 27. In a typical final step the protecting group is removed to give compound 28 using standard methods as previously described.

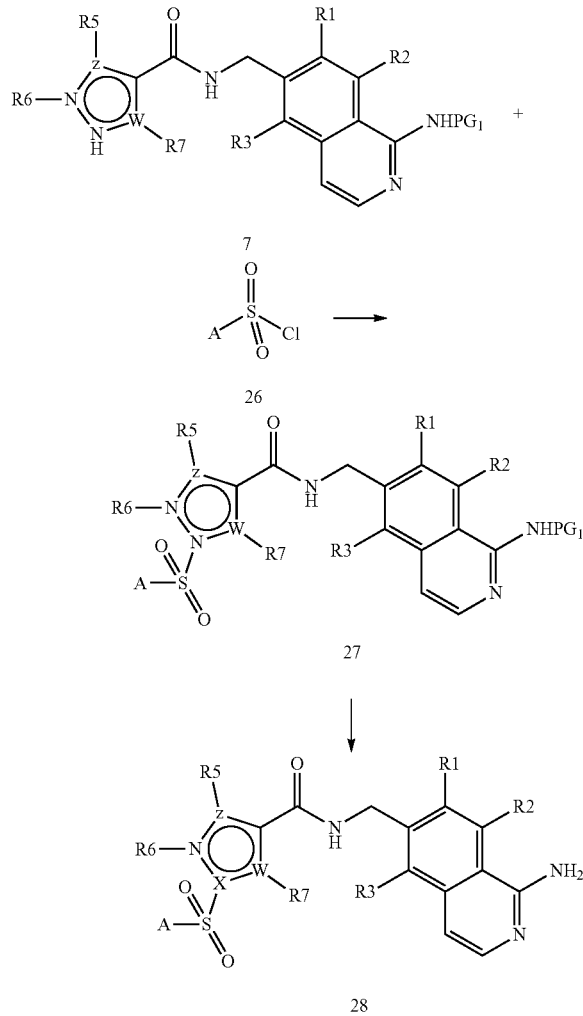

EXAMPLES

The invention is illustrated by the following non-limiting examples in which the following abbreviations and definitions are used:

| | |
|---|---|
| DCM | Dichloromethane |
| DMF | N,N-Dimethylformamide |
| EtOAc | Ethyl Acetate |
| HATU | 2-(3H-[1,2,3]triazolo[4,5-b]pyridin-3-yl)-1,1,3,3-tetramethylisouronium hexafluorophosphate(V) |
| hrs | Hours |
| HOBt | Hydroxybenzotriazole |
| LCMS | Liquid chromatography mass spectrometry |
| Me | Methyl |
| MeCN | Acetonitrile |
| MeOH | Methanol |
| Min | Minutes |
| MS | Mass spectrum |
| NMR | Nuclear magnetic resonance spectrum-NMR spectra were recorded at a frequency of 400 M Hz unless otherwise indicated |
| Pet. Ether | Petroleum ether fraction boiling at 60-80° C. |
| Ph | Phenyl |
| rt | room temperature |
| THF | Tetrahydrofuran |
| TFA | Trifluoroacetic acid |

All reactions were carried out under an atmosphere of nitrogen unless specified otherwise.

$^1$H NMR spectra were recorded on a Bruker (400 MHz) spectrometer with reference to deuterium solvent and at rt.

Molecular ions were obtained using LCMS which was carried out using a Chromolith Speedrod RP-18e column, 50×4.6 mm, with a linear gradient 10% to 90% 0.1% HCO$_2$H/MeCN into 0.1% HCO$_2$H/H$_2$O over 13 min, flow rate 1.5 mL/min, or using Agilent, X-Select, acidic, 5-95% MeCN/water over 4 min. Data was collected using a Thermofinnigan Surveyor MSQ mass spectrometer with electospray ionisation in conjunction with a Thermofinnigan Surveyor LC system.

Chemical names were generated using the Autonom software provided as part of the ISIS draw package from MDL Information Systems.

Where products were purified by flash chromatography, 'silica' refers to silica gel for chromatography, 0.035 to 0.070 mm (220 to 440 mesh) (e.g. Merck silica gel 60), and an applied pressure of nitrogen up to 10 p.s.i accelerated column elution. Reverse phase preparative HPLC purifications were carried out using a Waters 2525 binary gradient pumping system at flow rates of typically 20 mL/min using a Waters 2996 photodiode array detector.

All solvents and commercial reagents were used as received.

Example 1

2,5-Dimethyl-1-(2-phenyl-thiazol-4-ylmethyl)-1H-pyrrole-3-carboxylic acid (1-amino-isoquinolin-6-ylmethyl)-amide

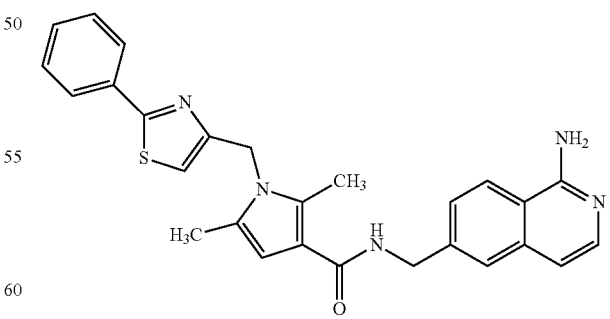

A. 2-Acetyl-4-oxo-pentanoic acid ethyl ester

Ethylacetoacetate sodium salt (17.10 g, 112 mmol) was suspended in acetone (500 mL). Potassium carbonate (15.54 g, 112 mmol) and potassium iodide (3.73 g, 22.48 mmol) were added and the resulting solution was refluxed. Chloroacetone (11.41 g, 124 mmol) was added dropwise over a period of 5 min. Once the addition was complete the mixture was heated under reflux for a further 2 hrs. The reaction mixture was allowed to cool to rt and the solid material was filtered off and washed with acetone. The resultant filtrate was evaporated and purified by flash chromatography (silica), eluent 75% Pet. Ether, 25% EtOAc, fractions combined and evaporated in vacuo to give a yellow oil identified as 2-acetyl-4-oxo-pentanoic acid ethyl ester (10.1 g, 54.2 mmol, 48% yield).

B. 1-[2-phenyl)-thiazol-4-ylmethyl]-2,5-dimethyl-1H-pyrrole-3-carboxylic acid ethyl ester 2-Acetyl-4-oxo-pentanoic acid ethyl ester (1.8 g, 9.66 mmol) was dissolved in toluene (35 mL), 2-phenyl-thiazoyl-4-methylamine (2.02 g, 10.62 mmol) and p-toluenesulphonic acid (183 mg, 0.97 mmol) were added. The reaction mixture was heated at reflux for 4 hrs after which time it was diluted with ethyl acetate and washed with $NaHCO_3$ (1×30 mL), water (1×30 mL), brine (1×30 mL), dried ($Na_2SO_4$) and evaporated in vacuo. The residue was purified by flash chromatography (silica), eluent 85% Pet. Ether, 15% EtOAc, fractions combined and evaporated in vacuo to give a colourless oil identified as 1-[2-phenyl)-thiazol-4-ylmethyl]-2,5-dimethyl-1H-pyrrole-3-carboxylic acid ethyl ester (1.26 g, 3.69 mmol, 38% yield). $[M+H]^+=341$.

C. 2,5-Dimethyl-1-(2-phenyl-thiazol-4-ylmethyl)-1H-pyrrole-3-carboxylic acid

1-[2-Phenyl)-thiazol-4-ylmethyl]-2,5-dimethyl-1H-pyrrole-3-carboxylic acid ethyl ester (1.07 g, 3.14 mmol) was dissolved in ethanol (50 mL). Sodium hydroxide (629 mg, 15.72 mmol) in water (5 mL) was added. The reaction mixture was heated at 90° C. for 3 days after which time the solvent was removed in vacuo. The residue was diluted with water and acidified to pH1 with 1M HCl and extracted with ethyl acetate (3×50 mL). The combined extracts were washed with water (1×30 mL), brine (1×30 mL), dried ($Na_2SO_4$) and evaporated in vacuo to give an off white solid identified as 2,5-dimethyl-1-(2-phenyl-thiazol-4-ylmethyl)-1H-pyrrole-3-carboxylic acid (980 mg, 3.14 mmol, 100% yield). $[M+H]^+=313$.

D. 2-((E)-2-Dimethylamino-vinyl)-terephthalonitrile ester

Methylterephthalonitrile (1.42 g, 9.99 mmol) and Bredereck's reagent (3.48 g, 19.98 mmol) were dissolved in DMF (15 mL). The reaction mixture was heated at 75° C. under nitrogen for 72 hrs after which time the solvent was removed in vacuo. Trituration with Pet. Ether gave a bright yellow solid identified as 2-((E)-2-dimethylamino-vinyl)-terephthalonitrile ester (1.88 g, 0.95 mmol, 95% yield).
$^1$H NMR ($CD_3OD$) δ: 3.20 (6H, s), 5.34 (1H, d, J=13.4 Hz), 7.21 (1H, dd, J=8.0 Hz, 1.4 Hz), 7.9 (1H, d, 13.4 Hz), 7.61 (1H, d, J=8.0 Hz), 7.94 (1H, d, J=1.2 Hz)

E. 1-Amino-2-(2,4-dimethoxy-benzyl)-1,2-dihydro-isoquinoline-6-carbonitrile 2-((E)-2-Dimethylamino-vinyl)-terephthalonitrile ester (1.85 g, 9.38 mmol) was dissolved in 1,3-dimethyl-3,4,5,6-tetrahydro-2(1H)-pyrimidinone (5 mL) and 2,4-dimethoxy-benzylamine (2.35 g, 14.07 mmol) was added. The reaction mixture was heated at 75° C. under nitrogen. After 3 hrs the reaction mixture was cooled and diethyl ether/Pet. Ether (15:85) was added. The yellow solid was filtered off, dried in vacuo, and identified as 1-amino-2-(2,4-dimethoxy-benzyl)-1,2-dihydro-isoquinoline-6-carbonitrile (2.65 g, 8.38 mmol, 89% yield)
$[M+H]^+=320$
$^1$H NMR ($CD_3OD$) δ: 3.85 (3H, s), 3.92 (3H, s), 5.02 (2H, s), 6.39 (1H, d, J=7.4 Hz), 6.57 (1H, dd, J=8.4 Hz, 2.4 Hz), 6.66 (1H, d, J=2.4 Hz), 7.18 (1H, d, J=8.4 Hz), 7.24 (1H, d, J=7.4 Hz), 7.72 (1H, dd, J=8.5 Hz, 1.4 Hz), 7.93 (1H, s), 8.45 (1H, d, J=8.5 Hz)

F. 1-Amino-isoquinoline-6-carbonitrile

1-Amino-2-(2,4-dimethoxy-benzyl)-1,2-dihydro-isoquinoline-6-carbonitrile (1.6 g, 5.0 mmol) was dissolved in anisole (17 mL) and trifluoroacetic acid (20 mL). The reaction mixture was heated at 105° C. under nitrogen for 12 hrs after which time the reaction mixture was cooled, diethyl ether/Pet. Ether (3:7) was added, the resultant solid was filtered off, dried in vacuo and identified as 1-amino-isoquinoline-6-carbonitrile (770 mg, 4.54 mmol, 91%).
$[M+H]^+=170$.
$^1$H NMR ($CD_3OD$) δ: 7.23-7.25 (1H, d, J=6.9 Hz), 7.65 (1H, d, J=6.8 Hz), 8.11 (1H, dd, J=8.7 Hz, 1.6 Hz), 8.33 (1H, s), 8.45 (1H, d, J=8.7 Hz).

G. (1-Amino-isoquinolin-6-ylmethyl)-carbamic acid tert-butyl ester

1-Amino-isoquinoline-6-carbonitrile (200 mg, 1.18 mmol) was dissolved in methanol (20 mL). This solution was cooled to 0° C. Nickel (II) chloride hexahydrate (28 mg, 0.12 mmol) and di-tertbutyl dicarbonate (516 g, 2.36 mmol) were added followed by sodium borohydride (313 g, 8.22 mmol) portionwise. The reaction mixture was stirred at 0° C. to room temp for 3 days. The MeOH was removed by evaporation. The residue was dissolved in $CHCl_3$ (70 mL), washed with sat $NaHCO_3$ (1×30 mL), water (1×30 mL), brine (1×30 mL), dried ($Na_2SO_4$) and evaporated in vacuo to give a yellow oil identified as (1-amino-isoquinolin-6-ylmethyl)-carbamic acid tert-butyl ester (110 mg, 0.4 mmol, 34% yield).
$[M+H]^+=274$.

H. 6-Aminomethyl-isoquinolin-1-ylamine hydrochloride (1-Amino-isoquinolin-6-ylmethyl)-carbamic acid tert-butyl ester (110 mg, 0.40 mmol) was dissolved in 4M HCl in dioxane (40 mL). After 18 hrs at rt the solvent was removed in vacuo to give a pale brown solid identified as 6-aminomethyl-isoquinolin-1-ylamine hydrochloride (67 mg, 0.39 mmol, 96% yield).
$[M+H]^+=174$.

I. 2,5-Dimethyl-1-(2-phenyl-thiazol-4-ylmethyl)-1H-pyrrole-3-carboxylic acid (1-amino-isoquinolin-6-ylmethyl)-amide 2,5-Dimethyl-1-(2-phenyl-thiazol-4-ylmethyl)-1H-pyrrole-3-carboxylic acid (87 mg, 0.28 mmol) was dissolved in $CH_2Cl_2$ (15 mL). This solution was cooled to 0° C. 6-Aminomethyl-isoquinolin-1-ylamine hydrochloride (48 mg, 0.28 mmol) was added followed by HOBt (45 mg, 0.31 mmol)

and triethylamine (147 mg, 1.4 mmol). Water soluble carbodiimide (75 mg, 0.39 mmol) was then added. After 18 hrs at 0° C. to rt, reaction mixture was diluted with chloroform (200 mL) and washed with NaHCO$_3$ (1×50 mL), water (1×50 mL), brine (1×50 mL), dried (Na$_2$SO$_4$) and evaporated in vacuo. The residue was purified by flash chromatography (silica), eluent dichloromethane:MeOH:NH$_3$ (100:10:1), fractions combined and evaporated in vacuo to give a white solid identified as 2,5-dimethyl-1-(2-phenyl-thiazol-4-ylmethyl)-1H-pyrrole-3-carboxylic acid (1-amino-isoquinolin-6-ylmethyl)-amide (68 mg, 0.14 mmol, 52% yield).

[M+H]$^+$=468.

$^1$H NMR: (d6-DMSO), δ: 2.28 (3H, s), 2.56 (3H, s), 4.52 (2H, d, J=5.9 Hz), 5.18 (2H, s), 6.33 (1H, s), 7.05 (1H, d, J=6.4 Hz), 7.31 (1H, s), 7.48-7.52 (3H, m), 7.55 (1H, d, J=9.9 Hz), 7.65 (1H, s), 7.68 (1H, d, J=6.5 Hz), 7.81-8.00 (2H, s, br.), 7.89-7.91 (2H, m), 8.25 (1H, t, J=5.9 Hz), 8.32 (1H, d, J=8.6 Hz).

Example 2

2,5-Dimethyl-1-(2-phenyl-thiazol-4-ylmethyl)-1H-pyrrole-3-carboxylic acid (1-amino-isoquinolin-7-ylmethyl)-amide

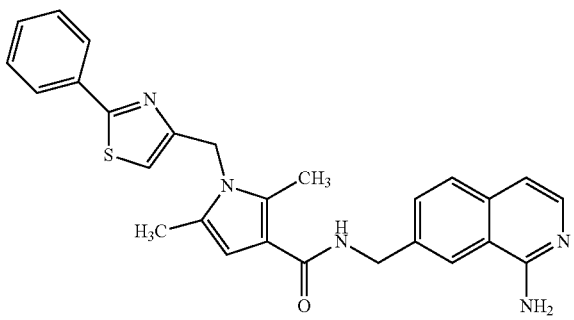 [SMILES: Cc1cc(C(=O)NCc2ccc3ccnc(N)c3c2)c(C)n1Cc1csc(-c2ccccc2)n1]

A. 2,5-Dimethyl-1-(2-phenyl-thiazol-4-ylmethyl)-1H-pyrrole-3-carboxylic acid (1-amino-isoquinolin-7-ylmethyl)-amide 2,5-Dimethyl-1-(2-phenyl-thiazol-4-ylmethyl)-1H-pyrrole-3-carboxylic acid (93 mg, 0.30 mmol) was dissolved in CH$_2$Cl$_2$ (15 mL). This solution was cooled to 0° C. 7-Aminomethyl-isoquinolin-1-ylamine hydrochloride (C. A. A. Van Boeckel et al., WO 98/47876) (56 mg, 0.33 mmol) was added followed by HOBt (48 mg, 0.32 mmol) and triethylamine (211 mg, 2.1 mmol). Water soluble carbodiimide (80 mg, 0.42 mmol) was then added. After 18 hrs at 0° C. to rt reaction mixture was diluted with chloroform (200 mL) and washed with NaHCO$_3$ (1×50 mL), water (1×50 mL), brine (1×50 mL), dried (Na$_2$SO$_4$) and evaporated in vacuo. The residue was purified by flash chromatography (silica), eluent dichloromethane:MeOH:NH$_3$ (100:10:1), fractions combined and evaporated in vacuo to give a white solid identified as 2,5-dimethyl-1-(2-phenyl-thiazol-4-ylmethyl)-1H-pyrrole-3-carboxylic acid (1-amino-isoquinolin-7-ylmethyl)-amide (30 mg, 0.06 mmol, 21% yield).

[M+H]$^+$=468.

$^1$H NMR: (d6-DMSO), δ: 2.26 (3H, s), 2.57 (3H, s), 4.49 (2H, d, J=5.9 Hz), 5.17 (2H, s), 6.32 (1H, s), 6.85 (2H, s, br), 6.88 (1H, d, J=5.9 Hz), 7.28 (1H, s), 7.46-7.52 (3H, m), 7.58 (1H, dd, J=8.1, 0.9 Hz), 7.65 (1H, d, J=8.4 Hz), 7.73 (1H, d, J=5.9 Hz), 7.89-7.92 (2H, m), 8.10 (1H, s, br), 8.17 (1H, t, J=5.9 Hz).

Example 3

2,5-Dimethyl-1-(2-phenyl-thiazol-4-ylmethyl)-1H-pyrrole-3-carboxylic acid (1H-pyrrolo[2,3-b]pyridin-5-ylmethyl)-amide

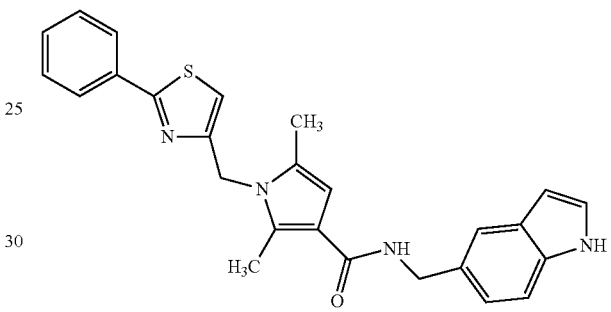

A. 2,5-Dimethyl-1-(2-phenyl-thiazol-4-ylmethyl)-1H-pyrrole-3-carboxylic acid (1H-pyrrolo[2,3-b]pyridin-5-ylmethyl)-amide 2,5-Dimethyl-1-(2-phenyl-thiazol-4-ylmethyl)-1H-pyrrole-3-carboxylic acid (120 mg, 0.38 mmol) was dissolved in CH$_2$Cl$_2$ (20 mL) and DMF (2 mL). This solution was cooled to 0° C. 5-Aminomethyl-7-azaindole hydrochloride (57 mg, 0.38 mmol), HOBt (62 mg, 0.41 mmol) and triethylamine (192 mg, 1.92 mmol). and water soluble carbodiimide (104 mg, 0.54 mmol) were then added. After 18 hrs at 0° C. to rt reaction mixture was diluted with chloroform (100 mL) and washed with NaHCO$_3$ (1×30 mL), water (1×50 mL), brine (1×30 mL), dried (Na$_2$SO$_4$) and evaporated in vacuo. The residue was purified by flash chromatography (silica), eluent 4% MeOH, 96% dichloromethane, fractions combined and evaporated in vacuo to give a white solid identified as 2,5-dimethyl-1-(2-phenyl-thiazol-4-ylmethyl)-1H-pyrrole-3-carboxylic acid (1H-pyrrolo[2,3-b]pyridin-5-ylmethyl)-amide (62 mg, 0.14 mmol, 37% yield).

[M+H]$^+$=442

$^1$H NMR: (d6-DMSO), δ: 2.24 (3H, s), 2.55 (3H, s), 4.43 (2H, d, J=6.0 Hz), 5.15 (2H, s), 6.27 (1H, s), 6.38-6.39 (1H, m), 7.22 (1H, s), 7.41 (1H, t, J=2.9 Hz), 7.46-7.51 (3H, m), 7.83 (1H, d, J=1.6 Hz), 7.85-7.90 (2H, m), 8.09 (1H, t, J=6.0 Hz), 8.17 (1H, d, J=1.9 Hz), 11.51 (1H, s).

Reference Example 4

1-[4-(2-Oxo-2H-pyridin-1-ylmethyl)-benzyl]-1H-pyrazole-4-carboxylic acid (1-amino-isoquinolin-6-ylmethyl)-amide

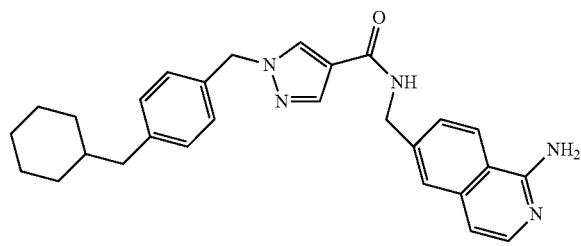 [SMILES: Nc1nccc2cc(CNC(=O)c3cnn(Cc4ccc(CC5CCCCC5)cc4)c3)ccc12]

A. 1-(4-Hydroxymethyl-benzyl)-1H-pyridin-2-one 4-(Chloromethyl)benzylalcohol (5.0 g, 31.93 mmol) was dissolved in acetone (150 mL) 2-hydroxypyridine (3.64 g, 38.3 mmol) and potassium carbonate (13.24 g, 95.78 mmol) were added and the reaction mixture was stirred at 50° C. for 3 hrs after which time the solvent was removed in vacuo and the residue taken up in chloroform (100 mL), this solution was washed with water (1×30 mL), brine (1×30 mL), dried (Na$_2$SO$_4$) and evaporated in vacuo. The residue was purified by flash chromatography (silica), eluent 3% MeOH, 97% CHCl$_3$, fractions combined and evaporated in vacuo to give a white solid identified as 1-(4-hydroxymethyl-benzyl)-1H-pyridin-2-one (5.30 g, 24.62 mmol, 77% yield).

[M+Na]$^+$=238

B. 1-(4-Bromomethyl-benzyl)-1H-pyridin-2-one 1-(4-Hydroxymethyl-benzyl)-1H-pyridin-2-one (2.30 g, 6.97 mmol) was dissolved in dichloromethane (250 mL). To this solution was added phosphorous tribromide (5.78 g, 21.37 mmol) The reaction mixture was stirred at rt for 18 hrs and diluted with CHCl$_3$ (250 mL) the filtrate was washed with saturated NaHCO$_3$ (1×30 mL), water (1×30 mL), brine (1×30 mL), dried (Na$_2$SO$_4$) and evaporated in vacuo to give a white solid which was identified as 1-(4-bromomethyl-benzyl)-1H-pyridin-2-one (2.90 g, 10.43 mmol, 98% yield).

[M+H]$^+$=278

C. 1-[4-(2-Oxo-2H-pyridin-1-ylmethyl)-benzyl]-1H-pyrazole-4-carboxylic acid ethyl ester 1-(4-Bromomethyl-benzyl)-1H-pyridin-2-one (2.80 g, 10.07 mmol) was dissolved in DMF (50 mL) ethyl 1H-pyrazole-4-carboxylate (1.69 g, 12.08 mmol) and caesium carbonate (9.84 g, 30.2 mmol) were added and the reaction mixture was stirred at 50° C. for 18 hrs after which time the reaction mixture was diluted with EtOAc (100 mL), this solution was washed with water (1×30 mL), brine (1×30 mL), dried (Na$_2$SO$_4$) and evaporated in vacuo. The residue was purified by flash chromatography (silica), eluent 3% MeOH, 97% CHCl$_3$, fractions combined and evaporated in vacuo to give a white foamy solid identified as 1-[4-(2-oxo-2H-pyridin-1-ylmethyl)-benzyl]-1H-pyrazole-4-carboxylic acid ethyl ester (3.20 g, 9.49 mmol, 94% yield).

[M+H]$^+$=338

D. 1-[4-(2-Oxo-2H-pyridin-1-ylmethyl)-benzyl]-1H-pyrazole-4-carboxylic acid 1-[4-(2-Oxo-2H-pyridin-1-ylmethyl)-benzyl]-1H-pyrazole-4-carboxylic acid ethyl ester (3.20 g, 9.49 mmol) was dissolved in THF (50 mL) and water (5 mL) lithium hydroxide (1.13 g, 47.43 mmol) was added. The reaction mixture was stirred at 50° C. for 48 hrs after which time the solvent was concentrated in vacuo and the residue taken up in CHCl$_3$ (150 mL), the aqueous layer was extracted and acidified with 1M HCl to pH2 and extracted with CHCl$_3$ (3×50 mL), the combined extracts were washed with water (1×30 mL), brine (1×30 mL), dried (Na$_2$SO$_4$) and evaporated in vacuo, the residue was triturated with EtOAc and Pet. Ether to give a white solid identified as 1-[4-(2-oxo-2H-pyridin-1-ylmethyl)-benzyl]-1H-pyrazole-4-carboxylic acid (3.20 g, 6.14 mmol, 65% yield).

[M+H]$^+$=310, 332 (M+Na)

E. 1-[4-(2-Oxo-2H-pyridin-1-ylmethyl)-benzyl]-1H-pyrazole-4-carboxylic acid (1-amino-isoquinolin-6-ylmethyl)-amide 1-[4-(2-Oxo-2H-pyridin-1-ylmethyl)-benzyl]-1H-pyrazole-4-carboxylic acid (80 mg, 0.26 mmol) was dissolved in CH$_2$Cl$_2$ (2.5 mL). HATU (108 mg, 0.28 mmol) was added followed by 6-(aminomethyl)isoquinolin-1-amine (49 mg, 0.28 mmol) and N,N-diisopropylethylamine (67 mg, 0.52 mmol). After 18 hrs at rt the reaction mixture was diluted with chloroform (400 mL) washed with NH$_4$Cl (1×30 mL), water (1×30 mL), brine (1×30 mL), dried (Na$_2$SO$_4$) and evaporated in vacuo giving a yellow oil. The residue was purified by flash chromatography (silica), eluent dichloromethane:MeOH:NH$_3$ (100:10:1). Fractions combined and evaporated in vacuo to give a white solid identified as 1-[4-(2-oxo-2H-pyridin-1-ylmethyl)-benzyl]-1H-pyrazole-4-carboxylic acid (1-amino-isoquinolin-6-ylmethyl)-amide (22 mg, 0.046 mmol, 18% yield).

[M+H]$^+$=465

$^1$H NMR: (d6-DMSO, δ: 4.55 (2H, d, J=6.0 Hz), 5.08 (2H, s), 5.33 (2H, s), 6.23 (1H, td, J=1.4, 6.7 Hz), 6.40 (1H, dd, J=1.3, 9.5 Hz), 6.94 (1H, d, J=6.1 Hz), 7.10-7.32 (5H, m), 7.38-7.47 (2H, m), 7.59 (1H, s, br), 7.71-7.81 (2H, m), 7.92 (1H, s), 8.21 (1H, d, J=8.6 Hz), 8.28 (1H, s), 8.72 (1H, t, J=5.9 Hz).

Reference Example 5

1-[4-(2-Oxo-2H-pyridin-1-ylmethyl)-benzyl]-1H-[1,2,3]triazole-4-carboxylic acid (1-amino-isoquinolin-6-ylmethyl)-amide

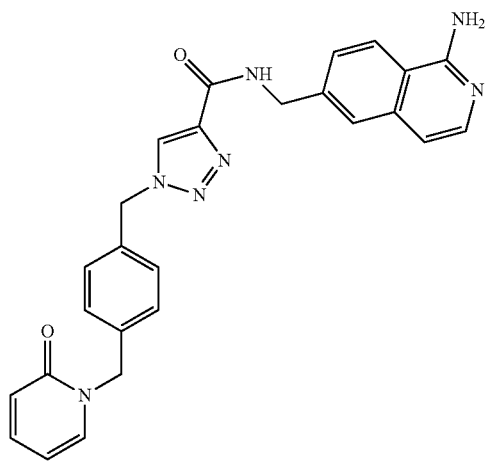 [SMILES: Nc1nccc2cc(CNC(=O)c3cn(Cc4ccc(Cn5ccccc5=O)cc4)nn3)ccc12]

A. 1-(4-Azidomethyl-benzyl)-1H-pyridin-2-one 1-(4-Hydroxymethyl-benzyl)-1H-pyridin-2-one (570 mg, 2.65 mmol) and 1,8-diazabicyclo[5.4.0]undec-7-ene (806 mg, 5.30 mmol) were dissolved in DMF (20 mL). Diphenylphosphoryl azide (1.09 g, 3.97 mmol) was added and the reaction mixture was stirred at rt for 3 hrs after which time the reaction mixture was diluted with EtOAc (100 mL), this solution was washed with water (1×30 mL), brine (1×30 mL), dried ($Na_2SO_4$) and evaporated in vacuo. The residue was purified by flash chromatography (silica), eluent 3% MeOH, 97% $CHCl_3$, fractions combined and evaporated in vacuo to give a white foamy solid identified as 1-(4-azidomethyl-benzyl)-1H-pyridin-2-one (430 mg, 1.79 mmol, 68% yield).

$[M+Na]^+=361$

B. 1-[4-(2-Oxo-2H-pyridin-1-ylmethyl)-benzyl]-1H-[1,2,3]triazole-4-carboxylic acid ethyl ester 1-(4-Azidomethyl-benzyl)-1H-pyridin-2-one (340 mg, 1.41 mmol), ethyl propiolate (139 mg, 1.41 mmol), (+)-sodium L-ascorbate (280 mg, 1.41 mmol) and copper (II) sulphate pentahydrate (71 mg, 0.28 mmol) were dissolved in tert-butanol (20 mL) and water (5 mL). The reaction mixture was stirred at rt for 18 hrs after which time the reaction mixture was diluted with chloroform (100 mL), this solution was washed with water (1×30 mL), brine (1×30 mL), dried ($Na_2SO_4$) and evaporated in vacuo. The residue was triturated with ethyl acetate and Pet. Ether to give a white solid identified as 1-[4-(2-oxo-2H-pyridin-1-ylmethyl)-benzyl]-1H-[1,2,3]triazole-4-carboxylic acid ethyl ester (430 mg, 1.27 mmol, 90% yield).

$[M+H]^+=486$

C. 1-[4-(2-Oxo-2H-pyridin-1-ylmethyl)-benzyl]-1H-[1,2,3]triazole-4-carboxylic acid 1-[4-(2-Oxo-2H-pyridin-1-ylmethyl)-benzyl]-1H-[1,2,3]triazole-4-carboxylic acid ethyl ester (110 mg, 0.32 mmol) was dissolved in THF (50 mL) and water (5 mL), lithium hydroxide (39 mg, 1.62 mmol) was added. The reaction mixture was stirred at 50° C. for 18 hrs after which time the solvent was concentrated in vacuo and the residue taken up in EtOAc (50 mL), the aqueous layer was separated, acidified with 1M HCl to pH2 and extracted $CHCl_3$ (3×50 mL) the combined extracts were washed with water (1×30 mL), brine (1×30 mL), dried ($Na_2SO_4$) and evaporated in vacuo. The residue was purified by flash chromatography (silica), eluent 3% MeOH, 97% $CHCl_3$, fractions combined and evaporated in vacuo to give a colourless oil identified as 1-[4-(2-oxo-2H-pyridin-1-ylmethyl)-benzyl]-1H-[1,2,3]triazole-4-carboxylic acid (140 mg, 0.45 mmol, 49% yield).

D. 1-[4-(2-Oxo-2H-pyridin-1-ylmethyl)-benzyl]-1H-[1,2,3]triazole-4-carboxylic acid (1-amino-isoquinolin-6-ylmethyl)-amide 1-[4-(2-oxo-2H-pyridin-1-ylmethyl)-benzyl]-1H-[1,2,3]triazole-4-carboxylic acid (100 mg, 0.26 mmol) was dissolved in $CH_2Cl_2$ (3.5 mL). HATU (147 mg, 0.39 mmol) and 6-(aminomethyl)isoquinolin-1-amine (61.4 mg, 0.35 mmol) were added followed by N,N-diisopropylethylamine (67 mg, 0.52 mmol). After 1 hour at rt the reaction mixture was diluted with chloroform (400 mL) washed with $NH_4Cl$ (1×30 mL), water (1×30 mL), brine (1×30 mL), dried ($Na_2SO_4$) and evaporated in vacuo giving a yellow oil. Trituration with methanol/diethyl ether (3:7, 10 mL) gave a yellow solid identified as 1-[4-(2-oxo-2H-pyridin-1-ylmethyl)-benzyl]-1H-[1,2,3]triazole-4-carboxylic acid (1-amino-isoquinolin-6-ylmethyl)-amide (107 mg, 0.22 mmol, 85% yield).

$[M+H]^+=466$ $^1$H NMR: (d6-DMSO), δ: 4.61 (2H, d, J=6.2 Hz), 5.08 (2H, s), 5.63 (2H, s), 6.22 (1H, td, J=1.4, 6.7 Hz), 6.34-6.48 (1H, m), 7.12 (1H, d, J=6.7 Hz), 7.29 (2H, d, J=8.3 Hz), 7.34 (2H, d, J=8.3 Hz), 7.41 (1H, ddd, J=2.1, 6.6, 8.9 Hz), 7.63 (1H, dd, J=1.5, 8.7 Hz), 7.67 (1H, d, J=6.7 Hz), 7.72 (1H, s); 7.74-7.81 (1H, m), 8.42 (3H, d, J=8.7 Hz), 8.67 (1H, s), 9.26 (1H, t, J=6.2 Hz).

Example 6

1-Ethyl-4-methyl-5-[4-(2-oxo-2H-pyridin-1-ylmethyl)-benzyl]-1H-pyrrole-2-carboxylic acid (1-amino-isoquinolin-6-ylmethyl)-amide

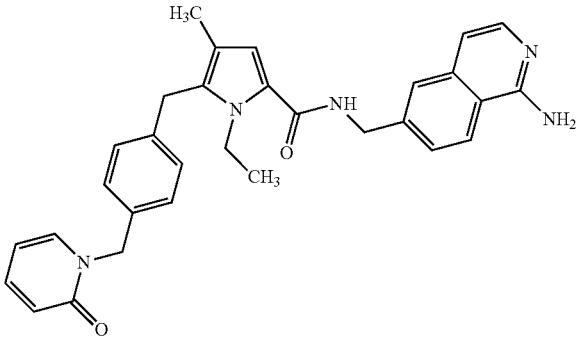 [SMILES: CCn1c(C(=O)NCc2ccc3c(N)nccc3c2)cc(C)c1Cc1ccc(Cn2ccccc2=O)cc1]

A. Ethyl 1-ethyl-4-methyl-1H-pyrrole-2-carboxylate

To a colourless solution of ethyl 4-methyl-1H-pyrrole-2-carboxylate (0.5 g, 3.26 mmol) in DMF (5 mL) at 0° C. was added sodium hydride (0.137 g, 3.43 mmol) (effervescence). After stirring for 30 min, ethyl iodide (0.317 mL, 3.92 mmol) was added to the suspension. The resultant white thick suspension was stirred at RT over the week-end. The reaction mixture was diluted with water (10 mL) and EtOAc (50 mL) was added. The layers were separated and the organic phase was washed with water (4×10 mL) and saturated brine (20 mL). The organic was dried over $Na_2SO_4$, filtered and concentrated in vacuo to afford a pale yellow oil (0.6456 g) that was dried further to afford ethyl 1-ethyl-4-methyl-1H-pyrrole-2-carboxylate (0.5657 g, 3.06 mmol, 94% yield).

$[M+H]^+=182$

B. Ethyl 5-(4-(chloromethyl)benzoyl)-1-ethyl-4-methyl-1H-pyrrole-2-carboxylate The zinc(II) chloride (3.35 g, 24.61 mmol) was weighed out to a 100 mL flask and dried under vacuum at 120° C. for 2 hrs to remove any water. The flask was placed under nitrogen and a solution of 4-(chloromethyl)benzoyl chloride (4.0 g, 21.16 mmol) in anhydrous dichloroethane (25 mL) was added. The mixture was cooled in an ice-bath and a solution of ethyl 1-ethyl-4-methyl-1H-pyrrole-2-carboxylate (2.23 g, 12.30 mmol) in anhydrous dichloroethane (8 mL) was added dropwise. After 10 min, the ice-bath was removed and the reaction allowed to stir at 40° C. for 1 h 30 min. The mixture was allowed to heat for a further 30 min, then poured into ice-water (200 mL) and extracted with DCM (3×125 mL). The combined organics were washed with water (100 mL), 1M HCl (100 mL) and brine (100 mL), then dried (Na$_2$SO$_4$), filtered and concentrated. The crude mixture was purified by chromatography (silica) eluting with a gradient of 0 to 15% EtOAc/Iso-Hexanes, holding at 0% and 10% EtOAc to afford the desired product ethyl 5-(4-(chloromethyl)benzoyl)-1-ethyl-4-methyl-1H-pyrrole-2-carboxylate (2.12 g, 6.16 mmol, 50.1% yield) as a pale yellow solid and the undesired isomer ethyl 3-(4-(chloromethyl)benzoyl)-1-ethyl-4-methyl-1H-pyrrole-2-carboxylate (1.00 g, 2.097 mmol, 17.04% yield) as a gummy solid, contaminated with 4-chloromethylbenzoic acid.

[M+H]$^+$=334/336

C. Ethyl 5-((4-(chloromethyl)phenyl)(hydroxy) methyl)-1-ethyl-4-methyl-1H-pyrrole-2-carboxylate A solution of ethyl 5-(4-(chloromethyl)benzoyl)-1-ethyl-4-methyl-1H-pyrrole-2-carboxylate (2.26 g, 6.77 mmol) in anhydrous THF (20 mL) and anhydrous MeOH (3 mL) was treated with sodium borohydride (0.512 g, 13.54 mmol) portionwise (an ice-bath was added after 5 min to control exotherm) and the mixture stirred at ambient temperature for 1 hour. HPLC (XSelect, 4 min) indicated >95% conversion to the desired compound. A further 100 mg of sodium borohydride were added and the mixture stirred for a further 30 min. The reaction mixture was poured into saturated aqueous NH$_4$Cl solution (120 mL) and stirred for 5 min. The aqueous layer was extracted with DCM (3×50 mL) and the combined organics washed with brine (50 mL), dried (Na$_2$SO$_4$), filtered and concentrated to afford ethyl 5-((4-(chloromethyl)phenyl)(hydroxy)methyl)-1-ethyl-4-methyl-1H-pyrrole-2-carboxylate (2.30 g, 6.84 mmol) as a clear oily foam.

[M−H$_2$O+H]$^+$=318/320

D. Ethyl 5-(4-(chloromethyl)benzyl)-1-ethyl-4-methyl-1H-pyrrole-2-carboxylate A solution of ethyl 5-((4-(chloromethyl)phenyl)(hydroxy)methyl)-1-ethyl-4-methyl-1H-pyrrole-2-carboxylate (2.16 g, 6.43 mmol) in anhydrous DCM (22 mL) was cooled in an ice-bath and treated with 2,2,2-trifluoroacetic acid (9.85 mL, 129 mmol) then triethylsilane (1.233 mL, 7.72 mmol). The mixture was allowed to stir at ambient temperature for 45 min. The mixture was poured carefully into saturated aqueous NaHCO$_3$ solution (250 mL, cooled in an ice-bath) and the biphasic mixture stirred for 15 min before extraction with DCM (3×75 mL). The combined organics were washed with water (100 mL), brine (100 mL), dried (Na$_2$SO$_4$), filtered and concentrated. The crude mixture was purified by chromatography (silica) eluting with a gradient of 0 to 10% EtOAc/Iso-Hexanes to afford ethyl 5-(4-(chloromethyl)benzyl)-1-ethyl-4-methyl-1H-pyrrole-2-carboxylate (1.46 g, 4.34 mmol, 64.4% yield) as a clear gummy oil.

[M+H]$^+$=320/322

E. Ethyl 1-ethyl-4-methyl-5-(4-((2-oxopyridin-1 (2H)-yl)methyl)benzyl)-1H-pyrrole-2-carboxylate Ethyl 5-(4-(chloromethyl)benzyl)-1-ethyl-4-methyl-1H-pyrrole-2-carboxylate (715 mg, 2.236 mmol) and pyridin-2 (1H)-one (425 mg, 4.47 mmol) were dissolved in anhydrous MeCN (8 mL) and potassium carbonate (618 mg, 4.47 mmol) added. The mixture was stirred at 67° C. (DrySyn bath temperature) overnight. The mixture was partitioned between EtOAc (30 mL) and water (30 mL). The pH was adjusted to ~7 with 1M HCl and the organic layer collected. The aqueous was extracted with further EtOAc (2×30 mL) and the combined organics washed with brine (30 mL), dried (MgSO$_4$), filtered and concentrated. The crude product was purified by chromatography (silica) eluting with a gradient of 10 to 90% EtOAc/Iso-Hexanes, holding at ~65% to elute product. Product containing fractions were combined to afford ethyl 1-ethyl-4-methyl-5-(4-((2-oxopyridin-1(2H)-yl) methyl)benzyl)-1H-pyrrole-2-carboxylate (715 mg, 1.851 mmol, 83% yield) as a pale yellow gum after drying overnight under vacuum.

[M+H]$^+$=379

F. 1-Ethyl-4-methyl-5-(4-((2-oxopyridin-1(2H)-yl) methyl)benzyl)-1H-pyrrole-2-carboxylic acid A solution of ethyl 1-ethyl-4-methyl-5-(4-((2-oxopyridin-1(2H)-yl)methyl)benzyl)-1H-pyrrole-2-carboxylate (621 mg, 1.641 mmol) in THF (11 mL), MeOH (7 mL) and water (10 mL) was treated with lithium hydroxide (295 mg, 12.31 mmol) and the mixture heated at 65° C. with stirring overnight. The majority of the solvents were removed under vacuum. The resultant cloudy mixture was partitioned between EtOAc (20 mL) and water (20 mL) containing 1M NaOH (1 mL). The organic layer was discarded and the aqueous layer acidified to ~pH 6 with 1M HCl forming a precipitate. This was allowed to stand for 20 min before filtration, washing with water (10 mL). The solid was dried under vacuum in the presence of CaCl$_2$ for 3 hrs to afford 1-ethyl-4-methyl-5-(4-((2-oxopyridin-1(2H)-yl)methyl) benzyl)-1H-pyrrole-2-carboxylic acid (543 mg, 1.534 mmol, 93% yield).

[M+H]$^+$=351

G. 1-Ethyl-4-methyl-5-[4-(2-oxo-2H-pyridin-1-ylmethyl)-benzyl]-1H-pyrrole-2-carboxylic acid (1-amino-isoquinolin-6-ylmethyl)-amide A scintillation vial was charged with 1-ethyl-4-methyl-5-(4-((2-oxopyridin-1(2H)-yl)methyl)benzyl)-1H-pyrrole-2-carboxylic acid (75 mg, 0.214 mmol), 6-(aminomethyl) isoquinolin-1-amine (40.8 mg, 0.235 mmol), HATU (90 mg, 0.235 mmol) and DCM (3.5 mL). N,N-diisopropylethylamine (74.6 µL, 0.428 mmol) was added and the mixture allowed to stir over a weekend.

The mixture was diluted with DCM (containing trace MeOH for solubility) (3 mL) and saturated aqueous NH$_4$Cl (4 mL) and shaken, then left to stand until the layers separated. The mixture was passed through a phase separation cartridge (15 mL), the organic layer collected then concentrated under vacuum. The crude material was purified by chromatography (silica) eluting with a gradient of 0.5 to 6.5% MeOH (1% NH3)/DCM to afford 1-ethyl-4-methyl-5-[4-(2-oxo-2H-pyridin-1-ylmethyl)-benzyl]-1H-pyrrole-2-carboxylic acid (1-amino-isoquinolin-6-ylmethyl)-amide (97 mg, 0.188 mmol, 88% yield) as an off-white foam.

$^1$H NMR: (d6-DMSO, δ: 0.94 (3H, t, J=7.0 Hz), 2.00 (3H, s), 3.93 (2H, s), 4.15 (2H, q, J=6.9 Hz), 4.49 (2H, d, J=6.0 Hz), 5.04 (2H, s), 6.21 (1H, td, J=6.7, 1.4 Hz), 6.39 (1H, d, J=9.1 Hz), 6.70-6.74 (3H, m), 6.84 (1H, d, J=5.6 Hz), 7.04 (2H, d, J=8.2 Hz), 7.20 (2H, d, J=8.2 Hz), 7.33-7.44 (2H, m), 7.51 (1H, s), 7.68-7.81 (2H, m), 8.12 (1H, d, J=8.6 Hz), 8.48 (1H, t, J=6.1 Hz).

[M+H]$^+$=506

Example 7

1-[4-(2-Oxo-2H-pyridin-1-ylmethyl)-benzyl]-3-trifluoromethyl-1H-pyrazole-4-carboxylic acid (1H-pyrrolo[2,3-b]pyridin-5-ylmethyl)-amide

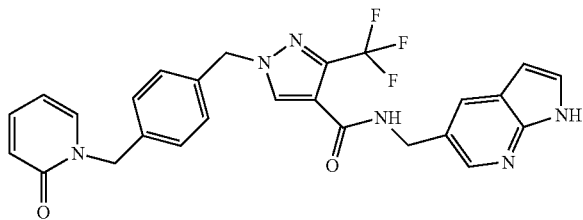 [SMILES: O=C(NCc1cnc2[nH]ccc2c1)c1cn(Cc2ccc(Cn3ccccc3=O)cc2)nc1C(F)(F)F]

A. 1-(4-Chloromethyl-benzyl)-3-trifluoromethyl-1H-pyrazole-4-carboxylic acid ethyl ester Polymer-supported triphenylphospine (3.0 mmol/g, 3 equiv, 1.0 g) was swollen in THF/dichloromethane (1:1, 100 mL). Under a nitrogen atmosphere ethyl 3-trifluoromethyl-1H-pyrazole-4-carboxylate (1.0 g, 4.80 mmol) and 4-(chloromethyl)benzylalcohol (903 mg, 5.76 mmol) were added followed by a solution of diisopropyl azodicarboxylate (1.46 g, 7.21 mmol) in THF/dichloromethane (1:1, 10 mL) over a period of 30 min. The reaction mixture was stirred at rt for 18 hrs, the mixture was filtered and the resin was washed with 3 cycles of dichloromethane/methanol (15 mL). The combined filtrates were evaporated in vacuo. Two main products were identified which were separated by flash chromatography (silica), eluent 20% EtOAc, 80% Pet. Ether, fractions combined and evaporated in vacuo to give white solids identified as 1-(4-chloromethyl-benzyl)-5-trifluoromethyl-1H-pyrazole-4-carboxylic acid ethyl ester (450 mg, 1.3 mmol, 27% yield) and 1-(4-chloromethyl-benzyl)-3-trifluoromethyl-1H-pyrazole-4-carboxylic acid ethyl ester (1.12 g, 3.23 mmol, 67% yield)

$[M+H]^+=347$

B. 1-[4-(2-Oxo-2H-pyridin-1-ylmethyl)-benzyl]-3-trifluoromethyl-1H-pyrazole-4-carboxylic acid ethyl ester 1-(4-Chloromethyl-benzyl)-3-trifluoromethyl-1H-pyrazole-4-carboxylic acid ethyl ester (980 mg, 2.84 mmol) was dissolved in acetone (50 mL). 2-Hydroxypyridine (323 mg, 3.39 mmol) and potassium carbonate (1.17 g, 8.48 mmol) were added and the reaction mixture was stirred at 50° C. for 3 hrs after which time the solvent was removed in vacuo and the residue taken up in EtOAc (100 mL), this solution was washed with water (1×30 mL) and brine (1×30 mL), dried (Na₂SO₄) and evaporated in vacuo. The residue was purified by flash chromatography (silica), eluent 3% MeOH, 97% CHCl₃, fractions combined and evaporated in vacuo to give a colourless oil identified as 1-[4-(2-oxo-2H-pyridin-1-ylmethyl)-benzyl]-3-trifluoromethyl-1H-pyrazole-4-carboxylic acid ethyl ester (1.10 g, 2.71 mmol, 96% yield).

$[M+H]^+=406$

C. 1-[4-(2-Oxo-2H-pyridin-1-ylmethyl)-benzyl]-3-trifluoromethyl-1H-pyrazole-4-carboxylic acid 1-[4-(2-Oxo-2H-pyridin-1-ylmethyl)-benzyl]-3-trifluoromethyl-1H-pyrazole-4-carboxylic acid ethyl ester (1.10 g, 2.71 mmol) was dissolved in THF (50 mL) and water (5 mL), and lithium hydroxide (325 mg, 13.57 mmol) was added. The reaction mixture was stirred at 50° C. for 18 hrs after which time the solvent was concentrated in vacuo and the residue taken up in EtOAc (50 mL), the aqueous layer was extracted and acidified with 1M HCl to pH2 and extracted CHCl₃ (3×50 mL). The combined extracts were washed with water (1×30 mL) and brine (1×30 mL), dried (Na₂SO₄) and evaporated in vacuo to give a white solid identified as 1-[4-(2-oxo-2H-pyridin-1-ylmethyl)-benzyl]-3-trifluoromethyl-1H-pyrazole-4-carboxylic acid (980 mg, 2.60 mmol, 96% yield).

$[M+H]^+=379$

D. 1-[4-(2-Oxo-2H-pyridin-1-ylmethyl)-benzyl]-3-trifluoromethyl-1H-pyrazole-4-carboxylic acid (1H-pyrrolo[2,3-b]pyridin-5-ylmethyl)-amide 1-[4-(2-Oxo-2H-pyridin-1-ylmethyl)-benzyl]-3-trifluoromethyl-1H-pyrazole-4-carboxylic acid (80 mg, 0.21 mmol) was dissolved in CH₂Cl₂ (50 mL) and DMF (2.5 mL). This solution was cooled to 0° C. 5-aminomethyl-7-azaindole hydrochloride (37 mg, 0.25 mmol) was added followed by HOBt (32 mg, 0.23 mmol) and triethylamine (64 mg, 0.64 mmol). Water soluble carbodiimide (49 mg, 0.25 mmol) was then added. After 18 hrs at 0° C. to rt reaction mixture was diluted with chloroform (200 mL), NaHCO₃ (1×30 mL), water (1×30 mL), brine (1×30 mL), dried (Na₂SO₄) and evaporated in vacuo. The residue was purified by flash chromatography (silica), eluent 8% MeOH, 92% CHCl₃, fractions combined and evaporated in vacuo. The residue was freeze dried from water/acetonitrile to give a white solid identified as 1-[4-(2-oxo-2H-pyridin-1-ylmethyl)-benzyl]-3-trifluoromethyl-1H-pyrazole-4-carboxylic acid (1H-pyrrolo[2,3-b]pyridin-5-ylmethyl)-amide (55 mg, 0.11 mmol, 51% yield).

$[M+H]^+=507$

¹H NMR: (d6-DMSO), δ: 4.45 (2H, d, J=5.7 Hz), 5.07 (2H, s), 5.39 (2H, s), 6.20 (1H, q, J=7.6 Hz), 6.38-6.41 (2H, m), 7.28 (4H, s), 7.41-7.46 (2H, m), 7.76 (1H, q, J=6.8 Hz), 7.85 (1H, d, J=1.7 Hz), 8.17 (1H, d, J=2.0 Hz), 8.41 (1H, s), 8.75-8.77 (1H, m), 11.59 (1H, s).

Example 8

1-[4-(2-Oxo-2H-pyridin-1-ylmethyl)-benzyl]-3-trifluoromethyl-1H-pyrazole-4-carboxylic acid (4,6-dimethyl-1H-pyrrolo[2,3-b]pyridin-5-ylmethyl)-amide

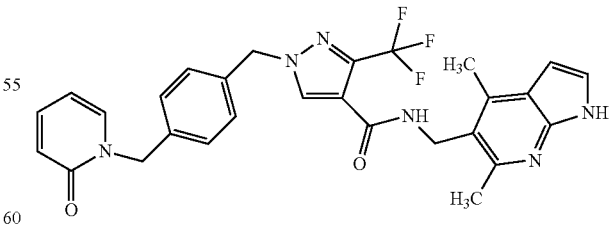

A. 1-tert-Butyl-4,6-dimethyl-1H-pyrrolo[2,3-b]pyridine-3-carbonitrile

A mixture of 5-amino-1-tert-butyl-1H-pyrrole-3-carbonitrile (2.6 g, 15.93 mmol) and pentane-2,4-dione (1.595 g, 15.93 mmol) were dissolved in ethanol (80 mL) and concentrated HCl (0.2 mL) was added. The reaction mixture was heated at reflux for 18 hrs. The mixture was concentrated in vacuo and the crude purified by flash chromatography (silica) eluting in step gradients 95:5 to 9:1 Pet. Ether/ethyl acetate to give a yellow oil identified as 1-tert-butyl-4,6-dimethyl-1H-pyrrolo[2,3-b]pyridine-3-carbonitrile (3.05 g, 13 mmol, 84% yield).

[M+H]$^+$=228.4

$^1$H NMR: (CDCl$_3$), δ: 1.81 (9H, s), 2.58 (3H, s), 2.70 (3H, s), 6.84 (1H, s), 7.75 (1H, s)

B. 5-Bromo-1-tert-butyl-4,6-dimethyl-1H-pyrrolo[2,3-b]pyridine-3-carbonitrile A solution of 1-tert-butyl-4,6-dimethyl-1H-pyrrolo[2,3-b]pyridine-3-carbonitrile (2.820 g, 12.4 mmol) in dichloromethane (50 mL) under an atmosphere of N$_2$ was cooled to at least −5° C. (Ice/NaCl, 3:1). 1,3-Dibromo-5,5-dimethylhydantoin (1.774 g, 6.203 mmol) was then added and the reaction was stirred at −5° C. or below. After stirring at −5° C. further 1,3-dibromo-5,5-dimethylhydantoin (88 mg, 0.31 mmol) was added and stirring continued at −5° C. for a further 3 hrs The reaction mixture was quenched with Na$_2$SO$_3$ (aq) before warming the reaction to rt. 1M NaOH was added and the layers separated. The aqueous phase was extracted with dichloromethane (2×10 mL), the combined organic extracts were washed with brine (2×10 mL) and concentrated in vacuo. The crude product was purified by flash column chromatography on silica eluting with Pet. Ether/ethyl acetate 95:5. Fractions containing product were concentrated and the residue recrystallised from ethyl acetate/Pet. Ether to give a white solid identified as 5-bromo-1-tert-butyl-4,6-dimethyl-1H-pyrrolo[2,3-b]pyridine-3-carbonitrile (3.19 g, 10.42 mmol, 84% yield).

[M+H]$^+$=305.7

$^1$H NMR: (CDCl$_3$), δ: 1.81 (9H, s), 2.78 (3H, s), 2.82 (3H, s), 7.78 (1H, s)

C. 5-Bromo-4,6-dimethyl-1H-pyrrolo[2,3-b]pyridine-3-carbonitrile

5-Bromo-1-(tert-butyl)-4,6-dimethyl-1H-pyrrolo[2,3-b]pyridine-3-carbonitrile (2.1 g, 6.87 mmol) was added portionwise to a stirring suspension of aluminum trichloride (2.75 g, 20.6 mmol) in chlorobenzene (160 mL). After the addition, the mixture was heated to 100° C. overnight forming a black gummy solution. After 24 hrs, the reaction was allowed to cool then poured into water (300 mL) and dichloromethane (300 mL). The mixture was treated cautiously with conc. HCl (135 mL) and the mixture stirred for 10 min then filtered, washing with water and dichloromethane. The resultant solid was dried under vacuum in the presence of CaCl$_2$ over a weekend to give a pale grey solid identified as 5-bromo-4,6-dimethyl-1H-pyrrolo[2,3-b]pyridine-3-carbonitrile (1.56 mg, 6.16 mmol, 90% yield).

D. 5-Bromo-4,6-dimethyl-1H-pyrrolo[2,3-b]pyridine

A suspension of 5-bromo-4,6-dimethyl-1H-pyrrolo[2,3-b]pyridine-3-carbonitrile (1.56 g, 6.16 mmol) in conc. hydrochloric acid, 37% (235 mL) was heated at reflux overnight. Further conc. HCl (100 mL) was added and the reaction was heated at reflux for a further 20 hrs. The mixture was cooled and poured into ice-water (1 L) and neutralised with 2N NaOH until pH 9, forming a precipitate. This was filtered, washed with water then dried under vacuum in the presence of CaCl$_2$ to give a grey solid identified as 5-bromo-4,6-dimethyl-1H-pyrrolo[2,3-b]pyridine (1.3 g, 5.72 mmol, 92% yield).

[M+H]$^+$=225.1

$^1$H NMR: (CDCl$_3$), δ: 2.66 (3H, s), 2.82 (3H, s), 6.49 (1H, dd, J=3.5, 2.1 Hz), 7.29 (1H, dd, J=3.4, 2.7 Hz), 11.14 (1H, br. s)

E. 4,6-Dimethyl-1H-pyrrolo[2,3-b]pyridine-5-carbonitrile

5-Bromo-4,6-dimethyl-1H-pyrrolo[2,3-b]pyridine (1.3 g, 5.72 mmol) was dissolved in N,N-dimethylacetamide (20 mL). The solution was degassed with N$_2$ before the addition of zinc powder (45 mg, 0.693 mmol), zinc acetate (127 mg, 0.693 mmol), 1,1'-bis(diphenylphosphino)ferrocene (128 mg, 0.23 mmol), Zn(CN)$_2$ (339 mg, 2.888 mmol) and tris(dibenzylideneacetone)dipalladium(0) (106 mg, 0.116 mmol). The reaction was heated at 120° C. for 48 hrs. After cooling to rt the reaction was diluted with ethyl acetate and washed with 2M NH$_4$OH and brine. Organic layer was dried over MgSO4 and filtered. After concentration in vacuo crude product was purified by flash column chromatography on silica eluting with 9:1, 8:2, 7:3, 1:1. (Pet. Ether/Ethyl acetate). Fractions were collected and concentrated in vacuo. The yellow solid was triturated in diethyl ether to give an off white solid identified as 4,6-dimethyl-1H-pyrrolo[2,3-b]pyridine-5-carbonitrile (660 mg, 3.83 mmol, 67% yield).

[M+H]$^+$=172.1

$^1$H NMR: (CDCl$_3$), δ: 2.76 (3H, s), 2.86 (3H, s), 6.59 (1H, dd, J=3.5, 2.0 Hz), 7.36 (1H, dd, J=3.5, 2.4 Hz), 10.86 (1H, br. s)

F. (4,6-Dimethyl-1H-pyrrolo[2,3-b]pyridin-5-ylmethyl)-carbamic acid tert-butyl ester 4,6-Dimethyl-1H-pyrrolo[2,3-b]pyridine-5-carbonitrile (610 mg, 3.56 mmol) was dissolved in methanol (75 mL). This solution was cooled to 0° C. Nickel (II) chloride hexahydrate (85 mg, 0.36 mmol) and di-tertbutyl dicarbonate (1.56 g, 7.13 mmol) were added followed by sodium borohydride (943 mg, 24.94 mmol) portionwise. The reaction mixture was stirred at 0° C. to room temp for 18 hrs. The MeOH was removed by evaporation. The residue was dissolved in CHCl$_3$ (70 mL), washed with sat NaHCO$_3$ (1×30 mL), water (1×30 mL) and brine (1×30 mL), dried (Na$_2$SO$_4$) and evaporated in vacuo to give a yellow oil. Purified by flash chromatography, (silica), eluant 40% Pet. Ether, 60% EtOAc to give white solid identified as identified as (4,6-dimethyl-1H-pyrrolo[2,3-b]pyridin-5-ylmethyl)-carbamic acid tert-butyl ester (710 mg, 2.56 mmol, 72% yield).

[M+H]$^+$=276.1

$^1$H NMR: (CDCl$_3$), 1.49 (9H, s), 2.61 (3H, s), 2.71 (3H, s), 4.46 (1H, br. s), 4.51 (2H, d, J=4.4 Hz), 6.50 (1H, dd, J=3.5, 2.0 Hz), 7.25 (1H, dd, J=3.4, 2.5 Hz), 9.64 (1H, br. s);

G. C-(4,6-Dimethyl-1H-pyrrolo[2,3-b]pyridin-5-yl)-methylamine hydrochloride 4,6-Dimethyl-1H-pyrrolo[2,3-b]pyridin-5-ylmethyl)-carbamic acid tert-butyl ester (710 mg, 2.56 mmol) was dissolved in 4M HCl in dioxane (10 mL). After 2 hrs at rt the solvent was removed in vacuo to give a yellow solid identified as C-(4,6-dimethyl-1H-pyrrolo[2,3-b]pyridin-5-yl)-methylamine hydrochloride (360 mg, 2.00 mmol, 80% yield).

[M+H]$^+$=176.4

¹H NMR: (d6-DMSO), 2.53 (3H, s), 2.60 (3H, s), 3.94 (2H, s), 4.76 (2H, br. s), 6.43 (1H, d, J=2.3 Hz), 7.28 (1H, dd, J=3.2, 1.9 Hz), 11.32 (1H, br. s)

H. 1-[4-(2-Oxo-2H-pyridin-1-ylmethyl)-benzyl]-3-trifluoromethyl-1H-pyrazole-4-carboxylic acid (4,6-dimethyl-1H-pyrrolo[2,3-b]pyridin-5-ylmethyl)-amide 1-[4-(2-Oxo-2H-pyridin-1-ylmethyl)-benzyl]-3-trifluoromethyl-1H-pyrazole-4-carboxylic acid (80 mg, 0.21 mmol) was dissolved in CH$_2$Cl$_2$ (50 mL) and DMF (2.5 mL). This solution was cooled to 0° C. C-(4,6-Dimethyl-1H-pyrrolo[2,3-b]pyridin-5-yl)-methylamine hydrochloride (44 mg, 0.25 mmol) was added followed by HOBt (32 mg, 0.23 mmol) and triethylamine (64 mg, 0.64 mmol). Water soluble carbodiimide (49 mg, 0.25 mmol) was then added. After 18 hrs at 0° C. to rt reaction mixture was diluted with chloroform (200 mL) and washed with NaHCO$_3$ (1×30 mL), water (1×30 mL) and brine (1×30 mL), dried (Na$_2$SO$_4$) and evaporated in vacuo. The residue was purified by flash chromatography (silica), eluent 8% MeOH, 92% CHCl$_3$, fractions combined and evaporated in vacuo. The residue was freeze dried from water/acetontrile to give a white solid identified as 1-[4-(2-oxo-2H-pyridin-1-ylmethyl)-benzyl]-3-trifluoromethyl-1H-pyrazole-4-carboxylic acid (4,6-dimethyl-1H-pyrrolo[2,3-b]pyridin-5-ylmethyl)-amide (55 mg, 0.11 mmol, 51% yield).

[M+H]$^+$=535

¹H NMR: (d6-DMSO), δ: 4.69 (2H, d, J=5.8 Hz), 5.07 (2H, s), 5.40 (2H, s), 6.21-6.24 (1H, m), 6.39 (1H, d, J=9.0 Hz), 7.00 (1H, d, J=6.9 Hz), 7.26-7.30 (5H, m), 7.39-7.44 (2H, m), 7.77 (1H, q, J=6.6 Hz), 8.14 (1H, s), 8.43 (1H, s), 8.89 (1H, t, J=5.8 Hz), 13.11 (1H, s).

Example 9

2,5-Dimethyl-1-[4-(4-methyl-pyrazol-1-ylmethyl)-benzyl]-1H-pyrrole-3-carboxylic acid (1-amino-isoquinolin-6-ylmethyl)-amide

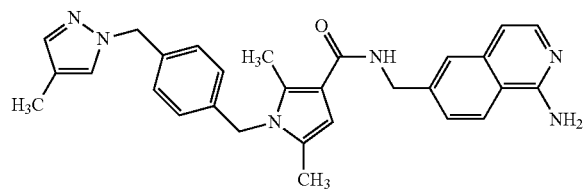 [SMILES: Cc1cnn(Cc2ccc(Cn3c(C)cc(C(=O)NCc4ccc5c(N)nccc5c4)c3C)cc2)c1]

A.
[4-(4-Methyl-pyrazol-1-ylmethyl)-phenyl]-methanol 4-(Chloromethyl)benzylalcohol (5.47 g, 34.9 mmol) was dissolved in acetone (50 mL) 4-methylpyrazole (2.86 g, 34.9 mmol) and potassium carbonate (5.07 g, 36.7 mmol) were added and the reaction mixture was stirred at rt for 18 hrs and at 60° C. for 30 hrs after which time the solvent was removed in vacuo and the residue taken up in EtOAc (100 mL), this solution was washed with water (1×30 mL), brine (1×30 mL), dried (MgSO$_4$) and evaporated in vacuo. The residue was purified by flash chromatography (silica), eluent gradient of 10 to 80% EtOAc in iso-Hexane, fractions combined and evaporated in vacuo to give a white solid identified as [4-(4-methyl-pyrazol-1-ylmethyl)-phenyl]-methanol (3.94 g, 18.90 mmol, 54% yield).

[M+H]$^+$=203

B.
1-(4-Chloromethyl-benzyl)-4-methyl-1H-pyrazole

[4-(4-Methyl-pyrazol-1-ylmethyl)-phenyl]-methanol (2.03 g, 10.04 mmol) and triethylamine (1.13 g, 11.54 mmol) was dissolved in dichloromethane (40 mL). To this solution was added methanesulphonyl chloride (1.26 g, 11.04 mmol) dropwise. The reaction mixture was stirred at rt for 18 hrs and diluted with CHCl$_3$ (250 mL) the filtrate was washed with saturated NH$_4$Cl (1×30 mL), water (1×30 mL), brine (1×30 mL), dried (Na$_2$SO$_4$) and evaporated in vacuo. The residue was purified by flash chromatography (silica), eluent gradient of 0 to 60% EtOAc in iso-Hexane, fractions combined and evaporated in vacuo to give a white solid identified as 1-(4-chloromethyl-benzyl)-4-methyl-1H-pyrazole (1.49 g, 6.62 mmol, 60% yield).

[M+H]$^+$=221, 223

C: 2,5-Dimethyl-1-[4-(4-methyl-pyrazol-1-ylmethyl)-benzyl]-1H-pyrrole-3-carboxylic acid methyl ester A solution of methyl 2,5-dimethyl-1H-pyrrole-3-carboxylate (0.382 g, 2.492 mmol) in anhydrous DMF (8 mL) was cooled in an ice-bath, then treated sequentially portionwise with sodium hydride (0.071 g, 2.95 mmol), then 1-(4-(chloromethyl)benzyl)-4-methyl-1H-pyrazole (0.50 g, 2.266 mmol) and the mixture allowed to stir at ~5° C. for 1 hour. The ice-bath was removed and the mixture stirred for a further 45 min. Further sodium hydride (0.5 eq) was added and the mixture allowed to stir overnight. The reaction was quenched with water (40 mL) and attempted to extract into DCM (3×40 mL), but presence of DMF caused emulsion. Combined DCM layers were washed with brine, dried (Na$_2$SO$_4$), filtered and concentrated. Brine (40 mL) was added to the initial aqueous layer and this extracted with EtOAc (3×40 mL). The combined EtOAc layers were washed with water (3×20 mL), brine (30 mL), dried (MgSO$_4$), and concentrated with the DCM extract residue (4 mbar @55° C.) to remove residual DMF. The compound was purified by chromatography (silica) eluting with a gradient of 0 to 70% EtOAc/Iso-Hexanes to afford 2,5-dimethyl-1-[4-(4-methyl-pyrazol-1-ylmethyl)-benzyl]-1H-pyrrole-3-carboxylic acid methyl ester (602 mg, 1.748 mmol, 77% yield) as a pale yellow oil which crystallized slowly on standing.

[M+H]$^+$=338

D: 2,5-Dimethyl-1-[4-(4-methyl-pyrazol-1-ylmethyl)-benzyl]-1H-pyrrole-3-carboxylic acid A solution of methyl 2,5-dimethyl-1-(4-((4-methyl-1H-pyrazol-1-yl)methyl)benzyl)-1H-pyrrole-3-carboxylate (459 mg, 1.360 mmol) in tetrahydrofuran (8 mL), methanol (5 mL) and water (7 mL) were treated with lithium hydroxide (163 mg, 6.80 mmol) and the mixture heated at 65° C. with stirring for 48 hrs until completion. The majority of the solvents were removed under vacuum. The resultant cloudy mixture was partitioned between EtOAc (50 mL) and water (50 mL) containing 1M NaOH (2 mL). The organic layer was discarded and the aqueous layer acidified to pH3 with 1M HCl (turned cloudy). The aqueous layer was extracted with EtOAc (3×50 mL) and the combined organics dried (MgSO$_4$), filtered and concentrated under vacuum to afford 2,5-dimethyl-1-(4-((4-methyl-1H-pyrazol-1-yl)methyl)benzyl)-1H-pyrrole-3-carboxylic acid (448 mg, 1.358 mmol, 90% yield) as a pale yellow solid.
[M+H]$^+$=324

E: 2,5-Dimethyl-1-[4-(4-methyl-pyrazol-1-ylmethyl)-benzyl]-1H-pyrrole-3-carboxylic acid (1-amino-isoquinolin-6-ylmethyl)-amide A scintillation vial was charged with 2,5-dimethyl-1-(4-((4-methyl-1H-pyrazol-1l)methyl)benzyl)-1H-pyrrole-3-carboxylic acid (93 mg, 0.289 mmol), 6-(aminomethyl)isoquinolin-1-amine (80 mg, 0.462 mmol), HATU (121 mg, 0.318 mmol) and 25% DMF/DCM (3.5 mL). Next, N,N-diisopropylethylamine (101 µl, 0.577 mmol) was added and the mixture allowed to stir overnight. The reaction mixture was diluted with MeOH (10 mL) to form a solution. This was passed through a strong cation exchange chromatography column (3 g), washing with MeOH, eluting with 1% NH$_3$/MeOH. The crude material was purified by chromatography (silica) eluting with a gradient of 0 to 8% MeOH/DCM (1% NH$_3$) to afford 2,5-dimethyl-1-[4-(4-methyl-pyrazol-1-ylmethyl)-benzyl]-1H-pyrrole-3-carboxylic acid (1-amino-isoquinolin-6-ylmethyl)-amide (66 mg, 0.134 mmol, 46.3% yield) as a pale yellow powder.
[M+H]$^+$=479
$^1$H NMR: (d6-DMSO), δ: 1.99 (3H, d, J=0.7 Hz), 2.07 (3H, s), 2.37 (3H, s), 4.50 (2H, d, J=6.0 Hz), 5.07 (2H, s), 5.20 (2H, s), 6.37 (1H, d, J=1.1 Hz), 6.70 (2H, s), 6.83-6.92 (3H, m), 7.16 (2H, d, J=8.2 Hz), 7.22 (1H, s), 7.39 (1H, dd, J=1.7, 8.6 Hz), 7.52 (2H, s, br), 7.76 (1H, d, J=5.8 Hz), 8.13 (1H, d, J=8.6 Hz), 8.21 (1H, t, J=6.1 Hz).

Example 10

1-[4-(4-Methyl-pyrazol-1-ylmethyl)-benzyl]-1H-imidazole-4-carboxylic acid (1-amino-isoquinolin-6-ylmethyl)-amide

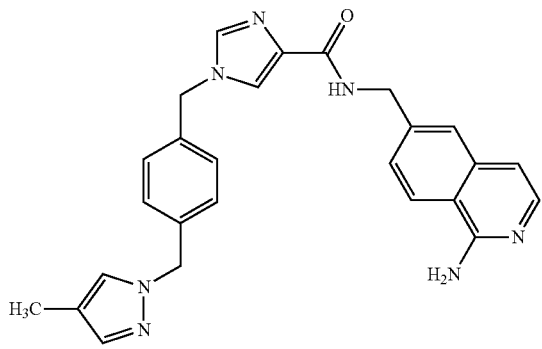 [SMILES: Cc1cnn(Cc2ccc(Cn3cnc(C(=O)NCc4ccc5c(N)nccc5c4)c3)cc2)c1]

A. 1-[4-(4-Methyl-pyrazol-1-ylmethyl)-benzyl]-1H-imidazole-4-carboxylic acid ethyl ester 1-(4-Chloromethyl-benzyl)-4-methyl-1H-pyrazole (986 mg, 4.47 mmol) was dissolved in DMF (28 mL) ethyl 1H-imidazole-4-carboxylate (626 mg, 4.47 mmol) and potassium carbonate (1.42 g, 10.28 mmol) were added and the reaction mixture was stirred at rt for 3 days after which time the reaction mixture was diluted with EtOAc (100 mL), this solution was washed with water (1×30 mL), brine (1×30 mL), dried (Na$_2$SO$_4$) and evaporated in vacuo. The residue was purified by flash chromatography (silica), eluent gradient of 50 to 100% EtOAc in iso-Hexane, 2 products eluted the first at ~90% EtOAc/Iso-Hexane with the second eluting at 100% EtOAc. Fractions combined and evaporated in vacuo.

The first product eluted was isolated as a white solid identified as 3-[4-(4-methyl-pyrazol-1-ylmethyl)-benzyl]-3H-imidazole-4-carboxylic acid ethyl ester (675 mg, 2.06 mmol, 46% yield).
[M+H]$^+$=325

The second product eluted was isolated as a clear gum identified as 1-[4-(4-methyl-pyrazol-1-ylmethyl)-benzyl]-1H-imidazole-4-carboxylic acid ethyl ester (540 mg, 1.652 mmol, 37% yield).
[M+H]$^+$=325

B. 1-[4-(4-Methyl-pyrazol-1-ylmethyl)-benzyl]-1H-imidazole-4-carboxylic acid

1-[4-(4-Methyl-pyrazol-1-ylmethyl)-benzyl]-1H-imidazole-4-carboxylic acid ethyl ester (471 mg, 1.45 mmol) was dissolved in THF (7 mL) ethanol (4.5 mL) and water (6.3 mL) lithium hydroxide (174 mg, 7.26 mmol) was added. The reaction mixture was stirred at 65° C. for 2 hrs after which time the solvent was concentrated in vacuo and the residue taken up in CHCl$_3$ (150 mL), the aqueous layer was extracted and acidified with 1M HCl to pH2 and extracted CHCl$_3$ (3×50 mL) the combined extracts were washed with water (1×30 mL), brine (1×30 mL), dried (Na$_2$SO$_4$) and evaporated in vacuo. The residue was purified by flash chromatography (silica), eluent dichloromethane:MeOH:NH$_3$ (100:10:1). Fractions combined and evaporated in vacuo to give a white solid identified as 1-[4-(4-methyl-pyrazol-1-ylmethyl)-benzyl]-1H-imidazole-4-carboxylic acid (245 mg, 0.82 mmol, 51% yield).
[M+H]$^+$=295

C. 1-[4-(4-Methyl-pyrazol-1-ylmethyl)-benzyl]-1H-imidazole-4-carboxylic acid (1-amino-isoquinolin-6-ylmethyl)-amide 1-[4-(4-Methyl-pyrazol-1-ylmethyl)-benzyl]-1H-imidazole-4-carboxylic acid (50 mg, 0.169 mmol) was dissolved in DMF/CH$_2$Cl$_2$ (1:3, 3 mL). HATU (71 mg, 0.186 mmol) was added followed by 6-(aminomethyl)isoquinolin-1-amine (80 mg, 0.464 mmol) and N,N-diisopropylethylamine (44 mg, 0.337 mmol). After 18 hrs at rt reaction mixture was diluted with chloroform (400 mL) washed with NH$_4$Cl (1×30 mL), water (1×30 mL), brine (1×30 mL), dried (Na$_2$SO$_4$) and evaporated in vacuo giving a yellow oil. The residue was purified by flash chromatography (silica), eluent dichloromethane:MeOH:NH$_3$ (100:10:1). fractions combined and evaporated in vacuo to give a white solid identified as 1-[4-(4-methyl-pyrazol-1-ylmethyl)-benzyl]-1H-imidazole-4-carboxylic acid (1-amino-isoquinolin-6-ylmethyl)-amide (47 mg, 0.102 mmol, 60% yield).
[M+H]$^+$=452
$^1$H NMR: (d6-DMSO), δ: 1.99 (3H, s), 4.52 (2H, d, J=6.3 Hz), 5.20 (1H, s), 5.22 (1H, s), 6.70 (2H, s), 6.83 (1H, d, J=5.8 Hz), 7.16-7.25 (3H, m), 7.26-7.32 (2H, m), 7.38 (1H, dd, J=1.7, 8.6 Hz), 7.46-7.56 (2H, m), 7.69-7.78 (2H, m), 7.85 (1H, d, J=1.3 Hz), 8.11 (1H, d, J=8.6 Hz), 8.58 (1H, t, J=6.3 Hz).

Example 11

3-Methyl-1-[4-(4-methyl-pyrazol-1-ylmethyl)-benzyl]-1H-pyrazole-4-carboxylic acid (1-amino-isoquinolin-6-ylmethyl)-amide

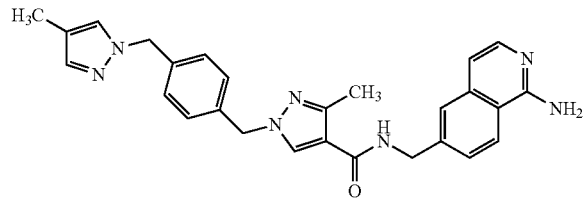 [SMILES: Cc1cnn(Cc2ccc(Cn3cc(C(=O)NCc4ccc5c(N)nccc5c4)c(C)n3)cc2)c1]

A. N'-[4-(4-Methyl-pyrazol-1-ylmethyl)-benzyl]-hydrazinecarboxylic acid tert-butyl ester A solution of 1-(4-(chloromethyl)benzyl)-4-methyl-1H-pyrazole (3.5 g, 15.86 mmol) and tert-butyl carbazate (8.38 g, 63.4 mmol) in absolute EtOH (21 mL) was treated with N,N-diisopropylethylamine (2.76 mL, 15.86 mmol) and the mixture stirred at 60° C. for 24 hrs. LCMS indicated desired product and reaction of product with a second equivalent of starting chloride [445]$^+$ in a 3:1 ratio. Solvents were removed under vacuum and the residue partitioned between EtOAc (150 mL) and saturated aqueous NH$_4$Cl (turned cloudy, some water added). The organic layer was separated and washed with water (75 mL) and brine (75 mL), dried (MgSO$_4$), filtered and concentrated. The residue was purified by chromatography (silica) eluting with a gradient of 0 to 50% EtOAc/Iso-Hexanes. Note chromaphore is weak; product streaked over many fractions. Every 5th fraction was examined by HPLC and the cleanest set of fractions combined to afford >7 g of material. $^1$H NMR (DMSO-d$_6$, 1119-13-1) showed 85% purity aside from the presence of excess tert butyl carbazate. The product was purified by Kugelrohr distillation (3 runs until no more material evident in collection bulb) at 2.9 mBar/110-115° C. (indicated). $^1$H NMR (DMSO-d$_6$) showed removal of the tert-butyl carbazate. The mixture was further purified by chromatography (silica) eluting with a gradient of 0 to 60% THF/DCM. The compound eluted more quickly than expected (in 15% THF). Some clean product fractions were obtained at the tail of the peak to afford 1.77 g of the desired compound at >95% purity by $^1$H NMR. Mixed fractions were also obtained and were consistent with the desired compound at 78% purity by $^1$H NMR.

[M+H]$^+$=317

B. [4-(4-Methyl-pyrazol-1-ylmethyl)-benzyl]-hydrazine

To a stirred solution of 4-tert-butyl 2-(4-((4-methyl-1H-pyrazol-1-1)methyl)benzyl) hydrazinecarboxylate (369 mg, 1.166 mmol) in dioxane (5 mL) was added HCl 4M in dioxane (1 mL, 32.9 mmol) dropwise, a thick precipitate formed and stirring continued for 2 hrs. Reaction mixture was diluted with diethyl ether (20 mL). The thick precipitate did not break up on sonication. Attempts to filter the material were difficult. Drying for 30 min on filter paper did not give dry solid. Material was slightly hygroscopic. The bulk was transferred into a flask and used directly in the next step without further purification

[M+H]$^+$=217

C. 3-Methyl-1-[4-(4-methyl-pyrazol-1-ylmethyl)-benzyl]-1H-pyrazole-4-carboxylic acid ethyl ester To a stirred suspension of 5-acetyl-uracil (150 mg, 0.971 mmol) and [4-(4-Methyl-pyrazol-1-ylmethyl)-benzyl]-hydrazine dihydrochloride (337 mg, 1.165 mmol) in EtOH (10 mL) was added conc HCl (0.5 mL) and the reaction heated at reflux (80° C.) for 24 hrs. A fine white suspension was observed. Analysis by LCMS showed the main peak [M+H]$^+$=353 corresponding to the imine intermediate. After a further 3 hrs no further reaction had occurred. The reaction mixture was charged with H$_2$SO$_4$ (conc.) (0.5 mL) and heated to 120° C. for 50 min in a microwave. The reaction mixture was evaporated to dryness and the residue taken up into EtOAc (100 mL). The organics were washed with NaOH (2M, 50 mL), brine (50 mL), dried over magnesium sulfate, filtered and evaporated to dryness. The crude product was purified by chromatography (12 g column, 0-50% EtOAc in isohexanes) to afford 3-methyl-1-[4-(4-methyl-pyrazol-1-ylmethyl)-benzyl]-1H-pyrazole-4-carboxylic acid ethyl ester (144 mg, 0.417 mmol, 42.9% yield) as a colourless oil. Analysis by HPLC, (PFP column, 40% Methanol, acidic, 225 nm detection) showed clean 3-regioisomer.

[M+H]$^+$=339

D. 3-Methyl-1-[4-(4-methyl-pyrazol-1-ylmethyl)-benzyl]-1H-pyrazole-4-carboxylic acid To a stirred solution of 3-methyl-1-[4-(4-methyl-pyrazol-1-ylmethyl)-benzyl]-1H-pyrazole-4-carboxylic acid ethyl ester (144 mg, 0.426 mmol) in THF (3 mL) and MeOH (2 mL) was added NaOH 2M (638 µl, 1.277 mmol) and left at RT overnight. Analysis showed clean conversion to the desired acid. Reaction mixture was acidified to pH5 using 1M HCl. The product was extracted into EtOAc (20 mL) and the organics washed with brine (2×20 mL), dried over magnesium sulfate, filtered and solvent removed to give a white solid identified as 3-methyl-1-(4-((4-methyl-1H-pyrazol-1-yl)methyl)benzyl)-1H-pyrazole-4-carboxylic acid (83 mg, 0.254 mmol, 59.7% yield).

[M+H]$^+$=311

E. 3-Methyl-1-[4-(4-methyl-pyrazol-1-ylmethyl)-benzyl]-1H-pyrazole-4-carboxylic acid (1-amino-isoquinolin-6-ylmethyl)-amide hydrochloride To a stirred solution of 3-methyl-1-(4-((4-methyl-1H-pyrazol-1-yl)methyl)benzyl)-1H-pyrazole-4-carboxylic acid (75 mg, 0.242 mmol) and 6-(aminomethyl)isoquinolin-1-amine, 2HCl (59.5 mg, 0.242 mmol) in DMF (3 mL) was added N,N-diisopropylethylamine (169 µl, 0.967 mmol) and HATU (96 mg, 0.254 mmol). The reaction was stirred at rt for 2 hrs. Analysis showed complete conversion to desired product. The reaction mixture was diluted with EtOAc (30 mL) and washed with NaOH (2M, 20 mL), brine (50 mL), dried over magnesium sulfate, filtered and the solvent evaporated under reduced pressure. The crude solid was pre-absorbed onto silica before purification by chromatography (12 g column, 0-10% MeOH (1% NH$_3$) in DCM, pausing at 5% to afford 3-Methyl-1-[4-(4-methyl-pyrazol-1-ylmethyl)-benzyl]-1H-pyrazole-4-carboxylic acid (1-amino-isoquinolin-6-ylmethyl)-amide hydrochloride (65.2 mg, 0.140 mmol, 58.0% yield) as a white powder. The free base was taken up into MeOH (1 mL) and HCl 4M in dioxane (35.0 µl, 0.140 mmol, 1 eq.) was added. A solid precipitated and the MeOH was removed under a flow of air. The dioxane was removed under vacuum. The residue was triturated from diethyl ether (5 mL) to afford 3-methyl-1-[4-(4-methyl-pyrazol-1-ylmethyl)-benzyl]-1H-pyrazole-4-carboxylic acid (1-amino-isoquinolin-6-ylmethyl)-amide hydrochloride (62 mg, 0.117 mmol, 48.6% yield) as white solid.

[M+H]$^+$=466

NMR (d6-DMSO) δ: 1.99 (3H, J=0.7 Hz), 2.31 (3H, s), 4.57 (2H, d, J=5.9 Hz), 5.23 (4H, d, J=7.4 Hz), 7.16-7.28 (6H, m), 7.54 (1H, t, J=0.9 Hz), 7.64-7.73 (2H, m), 7.79 (1H, d, J=1.6 Hz), 8.24 (1H, s), 8.54 (1H, d, J=8.7 Hz), 8.61 (1H, t, J=6.0 Hz), 9.05 (2H, br s), 13.14 (1H, s)

Example 12

3-Cyclopropyl-1-[4-(4-methyl-pyrazol-1-ylmethyl)-benzyl]-1H-pyrazole-4-carboxylic acid (1-amino-isoquinolin-6-ylmethyl)-amide

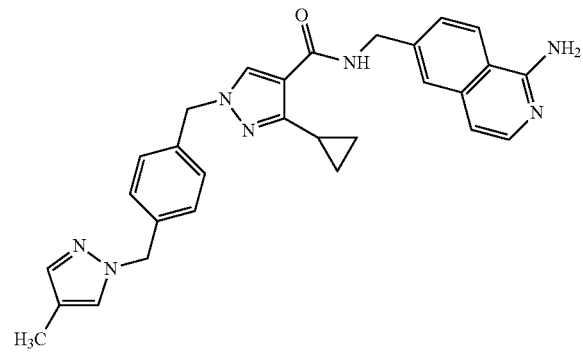 [SMILES: Cc1cnn(Cc2ccc(Cn3cc(C(=O)NCc4ccc5c(N)nccc5c4)c(C4CC4)n3)cc2)c1]

A.
1-(4-Bromomethyl-benzyl)-4-methyl-1H-pyrazole

[4-(4-Methyl-pyrazol-1-ylmethyl)-phenyl]-methanol (2.05 g, 10.1 mmol) was dissolved in dichloromethane (50 mL). To this solution was added triphenylphosphine (3.05 g, 11.6 mmol). The resultant solution was cooled in an ice bath before carbon tetrabromide (3.69 g, 11.1 mmol) was added portionwise. The reaction mixture was stirred at rt for 18 hrs and diluted with CHCl$_3$ (100 mL). The filtrate was washed with saturated NaHCO$_3$ (1×30 mL), water (1×30 mL) and brine (1×30 mL), dried (Na$_2$SO$_4$) and evaporated in vacuo. The residue was purified by flash chromatography (silica), eluent 95% Pet. Ether, 5% EtOAc, fractions combined and evaporated in vacuo to give a white solid which was identified as 1-(4-bromomethyl-benzyl)-4-methyl-1H-pyrazole (1.64 g, 6.19 mmol, 61% yield).

[M+H]$^+$=265

B. 3-Cyclopropyl-1-[4-(4-methyl-pyrazol-1-ylmethyl)-benzyl]-1H-pyrazole-4-carboxylic acid ethyl ester Ethyl 3-cyclopropyl-1H-pyrazole-4-carboxylate (100 mg, 0.56 mmol) was dissolved in DMF (20 mL). 1-(4-Bromomethyl-benzyl)-4-methyl-1H-pyrazole (155 mg, 0.58 mmol) and potassium carbonate (153 mg, 1.1 mmol) were added and the reaction mixture was stirred at rt for 2 days after which time the reaction mixture was diluted with EtOAc (100 mL), this solution was washed with water (1×30 mL) and brine (1×30 mL), dried (Na$_2$SO$_4$) and evaporated in vacuo. The residue was purified by flash chromatography (silica), eluent 98% dichloromethane, 2% methanol, fractions combined and evaporated in vacuo to give a white solid identified as 3-cyclopropyl-1-[4-(4-methyl-pyrazol-1-ylmethyl)-benzyl]-1H-pyrazole-4-carboxylic acid ethyl ester (190 mg, 0.52 mmol, 94% yield).

[M+H]$^+$=365

C. 3-Cyclopropyl-1-[4-(4-methyl-pyrazol-1-ylmethyl)-benzyl]-1H-pyrazole-4-carboxylic acid 3-Cyclopropyl-1-[4-(4-methyl-pyrazol-1-ylmethyl)-benzyl]-1H-pyrazole-4-carboxylic acid ethyl ester (190 mg, 0.52 mmol) was dissolved ethanol (10 mL) and sodium hydroxide (208 mg, 5.2 mmol) was added. The reaction mixture was stirred at reflux for 18 hrs after which time the solvent was concentrated in vacuo and the residue taken up in CHCl$_3$ (150 mL), the aqueous layer was extracted and acidified with 1M HCl to pH2 and extracted CHCl$_3$ (3×50 mL). The combined extracts were washed with water (1×30 mL) and brine (1×30 mL), dried (Na$_2$SO$_4$) and evaporated in vacuo. The residue was purified by flash chromatography (silica), eluent dichloromethane:MeOH:NH$_3$ (100:10:1) fractions combined and evaporated in vacuo to give a white solid identified as 3-cyclopropyl-1-[4-(4-methyl-pyrazol-1-ylmethyl)-benzyl]-1H-pyrazole-4-carboxylic acid (150 mg, 0.45 mmol, 86% yield).

[M+H]$^+$=337

D. 3-Cyclopropyl-1-[4-(4-methyl-pyrazol-1-ylmethyl)-benzyl]-1H-pyrazole-4-carboxylic acid (1-amino-isoquinolin-6-ylmethyl)-amide 3-Cyclopropyl-1-[4-(4-methyl-pyrazol-1-ylmethyl)-benzyl]-1H-pyrazole-4-carboxylic acid (65 mg, 0.19 mmol) was dissolved in CH$_2$Cl$_2$ (50 mL) and DMF (2.5 mL). This solution was cooled to 0° C. 6-Aminomethyl-isoquinolin-1-ylamine (34 mg, 0.19 mmol) was added followed by HOBt (31 mg, 0.23 mmol) and triethylamine (98 mg, 0.97 mmol). Water soluble carbodiimide (52 mg, 0.27 mmol) was then added. After 18 hrs at 0° C. to rt reaction mixture was diluted with chloroform (100 mL) and IPA (10 mL), washed with NaHCO$_3$ (1×30 mL), water (1×30 mL) and brine (1×30 mL), dried (Na$_2$SO$_4$) and evaporated in vacuo giving a yellow oil. The residue was purified by flash chromatography (silica), eluent dichloromethane:MeOH:NH$_3$ (100:10:1), fractions combined and evaporated in vacuo to give a white solid identified as 3-cyclopropyl-1-[4-(4-methyl-pyrazol-1-ylmethyl)-benzyl]-1H-pyrazole-4-carboxylic acid (1-amino-isoquinolin-6-ylmethyl)-amide (46 mg, 0.09 mmol, 48% yield).

[M+H]$^+$=496

$^1$H NMR: (d6-DMSO), δ: 0.73-0.76 (2H, m), 0.79-0.84 (2H, m), 1.98 (3H, s), 2.55-2.67 (1H, m), 4.50 (2H, d, J=5.9 Hz), 5.19 (2H, s), 5.21 (2H, s), 6.71 (2H, s), 6.85 (1H, d, J=5.8 Hz), 7.18 (4H, s), 7.23 (1H, s), 7.36-7.39 (1H, m), 7.52 (2H, s), 7.76 (1H, d, J=5.8 Hz), 8.12 (2H, d, J=8.4 Hz), 8.46 (1H, t, J=5.9 Hz).

Example 13

3-Isopropyl-1-[4-(4-methyl-pyrazol-1-ylmethyl)-benzyl]-1H-pyrazole-4-carboxylic acid (1-amino-isoquinolin-6-ylmethyl)-amide

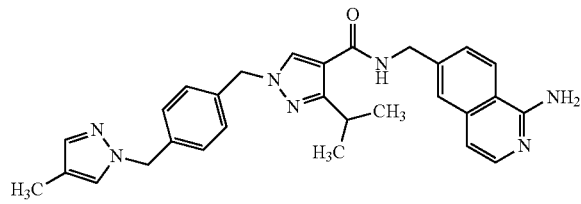 [SMILES: Cc1cnn(Cc2ccc(Cn3cc(C(=O)NCc4ccc5c(N)nccc5c4)c(C(C)C)n3)cc2)c1]

A. Ethyl 3-isopropyl-1-(4-((4-methyl-1H-pyrazol-1-yl)methyl)benzyl)-1H-pyrazole-4-carboxylate To a stirred solution of ethyl 3-isopropyl-1H-pyrazole-4-carboxylate (446 mg, 2.447 mmol) and 1-(4-(chloromethyl)benzyl)-4-methyl-1H-pyrazole (540 mg, 2.447 mmol) in DMF (8 mL) was added $K_2CO_3$ (676 mg, 4.89 mmol) and stirred at rt overnight. The reaction was diluted with brine (10 mL) and EtOAc (10 mL) and the layers separated. The aqueous was extracted with EtOAc (2×10 mL). The combined organic layers were dried ($Na_2SO_4$), filtered and evaporated under reduced pressure. The crude was purified by chromatography (24 g column, EtOAc in iso-Hexanes 0-50% yield) to afford ethyl 3-isopropyl-1-(4-((4-methyl-1H-pyrazol-1-yl)methyl)benzyl)-1H-pyrazole-4-carboxylate (702 mg, 1.762 mmol, 72.0% yield) as a thick pale yellow oil.

$[M+H]^+ = 367$

B. 3-Isopropyl-1-(4-((4-methyl-1H-pyrazol-1-yl)methyl)benzyl)-1H-pyrazole-4-carboxylic acid To a stirred mixture of ethyl 3-isopropyl-1-(4-((4-methyl-1H-pyrazol-1-yl)methyl)benzyl)-1H-pyrazole-4-carboxylate (690 mg, 1.883 mmol) and lithium hydroxide (135 mg, 5.65 mmol) in THF (8 mL) and water (4 mL) at rt was added lithium hydroxide (135 mg, 5.65 mmol). MeOH (1 mL) added to increase solubility. The reaction was stirred and heated at 50° C. for 5 hrs. The reaction was allowed to cool to rt, acidified to pH~3 with 1M HCl and extracted with EtOAc (3×5 mL). Organic dried ($Mg_2SO_4$), filtered and evaporated under reduced pressure to give) as a pale yellow solid. This sample crude was purified by chromatography (12 g column, (2:1 EtOAc-MeCN) in DCM 0-50% yield) to afford 3-isopropyl-1-(4-((4-methyl-1H-pyrazol-1-yl)methyl)benzyl)-1H-pyrazole-4-carboxylic acid (256 mg, 0.749 mmol, 40% yield). No undesired 5-regioisomer was observed.

$[M+H]^+ = 339$

C. 3-Isopropyl-1-[4-(4-methyl-pyrazol-1-ylmethyl)-benzyl]-1H-pyrazole-4-carboxylic acid (1-amino-isoquinolin-6-ylmethyl)-amide hydrochloride To a stirred solution of 3-isopropyl-1-(4-((4-methyl-1H-pyrazol-1-yl)methyl)benzyl)-1H-pyrazole-4-carboxylic acid (129 mg, 0.381 mmol), 6-(aminomethyl)isoquinolin-1-amine dihydrochloride (100 mg, 0.406 mmol) and HATU (174 mg, 0.457 mmol) in DMF (2 mL) was added N,N-diisopropylethylamine (266 µL, 1.525 mmol). The resulting mixture was stirred at rt overnight. The reaction was diluted with EtOAc (15 mL) and washed with 2M NaOH (2×20 mL). Organic dried ($Na_2SO_4$), filtered and evaporated under reduced pressure. The crude was purified by chromatography (4 g column, MeOH in DCM 0-5% and 1% $Et_3N$) to afford the desired compound as a free base. $^1$H NMR in DMSO-d6 was consistent with the free amine structure. The product was dissolved in DCM (1 mL), 4M HCl in dioxane (124 µL, 0.496 mmol) added and the resulting flocculent mixture stirred at rt for 15 min. The solvent was then evaporated under reduced pressure to give N-((1-aminoisoquinolin-6-yl)methyl)-3-isopropyl-1-(4-((4-methyl-1H-pyrazol-1-yl)methyl)benzyl)-1H-pyrazole-4-carboxamide, HCl (170 mg, 0.319 mmol, 84% yield) as a white solid.

$[M+H]^+ = 494$ $^1$H NMR: (d6-DMSO), δ: 1.17 (6H, d, J=6.9 Hz); 1.99 (3H, t, J=0.7 Hz); 3.57 (1H, hept, J=6.2 Hz); 4.56 (2H, d, J=5.8 Hz); 5.25 (4H, d, J=15.4 Hz); 7.16-7.27 (6H, m); 7.55 (1H, q, J=0.8 Hz); 7.63-7.72 (2H, m); 7.79 (1H, d, J=1.6 Hz); 8.19 (1H, s); 8.54 (1H, d, J=8.6 Hz); 8.64 (1H, t, J=5.9 Hz); 9.08 (2H, s); 13.22 (1H, s).

Example 14

3-Cyclobutyl-1-[4-(4-methyl-pyrazol-1-ylmethyl)-benzyl]-1H-pyrazole-4-carboxylic acid (1-amino-isoquinolin-6-ylmethyl)-amide

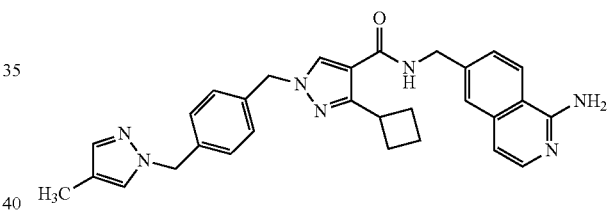

A. (E)-Ethyl 2-(cyclobutanecarbonyl)-3-(dimethylamino)acrylate

To a flask charged with ethyl 3-cyclobutyl-3-oxopropanoate (0.935 g, 5.49 mmol) was added 1,1-dimethoxy-N,N-dimethylmethanamine (0.876 mL, 6.59 mmol) and dioxane (30 mL). Heated at 70° C. for 7 hrs. Reaction mixture was azeotroped with toluene (2×30 mL) to remove any residual 1,1-dimethoxy-N,N-dimethylmethanamine. Quantitative yield assumed and material used directly in the next step.

$[M+H]^+ = 216$

B. Ethyl 3-cyclobutyl-1H-pyrazole-4-carboxylate

To a stirred solution of 1132-12 (E)-ethyl 2-(cyclobutanecarbonyl)-3-(dimethylamino)acrylate (1.24 g, 5.50 mmol) (crude) in EtOH (30 mL) was added hydrazine, $H_2O$ (0.803 mL, 8.26 mmol) and heated to reflux overnight. Reaction mixture evaporated to remove excess hydrazine. Crude material was taken up into EtOAc (150 mL) and washed with $NaHCO_3$ (aq, 100 mL), then brine (100 mL), dried over magnesium sulfate and solvent removed to afford ethyl 3-cyclobutyl-1H-pyrazole-4-carboxylate (709 mg, 3.54 mmol, 64.3% yield) as a waxy solid on standing.

$[M+H]^+ = 195$

C. 3-Cyclobutyl-1-[4-(4-methyl-pyrazol-1-ylmethyl)-benzyl]-1H-pyrazole-4-carboxylic acid (1-amino-isoquinolin-6-ylmethyl)-amide hydrochloride Procedure as for Example 13 methods A-C

[M+H]$^+$=506

$^1$H NMR: (d6-DMSO), δ: 1.70-1.83 (1H, m); 1.81-1.98 (1H, m); 1.99 (3H, d, J=0.8 Hz); 2.12-2.25 (4H, m); 4.55 (2H, d, J=5.8 Hz); 5.23 (2H, s); 5.29 (2H, s); 7.15-7.29 (6H, m); 7.55 (1H, t, J=0.9 Hz); 7.63-7.72 (2H, m); 7.78 (1H, d, J=1.5 Hz); 8.20 (1H, s); 8.49-8.61 (2H, m); 9.03 (2H, s); 13.11 (1H, s).

Example 15

3-Hydroxymethyl-1-[4-(4-methyl-pyrazol-1-ylmethyl)-benzyl]-1H-pyrazole-4-carboxylic acid (1-amino-isoquinolin-6-ylmethyl)-amide

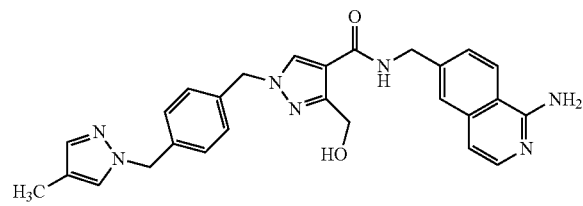 [SMILES: Cc1cnn(Cc2ccc(Cn3cc(C(=O)NCc4ccc5c(N)nccc5c4)c(CO)n3)cc2)c1]

A. 3-Hydroxymethyl-1-[4-(4-methyl-pyrazol-1-ylmethyl)-benzyl]-1H-pyrazole-4-carboxylic acid (1-amino-isoquinolin-6-ylmethyl)-amide hydrochloride Tribromoborane (118 μl, 0.118 mmol) was added to a stirred solution of 3-methoxymethyl-1-[4-(4-methyl-pyrazol-1-ylmethyl)-benzyl]-1H-pyrazole-4-carboxylic acid (1-amino-isoquinolin-6-ylmethyl)-amide (45 mg, 0.091 mmol) in DCM (0.3 mL). The resulting mixture was stirred at rt for 3 hrs. The solvent was evaporated under reduced pressure and the residue was absorbed on silica before purification by chromatography (4 g column, 0-10% MeOH in DCM, 1% Et$_3$N) to afford the free base of the desired compound as a white solid. This solid was dissolved in DCM (1 mL) and MeOH (0.5 mL). 4M HCl in dioxane (29.5 μl, 0.118 mmol) was added and the resulting mixture was stirred at rt for 15 min. The solvents were evaporated under reduced pressure to give 3-hydroxymethyl-1-[4-(4-methyl-pyrazol-1-ylmethyl)-benzyl]-1H-pyrazole-4-carboxylic acid (1-amino-isoquinolin-6-ylmethyl)-amide hydrochloride (39 mg, 0.075 mmol, 82% yield) as a white solid.

[M+H]$^+$=482.3

$^1$H NMR: (d6-DMSO), δ: 1.99 (3H, s), 4.56 (2H, s), 4.64 (2H, d, J=5.8 Hz), 5.22 (2H, s), 5.28 (2H, s), 7.16-7.31 (6H, m), 7.55 (1H, t, J=0.9 Hz), 7.63-7.74 (2H, m), 7.82 (1H, d, J=1.6 Hz), 8.34 (1H, s), 8.55 (1H, d, J=8.7 Hz), 8.90-9.05 (3H, m), 13.17 (1H, s).

Example 16

3-Cyano-1-[4-(4-methyl-pyrazol-1-ylmethyl)-benzyl]-1H-pyrazole-4-carboxylic acid (1-amino-isoquinolin-6-ylmethyl)-amide

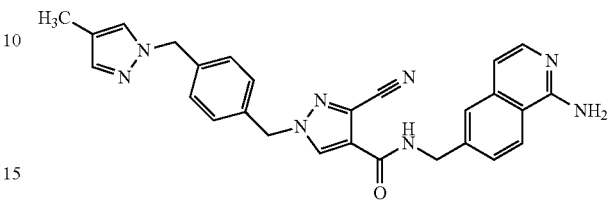

A. Ethyl 3-cyano-1-[4-(4-methyl-pyrazol-1-ylmethyl)-benzyl]-1H-pyrazole-4-carboxylate Procedure as Example 13 method A

[M+H]$^+$=350

B. 3-Cyano-1-[4-(4-methyl-pyrazol-1-ylmethyl)-benzyl]-1H-pyrazole-4-carboxylic acid A stirred solution of ethyl 3-cyano-1-(4-((4-methyl-1H-pyrazol-1-yl)methyl)benzyl)-1H-pyrazole-4-carboxylate (100 mg, 0.286 mmol) in THF (0.3 mL) and MeOH (0.3 mL) was treated with a solution of lithium hydroxide (10.28 mg, 0.429 mmol) in water (0.3 mL). The mixture was allowed to stir at ambient temperature for 18 hrs. Solvents were removed under vacuum and the residue partitioned between EtOAc (1 mL) and water (1 mL). The organic layer was removed and the aqueous layer adjusted to pH 4 with 1M HCl, forming a precipitate. This was briefly sonicated then filtered, washing with copious water. On drying under vacuum, 3-cyano-1-(4-((4-methyl-1H-pyrazol-1-yl)methyl)benzyl)-1H-pyrazole-4-carboxylic acid (70 mg, 0.196 mmol, 68.5% yield) was recovered as a white solid.

[M+H]$^+$=322

C. 3-Cyano-1-[4-(4-methyl-pyrazol-1-ylmethyl)-benzyl]-1H-pyrazole-4-carboxylic acid (1-amino-isoquinolin-6-ylmethyl)-amide hydrochloride A vial was charged with 3-cyano-1-(4-((4-methyl-1H-pyrazol-1-yl)methyl)benzyl)-1H-pyrazole-4-carboxylic acid (232 mg, 0.722 mmol), 6-(aminomethyl)isoquinolin-1-amine dihydrochloride (195 mg, 0.794 mmol), HATU (302 mg, 0.794 mmol), anhydrous DCM (4.5 mL) and anhydrous DMF (1.5 mL). N,N-Disopropylethylamine (503 μl, 2.89 mmol) was added and the mixture allowed to stir at ambient temperature. A precipitate formed. Solvents were removed under vacuum, slurried in methanol and filtered to give 293 mg of solid. This was purified by strong cation exchange chromatography (8 g), loading in a large quantity of MeOH/DCM (3:1, 150 mL), washing with MeOH, eluting with 1% NH$_3$/MeOH to afford 243 mg of material. This was purified by chromatography (silica) eluting with a gradient of 0 to 10% MeOH (1% NH$_3$/DCM) to afford 3-cyano-1-[4-(4-methyl-pyrazol-1-ylmethyl)-benzyl]-1H-pyrazole-4-carboxylic acid (1-amino-isoquinolin-6-ylmethyl)-amide hydrochloride (193 mg, 56% yield) as a white powder.

A sample of the product (60 mg) was dissolved in DCM (1 mL) and MeOH (0.5 mL) then treated with 4M HCl in dioxane (~100 µL), forming a precipitate. This was allowed to stand for 1 minute, then concentrated under vacuum to afford 63 mg of the mono-HCl salt

[M+H]+=477

$^1$H NMR: (d6-DMSO), δ: 1.98 (3H, s), 4.60 (2H, d, J=5.8 Hz), 5.24 (2H, s), 5.47 (2H, s), 7.17-7.28 (4H, m), 7.32 (2H, d, J=8.1 Hz), 7.55 (1H, s), 7.63-7.74 (2H, m), 7.82 (1H, s), 8.56 (1H, d, J=8.6 Hz), 8.61 (1H, s), 9.12 (2H, brs), 9.23 (1H, t, J=5.9 Hz), 13.29 (1H, s).

Example 17

4-[(1-Amino-isoquinolin-6-ylmethyl)-carbamoyl]-1-[4-(4-methyl-pyrazol-1-ylmethyl)-benzyl]-1H-pyrazole-3-carboxylic acid

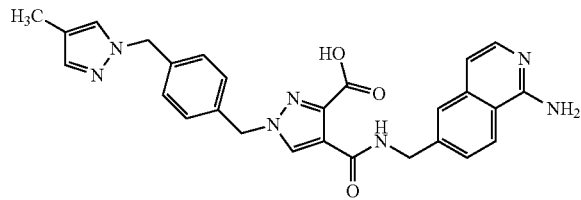 [SMILES: Cc1cnn(Cc2ccc(Cn3cc(C(=O)NCc4ccc5c(N)nccc5c4)c(C(=O)O)n3)cc2)c1]

A. 4-[(1-Amino-isoquinolin-6-ylmethyl)-carbamoyl]-1-[4-(4-methyl-pyrazol-1-ylmethyl)-benzyl]-1H-pyrazole-3-carboxylic acid hydrochloride A stirred suspension of 3-cyano-1-[4-(4-methyl-pyrazol-1-ylmethyl)-benzyl]-1H-pyrazole-4-carboxylic acid (1-amino-isoquinolin-6-ylmethyl)-amide (25 mg, 0.052 mmol) in MeOH (0.25 mL) was treated with a solution of lithium hydroxide (12.56 mg, 0.525 mmol) in water (0.25 mL). The mixture was allowed to stir at 60° C. (DrySyn bath temperature) overnight. The reaction was allowed to cool, then adjusted to pH 3 with 1M HCl. The precipitate was filtered, washing with water and dried under vacuum to afford a white powder. The mixture was taken up in DCM (0.5 mL) and MeOH (0.5 mL) and treated with 4M HCl in dioxane (29.5 µL, 0.118 mmol). The mixture was allowed to stand for 1 minute, then concentrated under vacuum to afford 4-[(1-amino-isoquinolin-6-ylmethyl)-carbamoyl]-1-[4-(4-methyl-pyrazol-1-ylmethyl)-benzyl]-1H-pyrazole-3-carboxylic acid hydrochloride (20 mg, 0.036 mmol, 68.1% yield) as a white powder.

[M+H]+=496

$^1$H NMR: (d6-DMSO), δ: 1.98 (3H, s), 4.69 (2H, d, J=5.8 Hz), 5.23 (2H, s), 5.43 (2H, s), 7.18-7.26 (4H, m), 7.31 (2H, d, J=8.1 Hz), 7.54 (1H, s), 7.63-7.77 (2H, m), 7.85 (1H, s), 8.57 (1H, d, J=8.6 Hz), 8.64 (1H, s), 9.13 (2H, brs), 10.04 (1H, t, J=5.8 Hz), 13.31 (1H, s), 14.85 (1H, brs).

Example 18

4-Methyl-2-[4-(4-methyl-pyrazol-1-ylmethyl)-benzyl]-thiazole-5-carboxylic acid (1-amino-isoquinolin-6-ylmethyl)-amide

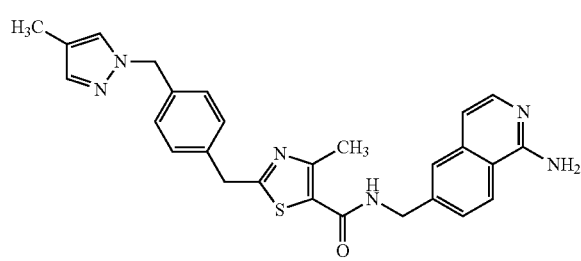 [SMILES: Cc1cnn(Cc2ccc(Cc3nc(C)c(C(=O)NCc4ccc5c(N)nccc5c4)s3)cc2)c1]

A. 2-(4-Bromo-benzyl)-4-methyl-thiazole-5-carboxylic acid ethyl ester

A solution of 2-(4-bromophenyl)ethanethioamide (1.98 g, 8.60 mmol) and ethyl 2-chloro-3-oxobutanoate (1.428 mL, 10.32 mmol) in pyridine (30 mL) and ethanol (30 mL) was stirred at 90° C. for 18 hrs. Then the reaction mixture was cooled to rt and concentrated under reduced pressure. The residue was diluted with ethyl acetate (100 mL), and 2N hydrochloric acid (100 mL) was added. The organic layer was separated, washed with saturated brine (50 mL), dried (Na$_2$SO$_4$), filtered and evaporated under reduced pressure. The crude was purified by chromatography (40 g column, EtOAc in Hex 0-50% yield) to afford 2-(4-bromo-benzyl)-4-methyl-thiazole-5-carboxylic acid ethyl ester (1.33 g, 5.00 mmol, 52.1% yield) as a white crystalline solid.

[M+H]+=340, 342

B. Potassium trifluoro(N-methylfomepizole)borate

Potassium hexamethyldisilazide (2.992 g, 15.00 mmol) was added dropwise to a stirred mixture of 4-methyl-1H-pyrazole (1.067 g, 13.00 mmol) and potassium bromomethyltrifluoroborate (2.008 g, 10 mmol) in dioxane (10 mL). The resulting mixture stirred at 85° C. overnight then at rt over the weekend. The reaction mixture was quenched with water (2 mL) and dried under reduced pressure (water bath at 50° C.). The crude solid was dissolved in a solution of hot HPLC grade acetone then filtered to remove KCl. The filtrate was concentrated under reduced pressure, dissolved in acetone (14 mL) and precipitated by addition of Et$_2$O (30 mL) to afford the desired product (660 mg, 2.91 mmol, 29.1% yield) as a white solid.

C. 4-Methyl-2-[4-(4-methyl-pyrazol-1-ylmethyl)-benzyl]-thiazole-5-carboxylic acid ethyl ester A mixture of potassium trifluoro(N-methylfomepizole) borate (386 mg, 1.911 mmol) and 2-(4-bromo-benzyl)-4-methyl-thiazole-5-carboxylic acid ethyl ester (591 mg, 1.737 mmol), in dioxane (4 mL) and water (1 mL) was stirred and heated at reflux for 1 hour. Sodium 2'-(dicyclohexylphosphino)-2,6-dimethoxy-[1,1'-biphenyl]-3-sulfonate (89 mg, 0.174 mmol), [PdCl(allyl)]$_2$ (31.8 mg, 0.087 mmol) and caesium carbonate (1698 mg, 5.21 mmol) in dioxane (8 mL) and water (2 mL) was degassed with argon for 15 min. Then, the mixture was heated and stirred at 100° C. overnight. The reaction mixture was diluted, absorbed on silica and purified by chromatography (12 g column, 0-50% EtOAc in isohexanes) to afford 4-methyl-2-[4-(4-methyl-pyrazol-1-ylmethyl)-benzyl]-thiazole-5-carboxylic acid ethyl ester (278 mg, 0.547 mmol, 31.5% yield) as a yellow thick oil.

[M+H]$^+$=356

D. 4-Methyl-2-[4-(4-methyl-pyrazol-1-yl methyl)-benzyl]-thiazole-5-carboxylic acid To a stirred mixture of 4-methyl-2-[4-(4-methyl-pyrazol-1-ylmethyl)-benzyl]-thiazole-5-carboxylic acid ethyl ester (278 mg, 0.782 mmol) in THF (1 mL) and water (0.5 mL) at rt was added sodium hydroxide (130 mg, 3.25 mmol). The resulting solution was stirred at rt overnight and evaporated under reduced pressure. The residue was redissolved in 2M NaOH (5 mL) and extracted with EtOAc (3×5 mL). Then, the aqueous was acidified to pH~3 and extracted with EtOAc (3×5 mL). Combined organics were dried (MgSO$_4$), filtered and evaporated under reduced pressure to give 4-methyl-2-[4-(4-methyl-pyrazol-1-yl methyl)-benzyl]-thiazole-5-carboxylic acid (232 mg, 0.602 mmol, 77% yield) as a pale yellow solid.

[M+H]$^+$=328

E. 4-Methyl-2-[4-(4-methyl-pyrazol-1-ylmethyl)-benzyl]-thiazole-5-carboxylic acid (1-amino-isoquinolin-6-ylmethyl)-amide hydrochloride Procedure as for Example 13 method C
[M+H]$^+$=483
$^1$H NMR: (d6-DMSO), δ: 2.00 (3H, s); 2.55 (3H, s); 4.28 (2H, s); 4.56 (2H, d, J=5.8 Hz); 5.23 (2H, s); 7.15-7.36 (6H, m); 7.56 (1H, t, J=0.9 Hz); 7.62-7.71 (2H, m); 7.78 (1H, d, J=1.6 Hz); 8.52 (1H, d, J=8.7 Hz); 8.80 (1H, t, J=5.9 Hz); 9.00 (2H, s); 13.04 (1H, s)

Example 19

1-[4-(4-Methyl-pyrazol-1-ylmethyl)-benzyl]-3-oxo-2,3-dihydro-1H-pyrazole-4-carboxylic acid (1-amino-isoquinolin-6-ylmethyl)-amide

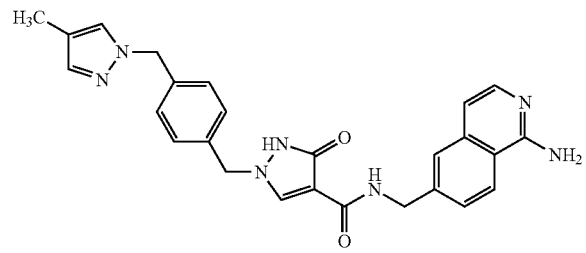 [SMILES: Cc1cnn(Cc2ccc(Cn3cc(C(=O)NCc4ccc5c(N)nccc5c4)c(=O)[nH]3)cc2)c1]

A. Ethyl 1-[4-(4-methyl-pyrazol-1-ylmethyl)-benzyl]-3-oxo-2,3-dihydro-1H-pyrazole-4-carboxylate To a solution of sodium ethanolate (1418 mg, 20.83 mmol) and diethyl 2-(ethoxymethylene)malonate (842 µl, 4.17 mmol) in EtOH (10 mL) was added dropwise a solution of 1-(4-(hydrazinylmethyl)benzyl)-4-methyl-1H-pyrazole, 2HCl (1446 mg, 5 mmol) in EtOH (20 mL) with cooling in an ice-water bath. The resulting mixture was stirred allowed to warm to rt overnight. The reaction mixture was concentrated under vacuum, then partitioned between DCM (50 mL) and water (50 mL, adjusted to pH 5 with 1N HCl). The aqueous layer was extracted with DCM (2×50 mL) and the combined organics washed with brine (50 mL), dried (Na$_2$SO$_4$), filtered and concentrated to a yellow oil. This was purified by chromatography (silica) eluting with a gradient of 0 to 40% MeCN/DCM to afford 210 mg of ethyl 1-[4-(4-methyl-pyrazol-1-ylmethyl)-benzyl]-3-oxo-2,3-dihydro-1H-pyrazole-4-carboxylate.

[M+H]$^+$=341

B. 1-[4-(4-Methyl-pyrazol-1-ylmethyl)-benzyl]-3-oxo-2,3-dihydro-1H-pyrazole-4-carboxylic acid A solution of ethyl 1-[4-(4-methyl-pyrazol-1-ylmethyl)-benzyl]-3-oxo-2,3-dihydro-1H-pyrazole-4-carboxylate (200 mg, 0.588 mmol) in a mixture of THF (2 mL) and MeOH (0.5 mL) was treated with lithium hydroxide (70.4 mg, 2.94 mmol) and water (0.75 mL). The mixture was allowed to stir at ambient temperature for 1 hour. Further water (0.5 mL) was added to clarify, and the mixture heated at 50° C. overnight. Organics were removed under vacuum and the aqueous transferred to a separating funnel with water (7 mL). The aqueous (at pH 10) was extracted with EtOAc (10 mL). The aqueous layer was collected and adjusted to pH 4 with 1M HCl, forming a precipitate. This was allowed to stand for 5 min, then sonicated to a fine powder before being collected by filtration, washing with a small quantity of water. On drying under vacuum in the presence of CaCl$_2$, 1-[4-(4-methyl-pyrazol-1-ylmethyl)-benzyl]-3-oxo-2,3-dihydro-1H-pyrazole-4-carboxylic acid (147 mg, 0.466 mmol, 79% yield) was isolated as an off-white powder.

[M+H]$^+$=313

C. 1-[4-(4-Methyl-pyrazol-1-ylmethyl)-benzyl]-3-oxo-2,3-dihydro-1H-pyrazole-4-carboxylic acid (1-amino-isoquinolin-6-ylmethyl)-amide A scintillation vial was charged with 1-(4-((4-methyl-1H-pyrazol-1-yl)methyl)benzyl)-3-oxo-2,3-dihydro-1H-pyrazole-4-carboxylic acid (75 mg, 0.240 mmol), 6-(aminomethyl)isoquinolin-1-amine dihydrochloride (65.0 mg, 0.264 mmol), HATU (100 mg, 0.264 mmol) and anhydrous DCM (2 mL) and anhydrous DMF (0.3 mL). N,N-Diisopropylethylamine (167 µl, 0.961 mmol) was added and the mixture allowed to stir at ambient temperature for 2 hrs. Further HATU (30 mg), N,N-diisopropylethylamine (80 µL) and amine (20 mg) were added, along with DMF (1 mL). The mixture was heated at 40° C. for 2.5 hrs. The reaction was partitioned between EtOAc (25 mL) and 2N NaOH (15 mL). The aqueous layer was extracted with further EtOAc (2×25 mL) and the combined organics dried (MgSO$_4$), filtered and concentrated. HPLC of the aqueous and isolated organics indicated that all product was in the aqueous layer. This was adjusted to pH 7 with conc. HCl (forming some relatively insoluble material) and extracted with EtOAc (containing trace MeOH, 2×30 mL) and DCM (containing trace MeOH, 30 mL). The combined organics were dried (Na$_2$SO$_4$), filtered and concentrated. The residue was triturated with DCM and then MeOH to afford 15 mg of a yellow solid. Chromatography (silica) eluting with THF afforded 1-[4-(4-methyl-pyrazol-1-ylmethyl)-benzyl]-3-oxo-2,3-dihydro-1H-pyrazole-4-carboxylic acid (1-amino-isoquinolin-6-ylmethyl)-amide (9 mg, 0.012 mmol, 4.81% yield, 70% purity) as a white powder.

[M+H]⁺=468

NMR (d6-DMSO) δ: 1.98 (3H, s), 4.55 (2H, d, J=6.0 Hz), 5.09 (2H, s), 5.21 (2H, s), 6.82 (2H, br. s), 6.87 (1H, d, J=6.2 Hz), 7.16-7.26 (5H, m), 7.38 (1H, dd, J=8.6, 1.8 Hz), 7.52 (2H, m), 7.74 (1H, d, J=5.8 Hz), 7.93 (1H, t, J=6.1 Hz), 8.04 (1H, s), 8.14 (1H, d, J=8.6 Hz), 11.10 (1H, br. s).

Example 20

3-(3,5-Dimethyl-isoxazol-4-yl)-1-[4-(4-methyl-pyrazol-1-ylmethyl)-benzyl]-1H-pyrazole-4-carboxylic acid (1-amino-isoquinolin-6-ylmethyl)-amide

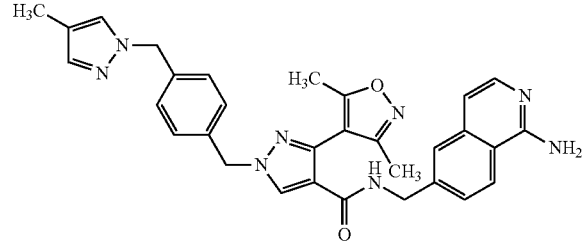 [SMILES: Cc1cnn(Cc2ccc(Cn3cc(C(=O)NCc4ccc5c(N)nccc5c4)c(-c4c(C)noc4C)n3)cc2)c1]

A: Ethyl 3-bromo-1H-pyrazole-4-carboxylate

To a solution of tert-butyl nitrite (3.04 mL, 25.6 mmol) in anhydrous MeCN (80 mL) was added copper(II) bromide (5.71 g, 25.6 mmol). The mixture was stirred at ambient temperature for 1 hour under $N_2$, then ethyl 3-amino-1H-pyrazole-4-carboxylate (3.39 g, 21.85 mmol) added in portions over 15 min. The mixture was stirred at ambient temperature for 30 min, then heated at 70° C. for 2 hrs. The reaction was allowed to cool and the acetonitrile removed under vacuum. The residue was dissolved in EtOAc (250 mL) and washed with brine (3×100 mL), dried (MgSO₄), filtered and concentrated to a dark green solid (5.64 g, 18.02 mmol, 82% yield, 70% purity). The product was used directly in the next step without purification.

[M+H]⁺=219/221

B: 3-Bromo-1-[4-(4-methyl-pyrazol-1-yl methyl)-benzyl]-1H-pyrazole-4-carboxylic acid ethyl ester To a stirred suspension of ethyl 3-bromo-1H-pyrazole-4-carboxylate (500 mg, 2.283 mmol) and 1-(4-(chloromethyl)benzyl)-4-methyl-1H-pyrazole (504 mg, 2.283 mmol) in DMF (2.5 mL) was added potassium carbonate (631 mg, 4.57 mmol) and the mixture stirred at ambient temperature for 1.5 hrs. Heating was increased to 50° C. for 24 hrs then the reaction was diluted with EtOAc (50 mL) and water (30 mL) containing brine (30 mL). The aqueous layer was extracted with further EtOAc (2×40 mL) and the combined organics dried (MgSO₄), filtered and concentrated. The crude material was purified by chromatography (silica) eluting with a gradient of 0 to 45% EtOAc/Iso-Hexanes holding at 40% to elute the two regioisomers.

5-Bromo-1-(4-((4-methyl-1H-pyrazol-1-yl)methyl)benzyl)-1H-pyrazole-4-carboxylic acid ethyl ester (54 mg, 0.100 mmol, 4.40% yield) was isolated as a clear gum which crystallised on standing, 2D nOesy showed no interaction between the benzylic protons and the pyrazole core ring proton (at 8.03 ppm).

[M+H]⁺=403/405

The desired isomer 3-bromo-1-(4-((4-methyl-1H-pyrazol-1-yl)methyl)benzyl)-1H-pyrazole-4-carboxylic acid ethyl ester (217 mg, 0.527 mmol, 23% yield) was isolated as a clear gum which crystallized on standing. 2D nOesy showed an interaction between one of the pairs of benzylic protons and the pyrazole core ring proton (at 8.52 ppm) confirming the desired isomer.

[M+H]⁺=403/405

C: 3-(3,5-Dimethyl-isoxazol-4-yl)-1-[4-(4-methyl-pyrazol-1-ylmethyl)-benzyl]-1H-pyrazole-4-carboxylic acid ethyl ester A mixture of 3-bromo-1-[4-(4-methyl-pyrazol-1-yl methyl)-benzyl]-1H-pyrazole-4-carboxylic acid ethyl ester (85 mg, 0.211 mmol), 3,5-dimethyl-4-(4,4,5,5-tetramethyl-1,3,2-dioxaborolan-2-yl)isoxazole (58.8 mg, 0.263 mmol), potassium carbonate (65.5 mg, 0.474 mmol) and tetrakis(triphenylphosphine)palladium(0) (24.36 mg, 0.021 mmol) were combined in a microwave vial and dioxane (0.6 mL) and water (0.2 mL) were added. The mixture was degassed with $N_2$ for 5 min, then heated at 100° C. for 5.5 hrs, then at ambient temperature overnight. The reaction mixture was partitioned between EtOAc (40 mL) and water (30 mL). The aqueous layer was extracted with further EtOAc (2×15 mL) and the combined organics washed with brine (20 mL), dried (MgSO₄), filtered and concentrated. The crude residue was purified by chromatography (silica) eluting with a gradient of 0 to 60% EtOAc/Iso-Hexanes to afford 3-(3,5-dimethyl-isoxazol-4-yl)-1-(4-((4-methyl-1H-pyrazol-1-yl)methyl)benzyl)-1H-pyrazole-4-carboxylic acid ethyl ester (37 mg, 0.086 mmol, 41.0% yield) as a white powder.

[M+H]⁺=420

D: 3-(3,5-Dimethyl-isoxazol-4-yl)-1-[4-(4-methyl-pyrazol-1-ylmethyl)-benzyl]-1H-pyrazole-4-carboxylic acid A stirred solution of 3-(3,5-dimethyl-isoxazol-4-yl)-1-[4-(4-methyl-pyrazol-1-ylmethyl)-benzyl]-1H-pyrazole-4-carboxylic acid ethyl ester (32.3 mg, 0.077 mmol) in THF (0.25 mL) and MeOH (0.25 mL) was treated with a solution of lithium hydroxide (4.61 mg, 0.193 mmol) in water (0.25 mL). A precipitate quickly formed. Further MeOH (0.5 mL) was added and the mixture was allowed to stir at ambient temperature for 3 hrs. LCMS indicated only 15% hydrolysis. Further THF was added until solution formed (total volume~2.5 mL). Further LiOH (5 mg) was added and the mixture heated at 50° C. for 3 hrs, then at ambient temperature overnight. Solvents were removed under vacuum and the residue partitioned between EtOAc (5 mL) and water (4 mL). The aqueous layer was adjusted to ~pH 4 with 1M HCl, forming a precipitate. This was filtered, washing with water, then dried under vacuum to afford 3-(3,5-dimethylisoxazol-4-yl)-1-(4-((4-methyl-1H-pyrazol-1-yl)methyl)benzyl)-1H-pyrazole-4-carboxylic acid (21 mg, 0.053 mmol, 69.0% yield) as a white solid.

[M+H]⁺=392

E: 3-(3,5-Dimethyl-isoxazol-4-yl)-1-[4-(4-methyl-pyrazol-1-ylmethyl)-benzyl]-1H-pyrazole-4-carboxylic acid (1-amino-isoquinolin-6-ylmethyl)-amide hydrochloride A scintillation vial was charged with 3-(3,5-dimethylisoxazol-4-yl)-1-(4-((4-methyl-1H-pyrazol-1-yl)methyl)benzyl)-1H-pyrazole-4-carboxylic acid (18.7 mg, 0.048 mmol), 6-(aminomethyl)isoquinolin-1-amine dihydrochloride (18.81 mg, 0.076 mmol), HATU (19.98 mg, 0.053 mmol), anhydrous DCM (0.5 mL) and anhydrous DMF (0.15 mL). N,N-Disopropylethylamine (33.3 µl, 0.191 mmol) was added and the mixture allowed to stir at ambient temperature overnight. Solvents were removed under vacuum. The residue was redissolved in MeOH (2 mL) and purified by strong cation exchange chromatography (1.5 g), washing with MeOH, eluting with 1% $NH_3$/MeOH. The resultant material was purified by chromatography (silica) eluting with a gradient of 0 to 10% MeOH (0.3% $NH_3$)/DCM to afford the free base as a white powder. The free base was dissolved in DCM (0.75 mL), then treated with 4M HCl in dioxane (26.3 µl, 0.105 mmol). This was allowed to stand for 10 min before being concentrated. On drying, 3-(3,5-dimethyl-isoxazol-4-yl)-1-[4-(4-methyl-pyrazol-1-ylmethyl)-benzyl]-1H-pyrazole-4-carboxylic acid (1-amino-isoquinolin-6-ylmethyl)-amide (19 mg, 0.030 mmol, 63.4% yield) was isolated as a pale yellow powder.

$[M+H]^+=547$

NMR (d6-DMSO): 1.98 (3H, s), 2.04 (3H, s), 2.21 (3H, s), 4.53 (2H, d, J=5.9 Hz), 5.23 (2H, s), 5.38 (2H, s), 7.15-7.26 (4H, m), 7.30 (2H, d, J=8.2 Hz), 7.54 (1H, s), 7.63-7.71 (2H, m), 7.76 (1H, s), 8.44 (1H, s), 8.53 (1H, d, J=8.6 Hz), 8.80 (1H, t, J=6.0 Hz), 9.09 (2H, brs), 13.26 (1H, brs).

Example 21

1-[4-(4-Methyl-pyrazol-1-ylmethyl)-benzyl]-3-morpholin-4-yl-1H-pyrazole-4-carboxylic acid (1-amino-isoquinolin-6-ylmethyl)-amide

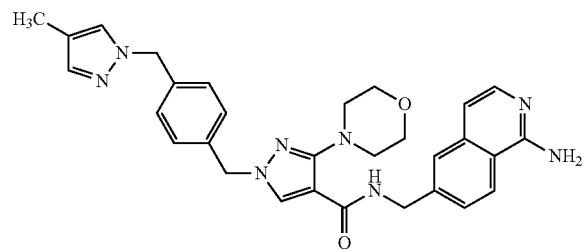 [SMILES: Cc1cnn(Cc2ccc(Cn3cc(C(=O)NCc4ccc5c(N)nccc5c4)c(N4CCOCC4)n3)cc2)c1]

A: 1-[4-(4-Methyl-pyrazol-1-ylmethyl)-benzyl]-3-morpholin-4-yl-1H-pyrazole-4-carboxylic acid ethyl ester A microwave vial was charged with 3-bromo-1-[4-(4-methyl-pyrazol-1-yl methyl)-benzyl]-1H-pyrazole-4-carboxylic acid ethyl ester (300 mg, 0.744 mmol), RuPhos Precatalyst, chloro(2-dicyclohexylphosphino-2',6'-diisopropoxy-1,1'-biphenyl)[2-(2'-amino-1,1'-biphenyl)]palladium(II) (34.7 mg, 0.045 mmol), dicyclohexyl(2',6'-diisopropoxy-[1,1'-biphenyl]-2-yl)phosphine—RuPhos (20.83 mg, 0.045 mmol), morpholine (386 µl, 4.46 mmol), caesium carbonate (630 mg, 1.934 mmol) and anhydrous THF (5 mL). The mixture was briefly degassed with $N_2$, and stirred at ambient temperature for 10 min, before heating to 85° C. (DrySyn bath temperature) overnight. LCMS indicated a ~1:1:1 mixture of starting material:debromination:product. Further RuPhos Precatalyst, chloro(2-dicyclohexylphosphino-2',6'-diisopropoxy-1,1'-biphenyl)[2-(2'-amino-1,1'-biphenyl)]palladium(II) (34.7 mg, 0.045 mmol), dicyclohexyl(2',6'-diisopropoxy-[1,1'-biphenyl]-2-yl)phosphine—RuPhos (20.83 mg, 0.045 mmol) and morpholine (150 µL) were added and the mixture stirred at 85° C. (DrySyn bath temperature) overnight. Solvents were removed under vacuum and the residue partitioned between EtOAc (10 mL) and water (10 mL). The aqueous was extracted with EtOAc (10 mL) and the combined organics washed with brine (5 mL), dried ($MgSO_4$), filtered and concentrated. The crude product was purified by chromatography (silica) eluting with a gradient of 0 to 80% EtOAc/Iso-Hexanes to afford 1-[4-(4-methyl-pyrazol-1-ylmethyl)-benzyl]-3-morpholin-4-yl-1H-pyrazole-4-carboxylic acid ethyl ester (128 mg, 0.309 mmol, 41.6% yield) as a clear gum.

$[M+H]^+=410$

B: 1-[4-(4-Methyl-pyrazol-1-ylmethyl)-benzyl]-3-morpholin-4-yl-1H-pyrazole-4-carboxylic acid A stirred solution of ethyl 1-[4-(4-Methyl-pyrazol-1-ylmethyl)-benzyl]-3-morpholin-4-yl-1H-pyrazole-4-carboxylic acid ethyl ester (125 mg, 0.305 mmol) in THF (1 mL) and MeOH (1 mL) was treated with a solution of lithium hydroxide (18.28 mg, 0.763 mmol) in water (1 mL) and the mixture heated at 40° C. over a weekend. Any remaining organic solvents were removed under vacuum and the residue partitioned between EtOAc (10 mL) and water (7 mL). The aqueous layer was adjusted to ~pH 4 with 1M HCl. The aqueous layer was extracted with EtOAc (3×10 mL) and the combined organics dried ($MgSO_4$), filtered and concentrated to afford 1-(4-((4-methyl-1H-pyrazol-1-yl)methyl)benzyl)-3-morpholino-1H-pyrazole-4-carboxylic acid (109 mg, 0.271 mmol, 89% yield) as a gummy yellow solid.

$[M+H]^+=382$

C: 1-[4-(4-Methyl-pyrazol-1-ylmethyl)-benzyl]-3-morpholin-4-yl-1H-pyrazole-4-carboxylic acid (1-amino-isoquinolin-6-ylmethyl)-amide A scintillation vial was charged with 1-(4-((4-methyl-1H-pyrazol-1-yl)methyl)benzyl)-3-morpholino-1H-pyrazole-4-carboxylic acid (106 mg, 0.278 mmol), 6-(aminomethyl)isoquinolin-1-amine dihydrochloride (82 mg, 0.333 mmol), HATU (116 mg, 0.306 mmol), anhydrous DCM (1 mL) and anhydrous DMF (0.3 mL). N,N-Disopropylethylamine (194 µl, 1.112 mmol) was added and the mixture allowed to stir at ambient temperature overnight. Solvents were removed under vacuum. The residue was redissolved in MeOH (2 mL) and purified by strong cation exchange chromatography (2.5 g), washing with MeOH, eluting with 1% $NH_3$/MeOH. The resultant material was purified by chromatography (silica) eluting with a gradient of 0 to 10% MeOH (0.3% $NH_3$)/DCM to afford the free base as a white foam. The free base was dissolved in DCM (0.75 mL) and MeOH (0.15 mL), then treated with 4M HCl in dioxane (153 µl, 0.611 mmol). This was allowed to stand for 10 min before being concentrated. On drying, 1-[4-(4-methyl-pyrazol-1-ylmethyl)-benzyl]-3-morpholin-4-yl-1H-pyrazole-4-carboxylic acid (1-amino-isoquinolin-6-ylmethyl)-amide (125 mg, 0.212 mmol, 76% yield) was isolated as a mono HCl salt, as a pale yellow powder.

$[M+H]^+=537$

NMR (d6-DMSO): 1.98 (3H, s), 3.03-3.10 (4H, m), 3.58-3.64 (4H, m), 4.58 (2H, d, J=5.8 Hz), 5.18 (2H, s), 5.23 (2H, s), 7.16-7.28 (6H, m), 7.55 (1H, s), 7.65-7.72 (2H, m), 7.79 (1H, s), 8.20 (1H, s), 8.48-8.60 (2H, m), 9.16 (2H, br. s), 13.39 (1H, br. s).

Example 22

1-[4-(4-Methyl-pyrazol-1-ylmethyl)-benzyl]-1H-pyrazole-4-carboxylic acid (6-methyl-1H-pyrrolo[2,3-b]pyridin-5-ylmethyl)-amide

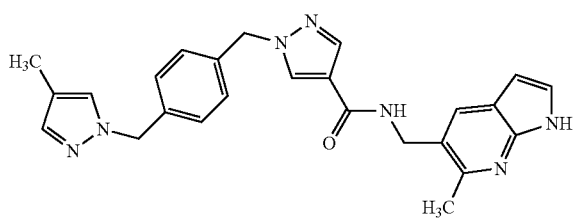 [SMILES: Cc1cnn(Cc2ccc(Cn3cc(C(=O)NCc4cc5cc[nH]c5nc4C)cn3)cc2)c1]

A. 6-Amino-5-iodo-2-methylnicotinonitrile

6-Amino-2-methylnicotinonitrile (3.0 g, 22.53 mmol) and 1-iodopyrrolidine-2,5-dione (8.62 g, 38.3 mmol) were dissolved in dry DMF (35 mL). The brown solution was heated to 80° C. for 24 hrs after which time the reaction mixture was diluted with water (50 mL). Extracted with EtOAc (4×75 mL). Combined organic layers were washed with water (5×30 mL), brine (50 mL) then dried (Na$_2$SO$_4$), filtered and concentrated in vacuo. The crude product was purified by chromatography on RediSep (80 g column, 0-30% EtOAc in iso-hexanes) to give a brown coloured solid identified as 6-amino-5-iodo-2-methylnicotinonitrile (3.0 g, 9.84 mmol, 43.7% yield)
[M+H]$^+$=260

B. 6-Amino-2-methyl-5-((trimethylsilyl)ethynyl)nicotinonitrile

To a dried flask under N$_2$ was added 6-amino-5-iodo-2-methylnicotinonitrile (4 g, 13.13 mmol), triethylamine (2.74 mL, 19.69 mmol), dry THF (30 mL) and dry DCM (10 mL) to give an orange solution. Degassed with N$_2$ for 5 min before bis(triphenylphosphine)palladium(II) chloride (0.276 g, 0.394 mmol) and copper(I) iodide (0.125 g, 0.656 mmol) were added to give a black coloured suspension. Next, ethynyltrimethylsilane (2.040 mL, 14.44 mmol) was added drop-wise over 5 min resulting in a red/brown coloured solution which was stirred at rt for 1 hour. The reaction mixture was partitioned with EtOAc (100 mL) and water (100 mL). The aqueous layer was extracted with EtOAc (2×50 mL) and the combined organic layers were washed with water (2×50 mL) and brine (50 mL) then dried (Na$_2$SO$_4$), filtered and concentrated in vacuo. The crude product was purified by chromatography on RediSep (80 g column, 0-25% EtOAc in iso-hexanes) to give a pale orange solid identified as 6-amino-2-methyl-5-((trimethylsilyl)ethynyl)nicotinonitrile (2.2 g, 9.40 mmol, 72% yield)
[M+H]$^+$=230

C. N-Acetyl-N-(5-cyano-6-methyl-3-((trimethylsilyl)ethynyl)pyridin-2-yl)acetamide To a flask under N$_2$ was added 6-amino-2-methyl-5-((trimethylsilyl)ethynyl)nicotinonitrile (2.2 g, 9.59 mmol) and pyridine (15 mL, 9.59 mmol). The mixture was cooled in an ice bath before acetyl chloride (1.569 mL, 22.06 mmol) was added drop-wise to give a light tan coloured suspension. Stirred for 10 min, allowed to warm to rt then heated at 40° C. for 1 hour. Dry THF (10 mL) was added and the reaction was stirred for a further 2 hrs. Dry DCM (10 mL) added and stirred at rt for 3 days. Heated to 60° C. for 2 hrs. Stirred at rt for a further 18 hrs. The volatiles were removed in vacuo and the residue was azeotroped with toluene (30 mL). LCMS showed mainly starting material and some evidence of mono and di acylation. Resuspended in DCM (20 mL) and treated with pyridine (1.940 mL, 23.98 mmol) then acetyl chloride (1.569 mL, 22.06 mmol). The resulting suspension was stirred at rt for 18 hrs. LCMS showed conversion to mono and bis acylation with evidence of starting material present in m/z trace. The reaction was heated to 40° C. for 1 hour. LCMS showed conversion to bis-acylated material (60% purity). Diluted with EtOAc (200 mL) and washed with 1N HCl (60 mL). Aqueous layer extracted with EtOAc (50 mL) and the combined organic layers were washed with saturated aqueous NaHCO$_3$ (30 mL), water (30 mL) and brine (30 mL) then dried (Na$_2$SO$_4$), filtered and concentrated in vacuo to a brown coloured residue (4.0 g). The crude product was purified by chromatography on RediSep (40 g column, 0-20% EtOAc in iso-hexanes). Material isolated (4.0 g) as a brown oil. Analysis by LCMS confirmed N-acetyl-N-(5-cyano-6-methyl-3-((trimethylsilyl)ethynyl)pyridin-2-yl)acetamide (60% purity by UV) along with 3 impurities (10-15% each). Material used in subsequent reaction without further purification/analysis.

D. 6-Methyl-1H-pyrrolo[2,3-b]pyridine-5-carbonitrile

To a flask under N$_2$ was added N-acetyl-N-(5-cyano-6-methyl-3-((trimethylsilyl)ethynyl)pyridin-2-yl)acetamide (4.3 g, 6.86 mmol), dry THF (20.0 mL) followed by tetra-butylammonium fluoride (1.0 M in THF) (10.29 mL, 10.29 mmol). The dark brown reaction mixture was heated to 70° C. before being diluted with EtOAc (100 mL), washed with water (50 mL) and brine (50 mL) then dried (Na$_2$SO$_4$), filtered and concentrated in vacuo. The crude product was purified by chromatography on RediSep (40 g column, 0-35% EtOAc in iso-hexanes) and two major peaks eluted. To a flask under N$_2$ was added N-(5-cyano-3-ethynyl-6-methylpyridin-2-yl)acetamide (1.03 g, 3.21 mmol), dry THF (2.0 mL) to give a pale yellow solution. Next, tetrabutylammonium fluoride (1.0 M in THF) (15 mL, 15.00 mmol) was added and heated to 72° C. for 1 h to give a dark orange solution. HPLC showed complete consumption of starting material. Allowed to cool to rt. Diluted with EtOAc (150 mL) and washed with water (100 mL). Aqueous layer extracted with EtOAc (2×50 mL) before the combined organic layers were washed with water (2×50 mL), brine (50 mL) and dried (Na$_2$SO$_4$), filtered and concentrated in vacuo to give an orange solid slurried in Et$_2$O:MeOH (9:1, 15 mL), collected by filtration and washed with Et$_2$O (15 mL). Dried by suction for 10 min then in vacuum oven for 1 h to give a tan solid identified as 6-methyl-1H-pyrrolo[2,3-b]pyridine-5-carbonitrile (0.69 g, 4.26 mmol, 74.7% yield).
[M+H]$^+$=158

E. tert-Butyl ((6-methyl-1H-pyrrolo[2,3-b]pyridin-5-yl)methyl)carbamate

To a flask under N$_2$ was added: 6-methyl-1H-pyrrolo[2,3-b]pyridine-5-carbonitrile (0.64 g, 4.07 mmol), di-tert-butyl dicarbonate (1.777 g, 8.14 mmol), nickel(II) chloride (0.053 g, 0.407 mmol) and MeOH (50 mL) to give a pale tan coloured suspension. Cooled in an ice bath before sodium borohydride (1.078 g, 28.5 mmol) was added portion-wise over 1 hrs. Allowed to warm to rt in ice bath for 18 hrs. Volatiles were removed in vacuo and the brown residue was partitioned between DCM (100 mL) and saturated NaHCO$_3$ (50 mL). Aqueous layer extracted with DCM (2×30 mL) before the combined organic layers were washed with brine (50 mL), dried (Na$_2$SO$_4$), filtered and concentrated in vacuo. Purified by column chromatography (RediSep 40 g, dry loaded, 0-100% EtOAc in iso-hexanes). Dried in vacuum oven (40° C.) overnight. Giving a white solid identified as tert-butyl ((6-methyl-1H-pyrrolo[2,3-b]pyridin-5-yl)methyl)carbamate (0.74 g, 2.78 mmol, 68.2% yield).

[M+H]$^+$=262

F. 6-Methyl-1H-pyrrolo[2,3-b]pyridin-5-yl)methanamine tert-Butyl ((6-methyl-1H-pyrrolo[2,3-b]pyridin-5-yl)methyl)carbamate (0.74 g, 2.83 mmol) was suspended in DCM (7.0 mL). TFA (5 mL, 64.9 mmol) was added and the resulting clear yellow solution was stirred at rt for 1 hr. Material isolated by capture and release using strong cation exchange chromatography, washing with MeOH (50 mL) and eluting with 1% NH$_3$ in MeOH (100 mL). Concentrated in vacuo and dried in vacuum oven (40° C. for 2 h) to give an off-white solid identified as 6-methyl-1H-pyrrolo[2,3-b]pyridin-5-yl)methanamine (0.47 g, 2.62 mmol, 93% yield).

[M+H]$^+$=162

G. Ethyl 1-(4-((4-methyl-1H-pyrazol-1-yl)methyl)benzyl)-1H-pyrazole-4-carboxylate A solution of (4-((4-methyl-1H-pyrazol-1-yl)methyl)phenyl)methanol (500 mg, 2.472 mmol), ethyl 1H-pyrazole-4-carboxylate (364 mg, 2.60 mmol) and triphenylphosphine (713 mg, 2.72 mmol) in anhydrous THF (8 mL) was treated dropwise with (E)-diisopropyl diazene-1,2-dicarboxylate (560 µL, 2.84 mmol). After 4 hrs at rt the reaction mixture was concentrated onto silica and purified by flash chromatography (silica) eluting with a gradient of 10 to 100% EtOAc/Iso-Hexanes (product eluted at ~70% EtOAc). Fractions were evaporated to give a white solid identified as ethyl 1-(4-((4-methyl-1H-pyrazol-1-yl)methyl)benzyl)-1H-pyrazole-4-carboxylate (610 mg, 1.862 mmol, 75% yield).

[M+H]$^+$=325

H. 1-(4-((4-methyl-1H-pyrazol-1-yl)methyl)benzyl)-1H-pyrazole-4-carboxylic acid A solution of ethyl 1-(4-((4-methyl-1H-pyrazol-1-yl)methyl)benzyl)-1H-pyrazole-4-carboxylate (610 mg, 1.881 mmol) in tetrahydrofuran (20 mL) and water (10 mL) was treated with lithium hydroxide (225 mg, 9.40 mmol) and the mixture heated at 50° C. with stirring overnight. Solvents were removed under vacuum and the residue suspended between EtOAc (50 mL) and water (50 mL). The aqueous phase was adjusted to pH 1 with 1M HCl and the organic layer collected. The aqueous was extracted with EtOAc (2×50 mL) and the combined organics washed with brine (50 mL), dried (MgSO$_4$), filtered and concentrated to give a white solid identified as 1-(4-((4-methyl-1H-pyrazol-1-yl)methyl)benzyl)-1H-pyrazole-4-carboxylic acid (518 mg, 1.713 mmol, 91% yield).

[M+H]$^+$=297.

I. 1-[4-(4-Methyl-pyrazol-1-ylmethyl)-benzyl]-1H-pyrazole-4-carboxylic acid (6-methyl-1H-pyrrolo[2,3-b]pyridin-5-ylmethyl)-amide A scintillation vial was charged with 1-(4-((4-methyl-1H-pyrazol-1-yl)methyl)benzyl)-1H-pyrazole-4-carboxylic acid (0.092 g, 0.310 mmol) and suspended in dry DCM (3 mL) to which was added (6-methyl-1H-pyrrolo[2,3-b]pyridin-5-yl)methanamine (0.050 g, 0.310 mmol), HATU (0.130 g, 0.341 mmol) and then N,N-disopropylethylamine (0.108 mL, 0.620 mmol), the suspension was left to stir at rt. The reaction mixture was evaporated and the resulting residue quenched with saturated solution of ammonium chloride (5 mL) and left to stir at rt overnight. The solid was filtered under reduced pressure and placed in the vacuum oven at 40° C. for 2 days. The solid was triturated with ethyl acetate (5 mL) doped with methanol (0.1 mL), sonicated and then filtered under reduced pressure to give a pale brown solid which was placed in the vacuum oven at 40° C. to give a white solid identified as 1-[4-(4-methyl-pyrazol-1-ylmethyl)-benzyl]-1H-pyrazole-4-carboxylic acid (6-methyl-1H-pyrrolo[2,3-b]pyridin-5-ylmethyl)-amide (62 mg, 0.14 mmol, 37% yield).

[M+H]$^+$=440

$^1$H NMR: (d6-DMSO), δ: 1.98 (3H, t, J=0.7 Hz), 2.51 (3H, s), 4.45 (2H, d, J=5.5 Hz), 5.20 (2H, s), 5.30 (2H, s), 6.34 (1H, dd, J=1.9, 3.4 Hz), 7.15-7.19 (2H, m), 7.20-7.25 (3H, m), 7.32 (1H, dd, J=2.4, 3.4 Hz), 7.51 (1H, t, J=0.9 Hz), 7.74 (1H, s), 7.90 (1H, d, J=0.7 Hz), 8.25 (1H, d, J=0.7 Hz), 8.41 (1H, t, J=5.5 Hz), 11.37 (1H, s).

Example 23

5-Amino-1-(4-pyrazol-1-ylmethyl-benzyl)-1H-pyrazole-4-carboxylic acid (1-amino-isoquinolin-6-ylmethyl)-amide

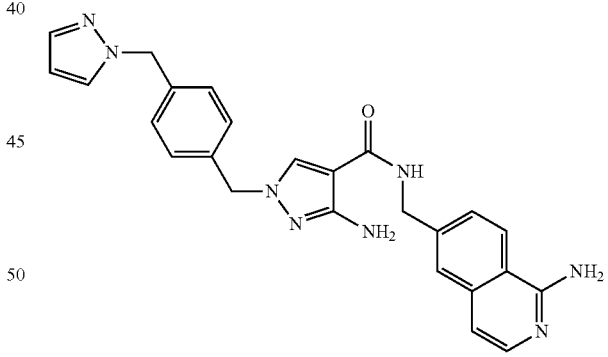

A. 1-(4-Hydroxymethyl-benzyl)-1H-pyrazole 4-(Chloromethyl)benzyl alcohol (650 mg, 4.15 mmol) and pyrazole (311 mg, 4.57 mmol) were taken up in MeCN (30 mL). K$_2$CO$_3$ (860.5 mg, 6.23 mmol) was added and the reaction was heated to 50° C. for 48 hrs. Volatiles were removed in vacuo. Ethyl acetate (60 mL) and water (20 mL) added. Organic layer filtered and evaporated under vacuum. Purified by flash chromatography (silica) eluting with 40% EtOAc in Pet. Ether to afford a colourless oil identified as 1-(4-hydroxymethyl-benzyl)-1H-pyrazole (480 mg, 61% yield).

B. 1-(4-Bromomethyl-benzyl)-1H-pyrazole 1-(Hydroxymethyl-benzyl)-1H-pyrazole (480 mg, 2.55 mmol) and triphenylphosphine (769 mg, 2.93 mmol) were taken up in DCM (15 mL). The resultant solution was cooled in an ice bath before carbon tetrabromide (930 mg, 2.81 mmol) was added portionwise. The mixture was stirred at RT for 18 hrs. The mixture was diluted with DCM, washed with water (2×50 mL) and brine (30 mL) and concentrated under vacuum. The crude material was purified via flash chromatography (silica) (20-40% EtOAC/Pet. Ether). The compound containing fractions were concentrated in vacuo to afford to an off white solid identified as 1-(4-bromomethyl-benzyl)-1H-pyrazole (410 mg, 64% yield).

C. 3-Amino-1-(4-pyrazol-1-ylmethyl-benzyl)-1H-pyrazole-4-carboxylic acid ethyl ester and 5-Amino-1-(4-pyrazol-1-ylmethyl-benzyl)-1H-pyrazole-4-carboxylic acid ethyl ester To 5-amino-1H-pyrazole-4-carboxylic acid ethyl ester (200 mg, 1.29 mmol) in acetonitrile (7 mL) was added potassium carbonate (356 mg, 2.58 mmol) and 1-(4-bromomethyl-benzyl)-1H-pyrazole (324 mg, 1.29 mmol) and the reaction stirred at rt for 18 hrs. The reaction mixture was concentrated and the residue purified by column chromatography (silica) eluting with 6:6:7 Acetonitrile:Ethyl acetate:Pet. Ether to afford 3-amino-1-(4-pyrazol-1-ylmethyl-benzyl)-1H-pyrazole-4-carboxylic acid ethyl ester (129 mg, 31% yield) and 5-amino-1-(4-pyrazol-1-ylmethyl-benzyl)-1H-pyrazole-4-carboxylic acid ethyl ester (119 mg, 28% yield).

D. 3-Amino-1-(4-pyrazol-1-ylmethyl-benzyl)-1H-pyrazole-4-carboxylic acid

To 3-amino-1-(4-pyrazol-1-ylmethyl-benzyl)-1H-pyrazole-4-carboxylic acid ethyl ester (119 mg, 0.37 mmol) in ethanol (20 mL) was added sodium hydroxide (102 mg, 2.56 mmol) and the reaction heated at reflux for 48 hrs. The reaction mixture was cooled and concentrated in vacuo. The crude residue was dissolved in water (2 mL) and the pH adjusted to pH~5 with 2M HCl (until reaction mixture turned opaque). EtOAc was added and solid went into organic layer but did not dissolve. Aqueous layer was removed and the organic layer filtered to afford an off white solid that was washed with diethyl ether to afford 3-amino-1-(4-pyrazol-1-ylmethyl-benzyl)-1H-pyrazole-4-carboxylic acid which was used in next step without further purification.

E. 3-Amino-1-(4-pyrazol-1-ylmethyl-benzyl)-1H-pyrazole-4-carboxylic acid (1-amino-isoquinolin-6-ylmethyl)-amide TFA salt To 3-amino-1-(4-pyrazol-1-ylmethyl-benzyl)-1H-pyrazole-4-carboxylic acid (49.1 mg, 0.17 mmol) in dichloromethane (15 mL) and DMF (2 mL) at 0° C. was added HOBt (26.8 mg, 0.20 mmol) and water soluble carbodiimide (44.3 mg, 0.23 mmol). After stirring for 15 min triethylamine (115 µL, 0.83 mmol) and 6-aminomethyl-isoquinolin-1-ylamine (28.6 mg, 0.17 mmol) was added and the reaction allowed to warm to rt and stirred for 18 hrs. The reaction mixture was partitioned between EtOAc (30 mL) and water (10 mL). The organic layer was washed with brine (30 mL). The organic layer was dried (MgSO$_4$), filtered and concentrated. Purification by prep HPLC afforded 3-amino-1-(4-pyrazol-1-ylmethyl-benzyl)-1H-pyrazole-4-carboxylic acid (1-amino-isoquinolin-6-ylmethyl)-amide TFA salt as an off white solid.

[M+H]$^+$=453

$^1$H NMR: (d6-DMSO), δ: 2.98 (1H, br s), 4.02 (2H, br s), 4.55 (2H, d, J=5.8 Hz), 5.07 (2H, s), 5.31 (2H, s), 6.26 (1H, t, J=2.0), 7.19-7.25 (5H, m), 7.44 (1H, d, 1.8 Hz), 7.64 (1H, d, J=7.0 Hz), 7.68 (1H, dd, J=8.7, 1.3 Hz), 7.79 (2H, dd, J=9.0, 2.0 Hz), 8.02 (1H, s), 8.49 (1H, d, J=8.6 Hz), 8.51 (1H, t, J=5.7 Hz), 8.93 (2H, br s), 12.84 (1H, br s).

Example 24

1-(6-Pyrrolidin-1-yl-pyridin-3-ylmethyl)-3-trifluoromethyl-1H-pyrazole-4-carboxylic acid (1-amino-isoquinolin-6-ylmethyl)-amide

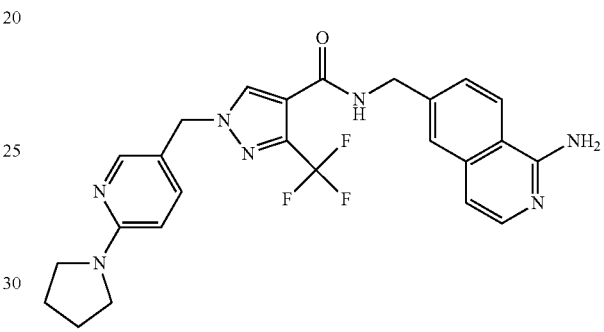

A. 5-Bromomethyl-2-fluoro-pyridine

2-Fuoro-5-methylpyridine (5.0 g, 45 mmol) was dissolved in 1,2-dichloroethane (120 mL). To this solution was added N-bromosuccinimide (9.61 g, 54 mmol) and azobisisobutyronitrile (AIBN) (739 mg, 4.5 mmol). The reaction was stirred at reflux. After 18 hrs the reaction mixture was diluted with chloroform (100 mL) and washed with water (1×50 mL) and brine (1×30 mL), dried (Na$_2$SO$_4$) and evaporated in vacuo. The residue was purified by flash chromatography (silica), eluent 95% Pet. Ether, 5% EtOAc, fractions combined and evaporated in vacuo to give a yellow oil identified as 5-bromomethyl-2-fluoro-pyridine (6.89 g, 36.25 mmol, 81% yield).

[M+H]$^+$=192

B. 1-(6-Fluoro-pyridin-3-ylmethyl)-3-trifluoromethyl-1H-pyrazole-4-carboxylic acid ethyl ester Ethyl 3-trifluoromethyl-1H-pyrazole-4-carboxylate (1.57 g, 7.53 mmol) was dissolved in DMF (20 mL), 5-bromomethyl-2-fluoro-pyridine (1.3 g, 6.84 mmol) and caesium carbonate (6.69 g, 20.53 mmol) were added and the reaction mixture was stirred at 50° C. After 18 hrs the reaction mixture was diluted with EtOAc (100 mL), this solution was washed with water (1×30 mL) and brine (1×30 mL), dried (Na$_2$SO$_4$) and evaporated in vacuo. The residue was purified by flash chromatography (silica), eluent 85% Pet. Ether, 15% EtOAc, fractions combined and evaporated in vacuo to give a white solid identified as 1-(6-fluoro-pyridin-3-ylmethyl)-3-trifluoromethyl-1H-pyrazole-4-carboxylic acid ethyl ester. (1.26 g, 3.97 mmol, 58% yield).

C. 1-(6-Fluoro-pyridin-3-ylmethyl)-3-trifluoromethyl-1H-pyrazole-4-carboxylic acid 1-(6-Fluoro-pyridin-3-ylmethyl)-3-trifluoromethyl-1H-pyrazole-4-carboxylic acid ethyl ester (1.26 g, 3.97 mmol) was dissolved in THF (50 mL) and water (5 mL) and lithium hydroxide (476 mg, 19.86 mmol) was added. The reaction mixture was stirred at 50° C. After 18 hrs the solvent was concentrated in vacuo and the residue taken up in EtOAc (50 mL), the aqueous layer was separated and acidified with 1M HCl to pH2 and extracted with CHCl$_3$ (3×50 mL). The combined extracts were washed with water (1×30 mL) and brine (1×30 mL), dried (Na$_2$SO$_4$) and evaporated in vacuo to give a colourless oil identified as 1-(6-fluoro-pyridin-3-ylmethyl)-3-trifluoromethyl-1H-pyrazole-4-carboxylic acid (980 mg, 3.39 mmol, 85% yield).
[M+H]$^+$=290

D. 1-(6-Pyrrolidin-1-yl-pyridin-3-ylmethyl)-3-trifluoromethyl-1H-pyrazole-4-carboxylic acid 1-(6-Fluoro-pyridin-3-ylmethyl)-3-trifluoromethyl-1H-pyrazole-4-carboxylic acid (300 mg, 1.04 mmol) was dissolved in dioxane (25 mL) and pyrrolidine (2 mL) and the reaction mixture was stirred at 80° C. After 18 hrs the reaction mixture was diluted with EtOAc (100 mL), this solution was washed with water (1×30 mL) and brine (1×30 mL), dried (Na$_2$SO$_4$) and evaporated in vacuo. The residue was purified by flash chromatography (silica), eluent 1% AcOH, 9% MeOH, 90% CHCl$_3$, fractions combined and evaporated in vacuo to give a white foamy solid identified as 1-(6-pyrrolidin-1-yl-pyridin-3-ylmethyl)-3-trifluoromethyl-1H-pyrazole-4-carboxylic acid. (267 mg, 0.785 mmol, 76% yield).
[M+H]$^+$=341

E. 1-(6-Pyrrolidin-1-yl-pyridin-3-ylmethyl)-3-trifluoromethyl-1H-pyrazole-4-carboxylic acid (1-amino-isoquinolin-6-ylmethyl)-amide 1-(6-Pyrrolidin-1-yl-pyridin-3-ylmethyl)-3-trifluoromethyl-1H-pyrazole-4-carboxylic acid (180 mg, 0.53 mmol) was dissolved in CH$_2$Cl$_2$ (50 mL) and DMF (2.5 mL). This solution was cooled to 0° C. 6-Aminomethyl-isoquinolin-1-ylamine.HCl (122 mg, 0.58 mmol) was added followed by HOBt (77 mg, 0.58 mmol) and triethylamine (161 mg, 1.58 mmol). Water soluble carbodiimide (122 mg, 0.63 mmol) was then added. After 18 hrs at 0° C. to rt reaction mixture was diluted with chloroform (100 mL) and isopropanol (10 mL) and washed with NaHCO$_3$ (1×30 mL), water (1×30 mL) and brine (1×30 mL), dried (Na$_2$SO$_4$) and evaporated in vacuo giving a yellow oil. The residue was purified by flash chromatography (silica), eluent 15% MeOH, 85% CHCl$_3$, fractions combined and evaporated in vacuo to give a white solid. The residue was treated with HCl in methanol (4 mL), the solvent was evaporated in vacuo and the residue freeze dried from water/acetonitrile to give a white solid identified as 1-(6-pyrrolidin-1-yl-pyridin-3-ylmethyl)-3-trifluoromethyl-1H-pyrazole-4-carboxylic acid (1-amino-isoquinolin-6-ylmethyl)-amide (135 mg, 0.254 mmol, 48% yield).
[M+H]$^+$=496
$^1$H NMR: (d6-DMSO), δ: 2.01 (4H, t, J=6.0 Hz), 3.47 (4H, t, J=6.3 Hz), 4.59 (2H, d, J=5.8 Hz), 5.45 (2H, s), 7.10 (1H, d, J=9.0 Hz), 7.20 (1H, d, J=7.1 Hz), 7.70 (2H, dd, J=1.2 and 8.3 Hz), 7.81 (1H, s), 7.94 (1H, d, J=8.8 Hz), 8.15 (1H, s), 8.58 (1H, d, J=8.7 Hz), 8.64 (1H, s), 9.17-9.20 (2H, m), 13.30 (1H, s).

Example 25

3-Cyclopropyl-1-(5-methoxy-6-pyrrolidin-1-yl-pyridin-3-ylmethyl)-1H-pyrazole-4-carboxylic acid (1-amino-isoquinolin-6-ylmethyl)-amide

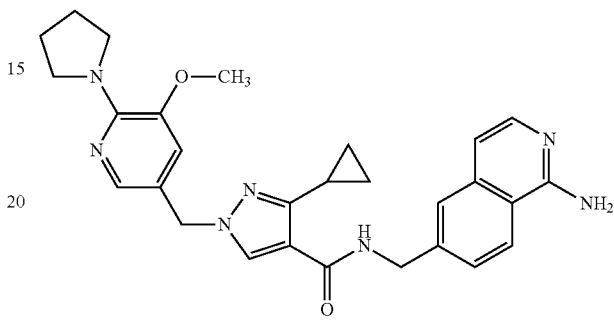

A: (6-Chloro-5-methoxy-pyridin-3-yl)-methanol

To a stirred solution of 6-chloro-5-methoxy-nicotinic acid methyl ester (0.5 g, 2.48 mmol) in anhydrous THF (20 mL) cooled to 0° C. under nitrogen, LiAlH$_4$ (104 mg, 2.728 mmol) was added. The reaction was allowed to warm to rt for 2 hrs. The reaction was cooled to 0° C. and quenched with water (5 mL). Potassium sodium tartrate (Rochelle's salt) was added to help break up the suspension. The mixture was filtered through Celite, washing well with water (20 mL) and ethyl acetate (100 mL). The filtrate was collected and the layers separated. The aqueous extracted with ethyl acetate (3×20 mL). The combined organic layers were washed with brine (50 mL), dried over MgSO$_4$ and the solvent removed in vacuo. The crude was purified by flash chromatography (silica) eluting in step gradients up to 40% Pet. Ether, 60% ethyl acetate. Pure fractions were concentrated affording the title compound (6-chloro-5-methoxy-pyridin-3-yl)-methanol as a white solid (360 mg, 2.074 mmol, 84% yield).
[M+H]$^+$=174

B. 5-Bromomethyl-2-chloro-3-methoxy-pyridine

Under an atmosphere of N$_2$, (6-chloro-5-methoxy-pyridin-3-yl)-methanol (360 mg, 2.074 mmol) and triphenylphosphine (626 mg, 2.385 mmol) were dissolved in dry DCM (5 mL). The resultant solution was cooled in an ice bath before carbon tetrabromide (756 mg, 2.281 mmol) was added portionwise. The mixture was stirred at ambient temperature for 18 hrs. The mixture was diluted with dichloromethane (30 mL), washed with water (2×50 mL) and brine (30 mL), dried (MgSO$_4$) and concentrated under vacuum. The crude material was purified by flash chromatography (silica) eluting in step gradients up to 85% Pet. Ether, 15% ethyl acetate. The compound containing fractions were concentrated in vacuo to afford a colourless oil identified as 5-bromomethyl-2-chloro-3-methoxy-pyridine (220 mg, 0.93 mmol, 45% yield).
[M+H]$^+$=238

¹H NMR (400 MHz, CDCl3) δ: 3.97 (3H, s), 4.47 (2H, s), 7.25 (1H, d, J=2.0 Hz), 8.01 (1H, d, J=2.0 Hz)

C. 1-(6-Chloro-5-methoxy-pyridin-3-ylmethyl)-3-cyclopropyl-1H-pyrazole-4-carboxylic acid ethyl ester 3-Cyclopropyl-1H-pyrazole-4-carboxylic acid ethyl ester (60 mg, 0.333 mmol) was taken up in DMF (2 mL) and treated with potassium carbonate (91 mg, 0.660 mmol). 5-Bromomethyl-2-chloro-3-methoxy-pyridine (78 mg, 0.330 mmol) was added and the reaction stirred at rt over the weekend. Ethyl acetate (60 mL) and water (20 mL) were added and the layers separated. The organic layer was washed with water (3×15 mL), brine (10 mL), filtered and evaporated. The crude product was purified by flash chromatography (silica) eluting in step gradients up to 60% Pet. Ether, 40% ethyl acetate. 1-(6-Chloro-5-methoxy-pyridin-3-ylmethyl)-3-cyclopropyl-1H-pyrazole-4-carboxylic acid ethyl ester was isolated as a colourless oil which solidified on standing to a white solid, (78 mg, 0.232 mmol, 70% yield).

$[M+H]^+=336$

D. 3-Cyclopropyl-1-(5-methoxy-6-pyrrolidin-1-yl-pyridin-3-ylmethyl)-1H-pyrazole-4-carboxylic acid ethyl ester A suspension of 1-(6-chloro-5-methoxy-pyridin-3-ylmethyl)-3-cyclopropyl-1H-pyrazole-4-carboxylic acid ethyl ester (78 mg, 0.232 mmol) in pyrrolidine (763 LS, 9.282 mmol) and 1,4-dioxane (300 μL) was heated at 90° C. overnight. The reaction was then cooled and taken up in ethyl acetate (20 mL), NaHCO₃ (10 mL) was added and the organic layer was separated, washed with brine, dried (MgSO₄) and concentrated. The crude product was purified by flash chromatography (silica) eluting in step gradients up to 60% Pet. Ether, 40% ethyl acetate. 3-Cyclopropyl-1-(5-methoxy-6-pyrrolidin-1-yl-pyridin-3-ylmethyl)-1H-pyrazole-4-carboxylic acid ethyl ester was isolated as a colourless oil (85 mg, 0.229 mmol, 98% yield).

$[M+H]^+=371$

E. 3-Cyclopropyl-1-(5-methoxy-6-pyrrolidin-1-yl-pyridin-3-ylmethyl)-1H-pyrazole-4-carboxylic acid To 3-cyclopropyl-1-(5-methoxy-6-pyrrolidin-1-yl-pyridin-3-ylmethyl)-1H-pyrazole-4-carboxylic acid ethyl ester (85 mg, 0.229 mmol) in ethanol (20 mL) was added sodium hydroxide (92 mg, 2.295 mmol). The reaction mixture was heated at reflux overnight. Then the reaction was cooled and concentrated under reduced pressure. The crude residue was dissolved in water (2 mL) and the pH adjusted to pH~4.7 with 2M HCl. The aqueous layer was washed with chloroform (3×10 mL). The combined organics were concentrated to afford the desired product 3-cyclopropyl-1-(5-methoxy-6-pyrrolidin-1-yl-pyridin-3-ylmethyl)-1H-pyrazole-4-carboxylic acid as a white solid (60 mg, 0.175 mmol, 76% yield).

$[M+H]^+=343$

F. 3-Cyclopropyl-1-(5-methoxy-6-pyrrolidin-1-yl-pyridin-3-ylmethyl)-1H-pyrazole-4-carboxylic acid (1-amino-isoquinolin-6-ylmethyl)-amide hydrochloride To 3-cyclopropyl-1-(5-methoxy-6-pyrrolidin-1-yl-pyridin-3-ylmethyl)-1H-pyrazole-4-carboxylic acid (60 mg, 0.175 mmol) in dichloromethane (5 mL) at 0° C. was added HOBt (28 mg, 0.210 mmol) and 1-ethyl-3-(3-dimethylaminopropyl)carbodiimide (47 mg, 0.245 mmol). After 10-15 min triethylamine (122 μl, 0.876 mmol) and 6-(aminomethyl)isoquinolin-1-amine (30 mg, 0.175 mmol) was added. DMF (3 mL) was added to aid solubility and the reaction allowed to warm to rt and stirred for 3 days. The reaction mixture was diluted with chloroform (50 mL) and saturated aqueous NaHCO₃ (15 mL) added. The layers were separated and the organic layer washed with water (5×20 mL), followed by brine (15 mL). The combined organic layers were dried over MgSO₄, filtered and concentrated under reduced pressure. The crude was purified by flash chromatography (silica) eluting in step gradients up to 3.5% methanol, 95.5% dichloromethane, 1% NH₄OH. The product was treated with HCl/dioxane for 30 min, concentrated in vacuo and freeze dried in acetonitrile/water. 3-Cyclopropyl-1-(5-methoxy-6-pyrrolidin-1-yl-pyridin-3-ylmethyl)-1H-pyrazole-4-carboxylic acid (1-amino-isoquinolin-6-ylmethyl)-amide was isolated as the di hydrochloride salt as an off white solid (50 mg, 0.088 mmol, 99% yield).

$[M+H]^+=498$

1H NMR (d6-DMSO): 0.75-0.79 (2H, m), 0.81-0.87 (2H, m), 1.11-1.95 (4H, m), 2.57-2.63 (1H, m), 3.77 (4H, br. s), 3.86 (3H, s), 4.58 (2H, d, J=5.8 Hz), 5.19 (2H, s), 7.21 (1H, d, J=7.0 Hz), 7.41 (1H, d, J=1.3 Hz), 7.54 (1H, d, J=1.0 Hz), 7.67-7.69 (1H, m), 7.69-7.72 (1H, m), 7.80 (1H, s), 8.31 (1H, s), 8.59 (1H, d, J=8.6 Hz), 8.79 (1H, t, J=5.8 Hz), 9.17 (2H, br. s), 13.39 (1H, s)

Example 26

1-(6-Ethoxy-pyridin-3-ylmethyl)-3-phenyl-1H-pyrazole-4-carboxylic acid (1-amino-isoquinolin-6-ylmethyl)-amide

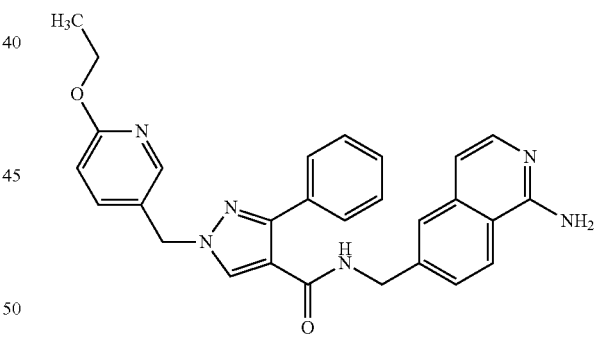

A: 5-Chloromethyl-2-fluoro-pyridine

A 500 mL flask was charged with 2-fluoro-5-methylpyridine (23.42 g, 211 mmol), 1-chloropyrrolidine-2,5-dione (42.2 g, 316 mmol), benzoic peroxyanhydride (1.361 g, 4.22 mmol), acetic acid (1 mL, 17.47 mmol) and acetonitrile (132 mL, 2527 mmol). The reaction mixture was heated to reflux giving a pale yellow solution which was left to reflux for 5 hrs. The reaction mixture was cooled and quenched with water (20 mL), followed by ethyl acetate (30 mL) and brine (30 mL). The two phases were separated and the aqueous re-extracted with ethyl acetate (30 mL). The combined organics were washed with brine (30 mL), dried over magnesium sulphate, filtered and evaporated to give a viscous orange suspension. The product was triturated with DCM (100 mL) and the resulting solid removed by filtration. The filtrate was evaporated under reduced pressure to give a clear orange oil. The crude product was divided into two 19 g batches and purified on a 330 g silica column, liquid loaded in DCM and gradient eluted with ethyl acetate-Isohexane (5:95). Product containing fractions were combined and evaporated in vacuo to give a clear almost colourless oil identified as 5-(chloromethyl)-2-fluoropyridine (14.6 g, 99 mmol, 46.9% yield).
[M+H]$^+$=146

B. 1-(6-Fluoro-pyridin-3-ylmethyl)-3-phenyl-1H-pyrazole-4-carboxylic acid ethyl ester To a stirred solution of 5-(chloromethyl)-2-fluoropyridine (750 mg, 5.15 mmol) and ethyl 3-phenyl-1H-pyrazole-4-carboxylate (1114 mg, 5.15 mmol) in DMF (15 mL) was added K$_2$CO$_3$ (1424 mg, 10.30 mmol) and stirred at RT over the weekend. The reaction mixture was diluted with EtOAc (150 mL) and washed with water (100 mL) and brine (2×100 mL), dried over magnesium sulfate, filtered and crude material evaporated directly onto silica. The crude product was purified by chromatography (40 g column, 0-60% (3:1 EtOAc:MeCN) in isohexanes). 1-(6-Fluoro-pyridin-3-ylmethyl)-3-phenyl-1H-pyrazole-4-carboxylic acid ethyl ester (1.69 g, 4.16 mmol, 81% yield) was isolated as a waxy solid on standing, as a mixture of regioisomers. The material was used directly in the next step
[M+H]$^+$=326

C: 1-(6-Ethoxy-pyridin-3-ylmethyl)-3-phenyl-1H-pyrazole-4-carboxylic acid

To a stirred microwave vial containing ethanol (3 mL) was added sodium ethoxide (586 mg, 8.61 mmol) and 1-(6-fluoro-pyridin-3-ylmethyl)-3-phenyl-1H-pyrazole-4-carboxylic acid ethyl ester (700 mg, 2.152 mmol). The reaction vessel was sealed and heated to 90° C. overnight. The reaction mixture was allowed to cool to rt and diluted with EtOAc (100 mL), NH$_4$Cl (sat, 10 mL) and water (100 mL). The organics were washed with brine (100 mL) and solvent was removed. The crude material was taken up into THF (10 mL) and MeOH (3 mL) then 2M NaOH (2152 µl, 4.30 mmol) was added and left at RT for 2 hrs. The reaction mixture was acidified to ~pH 5 with 1M HCl and the product extracted into EtOAc (2×30 mL). The organics were washed with brine (30 mL), dried over magnesium sulfate, filtered and solvent removed. The crude product was purified by chromatography (40 g column, 0-70% (3:1 EtOAc:MeCN, 1% acetic acid) in isohexanes) to afford 1-((6-ethoxypyridin-3-yl)methyl)-3-phenyl-1H-pyrazole-4-carboxylic acid (65 mg, 0.191 mmol, 9% yield) as a white solid.
[M+H]$^+$=324

D: 1-(6-Ethoxy-pyridin-3-ylmethyl)-3-phenyl-1H-pyrazole-4-carboxylic acid (1-amino-isoquinolin-6-ylmethyl)-amide To a stirred solution of 1-((6-ethoxypyridin-3-yl)methyl)-3-phenyl-1H-pyrazole-4-carboxylic acid (65 mg, 0.201 mmol) and 6-(aminomethyl)isoquinolin-1-amine.2HCl (49.5 mg, 0.201 mmol) in DMF (2 mL) was added N,N-diisopropylethylamine (140 µl, 0.804 mmol) and HATU (84 mg, 0.221 mmol) and left at RT for 2 hrs. The reaction mixture was diluted with EtOAc (30 mL) and washed with NaOH (2 M, 20 mL) and then brine (2×40 mL). The organics were preabsorbed directly onto silica and purified by chromatography (12 g column, 0-7% MeOH (1% NH3) in DCM) to afford the free base of the title compound (54.2 mg, 0.100 mmol, 49.7% yield) as a white powder. The solid was azeotroped from toluene (3×5 mL) under high vacuum to remove any residual N,N-diisopropylethylamine before salt formation. The material was suspended in DCM (3 mL) and HCl 4M in dioxane (27.1 µl, 0.109 mmol, 1 eq) was added. The solvent was removed under vacuum. The residue was suspended in water (3 mL) and then freeze dried overnight to give 1-(6-ethoxy-pyridin-3-ylmethyl)-3-phenyl-1H-pyrazole-4-carboxylic acid (1-amino-isoquinolin-6-ylmethyl)-amide as a HCl salt, as a white solid (54.2 mg, 0.100 mmol, 49.7% yield).
[M+H]$^+$=479.3

Example 27

1-(6-Ethoxy-pyridin-3-ylmethyl)-3-(2-methoxy-acetylamino)-1H-pyrazole-4-carboxylic acid (1-amino-isoquinolin-6-ylmethyl)-amide

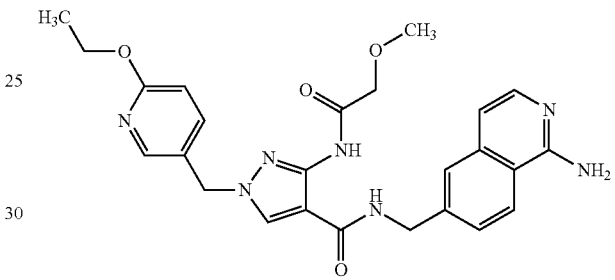

A. 3-Amino-1-(6-fluoro-pyridin-3-ylmethyl)-1H-pyrazole-4-carboxylic acid ethyl ester 1132-35

To a stirred solution of 3-amino-1H-pyrazole-4-carboxylic acid ethyl ester (1.785 g, 11.51 mmol) in ethanol (10 mL) was added sodium ethoxide (1.566 g, 23.01 mmol). After 5 min a solution of 5-(chloromethyl)-2-fluoropyridine (1.675 g, 11.51 mmol) in EtOH (3 mL) was added and the reaction heated to 80° C. After 90 min the reaction mixture was reduced in volume under vacuum and then diluted with EtOAc (200 mL) and water (100 mL). The organics were isolated and washed with brine (100 mL), dried over magnesium sulfate, filtered and solvent removed. The crude product was purified by chromatography (80 g column, slowly 0-40% (3:1 EtOAc:MeCN) in isohexanes). The undesired regioisomer 5-amino-1-(6-fluoro-pyridin-3-ylmethyl)-1H-pyrazole-4-carboxylic acid ethyl ester was isolated from the first set of fractions (768 mg, 2.76 mmol, 24% yield) as an oil that solidified to a waxy solid on standing. The desired isomer 3-amino-1-(6-fluoro-pyridin-3-ylmethyl)-1H-pyrazole-4-carboxylic acid ethyl ester (712 mg, 2.61 mmol, 22.7% yield) was isolated as a waxy solid from the second set of fractions.
[M+H]$^+$=265

B. 3-Amino-1-(6-ethoxy-pyridin-3-ylmethyl)-1H-pyrazole-4-carboxylic acid

To a microwave vial containing EtOH (5 mL) was added NaH (260 mg, 6.51 mmol) and allowed to stir for 10 min. To this was added a suspension of ethyl 3-amino-1-((6-fluoropyridin-3-yl)methyl)-1H-pyrazole-4-carboxylate (430 mg, 1.627 mmol) in EtOH (4 mL). The mixture was sealed and heated to 90° C. overnight. NaOH (2M, 2 mL) was added and heated to 50° C. for 1 hour. The reaction mixture was evaporated to dryness and the residue dissolved in water (10 mL) and the pH adjusted to pH5 then extracted with EtOAc (10×20 mL). The combined organics were then evaporated. The crude material was purified by chromatography (12 g column, 0-70% (3:1 EtOAc:MeCN, 1% acetic acid in isohexanes) to afford 3-amino-1-((6-ethoxypyridin-3-yl)methyl)-1H-pyrazole-4-carboxylic acid (195 mg, 0.736 mmol, 45.2% yield) as a white powder after azeotroping with toluene (2×20 mL).
[M+H]$^+$=263

C. 1-((6-Ethoxypyridin-3-yl)methyl)-3-(2-methoxy-acetamido)-1H-pyrazole-4-carboxylic acid To a stirred solution of 3-amino-1-((6-ethoxypyridin-3-yl)methyl)-1H-pyrazole-4-carboxylic acid (142 mg, 0.541 mmol) in DCM (3 mL) was added N,N-diisopropylethylamine (142 μL, 0.812 mmol) and 2-methoxyacetyl chloride (54.5 μL, 0.596 mmol) and stirred at rt for 1 hour. The reaction mixture was evaporated to remove DCM. The crude residue was sonicated in water (10 mL). Hydrochloric acid (2M, 1 mL) was added and the product extracted into EtOAc (30 mL). The organic layer was dried over magnesium sulfate and solvent evaporated under reduced pressure to afford 1-((6-ethoxypyridin-3-yl)methyl)-3-(2-methoxyacetamido)-1H-pyrazole-4-carboxylic acid as a yellow solid (160 mg, 0.469 mmol, 87% yield).
[M+H]$^+$=335

D. 1-(6-Ethoxy-pyridin-3-ylmethyl)-3-(2-methoxy-acetylamino)-1H-pyrazole-4-carboxylic acid (1-amino-isoquinolin-6-ylmethyl)-amide hydrochloride To a stirred solution of 1-((6-ethoxypyridin-3-yl)methyl)-3-(2-methoxyacetamido)-1H-pyrazole-4-carboxylic acid (81.0 mg, 0.242 mmol), 6-(aminomethyl)isoquinolin-1-amine dihydrochloride (65.6 mg, 0.267 mmol) and HATU (111 mg, 0.291 mmol) in DMF (2 mL) was added triethylamine (135 μL, 0.969 mmol). The resulting mixture was stirred at rt overnight. The reaction mixture was then diluted with EtOAc (15 mL) and washed with 2M NaOH (2×20 mL). The organic was dried (Na$_2$SO$_4$), filtered and evaporated under reduced pressure. The crude was purified by chromatography (4 g column, MeOH in DCM 0-5% and 1% Et$_3$N) to afford the desired product as a free base. The product was dissolved in DCM (1 mL), 4M HCl in dioxane (79 μl, 0.315 mmol) added and the resulting mixture stirred at rt for 15 min. The solvent was then evaporated under reduced pressure to give 1-(6-ethoxy-pyridin-3-ylmethyl)-3-(2-methoxy-acetylamino)-1H-pyrazole-4-carboxylic acid (1-amino-isoquinolin-6-ylmethyl)-amide hydrochloride (47.5 mg, 0.089 mmol, 36.5% yield) as a white solid.
[M+H]$^+$=490

NMR (d6-DMSO) 1.31 (3H, t, J=7.0 Hz), 3.36 (3H, s), 3.96 (2H, s), 4.30 (2H, q, J=7.0 Hz), 4.60 (2H, d, J=5.9 Hz), 5.27 (2H, s), 6.83 (1H, dd, J=0.7, 8.5 Hz), 7.17 (1H, d, J=6.8 Hz), 7.60-7.72 (3H, m), 7.73-7.78 (1H, m), 8.17-8.27 (2H, m), 8.40-8.50 (3H, m), 8.83 (1H, t, J=6.0 Hz), 10.51 (1H, s), 12.74 (1H, s).

The compounds in the following tables were synthesised as described for Examples 1-3 and 6-27 and Reference Examples 4 and 5.

TABLE 1

| Example Number | A | Free Base MW | [M + H]$^+$ |
|---|---|---|---|
| 28 | (4-methylpyrazol-1-yl)methyl | 492.6 | 493 |
| 29 | 2-phenylthiazol-4-yl | 481.6 | 482 |
| 30 | 6-(pyrrolidin-1-yl)pyridin-3-yl | 468.6 | 469 |

TABLE 2

| Example Number | W | Z | Y | Free Base MW | [M + H]$^+$ |
|---|---|---|---|---|---|
| 31 | CH | CH | N | 451.5 | 452 |
| 32 | CH | N | CH | 451.5 | 452 |

TABLE 2-continued

| | | | | | |
|---|---|---|---|---|---|
| 33 | CH | N | N | 452.5 | 453 |
| 34 | C—CH₃ | C—CH₃ | N | 479.6 | 480 |
| 35 | CH | C—Ph | N | 527.6 | 528 |
| 36 | CH | C—CF₃ | N | 519.5 | 520 |
| 37 | CH | C—NH₂ | N | 466.5 | 467 |
| 38 | CH | C—CH₂—O—CH₃ | N | 495.6 | 496 |
| 39 | CH | C—CHF₂ | N | 501.5 | 502 |
| 40 | CH | C—CH₂—CF₃ | N | 533.6 | 268 [M + 2H]/2 |
| 41 | CH | C—CON(CH₃)₂ | N | 522.6 | 523 |
| 42 | CH | C-(3-thienyl) | N | 533.7 | 534 |
| 43 | CH | C—Cl | N | 486.0 | 486 |

TABLE 3

[Structure: A-CH₂-N(triazole ring with W, Y)-C(=O)-NH-CH₂-(isoquinoline-1-amine)]

| Example Number | A | W | Y | Free Base MW | [M + H]⁺ |
|---|---|---|---|---|---|
| 44 | 1-(4-methylenephenyl)-2-oxopyridin-1(2H)-yl | C—CH₃ | C—CH₃ | 491.6 | 492 |
| 45 | 2,3-dihydro-1,4-benzodioxin-6-ylmethyl | CH | N | 429.5 | 430 |
| 46 | 4-[(N-methyl-N-(2,4-dimethylthiazol-5-yl))amino]benzyl | CH | N | 511.6 | 513 |

TABLE 3-continued

| Example Number | A | W | Y | Free Base MW | [M + H]+ |
|---|---|---|---|---|---|
| 47 | (6-phenoxypyridin-2-yl) | CH | N | 450.5 | 451 |
| 48 | (3-fluoropyridin-2-yl)oxyphenyl | CH | N | 468.5 | 469 |
| 49 | 4-(pyridin-2-yloxy)phenyl | CH | N | 450.6 | 451 |
| 50 | 4-((6-fluoropyridin-2-yl)oxymethyl)phenyl | CH | N | 482.5 | 483 |
| 51 | 2-(pyrrolidin-1-yl)pyridin-4-yl | C—CF$_3$ | N | 495.5 | 496 |

TABLE 3-continued
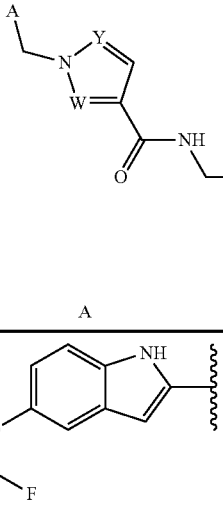
| Example Number | A | W | Y | Free Base MW | [M + H]+ |
|---|---|---|---|---|---|
| 52 | 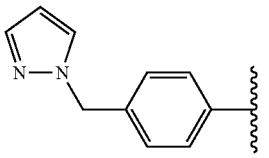 | CH | N | 480.4 | 481 |
| 53 | 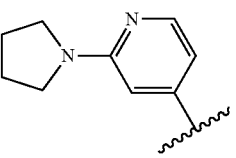 [SMILES: *c1ccnc(N2CCCC2)c1] | C—NH₂ | N | 452.5 | 453 |
TABLE 4
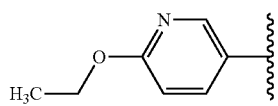
| Example Number | A | Free Base MW | [M + H]+ |
|---|---|---|---|
| 54 | 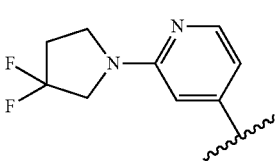 [SMILES: *c1ccnc(N2CCC(F)(F)C2)c1] | 495.5 | 496 |
| 55 | 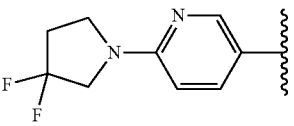 [SMILES: *c1ccc(N2CCC(F)(F)C2)nc1] | 470.5 | 471 |
| 56 | 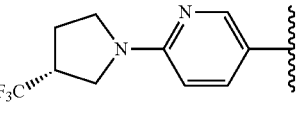 | 531.5 | 532 |
TABLE 4-continued
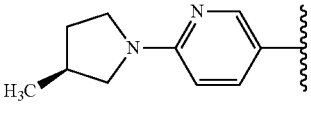 [SMILES: *c1ccc(N2CC[C@H](C)C2)nc1]
| Example Number | A | Free Base MW | [M + H]+ |
|---|---|---|---|
| 57 | 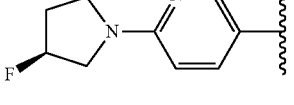 | 531.5 | 532 |
| 58 | | 509.5 | 510 |
| 59 | | 509.5 | 510 |
| 60 | | 513.5 | 514 |

TABLE 4-continued

[Structure: A-CH2-pyrazole(N-N, CF3)-C(=O)-NH-CH2-isoquinoline-NH2]

| Example Number | A | Free Base MW | [M + H]+ |
|---|---|---|---|
| 61 | (3-fluoropyrrolidin-1-yl)pyridin-yl | 513.5 | 514 |
| 62 | (2-methylpyrrolidin-1-yl)pyridin-yl | 509.5 | 510 |
| 63 | (2-methylpyrrolidin-1-yl)pyridin-yl | 509.5 | 510 |
| 64 | (pyrrolidin-1-yl)pyrimidin-yl | 496.5 | 497 |
| 65 | (pyrrolidin-1-yl)pyrazin-yl | 496.5 | 497 |
| 66 | (isopropoxy)pyridin-yl | 484.5 | 485 |
| 67 | (3-methylpyrrolidin-1-yl)pyridin-yl | 509.5 | 510 |
| 68 | (3-methylpyrrolidin-1-yl)pyridin-yl | 509.5 | 510 |
| 69 | (±)-(3-hydroxymethylpyrrolidin-1-yl)pyridin-yl | 525.5 | 526 |
| 70 | (3-hydroxymethylpyrrolidin-1-yl)pyridin-yl | 525.5 | 526 |
| 71 | (propoxy)pyridin-yl | 484.5 | 485 |
| 72 | (sec-butoxy)pyridin-yl | 498.5 | 499 |
| 73 | (3-fluoro-2-pyrrolidin-1-yl)pyridin-yl | 513.5 | 514 |
| 74 | (2-chloro-3-ethoxy)pyridin-yl | 504.9 | 505 |
| 75 | (2-ethoxy-3-fluoro)pyridin-yl | 488.4 | 489 |

TABLE 4-continued

| Example Number | A | Free Base MW | [M + H]+ |
|---|---|---|---|
| 76 | pyrazol-1-ylmethyl-phenyl | 505.5 | 506 |
| 77 | 4-cyano-pyrazol-1-ylmethyl-phenyl | 530.5 | 531 |
| 78 | 4-carboxamide-pyrazol-1-ylmethyl-phenyl | 548.5 | 549 |
| 79 | pyrazol-1-ylmethyl-pyridinyl | 506.5 | 507 |
| 80 | 6-ethoxy-pyridin-3-yl | 470.5 | 471 |
| 81 | thiazol-pyrazol-1-ylmethyl | 512.5 | 513 |
| 82 | thiazol-(4-methyl-pyrazol-1-yl)methyl | 526.5 | 527 |
| 83 | 1,2,4-triazol-1-ylmethyl-phenyl | 506.5 | 507 |
| 84 | (3-methyl-1H-pyrazol-5-yloxy)methyl-phenyl | 535.5 | 536 |
| 85 | (5-methyl-3-oxo-2,3-dihydro-pyrazol-1-yl)methyl-phenyl | 535.5 | 536 |

TABLE 5

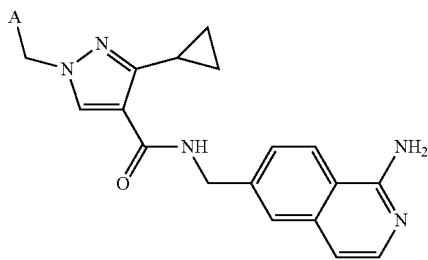

| Example Number | A | Free Base MW | [M + H]+ |
|---|---|---|---|
| 86 | H3C—O—CH2CH2—N(CH3)—pyridine | 485.6 | 486 |
| 87 | 3,3-difluoropyrrolidinyl-pyridine | 503.6 | 504 |
| 88 | pyrrolidinyl-methoxy-pyridine | 497.6 | 498 |
| 89 | pyrrolidinyl-methoxy-pyridine | 497.6 | 498 |
| 90 | pyrrolidinyl-pyridine | 467.6 | 468 |
| 91 | triazolyl-benzyl | 478.6 | 479 |
| 92 | CF3CH2O-pyridine | 496.5 | 497 |

TABLE 5-continued

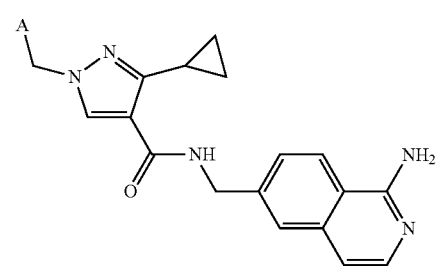

| Example Number | A | Free Base MW | [M + H]+ |
|---|---|---|---|
| 93 | phenoxy-pyridine | 490.6 | 491 |
| 94 | ethoxy-chloro-pyridine | 477 | 477 |
| 95 | diethylamino-fluoro-pyridine | 487.6 | 488 |
| 96 | diethylamino-pyridine | 469.6 | 470 |
| 97 | pyrrolidinyl-chloro-pyridine | 502.0 | 502 |

TABLE 6

[Core structure: A-CH2-triazole(N1,N2,N3)-C(=O)-NH-CH2-(6-position of 1-aminoisoquinoline), with Z at position 4 of triazole]

| Example Number | A | Z | Free Base MW | [M + H]+ |
|---|---|---|---|---|
| 98 | 6-ethoxypyridin-3-yl (H3C-CH2-O-pyridine) | C—NH2 | 417.5 | 418 |
| 99 | 6-(pyrrolidin-1-yl)pyridin-3-yl | C—NH2 | 442.5 | 443 |
| 100 | 6-(pyrrolidin-1-yl)pyridin-3-yl | C—N(CH3)2 | 470.6 | 471 |
| 101 | 6-(pyrrolidin-1-yl)pyridin-3-yl | C-(1-methyl-5-oxopyrrolidin-3-yl) | 524.6 | 525 |
| 102 | 6-(pyrrolidin-1-yl)pyridin-3-yl | C-(3,5-dimethylisoxazol-4-yl) | 522.6 | 523 |
| 103 | 6-(pyrrolidin-1-yl)pyridin-3-yl | C-(thiophen-3-yl) | 509.6 | 256 [M + 2H]/2 |
| 104 | 6-(pyrrolidin-1-yl)pyridin-3-yl | C-(morpholin-4-yl) | 512.6 | 513 |

TABLE 7

[Structure: triazole-carboxamide linked to azaindazole core with A, V, U, Z variable positions]

| Example Number | A | V | U | Z | Free Base MW | [M + H]+ |
|---|---|---|---|---|---|---|
| 105 | 2,4-dimethylthiazol-5-yl-N(CH3)-benzyl group | N | CH | CH | 485.6 | 486 |
| 106 | 3-(3-fluoropyridin-2-yloxy)phenyl | N | CH | CH | 442.5 | 443 |
| 107 | 4-(pyridin-2-yloxy)phenyl | N | CH | CH | 424.5 | 425 |
| 108 | 3-phenoxyphenyl | N | CH | CH | 423.5 | 424 |
| 109 | 4-((6-fluoropyridin-2-yloxy)methyl)phenyl | N | CH | CH | 456.5 | 457 |

TABLE 7-continued
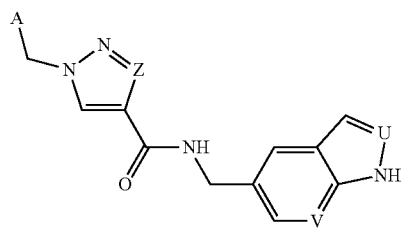
| Example Number | A | V | U | Z | Free Base MW | [M + H]+ |
|---|---|---|---|---|---|---|
| 110 | 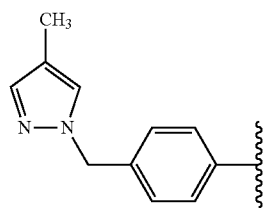 [SMILES: *c1ccc(Cn2cc(C)cn2)cc1] | CH | C—CH₃ | C—CF₃ | 506.5 | 507 |
| 111 | 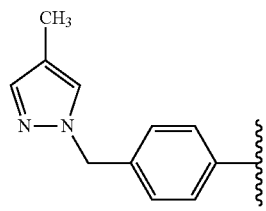 [SMILES: *c1ccc(Cn2cc(C)cn2)cc1] | CH | N | C—CF₃ | 493.5 | 494 |
| 112 | 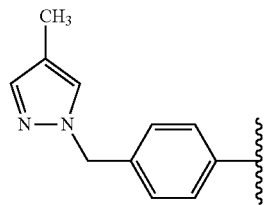 [SMILES: *c1ccc(Cn2cc(C)cn2)cc1] | CH | CH | C—CF₃ | 492.5 | 493.1 |
| 113 | 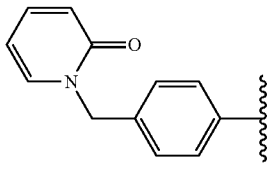 [SMILES: *c1ccc(Cn2ccccc2=O)cc1] | CH | N | C—NH₂ | 453.5 | 454 |
| 114 | 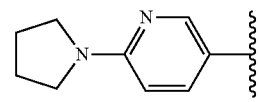 | N | CH | C—CF₃ | 469.5 | 470 |

TABLE 8
| Example Number | R1 | R3 | Z | Free Base MW | [M + H]+ |
|---|---|---|---|---|---|
| 115 | H | H | N | 426.5 | 427 |
| 116 | H | CH3 | N | 440.5 | 441 |
| 117 | H | H | CH | 425.5 | 426 |
| 118 | CH3 | CH3 | CH | 453.5 | 454 |
| 119 | CH3 | CH3 | C—CF3 | 453.5 | 454 |
| 120 | H | H |  | 465.6 | 466 |
| 121 | H | H | C—CF3 | 493.5 | 494 |
| 122 | CH3 | CH3 | 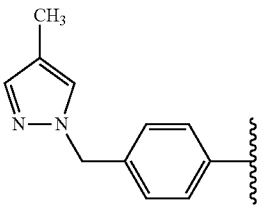 [SMILES: *c1ccc(Cn2cc(C)cn2)cc1] | 493.6 | 494 |
TABLE 9
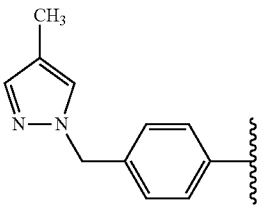 [SMILES: *c1ccc(Cn2cc(C)cn2)cc1]
| Example Number | A | U | V | Free Base MW | [M + H]+ |
|---|---|---|---|---|---|
| 123 | 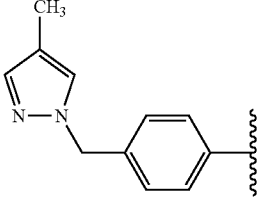 [SMILES: *c1ccc(Cn2cc(C)cn2)cc1] | CH | CH | 492.5 | 493 |
| 124 | 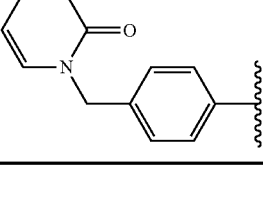 | N | CH | 493.5 | 494 |
| 125 | 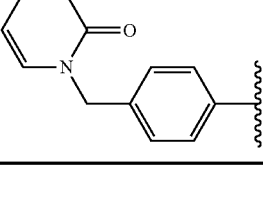 | CH | N | 493.5 | 494 |
| 126 | 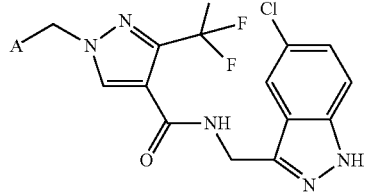 | N | CH | 506.5 | 507 |
TABLE 10
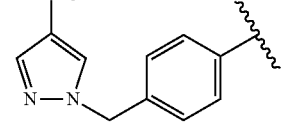
| Example Number | A | Free Base MW | [M + H]+ |
|---|---|---|---|
| 127 | 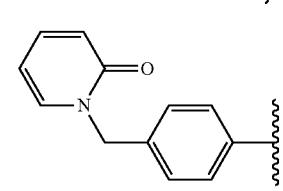 | 527.9 | 528 |
| 128 | | 503.9 | 504 |
| 129 | | 540.9 | 541 |
TABLE 11
| Example Number | Name |
|---|---|
| 28 | 1-Ethyl-4-methyl-5-[4-(4-methyl-pyrazol-1-ylmethyl)-benzyl]-1H-pyrrole-2-carboxylic acid (1-amino-isoquinolin-6-ylmethyl)-amide |

TABLE 11-continued

| Example Number | Name |
|---|---|
| 29 | 1-Ethyl-4-methyl-5-(2-phenyl-thiazol-4-ylmethyl)-1H-pyrrole-2-carboxylic acid (1-amino-isoquinolin-6-ylmethyl)-amide |
| 30 | 1-Ethyl-4-methyl-5-(6-pyrrolidin-1-yl-pyridin-3-ylmethyl)-1H-pyrrole-2-carboxylic acid (1-amino-isoquinolin-6-ylmethyl)-amide |
| 31 | 1-[4-(4-Methyl-pyrazol-1-ylmethyl)-benzyl]-1H-pyrazole-4-carboxylic acid (1-amino-isoquinolin-6-ylmethyl)-amide |
| 32 | 1-[4-(4-Methyl-pyrazol-1-ylmethyl)-benzyl]-1H-imidazole-4-carboxylic acid (1-amino-isoquinolin-6-ylmethyl)-amide |
| 33 | 1-[4-(4-Methyl-pyrazol-1-ylmethyl)-benzyl]-1H-[1,2,3]triazole-4-carboxylic acid (1-amino-isoquinolin-6-ylmethyl)-amide |
| 34 | 3,5-Dimethyl-1-[4-(4-methyl-pyrazol-1-ylmethyl)-benzyl]-1H-pyrazole-4-carboxylic acid (1-amino-isoquinolin-6-ylmethyl)-amide |
| 35 | 1-[4-(4-Methyl-pyrazol-1-ylmethyl)-benzyl]-3-phenyl-1H-pyrazole-4-carboxylic acid (1-amino-isoquinolin-6-ylmethyl)-amide |
| 36 | 1-[4-(4-Methyl-pyrazol-1-ylmethyl)-benzyl]-3-trifluoromethyl-1H-pyrazole-4-carboxylic acid (1-amino-isoquinolin-6-ylmethyl)-amide |
| 37 | 3-Amino-1-[4-(4-methyl-pyrazol-1-ylmethyl)-benzyl]-1H-pyrazole-4-carboxylic acid (1-amino-isoquinolin-6-ylmethyl)-amide |
| 38 | 3-Methoxymethyl-1-[4-(4-methyl-pyrazol-1-ylmethyl)-benzyl]-1H-pyrazole-4-carboxylic acid (1-amino-isoquinolin-6-ylmethyl)-amide |
| 39 | 3-Difluoromethyl-1-[4-(4-methyl-pyrazol-1-ylmethyl)-benzyl]-1H-pyrazole-4-carboxylic acid (1-amino-isoquinolin-6-ylmethyl)-amide |
| 40 | 1-[4-(4-Methyl-pyrazol-1-ylmethyl)-benzyl]-3-(2,2,2-trifluoro-ethyl)-1H-pyrazole-4-carboxylic acid (1-amino-isoquinolin-6-ylmethyl)-amide |
| 41 | 1-[4-(4-Methyl-pyrazol-1-ylmethyl)-benzyl]-1H-pyrazole-3,4-dicarboxylic acid 4-[(1-amino-isoquinolin-6-ylmethyl)-amide] 3-dimethylamide |
| 42 | 1-[4-(4-Methyl-pyrazol-1-ylmethyl)-benzyl]-3-thiophen-3-yl-1H-pyrazole-4-carboxylic acid (1-amino-isoquinolin-6-ylmethyl)-amide |
| 43 | 3-Chloro-1-[4-(4-methyl-pyrazol-1-ylmethyl)-benzyl]-1H-pyrazole-4-carboxylic acid (1-amino-isoquinolin-6-ylmethyl)-amide |
| 44 | 2,5-Dimethyl-1-[4-(2-oxo-2H-pyridin-1-ylmethyl)-benzyl]-1H-pyrrole-3-carboxylic acid (1-amino-isoquinolin-6-ylmethyl)-amide |
| 45 | 1-[2-(2,3-Dihydro-benzo[1,4]dioxin-6-yl)-ethyl]-1H-pyrazole-4-carboxylic acid (1-amino-isoquinolin-6-ylmethyl)-amide |
| 46 | 1-(4-{[(2,4-Dimethyl-thiazol-5-yl)-methyl-amino]-methyl}-benzyl)-1H-pyrazole-4-carboxylic acid (1-amino-isoquinolin-6-ylmethyl)-amide |
| 47 | 1-(6-Phenoxy-pyridin-2-ylmethyl)-1H-pyrazole-4-carboxylic acid (1-amino-isoquinolin-6-ylmethyl)-amide |
| 48 | 1-[3-(3-Fluoro-pyridin-2-yloxy)-benzyl]-1H-pyrazole-4-carboxylic acid (1-amino-isoquinolin-6-ylmethyl)-amide |
| 49 | 1-[4-(Pyridin-2-yloxy)-benzyl]-1H-pyrazole-4-carboxylic acid (1-amino-isoquinolin-6-ylmethyl)-amide |
| 50 | 1-[4-(6-Fluoro-pyridin-2-yloxymethyl)-benzyl]-1H-pyrazole-4-carboxylic acid (1-amino-isoquinolin-6-ylmethyl)-amide |
| 51 | 1-(2-Pyrrolidin-1-yl-pyridin-4-ylmethyl)-5-trifluoromethyl-1H-pyrazole-4-carboxylic acid (1-amino-isoquinolin-6-ylmethyl)-amide |
| 52 | 1-(5-Trifluoromethoxy-1H-indol-2-ylmethyl)-1H-pyrazole-4-carboxylic acid (1-amino-isoquinolin-6-ylmethyl)-amide |
| 53 | 5-Amino-1-(4-pyrazol-1-ylmethyl-benzyl)-1H-pyrazole-4-carboxylic acid (1-amino-isoquinolin-6-ylmethyl)-amide |
| 54 | 1-(2-Pyrrolidin-1-yl-pyridin-4-ylmethyl)-3-trifluoromethyl-1H-pyrazole-4-carboxylic acid (1-amino-isoquinolin-6-ylmethyl)-amide |
| 55 | 1-(6-Ethoxy-pyridin-3-ylmethyl)-3-trifluoromethyl-1H-pyrazole-4-carboxylic acid (1-amino-isoquinolin-6-ylmethyl)-amide |
| 56 | 1-[2-(3,3-Difluoro-pyrrolidin-1-yl)-pyridin-4-ylmethyl]-3-trifluoromethyl-1H-pyrazole-4-carboxylic acid (1-amino-isoquinolin-6-ylmethyl)-amide |
| 57 | 1-[6-(3,3-Difluoro-pyrrolidin-1-yl)-pyridin-3-ylmethyl]-3-trifluoromethyl-1H-pyrazole-4-carboxylic acid (1-amino-isoquinolin-6-ylmethyl)-amide |
| 58 | 1-[6-((R)-3-Methyl-pyrrolidin-1-yl)-pyridin-3-ylmethyl]-3-trifluoromethyl-1H-pyrazole-4-carboxylic acid (1-amino-isoquinolin-6-ylmethyl)-amide |
| 59 | 1-[6-((S)-3-Methyl-pyrrolidin-1-yl)-pyridin-3-ylmethyl]-3-trifluoromethyl-1H-pyrazole-4-carboxylic acid (1-amino-isoquinolin-6-ylmethyl)-amide |
| 60 | 1-[6-((S)-3-Fluoro-pyrrolidin-1-yl)-pyridin-3-ylmethyl]-3-trifluoromethyl-1H-pyrazole-4-carboxylic acid (1-amino-isoquinolin-6-ylmethyl)-amide |
| 61 | 1-[6-((R)-3-Fluoro-pyrrolidin-1-yl)-pyridin-3-ylmethyl]-3-trifluoromethyl-1H-pyrazole-4-carboxylic acid (1-amino-isoquinolin-6-ylmethyl)-amide |
| 62 | 1-[6-((S)-2-Methyl-pyrrolidin-1-yl)-pyridin-3-ylmethyl]-3-trifluoromethyl-1H-pyrazole-4-carboxylic acid (1-amino-isoquinolin-6-ylmethyl)-amide |
| 63 | 1-[6-((R)-2-Methyl-pyrrolidin-1-yl)-pyridin-3-ylmethyl]-3-trifluoromethyl-1H-pyrazole-4-carboxylic acid (1-amino-isoquinolin-6-ylmethyl)-amide |
| 64 | 1-(2-Pyrrolidin-1-yl-pyrimidin-5-ylmethyl)-3-trifluoromethyl-1H-pyrazole-4-carboxylic acid (1-amino-isoquinolin-6-ylmethyl)-amide |
| 65 | 1-(5-Pyrrolidin-1-yl-pyrazin-2-ylmethyl)-3-trifluoromethyl-1H-pyrazole-4-carboxylic acid (1-amino-isoquinolin-6-ylmethyl)-amide |
| 66 | 1-(2-Isopropoxy-pyridin-4-ylmethyl)-3-trifluoromethyl-1H-pyrazole-4-carboxylic acid (1-amino-isoquinolin-6-ylmethyl)-amide |

TABLE 11-continued

| Example Number | Name |
|---|---|
| 67 | 1-[2-((R)-3-Methyl-pyrrolidin-1-yl)-pyridin-4-ylmethyl]-3-trifluoromethyl-1H-pyrazole-4-carboxylic acid (1-amino-isoquinolin-6-ylmethyl)-amide |
| 68 | 1-[2-((S)-3-Methyl-pyrrolidin-1-yl)-pyridin-4-ylmethyl]-3-trifluoromethyl-1H-pyrazole-4-carboxylic acid (1-amino-isoquinolin-6-ylmethyl)-amide |
| 69 | 1-[6-(3-Hydroxymethyl-pyrrolidin-1-yl)-pyridin-3-ylmethyl)-3-trifluoromethyl-1H-pyrazole-4-carboxylic acid (1-amino-isoquinolin-6-ylmethyl)-amide |
| 70 | 1-[6-((R)-3-Hydroxymethyl-pyrrolidin-1-yl)-pyridin-3-ylmethyl)-3-trifluoromethyl-1H-pyrazole-4-carboxylic acid (1-amino-isoquinolin-6-ylmethyl)-amide |
| 71 | 1-(6-Propoxy-pyridin-3-ylmethyl)-3-trifluoromethyl-1H-pyrazole-4-carboxylic acid (1-amino-isoquinolin-6-ylmethyl)-amide |
| 72 | 1-(6-sec-Butoxy-pyridin-3-ylmethyl)-3-trifluoromethyl-1H-pyrazole-4-carboxylic acid (1-amino-isoquinolin-6-ylmethyl)-amide |
| 73 | 1-(5-Fluoro-6-pyrrolidin-1-yl-pyridin-3-ylmethyl)-3-trifluoromethyl-1H-pyrazole-4-carboxylic acid (1-amino-isoquinolin-6-ylmethyl)-amide |
| 74 | 1-(6-Chloro-5-ethoxy-pyridin-3-ylmethyl)-3-trifluoromethyl-1H-pyrazole-4-carboxylic acid (1-amino-isoquinolin-6-ylmethyl)-amide |
| 75 | 1-(6-Ethoxy-5-fluoro-pyridin-3-ylmethyl)-3-trifluoromethyl-1H-pyrazole-4-carboxylic acid (1-amino-isoquinolin-6-ylmethyl)-amide |
| 76 | 1-(4-Pyrazol-1-ylmethyl-benzyl)-3-trifluoromethyl-1H-pyrazole-4-carboxylic acid (1-amino-isoquinolin-6-ylmethyl)-amide |
| 77 | 1-[4-(4-Cyano-pyrazol-1-ylmethyl)-benzyl]-3-trifluoromethyl-1H-pyrazole-4-carboxylic acid (1-amino-isoquinolin-6-ylmethyl)-amide |
| 78 | 1-[4-(4-Carbamoyl-pyrazol-1-ylmethyl)-benzyl]-3-trifluoromethyl-1H-pyrazole-4-carboxylic acid (1-amino-isoquinolin-6-ylmethyl)-amide |
| 79 | 1-(6-Pyrazol-1-ylmethyl-pyridin-3-ylmethyl)-3-trifluoromethyl-1H-pyrazole-4-carboxylic acid (1-amino-isoquinolin-6-ylmethyl)-amide |
| 80 | 1-(2-Ethoxy-pyridin-4-ylmethyl)-3-trifluoromethyl-1H-pyrazole-4-carboxylic acid (1-amino-isoquinolin-6-ylmethyl)-amide |
| 81 | 1-(2-Pyrazol-1-ylmethyl-thiazol-4-ylmethyl)-3-trifluoromethyl-1H-pyrazole-4-carboxylic acid (1-amino-isoquinolin-6-ylmethyl)-amide |
| 82 | 1-[2-(4-Methyl-pyrazol-1-ylmethyl)-thiazol-4-ylmethyl]-3-trifluoromethyl-1H-pyrazole-4-carboxylic acid (1-amino-isoquinolin-6-ylmethyl)-amide |
| 83 | 1-(4-[1,2,4]Triazol-1-ylmethyl-benzyl)-3-trifluoromethyl-1H-pyrazole-4-carboxylic acid (1-amino-isoquinolin-6-ylmethyl)-amide |
| 84 | 1-[4-(5-Methyl-2H-pyrazol-3-yloxymethyl)-benzyl]-3-trifluoromethyl-1H-pyrazole-4-carboxylic acid (1-amino-isoquinolin-6-ylmethyl)-amide |
| 85 | 1-[4-(3-Methyl-5-oxo-4,5-dihydro-pyrazol-1-ylmethyl)-benzyl]-3-trifluoromethyl-1H-pyrazole-4-carboxylic acid (1-amino-isoquinolin-6-ylmethyl)-amide |
| 86 | 3-Cyclopropyl-1-{6-[(2-methoxy-ethyl)-methyl-amino]-pyridin-3-ylmethyl}-1H-pyrazole-4-carboxylic acid (1-amino-isoquinolin-6-ylmethyl)-amide |
| 87 | 3-Cyclopropyl-1-[6-(3,3-difluoro-pyrrolidin-1-yl)-pyridin-3-ylmethyl]-1H-pyrazole-4-carboxylic acid (1-amino-isoquinolin-6-ylmethyl)-amide |
| 88 | 3-Cyclopropyl-1-(2-methoxy-6-pyrrolidin-1-yl-pyridin-4-ylmethyl)-1H-pyrazole-4-carboxylic acid (1-amino-isoquinolin-6-ylmethyl)-amide |
| 89 | 3-Cyclopropyl-1-(4-methoxy-6-pyrrolidin-1-yl-pyridin-3-ylmethyl)-1H-pyrazole-4-carboxylic acid (1-amino-isoquinolin-6-ylmethyl)-amide |
| 90 | 3-Cyclopropyl-1-(6-pyrrolidin-1-yl-pyridin-3-ylmethyl)-1H-pyrazole-4-carboxylic acid (1-amino-isoquinolin-6-ylmethyl)-amide |
| 91 | 3-Cyclopropyl-1-(4-[1,2,3]triazol-1-ylmethyl-benzyl)-1H-pyrazole-4-carboxylic acid (1-amino-isoquinolin-6-ylmethyl)-amide |
| 92 | 3-Cyclopropyl-1-[6-(2,2,2-trifluoro-ethoxy)-pyridin-3-ylmethyl]-1H-pyrazole-4-carboxylic acid (1-amino-isoquinolin-6-ylmethyl)-amide |
| 93 | 3-Cyclopropyl-1-(6-phenoxy-pyridin-3-ylmethyl)-1H-pyrazole-4-carboxylic acid (1-amino-isoquinolin-6-ylmethyl)-amide |
| 94 | 1-(5-Chloro-6-ethoxy-pyridin-3-ylmethyl)-3-cyclopropyl-1H-pyrazole-4-carboxylic acid (1-amino-isoquinolin-6-ylmethyl)-amide |
| 95 | 3-Cyclopropyl-1-(6-diethylamino-5-fluoro-pyridin-3-ylmethyl)-1H-pyrazole-4-carboxylic acid (1-amino-isoquinolin-6-ylmethyl)-amide |
| 96 | 3-Cyclopropyl-1-(6-diethylamino-pyridin-3-ylmethyl)-1H-pyrazole-4-carboxylic acid (1-amino-isoquinolin-6-ylmethyl)-amide |
| 97 | 1-(5-Chloro-6-pyrrolidin-1-yl-pyridin-3-ylmethyl)-3-cyclopropyl-1H-pyrazole-4-carboxylic acid (1-amino-isoquinolin-6-ylmethyl)-amide |
| 98 | 3-Amino-1-(6-ethoxy-pyridin-3-ylmethyl)-1H-pyrazole-4-carboxylic acid (1-amino-isoquinolin-6-ylmethyl)-amide |
| 99 | 3-Amino-1-(6-pyrrolidin-1-yl-pyridin-3-ylmethyl)-1H-pyrazole-4-carboxylic acid (1-amino-isoquinolin-6-ylmethyl)-amide |
| 100 | 3-Dimethylamino-1-(6-pyrrolidin-1-yl-pyridin-3-ylmethyl)-1H-pyrazole-4-carboxylic acid (1-amino-isoquinolin-6-ylmethyl)-amide |
| 101 | 3-(1-Methyl-5-oxo-pyrrolidin-3-yl)-1-(6-pyrrolidin-1-yl-pyridin-3-ylmethyl)-1H-pyrazole-4-carboxylic acid (1-amino-isoquinolin-6-ylmethyl)-amide |
| 102 | 3-(3,5-Dimethyl-isoxazol-4-yl)-1-(6-pyrrolidin-1-yl-pyridin-3-ylmethyl)-1H-pyrazole-4-carboxylic acid (1-amino-isoquinolin-6-ylmethyl)-amide |
| 103 | 1-(6-Pyrrolidin-1-yl-pyridin-3-ylmethyl)-3-thiophen-3-yl-1H-pyrazole-4-carboxylic acid (1-amino-isoquinolin-6-ylmethyl)-amide |
| 104 | 3-Morpholin-4-yl-1-(6-pyrrolidin-1-yl-pyridin-3-ylmethyl)-1H-pyrazole-4-carboxylic acid (1-amino-isoquinolin-6-ylmethyl)-amide |

TABLE 11-continued

| Example Number | Name |
|---|---|
| 105 | 1-(4-{[(2,4-Dimethyl-thiazol-5-yl)-methyl-amino]-methyl}-benzyl)-1H-pyrazole-4-carboxylic acid (1H-pyrrolo[2,3-b]pyridin-5-ylmethyl)-amide |
| 106 | 1-[3-(3-Fluoro-pyridin-2-yloxy)-benzyl]-1H-pyrazole-4-carboxylic acid (1H-pyrrolo[2,3-b]pyridin-5-ylmethyl)-amide |
| 107 | 1-[4-(Pyridin-2-yloxy)-benzyl]-1H-pyrazole-4-carboxylic acid (1H-pyrrolo[2,3-b]pyridin-5-ylmethyl)-amide |
| 108 | 1-(3-Phenoxy-benzyl)-1H-pyrazole-4-carboxylic acid (1H-pyrrolo[2,3-b]pyridin-5-ylmethyl)-amide |
| 109 | 1-[4-(6-Fluoro-pyridin-2-yloxymethyl)-benzyl]-1H-pyrazole-4-carboxylic acid (1H-pyrrolo[2,3-b]pyridin-5-ylmethyl)-amide |
| 110 | 1-[4-(4-Methyl-pyrazol-1-ylmethyl)-benzyl]-3-trifluoromethyl-1H-pyrazole-4-carboxylic acid (2-methyl-1H-indol-5-ylmethyl)-amide |
| 111 | 1-[4-(4-Methyl-pyrazol-1-ylmethyl)-benzyl]-3-trifluoromethyl-1H-pyrazole-4-carboxylic acid (1H-indazol-5-ylmethyl)-amide |
| 112 | 1-[4-(4-Methyl-pyrazol-1-ylmethyl)-benzyl]-3-trifluoromethyl-1H-pyrazole-4-carboxylic acid (1H-indol-5-ylmethyl)-amide |
| 113 | 3-Amino-1-[4-(2-oxo-2H-pyridin-1-ylmethyl)-benzyl]-1H-pyrazole-4-carboxylic acid (1H-indazol-4-ylmethyl)-amide |
| 114 | 1-(6-Pyrrolidin-1-yl-pyridin-3-ylmethyl)-3-trifluoromethyl-1H-pyrazole-4-carboxylic acid (1H-pyrrolo[2,3-b]pyridin-5-ylmethyl)-amide |
| 115 | 1-[4-(4-Methyl-pyrazol-1-ylmethyl)-benzyl]-1H-[1,2,3]triazole-4-carboxylic acid (1H-pyrrolo[2,3-b]pyridin-5-ylmethyl)-amide |
| 116 | 1-[4-(4-Methyl-pyrazol-1-ylmethyl)-benzyl]-1H-[1,2,3]triazole-4-carboxylic acid (6-methyl-1H-pyrrolo[2,3-b]pyridin-5-ylmethyl)-amide |
| 117 | 1-[4-(4-Methyl-pyrazol-1-ylmethyl)-benzyl]-1H-pyrazole-4-carboxylic acid (1H-pyrrolo[2,3-b]pyridin-5-ylmethyl)-amide |
| 118 | 1-[4-(4-Methyl-pyrazol-1-ylmethyl)-benzyl]-1H-pyrazole-4-carboxylic acid (4,6-dimethyl-1H-pyrrolo[2,3-b]pyridin-5-ylmethyl)-amide |
| 119 | 1-[4-(4-Methyl-pyrazol-1-ylmethyl)-benzyl]-3-trifluoromethyl-1H-pyrazole-4-carboxylic acid (4,6-dimethyl-1H-pyrrolo[2,3-b]pyridin-5-ylmethyl)-amide |
| 120 | 3-Cyclopropyl-1-[4-(4-methyl-pyrazol-1-ylmethyl)-benzyl]-1H-pyrazole-4-carboxylic acid (1H-pyrrolo[2,3-b]pyridin-5-ylmethyl)-amide |
| 121 | 1-[4-(4-Methyl-pyrazol-1-ylmethyl)-benzyl]-3-trifluoromethyl-1H-pyrazole-4-carboxylic acid (1H-pyrrolo[2,3-b]pyridin-5-ylmethyl)-amide |
| 122 | 3-Cyclopropyl-1-[4-(4-methyl-pyrazol-1-ylmethyl)-benzyl]-1H-pyrazole-4-carboxylic acid (4,6-dimethyl-1H-pyrrolo[2,3-b]pyridin-5-ylmethyl)-amide |
| 123 | 1-[4-(4-Methyl-pyrazol-1-ylmethyl)-benzyl]-3-trifluoromethyl-1H-pyrazole-4-carboxylic acid (1H-indol-4-ylmethyl)-amide |
| 124 | 1-[4-(4-Methyl-pyrazol-1-ylmethyl)-benzyl]-3-trifluoromethyl-1H-pyrazole-4-carboxylic acid (1H-indazol-4-ylmethyl)-amide |
| 125 | 1-[4-(4-Methyl-pyrazol-1-ylmethyl)-benzyl]-3-trifluoromethyl-1H-pyrazole-4-carboxylic acid (1H-pyrrolo[2,3-b]pyridin-4-ylmethyl)-amide |
| 126 | 1-[4-(2-Oxo-pyridin-1-ylmethyl)-benzyl]-3-trifluoromethyl-1H-pyrazole-4-carboxylic acid (1H-indazol-4-ylmethyl)-amide |
| 127 | 1-[4-(4-Methyl-pyrazol-1-ylmethyl)-benzyl]-3-trifluoromethyl-1H-pyrazole-4-carboxylic acid (5-chloro-1H-indazol-3-ylmethyl)-amide |
| 128 | 1-(6-Pyrrolidin-1-yl-pyridin-3-ylmethyl)-3-trifluoromethyl-1H-pyrazole-4-carboxylic acid (5-chloro-1H-indazol-3-ylmethyl)-amide |
| 129 | 1-[4-(2-Oxo-2H-pyridin-1-ylmethyl)-benzyl]-3-trifluoromethyl-1H-pyrazole-4-carboxylic acid (5-chloro-1H-indazol-3-ylmethyl)-amide |

TABLE 12

NMR data of examples (solvent d6 DMSO)

| Example Number | Chemical Shift (ppm) |
|---|---|
| 28 | 0.94 (3H, t, J = 7.0 Hz), 1.98 (3H, s), 2.00 (3H, s), 3.93 (2H, s), 4.15 (2H, q, J = 6.9 Hz), 4.49 (2H, d, J = 6.0 Hz), 5.17 (2H, s), 6.70 (2H, s, br), 6.73 (1H, s), 6.84 (1H, d, J = 5.7 Hz), 7.03 (2H, d, J = 8.2 Hz), 7.12 (2H, d, J = 8.2 Hz), 7.22 (1H, s), 7.37 (1H, dd, J = 8.6, 1.6 Hz), 7.45-7.55 (2H, m), 7.75 (1H, d, J = 5.8 Hz), 8.12 (1H, d, J = 8.6 Hz), 8.48 (1H, t, J = 6.1 Hz) |
| 29 | 1.10 (3H, t, J = 6.9 Hz), 2.08 (3H, s), 4.11 (2H, s), 4.41 (2H, q, J = 6.9 Hz), 4.56 (2H, d, J = 6.0 Hz), 6.74 (1H, s), 7.19 (1H, d, J = 6.9 Hz), 7.26 (1H, s), 7.46-7.50 (3H, m), 7.59-7.70 (2H, m), 7.76 (1H, d, J = 1.7 Hz); 7.86-7.94 (2H, m), 8.48 (1H, d, J = 8.7 Hz), 8.57 (1H, t, J = 6.1 Hz), 8.79 (1H, s), 12.93 (1H, s). |
| 30 | 0.97 (3H, t, J = 6.9 Hz), 1.86-1.95 (4H, m), 2.02 (3H, s), 3.29-3.34 (4H, m), 3.79 (2H, s), 4.19 (2H, q, J = 6.9 Hz), 4.49 (2H, d, J = 6.0 Hz), 6.35 (1H, d, J = 8.6 Hz), 6.67-6.78 (3H, m), 6.84 (1H, d, J = 6.0 Hz), 7.14 (1H, dd, J = 8.6, 2.5 Hz), 7.37 (1H, dd, J = 8.6, 1.7 Hz), 7.51 (1H, |

TABLE 12-continued

NMR data of examples (solvent d6 DMSO)

| Example Number | Chemical Shift (ppm) |
|---|---|
| | s), 7.74 (1H, d, J = 5.8 Hz), 7.82-7.87 (1H, m), 8.12 (1H, d, J = 8.6 Hz), 8.47 (1H, t, J = 6.1 Hz). |
| 31 | 1.98 (3H, s), 4.53 (2H, d, J = 5.9 Hz), 5.21 (2H, s), 5.32 (2H, s), 6.85 (2H, s, br), 6.87 (1H, s), 6.88-7.18 (2H, m), 7.22-7.25 (3H, m), 7.39 (1H, dd, J = 8.6, 1.5 Hz), 7.51-7.54 (2H, m), 7.74 (1H, d, J = 5.9 Hz), 7.92 (1H, s), 8.15 (1H, d, J = 8.6 Hz), 8.26 (1H, s), 8.70 (1H, t, J = 5.9 Hz). |
| 33 | 1.98 (3H, s), 4.56 (2H, d, J = 6.2 Hz), 5.22 (2H, s), 5.62 (2H, s), 6.79 (2H, s), 6.86 (1H, d, J = 5.8 Hz), 7.19-7.23 (3H, m), 7.32 (2H, d, J = 8.2 Hz), 7.41 (1H, dd, J = 8.6,1.6 Hz), 7.52-7.54 (2H, m), 7.74 (1H, d, J = 5.8 Hz), 8.13 (1H, d, J = 8.6 Hz), 8.65 (1H, s), 9.18 (1H, t, J = 6.2 Hz). |
| 35 | 1.98 (3H, s), 4.56 (2H, d, J = 5.9 Hz), 5.23 (2H, s), 5.37 (2H, s), 7.15 (1H, d, J = 6.8 Hz), 7.19 ? 7.24 (3H, m), 7.28 ? 7.37 (5H, m), 7.54 (1H, s), 7.65 (1H, d, J = 8.6 Hz), 7.70 (3H, dd, J = 3.1 , 7.2 Hz), 7.76 (1H, s), 8.33 (1H, s), 8.47 (1H, d, J = 8.6 Hz), 8.62 (2H, s), 8.78 (1H, t, J = 6.0 Hz), 13.07 (1H, br s). |
| 36 | 1.99 (3H, s), 4.51 (2H, d, J = 5.8 Hz), 5.23 (2H, s), 5.42 (2H, s), 6.73 (2H, br.s), 6.85 (1H, d, J = 5.8 Hz), 7.20 (1H, s), 7.22 (2H, d, J = 7.2 Hz), 7.29 (2H, d, J = 8.1 Hz), 7.37 (1H, dd, J = 8.6, 1.1 Hz), 7.54 (2H, br.s), 7.77 (1H, d, J = 5.8 Hz), 8.14 (1H, d, J = 8.6 Hz), 8.47 (1H, s), 8.88 (1H, t, J = 5.9 Hz) |
| 37 | 1.99 (3H, s), 4.55 (2H, d, J = 5.8 Hz), 5.07 (2H, s), 5.22 (2H, s), 5.41 (2H, s), 7.15-7.29 (6H, m), 7.54 (1H, t, J = 0.9 Hz), 7.59-7.71 (2H, m), 7.75 (1H, s), 8.03 (1H, s), 8.46 (1H, d, J = 8.6 Hz), 8.53 (1H, t, J = 6.0 Hz), 8.64 (2H, s), 12.95 (1H, s). |
| 38 | 1.99 (3H, t, J = 0.7 Hz); 3.22 (3H, s); 4.59 (4H, d, J = 15.7 Hz); 5.23 (2H, s); 5.31 (2H, s); 7.16-7.29 (6H, m); 7.55 (1H, t, J = 0.9 Hz); 7.69 (2H, td, J = 3.0 & 8.7 Hz); 7.81 (1H, d, J = 1.6 Hz); 8.31 (1H, s); 8.56 (1H, d, J = 8.6 Hz); 8.64 (1H, t, J = 5.9 Hz); 9.12 (2H, s); 13.29 (1H, s). |
| 39 | 1.99 (3H, s); 4.59 (2H, d, J = 5.8 Hz); 5.24 (2H, s); 5.41 (2H, s); 7.15-7.34 (7H, m); 7.55 (1H, t, J = 0.9 Hz); 7.69 (2H, td, J = 2.4 & 8.6 Hz); 7.81 (1H, d, J = 1.7 Hz); 8.46 (1H, t, J = 1.2 Hz); 8.55 (1H, d, J = 8.6 Hz); 9.03-9.21 (3H, m); 13.25 (1H, s). |
| 40 | 1.99 (3H, s), 3.95 (2H, q, J = 11.3 Hz), 4.58 (2H, d, J = 5.8 Hz), 5.23 (2H, s), 5.35 (2H, s), 7.13-7.32 (6H, m), 7.54 (1H, s), 7.63-7.72 (2H, m), 7.78 (1H, s), 8.35 (1H, s), 8.52 (1H, d, J = 8.7 Hz), 8.86 (1H, s), 9.00 (2H, s), 13.05 (1H, br s). |
| 41 | 1.98 (3H, s), 2.92 (3H, s), 2.96 (3H, s), 4.52 (2H, d, J = 5.8 Hz), 5.22 (2H, s), 5.35 (2H, s), 6.74 (2H, s), 6.84 (1H, d, J = 5.7 Hz), 7.19 (2H, d, J = 8.2 Hz), 7.20-7.30 (3H, m), 7.36 (1H, dd, J = 8.6, 1.7 Hz), 7.49-7.55 (2H, m), 7.76 (1H, d, J = 5.8 Hz), 8.13 (1H, d, J = 8.6 Hz), 8.35 (1H, s), 9.08 (1H, t, J = 5.9 Hz). |
| 42 | 1.97 (3H, s), 4.59 (2H, d, J = 5.8 Hz), 5.22 (2H, s), 5.35 (2H, s), 7.16-7.23 (3H, m), 7.24 (1H, s), 7.30 (2H, d, J = 8.1 Hz), 7.47 (1H, dd, J = 5.0, 3.0 Hz), 7.50-7.57 (2H, m), 7.63-7.74 (2H, m), 7.81 (1H, s), 8.13 (1H, dd, J = 3.0, 1.2 Hz), 8.36 (1H, s), 8.56 (1H, d, J = 8.6 Hz), 8.85 (1H, t, J = 5.9 Hz), 9.12 (2H, brs), 13.31 (1H, brs) |
| 43 | 1.98 (3H, s), 4.51 (2H, d, J = 5.9 Hz), 5.22 (2H, s), 5.29 (2H, s), 6.80 (2H, s), 6.87 (1H, d, J = 6.0 Hz), 7.19 (2H, d, J = 8.2 Hz), 7.23 (1H, s), 7.27 (2H, d, J = 8.2 Hz), 7.39 (1H, dd, J 8.6, 1.8 Hz), 7.50-7.57 (2H, m), 7.76 (1H, d, J = 5.8 Hz), 8.14 (1H, d, J = 8.6 Hz), 8.36 (1H, s), 8.58 (1H, t, J = 6.0 Hz) |
| 44 | 2.07 (3H, s), 2.37 (3H, s), 4.50 (2H, d, J = 6.0 Hz), 5.06 (2H, s), 5.07 (2H, s), 6.23 (1H, dt, J = 1.4, 6.7 Hz), 6.36 (1H, s), 6.39 (1H, d, J = 9.2 Hz), 6.69 (2H, s, br), 6.79-6.94 (3H, m), 7.20-7.30 (2H, m), 7.35-7.46 (2H, m), 7.52 (1H, d, J = 1.6 Hz), 7.73-7.77 (2H, m), 8.12 (1H, d, J = 8.6 Hz), 8.21 (1H, t, J = 6.1 Hz). |
| 45 | 2.98 (2H, t, J = 7.2 Hz), 4.18 (4H, s), 4.30 (2H, t, J = 7.2 Hz), 4.52 (2H, t, J = 5.9 Hz), 6.59 (1H, dd, J = 8.2, 2.1 Hz), 6.67 (1H, d, J = 2.0 Hz), 6.69-6.77 (3H, m), 6.84 (1H, d, J = 5.8 Hz), 7.36 (1H, dd, J = 8.6, 1.6 Hz), 7.51 (1H, s), 7.76 (1H, d, J = 5.8 Hz), 7.92 (1H, s), 8.08-8.16 (2H, m), 8.68 (1H, t, J = 6.0 Hz). |
| 46 | 2.10 (3H, s), 2.47 (3H, s), 2.55 (3H, s), 3.87 (2H, s), 4.53 (2H, d, J = 5.9 Hz), 5.33 (2H, s), 6.83 (2H, br. s), 6.88 (1H, d, J = 5.8 Hz), 7.20 (2H, d, J = 8.2 Hz), 7.26 (2H, d, J = 8.2 Hz), 7.39 (1H, dd, J = 1.3, 8.6 Hz), 7.54 (1H, br. s), 7.74 (1H, d, J = 5.8 Hz), 7.93 (1H, d, J = 0.6 Hz), 8.14 (1H, d, J = 8.6 Hz), 8.27 (1H, d, 0.6 Hz), 8.70 (1H, t, J = 6.0 Hz) |
| 47 | 4.55 (2H, d, J = 5.9 Hz), 5.33 (2H, s), 6.74 (2H, s), 6.81-6.92 (3H, m), 7.05-7.19 (3H, m), 7.33-7.42 (3H, m), 7.55 (1H, d, J = 1.7 Hz), 7.76 (1H, d, J = 5.8 Hz), 7.83 (1H, dd, J = 7.4, 8.2 Hz), 7.95 (1H, d, J = 0.7 Hz), 8.15 (1H, d, J = 8.6 Hz), 8.24 (1H, d, J = 0.8 Hz), 8.71 (1H, t, J = 6.0 Hz). |

TABLE 12-continued

NMR data of examples (solvent d6 DMSO)

| Example Number | Chemical Shift (ppm) |
|---|---|
| 48 | 4.54 (2H, d, J = 5.9 Hz), 5.37 (2H, s), 6.73 (2H, s), 6.86 (1H, d, J = 5.8 Hz), 7.14-7.23 (3H, m), 7.31-7.41 (3H, m), 7.53 (1H, d, J = 1.7 Hz), 7.75 (1H, d, J = 5.8 Hz), 7.86 (1H, ddd, J = 1.5, 8.0, 10.7 Hz), 7.92 (1H, dd, J = 1.5, 4.9 Hz), 7.96 (1H, d, J = 0.7 Hz), 8.13 (1H, d, J = 8.6 Hz), 8.34 (1H, d, J = 0.8 Hz), 8.73 (1H, t, J = 6.0 Hz). |
| 49 | 4.61 (2H, d, J = 5.9 Hz), 5.37 (2H, s), 7.03 (1H, dt, J = 0.9, 8.3 Hz), 7.09-7.15 (3H, m), 7.22 (1H, d, J = 7.0 Hz), 7.30-7.37 (2H, m), 7.63-7.72 (2H, m), 7.80 (1H, dd, J = 1.6 Hz), 7.85 (1H, dd, J = 2.0, 7.2, 8.3 Hz), 7.97 (1H, d, J = 0.7 Hz), 8.12 (1H, ddd, J = 0.8, 2.0, 5.0 Hz), 8.35 (1H, d, J = 0.8 Hz), 8.51 (1H, d, J = 8.6 Hz), 8.87 (1H, t, J = 6.0 Hz), 8.95 (1H, s), 13.04 (1H, s). |
| 50 | 4.53 (2H, d, J = 5.9 Hz), 5.28 (2H, s), 5.36 (2H, s), 6.71-6.73 (3H, m), 6.80 (1H, dd, J = 1.5, 8.0 Hz), 6.85 (1H, d, J = 5.8 Hz), 7.29 (2H, d, J = 8.2 Hz), 7.37 (1H, dd, J = 1.6, 8.6 Hz), 7.44 (2H d, J = 8.2 Hz), 7.52 (1H, br. s), 7.75 (1H, d, J = 5.8 Hz), 7.89 (1H, td, J = 8.0, 8.6 Hz), 7.93 (1H, d, J = 0.5 Hz), 8.13 (1H, d, J = 8.6 Hz), 8.29 (1H, d, J = 0.5 Hz), 8.70 (1H, t, J = 6.0 Hz). |
| 51 | 1.91-1.94 (4H, s), 3.31-3.33 (4H, m), 4.61 (2H, d, J = 5.88 Hz), 5.51(2H, s), 6.13 (1H, d, J = 5.24 Hz), 6.17 (1H, s), 7.15 (1H, d, J = 6.72 Hz), 7.65 (1H, d, J = 8.49 Hz), 7.70 (1H, d, J = 6.72 Hz), 7.78 (1H, s), 7.99 (1H, d, J = 5.16 Hz), 8.16 (1H, s), 8.47 (1H, d, J = 8.60 Hz), 8.57 (2H, br, s), 9.22(1H, t, J = 5.76 Hz). |
| 52 | 4.53 (2H, d, J = 5.9 Hz), 5.52 (2H, s), 6.50 (1H, d, J = 1.3 Hz),6.70 (2H, s), 6.84 (1H, d, J = 5.7 Hz), 7.05 (1H, dd, J = 8.8, 1.5 Hz), 7.36 (1H, dd, J = 8.6, 1.7 Hz), 7.43 (1H, d, J = 8.8 Hz), 7.51 (2H, s), 7.75 (1H, d, J = 5.8 Hz), 7.96 (1H, d, J = 0.6 Hz), 8.12 (1H, d, J = 8.6 Hz), 8.29-8.24 (1H, m), 8.72 (1H, t, J = 6.0 Hz), 11.51 (1H, s) |
| 53 | 3.40 (0.5H, br s), 4.57 (2H, d, J = 6.0 Hz), 5.07 (2H, s), 5.29 (2H, s), 6.25 (1H, t, J = 2.0 Hz), 6.32 (2H, br s), 6.52 (0.5H, br s), 7.13 (2H, d, J = 8.2 Hz), 7.17 (2H, d, J = 8.0 Hz), 7.24 (1H, d, J = 6.9 Hz), 7.43 (1H, d, J = 1.6 Hz), 7.64 (1H, d, J = 7.0 Hz), 7.69 (1H, dd, J = 8.6, 1.3 Hz), 7.76 (1H, s), 7.79 (2H, s), 8.45 (1H, t, J = 5.7 Hz), 8.50 (1H, d, J = 8.6 Hz), 8.92 (2H, br s), 12.88 (1H, br s). |
| 54 | 1.91-1.95 (4H, s), 3.33-3.37 (4H, m), 4.53 (2H, d, J = 5.8 Hz), 5.38(2H, s), 6.36 (2H, d, J = 1.8 Hz), 6.76 (2H, s), 6.9(1H, d, J = 5.8 Hz), 7.39 (1H, d, J = 8.6 Hz), 7.55 (1H, s), 7.77(1H, d, J = 5.8 Hz), 8.03(1H, t, J = 2.8 Hz), 8.15 (1H, d, J = 8.6 Hz), 8.52 (1H, s), 8.93(1H, t, J = 5.4 Hz). |
| 55 | 1.31(3H,t,J = 7.0 Hz), 4.30(2H,q,J = 7.0 Hz), 4.60(2H,d,J = 5.8 Hz), 5.42(2H,s), 6.83(1H,d,J = 8.5 Hz), 7.21(1H,d,J = 7.0 Hz), 7.66-7.73(3H,m), 7.81(1H,s), 8.24(1H,d,J = 2.4 Hz), 8.51(2H,d,J = 8.8 Hz), 9.02(1H,t,J = 5.7 Hz), 9.11(2H,br s), 13.33(1H,s) |
| 56 | 2.53-2.68 (2H, m), 3.73 (2H, t, J = 7.4 Hz), 3.97 (2H, t, J = 12.9 Hz), 4.60 (2H, d, J = 5.9 Hz), 5.53 (2H, s), 6.64 (1H, d, J = 5.7 Hz), 6.87 (1H, brs), 7.19 (1H, d, J = 7.0 Hz), 7.65-7.75 (2H, m), 7.82 (1H, s), 8.07 (1H, d, J = 5.6 Hz), 8.58 (1H, d, J = 8.6 Hz), 8.71 (1H, s), 9.15 (2H, brs), 9.25 (1H, t, J = 5.9 Hz), 13.33 (1H, s). |
| 57 | 2.53-2.66 (2H, m), 3.73 (2H, t, J = 7.4 Hz), 3.96 (2H, t, J = 13.0 Hz), 4.58 (2H, d, J = 5.9 Hz), 5.41 (2H, s), 6.79-6.92 (1H, m), 7.20 (1H, d, J = 7.0 Hz), 7.64-7.73 (2H, m), 7.78-7.88 (2H, m), 8.24 (1H, d, J = 2.1 Hz), 8.53-8.62 (2H, m), 8.86-9.39 (3H, m), 13.27 (1H, s). |
| 58 | 1.08 (3H, d, J = 6.6 Hz), 1.61 (1H, br.s), 2.12 (1H, br.s), 2.98 (3H, br.s), 3.37-3.65 (2H, m), 4.59 (2H, d, J = 5.8 Hz), 5.36 (2H, s), 7.21 (1H, d, J = 7.0 Hz), 7.66 (1H, d, J = 7.2 Hz), 7.69 (1H, d, J = 8.8 Hz), 7.80 (1H, s), 8.13 (1H, d, J = 1.8 Hz), 8.50 (1H, br.s), 8.52 (1H, d, J = 8.6 Hz), 8.93 (1H, br.s), 9.02 (1H, br.s), 12.87 (1H, br.s) |
| 59 | 1.08 (3H, d, J = 6.4 Hz), 1.63 (1H, dd, J = 11.9, 8.8 Hz), 2.15 (1H, d, J = 5.8 Hz), 3.00-3.04 (3H, m), 3.43-3.50 (2H, m), 4.59 (2H, d, J = 5.8 Hz), 5.41 (2H, s), 7.21 (1H, d, J = 7.0 Hz), 7.67 (1H, d, J = 8.5 Hz), 7.69 (1H, dd, J = 8.8, 1.4 Hz), 7.81 (1H, s), 8.14 (1H, d, J = 1.7 Hz), 8.54 (2H, d, J = 8.7 Hz), 9.01 (1H, br.s), 9.08 (1H, br.s), 13.03 (1H, br.s) |
| 60 | 2.11-2.44 (2H, m), 3.55-3.65 (1H, m), 3.73-3.94 (3H, m), 4.59 (2H, d, J = 5.8 Hz), 5.36-5.65 (3H, m), 7.06 (1H, brd, J = 9.1 Hz), 7.19 (1H, d, J = 6.9 Hz), 7.64-7.74 (2H, m), 7.80 (1H, s), 7.94 (1H, brd, J = 9.1 Hz), 8.21 (1H, d, J = 1.9 Hz), 8.59 (1H, d, J = 8.6 Hz), 8.64 (1H, s), 8.91-9.45 (3H, m), 13.39 (1H, s). |
| 61 | 2.12-2.42 (2H, m), 3.55-3.65 (1H, m), 3.70-3.93 (3H, m), 4.59 (2H, d, J = 5.9 Hz), 5.36-5.64 (3H, m), 7.06 (1H, brd, J = 9.1 Hz), 7.19 (1H, d, J = 7.0 Hz), 7.64-7.74 (2H, m), 7.80 (1H, s), 7.92 (1H, brd, J = 9.1 Hz), 8.21 (1H, d, J = 2.0 Hz), 8.59 (1H, d, J = 8.6 Hz), 8.64 (1H, s), 8.91-9.45 (3H, m), 13.41 (1H, s). |
| 62 | 1.16 (3H, d, J = 6.3 Hz), 1.69-1.84 (1H, m), 1.95-2.22 (3H, m), 3.38-3.47 (1H, m), 3.68-3.75 (1H, m), 4.33 (1H, br.s), 4.59 (2H, d, J = 5.9 Hz), 5.44 (2H, s), 7.11 (1H, br.s), 7.19 (1H, d, J = 7.0 Hz), 7.64-7.73 (2H, m), 7.81 (1H, s), 7.92 (1H, br.d, J = 9.1 Hz), 8.12-8.20 (1H, |

TABLE 12-continued

NMR data of examples (solvent d6 DMSO)

| Example Number | Chemical Shift (ppm) |
|---|---|
| | m), 8.60 (1H, d, J = 8.6 Hz), 8.66 (1H, s), 8.91-9.45 (3H, m), 13.40 (1H, s), 13.85 (1H, brs). |
| 63 | 1.16 (3H, d, J = 6.3 Hz), 1.70-1.84 (1H, m), 1.96-2.21 (3H, m), 3.37-3.47 (1H, m), 3.68-3.75 (1H, m), 4.32 (1H, brs), 4.59 (2H, d, J = 5.8 Hz), 5.44 (2H, s), 7.10 (1H, brs), 7.19 (1H, d, J = 7.0 Hz), 7.64-7.73 (2H, m), 7.81 (1H, s), 7.92 (1H, br.d, J = 9.2 Hz), 8.13-8.20 (1H, m), 8.59 (1H, d, J = 8.7 Hz), 8.66 (1H, s), 8.91-9.45 (3H, m), 13.38 (1H, s), 13.85 (1H, br.s). |
| 64 | 1.90-1.93(4H,m), 3.45-3.49(4H,m), 4.59(2H,d,J = 5.8 Hz), 5.30(2H,s), 7.22(1H,d,J = 7.0 Hz), 7.65-7.70(2H,m), 7.80(1H,s), 8.39-8.45(3H,m), 8.50(1H,d,J = 8.6 Hz), 8.96-8.99(3H,m),13.02(1H,s). |
| 65 | 1.93-1.96 (4H, m), 3.41-3.44 (4H, m), 4.59 (2H, d, J = 5.8 Hz), 5.39 (2H, s), 7.22 (1H, d, J = 7.0 Hz), 7.65 (1H, d, J = 7.0 Hz), 7.69 (1H, dd, J = 8.6,1.3 Hz), 7.80 (1H, s), 7.93 (1H, d, J = 1.3 Hz), 8.19 (1H, d, J = 1.2 Hz), 8.47 (1H, s), 8.51 (1H, d, J = 8.6 Hz), 8.97-9.00 (3H, m), 12.90 (1H, s). |
| 66 | 1.21-1.32 (6H, m), 4.61 (2H, d, J = 5.8 Hz), 5.23 (1H, hept, J = 6.2 Hz), 5.48 (2H, s), 6.51-6.56 (1H, m), 6.81 (1H, dd, J = 1.5, 5.3 Hz), 7.21 (1H, d, J = 7.0 Hz), 7.64-7.74 (2H, m), 7.82 (1H, d, J = 1.7 Hz), 8.14 (1H, dd, J = 0.7, 5.2 Hz), 8.51-8.61 (2H, m), 8.88-9.12 (3H, m), 13.12 (1H, s). |
| 67 | 1.09 (3H, d, J = 6.6 Hz), 1.63 (1H, br.s), 2.14 (1H, br.s), 2.40 (3H, br.s), 3.02 (3H, br.s), 3.58 (1H, br.s), 3.66 (1H, br.s), 4.61 (2H, d, J = 5.8 Hz), 5.53 (2H, br.s), 6.52 (1H, br.s), 7.21 (1H, d, J = 7.04 Hz), 7.66 (1H, br.s), 7.69 (1H, dd, J = 9.7, 8.3 Hz), 7.82 (1H, s), 7.97 (1H, d, J = 5.9 Hz), 8.53 (1H, d, J = 8.7 Hz), 8.62 (1H, s), 8.97 (1H, br.s), 9.12 (1H, br.s), 12.94 (1H, br.s) |
| 68 | 1.09 (3H, d, J = 6.6 Hz), 1.64 (1H, br.s), 2.14 (1H, br.s), 3.01 (3H, br.s), 3.58 (1H, br.s), 3.67 (1H, br.s), 4.61 (2H, d, J = 5.9 Hz), 5.54 (2H, br.s), 6.54 (1H, br.s), 7.21 (1H, d, J = 7.04 Hz), 7.66 (1H, br.s), 7.70 (1H, dd, J = 9.0, 7.7 Hz), 7.82 (1H, s), 7.97 (1H, d, J = 5.6 Hz), 8.54 (1H, d, J = 8.4 Hz), 8.63 (1H, s), 8.98 (1H, br.s), 9.13 (1H, br.s), 12.95 (1H, br.s) (isoquinoline NH2 obscured by solvent) |
| 69 | 1.76-1.90 (1H, m), 2.02-2.14 (1H, m), 2.44-2.52 (1H, m), 3.29-3.54 (5H, m), 3.60-3.67 (2H, m), 4.59 (2H, d, J = 6.0 Hz), 5.44 (2H, s), 7.05 (1H, br.s), 7.20 (1H, d, J = 6.9 Hz), 7.64-7.73 (2H, m), 7.81 (1H, s), 7.91 (1H, d, J = 9.0 Hz), 8.15 (1H, d, J = 1.8 Hz), 8.59 (1H, d, J = 8.7 Hz), 8.64 (1H, s), 8.96-9.41 (3H, m), 13.34 (1H, br.s), 13.70 (1H, br.s). |
| 70 | 1.75-1.89 (1H, m), 2.02-2.14 (1H, m), 2.44-2.52 (1H, m), 3.29-3.54 (5H, m), 3.61-3.68 (2H, m), 4.59 (2H, d, J = 6.0 Hz), 5.43 (2H, s), 7.04 (1H, brs), 7.20 (1H, d, J = 7.0 Hz), 7.64-7.73 (2H, m), 7.81 (1H, s), 7.91 (1H, d, J = 9.1 Hz), 8.15 (1H, d, J = 1.8 Hz), 8.58 (1H, d, J = 8.6 Hz), 8.64 (1H, s), 8.96-9.41 (3H, m), 13.33 (1H, brs), 13.70 (1H, brs). |
| 71 | 0.95 (3H, t, J = 7.4 Hz), 1.67-1.76 (2H, m), 4.21 (2H, t, J = 6.7 Hz), 4.60 (2H, d, J = 5.9 Hz), 5.42 (2H, s), 6.85 (1H, d, J = 8.6 Hz), 7.22 (1H, d, J = 7.0 Hz), 7.64-7.76 (3H, m), 7.81 (1H, s), 8.24 (1H, d, J = 2.0 Hz), 8.48-8.56 (2H, m), 9.03 (3H, s), 13.03 (1H, s). |
| 72 | 0.89 (3H, t, J = 7.4 Hz), 1.24 (3H, d, J = 6.2 Hz), 1.53-1.71 (2H, m), 4.60 (2H, d, J = 5.3 Hz), 5.08 (1H, q, J = 6.2 Hz), 5.41 (2H, s), 6.80 (1H, d, J = 9.0 Hz), 7.22 (1H, d, J = 7.0 Hz), 7.64-7.73 (3H, m), 7.81 (1H, s), 8.22 (1H, d, J = 2.1 Hz), 8.49-8.57 (2H, m), 8.84-9.18 (3H, m), 13.02 (1H, s). |
| 73 | 1.87 (4H, q, J = 6.6 Hz), 3.53 (4H, q, J = 6.3 Hz), 4.59 (2H, d, J = 5.8 Hz), 5.32 (2H, s), 7.21 (1H, d, J = 7.0 Hz), 7.46 (1H, dd, J = 1.7, 15.8 Hz), 7.65-7.70 (2H, m), 7.81 (1H, s), 8.00 (1H, s), 8.43 (1H, s), 8.50 (1H, d, J = 8.7 Hz), 8.98 (2H, t, J = 5.7 Hz), 12.93 (1H, s). |
| 74 | 1.37 (3H, t, J = 6.9 Hz), 4.16 (2H, q, J = 6.9 Hz), 4.59 (2H, d, J = 5.8 Hz), 5.52 (2H, s), 7.20 (1H, d, J = 6.9 Hz), 7.65-7.70 (3H, m), 7.80 (1H, s), 8.00 (1H, d, J = 1.7 Hz), 8.50 (2H, d, J = 7.5 Hz), 8.91 (1H, br.s), 8.98 (1H, t, J = 5.7 Hz), 12.87 (1H, s). |
| 75 | 1.34 (3H, t, J = 7.0 Hz), 4.00 (2H, q, J = 7.1 Hz), 4.59 (2H, d, J = 5.8 Hz), 5.44 (2H, s), 7.20 (1H, d, J = 7.0 Hz), 7.65-7.75 (3H, m), 7.80 (1H, s), 8.07 (1H, d, J = 1.7 Hz), 8.49 (2H, d, J = 10.7 Hz), 8.91 (1H, br.s), 8.98 (1H, t, J = 5.8 Hz), 12.92 (1H, s). |
| 76 | 4.58 (2H, d, J = 5.8 Hz), 5.33 (2H, s), 5.43 (2H,s), 6.26 (1H, t, J = 2.0 Hz), 7.18-7.23 (3H, m), 7.31 (2H,d, J = 8.1 Hz), 7.45 (1H, d, J = 1.7 Hz), 7.68-7.70 (2H, m), 7.80 (1H, s), 7.82 (1H, d, J = 2.1 Hz), 8.53-8.56 (2H,m), 9.04-9.07 (3H, m), 13.18 (1H, s) |
| 77 | 4.58 (2H, d, J = 5.8 Hz), 5.33 (2H, s), 5.43 (2H, s), 6.26 (1H, t, J = 2.0 Hz), 7.18-7.23 (3H, m), 7.31 (2H, d, J = 8.1 Hz), 7.45 (1H, d, J = 1.7 Hz), 7.68-7.70 (2H, m), 7.80 (1H, s), 7.82 (1H, d, J = 2.1 Hz), 8.53-8.56 (2H, m), 9.04-9.07 (3H, m), 13.18 (1H, s). |
| 78 | 4.58 (2H, d, J = 5.8 Hz), 5.33 (2H, s), 5.43 (2H, s), 6.26 (1H, t, J = 2.0 Hz), 7.18-7.23 (3H, m), 7.31 (2H, d, J = 8.1 Hz), 7.45 (1H, d, J = |

TABLE 12-continued

NMR data of examples (solvent d6 DMSO)

| Example Number | Chemical Shift (ppm) |
|---|---|
| | 1.7 Hz), 7.68-7.70 (2H, m), 7.80 (1H, s), 7.82 (1H, d, J = 2.1 Hz), 8.53-8.56 (2H, m), 9.04-9.07 (3H,m), 13.18 (1H, s). |
| 80 | 1.30 (3H, t, J = 7.0 Hz), 4.30 (2H, q, J = 7.0 Hz), 4.61 (2H, d, J = 5.9 Hz), 5.50 (2H, s), 6.59-6.65 (1H, m), 6.85 (1H, dd, J = 1.4, 5.3 Hz), 7.22 (1H, d, J = 7.0 Hz), 7.71 (2H, td, J = 3.4, 8.8 Hz), 7.83 (1H, d, J = 1.6 Hz), 8.16 (1H, dd, J = 0.7, 5.2 Hz), 8.53-8.63 (2H, m), 8.80-9.20 (3H, m), 13.22 (1H, s). |
| 86 | 0.72-0.80 (2H, m), 0.80-0.87 (2H, m), 2.55-2.63 (1H, m,), 3.02 (3H, s), 3.48 (2H, t, J = 5.8 Hz), 3.57 (3H, s), 3.68 (2H, t, J = 5.8 Hz), 4.58 (2H, d, J = 5.9 Hz), 5.07 (2H, s), 6.65 (1H, d, J = 6.7 Hz), 7.23 (1H, d, J = 6.9 Hz), 7.46 (1H, d, J = 8.6 Hz), 7.66 (1H, d, J = 7.0 Hz), 7.70 (1H, d, J = 8.7 Hz), 7.80 (1H, s), 8.07 (1H, d, J = 2.2 Hz), 8.12 (1H, s), 8.53 (1H, d, J = 8.6 Hz), 8.59 (1H, t, J = 6.0 Hz), 8.99 (2H, br s), 13.06 (1H, br s). |
| 87 | 0.74-0.79 (2H, m), 0.79-0.87 (2H, m), 2.52-2.63 (3H, m), 3.60 (2H, t, J = 7.3 Hz), 3.82 (2H, t, J = 13.3 Hz), 4.57 (2H, d, J = 5.9 Hz), 5.10 (2H, s), 6.56 (1H, d, J = 8.5 Hz), 7.18 (1H, d, J = 6.9 Hz), 7.53 (1H, dd, J = 2.4, 8.6 Hz), 7.59-7.70 (2H, m), 7.76 (1H, s), 8.06-8.16 (2H, m), 8.47 (1H, d, J = 8.6 Hz), 8.53-8.89 (3H, m), 13.02 (1H, s). |
| 88 | 0.73-0.77 (2H, m), 0.82-0.93 (2H, m), 1.91 (4H, t, J = 6.5 Hz), 3.33 (4H, t, J = 6.4 Hz), 3.75 (3H, s), 4.59 (2H, d, J = 5.8 Hz), 5.10 (2H, s), 5.68 (1H, s), 5.82 (1H, s), 7.24 (1H, d, J = 6.8 Hz), 7.65 (1H, br.s), 7.71 (1H, dd, J = 8.8, 1.4 Hz), 7.81 (1H, s), 8.18 (1H, s), 8.52 (1H, d, J = 8.7 Hz), 8.62 (1H, t, J = 5.5 Hz), 8.96 (2H, br.s), 12.91 (1H, s) |
| 89 | 0.71-0.75 (2H, m), 0.80-0.85 (2H, m), 2.02 (4H, s), 2.57-2.63 (1H, m), 3.53 (4H, br.s), 3.99 (3H, s), 4.59 (2H, d, J = 5.8 Hz), 5.11 (2H, s), 6.34 (1H, s), 7.22 (1H, d, J = 7.0 Hz), 7.66 (1H, d, J = 6.9 Hz), 7.71 (1H, d, J = 8.7 Hz), 7.82 (2H, d, J = 14.9 Hz), 8.16 (1H, s), 8.54 (1H, d, J = 8.6 Hz), 8.63 (1H, br.s), 9.01 (2H, br.s), 12.81 (1H, br.s), 13.05 (1H, br.s) |
| 90 | 0.70-0.80 (2H, m), 0.77-0.88 (2H, m), 1.95-2.05 (4H, m), 2.58 (1H, ddd, J = 3.2, 5.2, 8.3 Hz), 3.52-3.94 (4H, m), 4.58 (2H, d, J = 5.8 Hz), 5.22 (2H, s), 7.08 (1H, d, J = 9.4 Hz), 7.17-7.24 (1H, m), 7.64-7.74 (2H, m), 7.77-7.90 (2H, m), 7.98-8.04 (1H, m), 8.28 (1H, s), 8.59 (1H, d, J = 8.6 Hz), 8.73 (1H, t, J = 5.9 Hz), 9.18 (2H, s), 13.40 (1H, s), 13.82 (1H, s). |
| 91 | 0.72-0.84 (4H, m), 2.55-2.62 (1H, m), 4.57 (2H,d, J = 5.7 Hz), 5.22 (2H, s), 5.60 (2H,s), 7.16-7.24 (3H,m), 7.28 (1H, d, J = 8.1 Hz), 7.66-7.71 (2H, m), 7.74 (1H,s), 7.80 (1H, s), 8.20 (2H, d, J = 6.6 Hz), 8.56 (1H, d, J = 8.6 Hz), 8.64 (1H, t, J = 5.8 Hz), 9.12 (2H, br.s), 13.32 (1H,s). |
| 92 | 0.73-0.76 (2H, m), 0.77-0.82 (2H, m), 2.59 (1H, tt, J = 5.1, 8.3 Hz), 4.59 (2H, d, J = 5.8 Hz), 4.99 (2H, q, J = 9.1 Hz), 5.24 (2H, s), 7.01 (1H, dd, J = 0.7, 8.5 Hz), 7.23 (1H, d, J = 7.0 Hz), 7.64-7.76 (3H, m), 7.81 (1H, d, J = 1.6 Hz), 8.16-8.25 (2H, m), 8.55 (1H, d, J = 8.6 Hz), 8.65 (1H, t, J = 5.9 Hz), 9.09 (2H, s), 13.24 (1H, s). |
| 93 | 0.74-0.78 (2H, m), 0.80-0.86 (2H, m), 2.55-2.62 (1H, m), 4.58 (2H, d, J = 5.9 Hz), 5.23 (2H, s), 7.03 (1H, dd, J = 0.7, 8.5 Hz), 7.09-7.14 (2H, m), 7.21 (2H, m), 7.38-7.45 (2H, m), 7.66 (1H, d, J = 7.2 Hz), 7.70 (1H, dd, J = 1.7, 8.7 Hz), 7.76 (1H, dd, J = 2.5, 8.5 Hz), 7.80 (1H, d, J = 1.6 Hz), 8.12 (1H, dd, J = 0.8, 2.5 Hz), 8.20 (1H, s), 8.54 (1H, d, J = 8.6 Hz), 8.62 (1H, t, J = 5.9 Hz), 9.04 (2H, s, br), 13.13 (1H, s) |
| 94 | 0.75-0.77 (2H, m), 0.82-0.85 (2H, m), 1.33 (3H, t, J = 7.1 Hz), 2.54-2.60 (1H, m), 4.38 (2H, q, J = 7.0 Hz), 4.58 (2H, d, J = 5.8 Hz), 5.21 (2H, s), 7.23 (1H, d, J = 7.0 Hz), 7.65 (1H, d, J = 6.9 Hz), 7.69 (1H, q, J = 8.6 Hz), 7.85 (1H, d, J = 2.0 Hz), 8.11 (1H, d, J = 2.0 Hz), 8.16 (1H, s), 8.49 (1H, d, J = 8.7 Hz), 8.58 (1H, t, J = 5.92 Hz), 8.90 (2H, br. s), 12.89 (1H, s). |
| 95 | 0.76-0.77 (2H, m), 0.81-0.85 (2H, m), 1..11 (6H, t, J = 6.97 Hz), 2.55-2.61 (1H, m), 3.46 (4H, t, J = 7.0 Hz), 4.58 (2H, d, J = 5.85 Hz), 5.11 (2H, s), 7.04 (1H, s), 7.17 (1H, s), 7.22(1H, t, J = 6.92 Hz), 7.29 (1H, s), 7.65-7.71 (2H, m), 7.81 (1H, d, J = 4.89 Hz), 7.93 (1H, d, J = 1.52 Hz), 8.15 (1H, s), 8.52 (1H, d, J = 8.64 Hz), 8.61 (1H, t, J = 5.92 Hz), 9.02 (2H, br, s), 13.08 (1H, s). |
| 96 | 0.74-0.79 (2H, m), 0.8-0.88 (2H, m), 1.11 (6H, t, J = 6.9 Hz), 2.59 (1H, m), 3.55 (4H, d, J = 15.4 Hz), 4.58 (2H, d, J = 5.9 Hz), 5.11 (2H, s, br), 6.5-7.1 (0.5, s, br), 7.22 (1H, d, J = 7.0 Hz), 7.54 (0.5H, s, br), 7.66 (1H, d, J = 7.0 Hz), 7.70 (1H, dd, J = 1.7, 8.6 Hz), 7.80 (1H, d, J = 1.7 Hz), 8.02 (1H, d, J = 2.3 Hz), 8.17 (1H, s), 8.54 (1H, d, J = 8.6 Hz), 8.63 (1H, t, J = 6.0 Hz), 9.04 (2H, s, br), 13.12 (1H, s, br) |
| 97 | 0.75-0.77 (2H, m), 0.82-0.84 (2H, m), 1.85-1.88 (4H, m), 2.55-2.60 (1H, m), 3.61 (4H, t, J = 6.6 Hz), 4.58 (2H, d, J = 5.8 Hz), 5.12 (2H, s), 7.22 (1H, d, J = 7.0 Hz), 7.59-7.71 (2H, m), 7.80 (1H, s), 8.04 (1H, d, J = 1.9 Hz), 8.19 (1H, s), 8.55 (1H, d, J = 8.6 Hz), 8.58 (1H, t, J = 5.7 Hz), 9.10 (2H, br.s), 13.53 (1H, s). |

TABLE 12-continued

NMR data of examples (solvent d6 DMSO)

| Example Number | Chemical Shift (ppm) |
|---|---|
| 98 | 1.31 (3H, t, J = 7.0 Hz), 4.29 (2H, q, J = 7.0 Hz), 4.56 (2H, d, J = 5.8 Hz), 5.05 (2H, s), 5.41 (2H, br.s), 6.80 (1H, d, J = 8.5 Hz), 7.23 (1H, d, J = 7.0 Hz), 7.60-7.71 (3H, m), 7.79 (1H, s), 8.02 (1H, s), 8.14 (1H, d, J = 2.0 Hz), 8.50-8.57 (2H, m), 9.01 (2H, s), 13.06 (1H, s). |
| 99 | 1.95-2.07 (4H, m), 3.52-3.58 (4H, m), 4.56 (2H, d, J = 5.8 Hz), 5.13 (2H, s), 7.11 (1H, d, J = 9.4 Hz), 7.20 (1H, d, J = 7.0 Hz), 7.64-7.71 (2H, m), 7.79 (1H, s), 7.89 (1H, dd, J = 9.4, 2.1 Hz), 8.02 (1H, d, J = 1.8 Hz), 8.23 (1H, s), 8.59 (1H, d, J = 8.6 Hz), 8.82 (1H, t, J = 6.0 Hz), 9.19 (2H, brs), 13.41 (1H, s), 13.86 (1H, brs). |
| 100 | 1.94 (4H, m), 2.71 (6H, s), 3.38 (4H, m), 4.58 (2H, d, J = 5.9 Hz), 5.04 (2H, s), 6.57 (1H, s, br), 7.21 (1H, d, J = 7.0 Hz), 7.57 (1H, s, br), 7.63-7.71 (2H, m), 7.75-7.80 (1H, m), 8.00-8.08 (2H, m), 8.45 (1H, t, J = 6.0 Hz), 8.51 (1H, d, J = 8.6 Hz), 8.95 (2H, s, br), 13.05 (1H, s, br) |
| 101 | 1.87-1.96 (4H, m), 2.50-2.66 (2H, m), 2.70 (3H, s), 3.30-3.43 (5H, m), 3.69 (1H, dd, J = 9.5, 8.5 Hz), 3.97-4.07 (1H, m), 4.49 (2H, d, J = 5.9 Hz), 5.12 (2H, s), 6.43 (1H, d, J = 8.7 Hz), 6.80 (2H, s), 6.86 (1H, d, J = 6.0 Hz), 7.36 (1H, dd, J = 8.6, 1.7 Hz), 7.47 (1H, dd, J = 8.7, 2.4 Hz), 7.51 (1H, s), 7.75 (1H, d, J = 5.8 Hz), 8.10 (1H, d, J = 2.5 Hz), 8.13 (1H, d, J = 8.6 Hz), 8.17 (1H, s), 8.59 (1H, t, J = 6.0 Hz) |
| 105 | 2.09 (3H, s), 2.46 (3H, s), 2.55 (3H, s), 3.86 (2H, s), 4.47 (2H, d, J = 5.8 Hz), 5.31 (2H, s), 6.40 (1H, dd, J = 1.9, 3.4 Hz), 7.18 (2H, d, J = 8.1 Hz), 7.25 (2H, d, J = 8.1 Hz), 7.43 (1H, dd, J = 2.7, 3.2 Hz), 7.85 (1H, d, J = 1.6 Hz), 7.88 (1H, d, J = 0.6 Hz), 8.17 (1H, d, J = 2.0 Hz), 8.24 (1H, d, J = 0.6 Hz), 8.59 (1H, t, J = 5.9 Hz), 11.6 Hz (1H, s) |
| 106 | 4.48 (2H, d, J = 5.8 Hz), 5.36 (2H, s), 6.41 (1H, dd, J = 1.9, 3.4 Hz), 7.12-7.24 (3H, m), 7.26-7.37 (2H, m), 7.44 (1H, dd, J = 2.5, 3.4 Hz), 7.78-7.99 (4H, m), 8.18 (1H, d, J = 2.0 Hz), 8.30 (1H, d, J = 0.7 Hz), 8.62 (1H, t, J = 5.9 Hz), 11.57 (1H, s). |
| 107 | 4.48 (2H, d, J = 5.8 Hz), 5.35 (2H, s), 6.41 (1H, dd, J = 1.9, 3.4 Hz), 7.02 (1H, dt, J = 0.9, 8.3 Hz), 7.06-7.15 (3H, m), 7.27-7.36 (2H, m), 7.44 (1H, dd, J = 2.5, 3.4 Hz), 7.81-7.88 (2H, m), 7.91 (1H, d, J = 0.7 Hz), 8.12 (1H, ddd, J = 0.8, 2.0 , 4.9 Hz), 8.18 (1H, d, J = 2.1 Hz), 8.30 (1H, d, J = 0.8 Hz), 8.62 (1H, t, J = 5.9 Hz), 11.56 (1H, s). |
| 108 | 4.48 (2H, d, J = 5.8 Hz), 5.33 (2H, s), 6.41 (1H, dd, J = 1.9, 3.4 Hz); 6.90 (2H, ddq, J = 1.2, 2.5, 4.6 Hz), 6.99 (3H, dq, J = 1.3, 7.9 Hz), 7.08-7.19 (1H, m), 7.28-7.47 (4H, m), 7.81-7.92 (2H, m), 8.18 (1H, d, J = 2.0 Hz), 8.26 (1H, d, J = 0.7 Hz), 8.61 (1H, t, J = 5.9 Hz), 11.57 (1H, s). |
| 109 | 4.47 (2H, d, J = 5.9 Hz), 5.23 (2H, s), 5.34 (2H, s), 6.40 (1H, dd, J = 1.9, 3.4 Hz), 6.78 (1H, dd, J = 2.2, 7.8 Hz), 6.79 (1H, dd, J = 1.5, 8.0 Hz), 7.26 (2H, d, J = 8.1 Hz), 7.41-7.44 (3H, m), 7.84-7.85 (1H, m), 7.87-7.91 (2H, m), 8.17 (1H, d, J = 2.0 Hz), 8.25 (1H, s), 8.59 (1H, t, J = 5.9 Hz), 11.55 (1H, br. s) |
| 110 | 1.98 (3H, s), 2.36 (3H, s), 4.40 (2H, d, J = 5.8 Hz), 5.22 (2H, s), 5.39 (2H, s), 6.06 (1H, d, J = 0.9 Hz), 6.90 (1H, dd, J = 8.2, 1.5 Hz), 7.18 (3H, m), 7.23 (1H, s), 7.29-7.26 (3H, m), 7.53 (1H, s), 8.41 (1H, d, J = 0.7 Hz), 8.70 (1H, t, J = 5.8 Hz), 11.85 (1H, br s). |
| 111 | 1.98 (3H, s), 4.46 (2H, d, J = 5.9 Hz), 5.22 (2H, s), 5.40 (2H, s), 7.19 (2H, d, J = 8.2 Hz), 7.23 (1H, s), 7.30-7.27 (3H, m), 7.49 (1H, d, J = 8.6 Hz), 7.54 (1H, s), 7.64 (1H, s), 8.03 (1H, s), 8.43 (1H, s), 8.81 (1H, t, J = 5.8 Hz), 13.03 (1H, br s). |
| 112 | 1.98 (3H, s), 4.42 (2H, d, J = 5.8 Hz), 5.22 (2H, s), 5.39 (2H, s), 6.37-6.38 (1H, m), 7.02 (1H, dd, J = 8.4, 1.6 Hz), 7.19 (2H, d, J = 8.2 Hz), 7.23 (1H, s), 7.27 (2H, d, J = 8.1 Hz), 7.31-7.34 (2H, m), 7.44 (1H, s), 7.54 (1H, s), 8.42 (1H, d, J = 0.7 Hz), 8.73 (1H, t, J = 5.8 Hz), 11.05 (1H, br.s). |
| 113 | 4.67 (2H, d, J = 5.8 Hz), 5.03 (2H, s), 5.06 (2H,s), 5.40 (2H, s), 6.20-6.24 (1H,m), 6.39 (1H, d, J = 9.1 Hz), 6.98 (1H, d, J = 6.9 Hz), 7.19 (2H, d, J = 8.1 Hz), 7.25-7.29 (3H, m), 7.38-7.42 (2H, m), 7.75 (1H, dd, J = 6.7, 1.9 Hz), 7.99 (1H, s), 8.15 (1H, s), 8.37 (1H, t, J = 5.8 Hz), 13.06 (1H, s). |
| 114 | 1.90-1.93 (4H, m), 3.33-3.36 (4H, m), 4.45 (2H, d, J = 5.7 Hz), 5.24 (2H, s), 6.40-6.44 (2H, m), 7.44-7.47 (2H, m), 7.84 (1H, d, J = 1.6 Hz), 8.12 (1H, d, J = 1.7 Hz), 8.16 (1H, d, J = 1.9 Hz), 8.33 (1H, s), 8.73-8.74 (1H, m), 11.57 (1H, s). |
| 115 | 1.98 (3H, s), 4.50 (2H, d, J = 6.2 Hz), 5.21 (2H, s), 5.60 (2H, s), 6.39 (1H, dd, J = 1.9, 3.4 Hz), 7.15-7.24 (3H, m), 7.25-7.32 (2H, m), 7.43 (1H, dd, J = 2.5, 3.4 Hz), 7.51 (1H, t, J = 0.9 Hz), 7.87 (1H, d, J = 2.1 Hz), 8.19 (1H, d, J = 2.0 Hz), 8.61 (1H, s), 9.08 (1H, t, J = 6.2 Hz), 11.54 (1H, s). |
| 116 | 1.98 (3H, t, J = 0.7 Hz), 2.53 (3H, s), 4.50 (2H, d, J = 5.9 Hz), 5.22 (2H, s), 5.61 (2H, s), 6.33 (1H, dd, J = 1.9, 3.4 Hz), 7.16-7.24 (3H, m), 7.28-7.34 (3H, m), 7.49-7.56 (1H, m), 7.75 (1H, s), 8.63 (1H, s), 8.94 (1H, t, J = 6.0 Hz), 11.36 (1H, s). |

TABLE 12-continued

NMR data of examples (solvent d6 DMSO)

| Example Number | Chemical Shift (ppm) |
|---|---|
| 117 | 1.98 (3H, t, J = 0.7 Hz), 4.47 (2H, d, J = 5.8 Hz), 5.20 (2H, s), 5.30 (2H, s), 6.40 (1H, dd, J = 1.9, 3.4 Hz), 7.12-7.26 (5H, m), 7.43 (1H, dd, J = 2.5, 3.4 Hz), 7.51 (1H, t, J = 0.9 Hz), 7.82-7.92 (2H, m), 8.17 (1H, d, J = 2.0 Hz), 8.23 (1H, d, J = 0.7 Hz), 8.57 (1H, t, J = 5.9 Hz), 11.55 (1H, s). |
| 118 | 1.97 (3H, s), 2.49 (3H, s), 2.54 (3H, s), 4.51 (2H, d, J = 4.6 Hz), 5.19 (2H, s), 5.27 (2H, s), 6.43 (1H, dd, J = 3.5, 1.9 Hz), 7.12-7.24 (5H, m), 7.28 (1H, dd, J = 3.5, 2.4 Hz), 7.50 (1H, s), 7.86 (1H, s), 7.97 (1H, t, J = 4.6 Hz), 8.22 (1H, s), 11.32 (1H, s). |
| 119 | 2.03 (3H, s), 2.57 (3H, s), 2.60 (3H, s), 4.56 (2H, d, J = 4.6 Hz), 5.25 (2H, s), 5.41 (2H, s), 6.49-6.50 (1H, m), 7.22 (2H, d, J = 8.1 Hz), 7.27-7.30 (3H, m), 7.35 (1H, t, J = 5.9 Hz), 7.57(1H, s), 8.29 (1H, t, J = 4.5 Hz), 8.42 (1H, s), 11.39 (1H, s). |
| 120 | 0.71-0.77 (2H, m), 0.79-0.84 (2H, m), 1.98 (3H,s), 2.55-2.67 (1H, m), 4.45 (2H, d, J = 5.7 Hz), 5.17 (2H, s), 5.20 (2H, s), 6.40 (1H, d, J = 3.3 Hz), 7.16 (4H, s), 7.22 (1H, s), 7.44 (1H, d, J = 3.3 Hz), 7.51 (1H, s), 7.85 (1H, s), 8.08 (1H, s), 8.17 (1H, d, J = 1.3 Hz), 8.36 (1H, t, J = 5.7 Hz), 11.56 (1H, s) |
| 121 | 1.98 (3H,s), 4.55 (2H, d, J = 5.7 Hz), 5.21 (2H, s), 5.39 (2H, s), 6.40-6.41 (1H, m), 7.19 (2H, d, J = 8.1 Hz), 7.23 (1H, s), 7.26 (2H, d, J = 8.0 Hz), 7.45 (1H, t, J = 2.9 Hz), 7.52 (1H, s), 7.85 (1H, d, J = 1.6 Hz), 8.17 (1H, d, J = 1.9 Hz), 8.40 (1H, s), 8.75 (1H, t, J = 5.6 Hz), 11.57 (1H, s). |
| 123 | (1.98 (3H, s), 4.63 (2H, d, J = 5.8 Hz), 5.21 (2H, s), 5.39 (2H, s), 6.51 (1H, m), 6.90 (1H, d, J = 7.0 Hz), 7.03 (1H, dd, J = 8.0, 7.4 Hz), 7.18 (2H, d, J = 8.2 Hz), 7.23 (1H, s), 7.33-7.26 (4H, m), 7.53 (1H, s), 8.41 (1H, d, J = 0.6 Hz), 8.74 (1H, t, J = 5.8 Hz), 11.14 (1H, br s). |
| 124 | 1.98 (3H, s), 4.69 (2H, d, J = 5.8 Hz), 5.22 (2H, s), 5.40 (2H, s), 7.00 (1H, d, J = 7.0 Hz), 7.18 (2H, d, J = 8.2 Hz), 7.23 (1H, s), 7.30-7.26 (3H, m), 7.44 (1H, d, J = 8.3 Hz), 7.54 (1H, s), 8.14 (1H, d, J = 0.6 Hz), 8.43 (1H, s), 8.89 (1H, t, J = 5.9 Hz), 13.11 (1H, br s). |
| 125 | 2.33 (3H, s), 4.66 (2H, d, J = 5.8 Hz), 5.22 (2H, s), 5.41 (2H, s), 6.54-6.55 (1H, m), 6.95 (1H, d, J = 4.8 Hz), 7.20 (2H, d, J = 8.1 Hz), 7.23 (1H, s), 7.29 (2H, d, J = 8.2 Hz), 7.44 (1H, t, J = 3.0 Hz), 7.53 (1H, s), 8.15 (1H,d, J = 4.8 Hz), 8.45 (1H, s), 8.88 (1H, t, J = 5.9 Hz), 11.64 (1H, s). |
| 126 | 4.69 (2H, d, J = 5.8 Hz), 5.07 (2H, s), 5.40 (2H, s), 6.21-6.24 (1H, m), 6.39 (1H, d, J = 8.9 Hz), 7.00 (1H, d, J = 6.9 Hz), 7.26-7.30 (5H, m), 7.39-7.44 (2H, m), 7.77 (1H, q, J = 6.6 Hz), 8.14 (1H, s), 8.43 (1H, s), 8.89 (1H, t, J = 5.8 Hz), 13.11 (1H, s). |
| 127 | 1.98 (3H, s), 4.69 (2H, d, J = 5.8 Hz), 5.21 (2H,s), 5.38 (2H, s), 7.17-7.26 (5H, m), 7.33 (1H, dd, J = 8.9, 2.0 Hz), 7.51-7.53 (2H, m), 7.84 (1H, d, J = 1.8 Hz), 8.36 (1H, s), 8.87 (1H, t, J = 5.8 Hz), 13.05 (1H, s). |
| 128 | 1.89-1.93 (4H,s), 3.35-3.42 (4H, m), 4.68 (2H, d, J = 5.88 Hz), 5.24(2H, s), 6.42 (1H, s, br), 7.34(1H, dd, J = 1.96, 8.92 Hz), 7.48 (2H, d, J = 6.80 Hz), 7.51 (1H, d, J = 8.92 Hz), 7.83 (1H, d, J = 1.80 Hz), 8.11 (1H, d, J = 2.2 Hz), 8.28 (1H, d, J = 4.96 Hz), 13.04 (1H, s). |
| 129 | 4.69 (2H, d, J = 5.84 Hz), 5.06 (2H, s), 5.38 (2H, s), 6.20-6.23 (1H, m), 6.39 (1H, d, J = 9.04 Hz), 7.27 (4H, s), 7.32-7.34 (1H, m),7.39-7.43 (1H, m), 7.52 (1H, d, J = 8.88 Hz), 7.74-7.82 (1H, m), 7.84 (1H, d, J = 1.64 Hz), 8.36 (1H, s), 8.86 (1H, d, J = 5.44 Hz), 13.04 (1H, s). |

Biological Methods

The ability of the compounds of formula (I) to inhibit plasma kallikrein may be determined using the following biological assays:

Determination of the $IC_{50}$ for Plasma Kallikrein

Plasma kallikrein inhibitory activity in vitro was determined using standard published methods (see e.g. Johansen et al., Int. J. Tiss. Reac. 1986, 8, 185; Shori et al., Biochem. Pharmacol., 1992, 43, 1209; Sturzebecher et al., Biol. Chem. Hoppe-Seyler, 1992, 373, 1025). Human plasma kallikrein (Protogen) was incubated at 37° C. with the fluorogenic substrate H-DPro-Phe-Arg-AFC and various concentrations of the test compound. Residual enzyme activity (initial rate of reaction) was determined by measuring the change in optical absorbance at 410 nm and the $IC_{50}$ value for the test compound was determined.

Data acquired from these assays are shown in Table 13 below:

TABLE 13

| Example Number | $IC_{50}$ (human PKaI) nM |
|---|---|
| 1 | 54.7 |
| 2 | 2110 |
| 3 | 2690 |
| 6 | 9460 |
| 7 | 5.38 |
| 8 | 3.72 |
| 9 | 14.3 |
| 10 | 2.4 |
| 11 | 1.89 |
| 12 | 2.58 |
| 13 | 2.14 |
| 14 | 4.62 |
| 15 | 1.17 |
| 16 | 0.74 |
| 17 | 1190 |
| 18 | 32.0 |

TABLE 13-continued

| Example Number | IC$_{50}$ (human PKaI) nM |
|---|---|
| 19 | 994.0 |
| 20 | 0.89 |
| 21 | 6.46 |
| 22 | 132 |
| 23 | 0.33 |
| 24 | 9.66 |
| 25 | 7.31 |
| 26 | 205 |
| 27 | 128 |
| 28 | 63.7 |
| 29 | 620 |
| 30 | 1470 |
| 31 | 2.0 |
| 32 | 2.4 |
| 33 | 2.8 |
| 34 | 142 |
| 35 | 3.68 |
| 36 | 2.16 |
| 37 | 0.67 |
| 38 | 1.27 |
| 39 | 1.68 |
| 42 | 4.85 |
| 44 | 3.9 |
| 45 | 3060 |
| 46 | 803 |
| 47 | 2030 |
| 48 | 820 |
| 49 | 186 |
| 50 | 203 |
| 51 | 576 |
| 52 | 300 |
| 53 | 16.8 |
| 54 | 46.7 |
| 55 | 79.2 |
| 56 | 71.8 |
| 57 | 14.9 |
| 58 | 13.3 |
| 59 | 5.84 |
| 60 | 9.61 |
| 61 | 18.1 |
| 62 | 13.58 |
| 63 | 12.3 |
| 64 | 10.4 |
| 65 | 14.9 |
| 66 | 281 |
| 67 | 108 |
| 68 | 59.0 |
| 69 | 32.3 |
| 70 | 66.9 |
| 71 | 63.6 |
| 72 | 118 |
| 73 | 22.6 |
| 74 | 425 |
| 75 | 98.3 |
| 76 | 0.92 |
| 77 | 85.4 |
| 78 | 91.1 |
| 79 | 2.29 |
| 80 | 206 |
| 81 | 26.5 |
| 82 | 21.2 |
| 86 | 56.1 |
| 87 | 23.2 |
| 88 | 112 |
| 89 | 17.8 |
| 90 | 11.6 |
| 91 | 13.8 |
| 92 | 109 |
| 93 | 75.1 |
| 94 | 53.2 |
| 95 | 34.0 |
| 97 | 18.5 |
| 98 | 62.4 |
| 99 | 4.15 |
| 105 | 17000 |
| 106 | 12000 |
| 107 | 2300 |
| 108 | 22000 |
| 109 | 4200 |
| 110 | 562 |
| 111 | 217 |
| 112 | 60.6 |
| 113 | 13.3 |
| 114 | 304 |
| 115 | 177 |
| 116 | 507 |
| 117 | 78 |
| 118 | 14 |
| 119 | 86.6 |
| 120 | 118 |
| 121 | 62.0 |
| 122 | 101 |
| 123 | 545 |
| 124 | 146 |
| 125 | 4010 |
| 126 | 22.9 |
| 127 | 537 |
| 128 | 24.9 |
| 129 | 2.14 |

Selected compounds were further screened for inhibitory activity against the related enzyme KLK1. The ability of the compounds of formula (I) to inhibit KLK1 may be determined using the following biological assay:

Determination of the IC$_{50}$ for KLK1

KLK1 inhibitory activity in vitro was determined using standard published methods (see e.g. Johansen et al., Int. J. Tiss. Reac. 1986, 8, 185; Shori et al., Biochem. Pharmacol., 1992, 43, 1209; Sturzebecher et al., Biol. Chem. Hoppe-Seyler, 1992, 373, 1025). Human KLK1 (Callbiochem) was incubated at 37° C. with the fluorogenic substrate H-DVal-Leu-Arg-AFC and various concentrations of the test compound. Residual enzyme activity (initial rate of reaction) was determined by measuring the change in optical absorbance at 410 nm and the IC$_{50}$ value for the test compound was determined.

Data acquired from this assay are shown in Table 14 below:

TABLE 14

(KLK1 Activity)

| Example Number | IC50 (human KLK1) nM |
|---|---|
| 1 | >10000 |
| 2 | >10000 |
| 3 | >10000 |
| 6 | 9460 |
| 7 | >10000 |
| 8 | >10000 |
| 9 | >10000 |
| 10 | >10000 |
| 11 | 8860 |
| 12 | 6060 |
| 13 | 5160 |
| 14 | 5970 |
| 15 | 6640 |
| 16 | 5730 |
| 17 | >10000 |
| 18 | >10000 |
| 19 | >10000 |
| 20 | >10000 |
| 21 | >10000 |
| 22 | >10000 |
| 23 | >10000 |
| 24 | >4000 |

TABLE 14-continued (KLK1 Activity)

| Example Number | IC50 (human KLK1) nM |
|---|---|
| 25 | 2210 |
| 26 | 4730 |
| 27 | 3200 |
| 28 | >10000 |
| 29 | >10000 |
| 30 | 5750 |
| 31 | >10000 |
| 32 | >10000 |
| 33 | >10000 |
| 34 | 18170 |
| 35 | >10000 |
| 36 | >40000 |
| 37 | 3530 |
| 38 | 7840 |
| 39 | 8050 |
| 42 | 9050 |
| 44 | 7090 |
| 45 | 18570 |
| 46 | 27200 |
| 47 | 15750 |
| 48 | 4320 |
| 49 | 8090 |
| 50 | >40000 |
| 51 | 11720 |
| 52 | >40000 |
| 53 | >10000 |
| 54 | 18250 |
| 55 | 3810 |
| 56 | >10000 |
| 57 | >10000 |
| 58 | 3110 |
| 59 | 4000 |
| 60 | 9570 |
| 61 | 7660 |
| 62 | >10000 |
| 63 | 5700 |
| 64 | 2790 |
| 65 | 960 |
| 66 | >10000 |
| 67 | 8880 |
| 68 | 9760 |
| 69 | 4740 |
| 70 | 4910 |
| 71 | >10000 |
| 72 | >10000 |
| 73 | 1570 |
| 74 | 2770 |
| 75 | 1300 |
| 76 | >1000 |
| 77 | >10000 |
| 78 | >10000 |
| 79 | >10000 |
| 80 | 9280 |
| 81 | 8970 |
| 82 | 4710 |
| 86 | 8790 |
| 87 | 6460 |
| 88 | 9630 |
| 89 | 960 |
| 90 | 4700 |
| 91 | >10000 |
| 92 | >10000 |
| 93 | >10000 |
| 94 | 2000 |
| 95 | 9640 |
| 97 | 3010 |
| 98 | 3140 |
| 99 | 3460 |
| 105 | >40000 |
| 106 | >40000 |
| 107 | 38100 |
| 108 | 20630 |
| 109 | >40000 |
| 110 | >10000 |
| 111 | 7170 |
| 112 | >10000 |
| 113 | 5950 |
| 114 | 1210 |
| 115 | >10000 |
| 116 | >10000 |
| 117 | >10000 |
| 118 | >40000 |
| 119 | >4000 |
| 120 | >10000 |
| 121 | >10000 |
| 122 | >10000 |
| 123 | >10000 |
| 124 | 7230 |
| 125 | >10000 |
| 126 | >10000 |
| 127 | >10000 |
| 128 | >10000 |
| 129 | >10000 |

Selected compounds were further screened for inhibitory activity against the related enzymes plasmin, thrombin, trypsin, Factor Xa and Factor XIIa. The ability of the compounds of formula (I) to these enzymes may be determined using the following biological assays:

Determination of Enzyme Selectivity

Human serine protease enzymes plasmin, thrombin, trypsin, Factor Xa and Factor XIIa were assayed for enzymatic activity using an appropriate fluorogenic substrate. Protease activity was measured by monitoring the accumulation of liberated fluorescence from the substrate over 5 minutes. The linear rate of fluorescence increase per minute was expressed as percentage (%) activity. The Km for the cleavage of each substrate was determined by standard transformation of the Michaelis-Menten equation. The compound inhibitor assays were performed at substrate Km concentration and activities were calculated as the concentration of inhibitor giving 50% inhibition ($IC_{50}$) of the uninhibited enzyme activity (100%).

Data acquired from these assays are shown in Table 15 below:

TABLE 15

(Selectivity data)

| Example Number | IC50 (nM) | | | |
|---|---|---|---|---|
| | Factor XIIa | Thrombin | Trypsin | Plasmin |
| 1 | >10000 | >40000 | >40000 | >40000 |
| 2 | >10000 | | | |
| 6 | >10000 | | | |
| 11 | >10000 | | | |
| 12 | >10000 | | | |
| 13 | >10000 | | | |
| 14 | >10000 | | | |
| 18 | >10000 | | | |
| 22 | >10000 | | | |
| 24 | >1000 | | | |
| 28 | >10000 | | | |
| 30 | >10000 | | | |
| 33 | >10000 | | | |
| 34 | >40000 | | | |
| 35 | >10000 | | | |
| 36 | >10000 | | | |
| 37 | >10000 | | | |
| 38 | >10000 | | | |
| 39 | >10000 | | | |

TABLE 15-continued (Selectivity data)

| Example Number | IC50 (nM) | | | |
|---|---|---|---|---|
| | Factor XIIa | Thrombin | Trypsin | Plasmin |
| 44 | >10000 | | | |
| 45 | >40000 | | | |
| 46 | >40000 | | | |
| 47 | >40000 | | | |
| 48 | >40000 | | | |
| 49 | >40000 | | | |
| 50 | >40000 | | | |
| 51 | >40000 | | | |
| 52 | >40000 | | | |
| 54 | >4000 | | | |
| 55 | >10000 | | | |
| 56 | >10000 | | | |
| 57 | >10000 | | | |
| 59 | >1000 | | | |
| 60 | >10000 | | | |
| 61 | >10000 | | | |
| 62 | >10000 | | | |
| 63 | >10000 | | | |
| 67 | >10000 | | | |
| 68 | >10000 | | | |
| 105 | >40000 | | | |
| 106 | >40000 | | | |
| 107 | >40000 | | | |
| 108 | >40000 | | | |
| 109 | >40000 | | | |
| 110 | >10000 | | | |
| 111 | >10000 | | | |
| 112 | >10000 | | | |
| 115 | >10000 | | | |
| 116 | >10000 | | | |
| 117 | >10000 | | | |
| 118 | >40000 | | | |
| 119 | >4000 | | | |
| 120 | >10000 | | | |
| 123 | >10000 | | | |
| 124 | >10000 | | | |
| 126 | >10000 | | | |

Pharmacokinetics

Pharmacokinetic studies of the compounds in Table 16 were performed to assess the pharmacokinetics following a single oral dose in male Sprague-Dawley rats. Two rats were given a single po dose of 5 mL/kg of a nominal 2 mg/mL (10 mg/kg) composition of test compound in 5% cremophor:5% ethanol:90% phosphate buffered saline. Following dosing, blood samples were collected over a period of 24 hours. Sample times were 5, 15 and 30 minutes then 1, 2, 4, 6, 8, 12 and 24 hours. Following collection, blood samples were centrifuged and the plasma fraction analysed for concentration of test compound by LCMS. Oral exposure data acquired from these studies are shown below:

TABLE 16

(Oral exposure data)

| Example Number | Dose po (mg/kg) | Cmax (ng/mL) | Tmax (min) |
|---|---|---|---|
| 11 | 10 | 134 | 23 |
| 12 | 10 | 155 | 30 |
| 24 | 4 | 97 | 420 |
| 36 | 10 | 642 | 75 |
| 117 | 10 | 98 | 45 |
| 126 | 10 | 56 | 30 |

The invention claimed is:

1. A compound of formula (I),

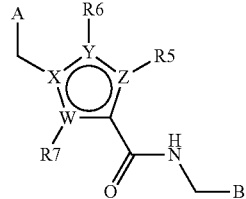

Formula (I)

wherein

B is a fused 6,5- or 6,6-heteroaromatic bicyclic ring, containing N and, optionally, one or two additional heteroatoms independently selected from N, O and S, which is optionally mono-, di or tri-substituted with a substituent selected from alkyl, alkoxy, OH, halo, CN, COOR8, CONR8R9, $CF_3$ and NR8R9; wherein when B is a fused 6,5-heteroaromatic bicyclic ring, it is linked to CONH—($CH_2$)— via its 6-membered ring component;

W, X, Y and Z are independently selected from C, N, O and S, such that the ring containing W, X, Y and Z is a five membered aromatic heterocycle;

wherein,

R5, R6 and R7 are independently absent or independently selected from H, alkyl, halo, OH, aryl, heteroaryl, —NR8R9, CN, COOR8, CONR8R9, —NR8COR9, $CF_3$, and R16; wherein at least one of R5, R6 and R7 is present and is independently selected from alkyl, halo, OH, aryl, heteroaryl, —NR8R9, CN, COOR8, CONR8R9, —NR8COR9, $CF_3$ and R16;

A is selected from aryl and heteroaryl;

R8 and R9 are independently selected from H and alkyl;

R16 is a carbon-containing 3-, 4-, 5- or 6-membered monocyclic ring system which may be aromatic, saturated or unsaturated non-aromatic and which may optionally contain 1, 2, 3 or 4 heteroatoms selected from N, O and S, wherein the ring system R16 is in turn optionally substituted with substituents selected from alkyl and oxo;

alkyl is a linear saturated hydrocarbon having up to 10 carbon atoms ($C_1$-$C_{10}$) or a branched saturated hydrocarbon of between 3 and 10 carbon atoms ($C_3$-$C_{10}$), optionally substituted with 1 or 2 substituents independently selected from ($C_1$-$C_6$)alkoxy, OH, CN, $CF_3$, COOR10, CONR10R11, fluoro and NR10R11;

alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$), optionally substituted with 1 or 2 substituents independently selected from OH, CN, $CF_3$, COOR10, CONR1OR11, fluoro and NR1OR11;

aryl is phenyl, biphenyl or naphthyl, optionally substituted with 1, 2 or 3 substituents independently selected from alkyl, alkoxy, methylenedioxy, ethylenedioxy, OH, halo, CN, morpholinyl, piperidinyl, heteroaryl, —($CH_2$)$_{0-3}$—O-heteroaryl, aryl$^b$, —O-aryl$^b$, —($CH_2$)$_{1-3}$-aryl$^b$, —($CH_2$)$_{1-3}$-heteroaryl, —COOR10, —CONR1OR11, —($CH_2$)$_{1-3}$—NR14R15, $CF_3$ and —NR1OR11;

aryl$^b$ is phenyl, biphenyl or naphthyl, optionally substituted with 1, 2 or 3 substituents independently selected from alkyl, alkoxy, OH, halo, CN, morpholinyl, piperidinyl, —COOR10, —CONR1OR11, CF₃ and NR10R11;

heteroaryl is a 5, 6, 9 or 10 membered mono- or bi-cyclic aromatic ring, containing, where possible, 1, 2 or 3 ring members independently selected from N, NR8, S and O, optionally substituted with 1, 2 or 3 substituents independently selected from alkyl, alkoxy, OH, OCF₃, halo, CN, aryl, morpholinyl, piperidinyl, —(CH₂)₁₋₃-aryl, heteroaryl^b, —COOR10, —CONR1OR11, CF₃ and —NR10R11;

heteroaryl^b is a 5, 6, 9 or 10 membered mono- or bi-cyclic aromatic ring, containing, where possible, 1, 2 or 3 ring members independently selected from N, NR8, S and O; wherein heteroaryl^b may be optionally substituted with 1, 2 or 3 substituents independently selected from alkyl, alkoxy, OH, halo, CN, morpholinyl, piperidinyl, aryl, —(CH₂)₁₋₃-aryl, —COOR10, —CONR1OR11, CF₃ and NR1OR11;

R10 and R11 are independently selected from H and alkyl or R10 and R11 together with the nitrogen atom to which they are attached form a carbon-containing 4-, 5-, 6- or 7-membered heterocyclic ring which may be saturated or unsaturated with 1 or 2 double bonds and which may be optionally mono- or di-substituted with substituents selected from oxo, alkyl, alkoxy, OH, F and CF₃;

R14 and R15 are independently selected from alkyl, aryl^b and heteroaryl^b; or R14 and R15 together with the nitrogen atom to which they are attached form a carbon-containing 4-, 5-, 6- or 7-membered heterocyclic ring which may be saturated or unsaturated with 1 or 2 double bonds, and optionally may be oxo substituted;

or a tautomer, isomer, stereoisomer, pharmaceutically acceptable salt or solvate thereof;

wherein the compound of formula (I) is not:

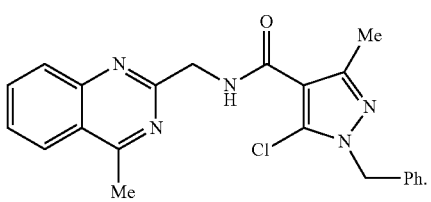 [SMILES: Cc1nn(Cc2ccccc2)c(Cl)c1C(=O)NCc1nc(C)c2ccccc2n1]

2. A compound according to claim 1, wherein B is a fused 6,6-heteroaromatic bicyclic ring, containing N and, optionally, one or two additional heteroatoms independently selected from N, O and S, which is optionally mono-, di or tri-substituted with a substituent selected from alkyl, alkoxy, OH, halo, CN, COOR8, CONR8R9, CF₃ and NR8R9.

3. A compound according to claim 2, wherein B is selected from optionally substituted quinoline, optionally substituted isoquinoline, optionally substituted quinoxaline, optionally substituted cinnoline, optionally substituted phthalazine, optionally substituted quinazoline, optionally substituted 1,2,4-benzotriazine, optionally substituted 1,2,3-benzotriazine, optionally substituted 1,7-naphthyridine, and optionally substituted 1,8-naphthyridine; wherein said optional substituents are selected from alkyl, alkoxy, OH, F, Cl, CN, COOR8, CONR8R9, CF₃ and NR8R9.

4. A compound according to claim 1, wherein B is selected from optionally mono-, di or tri-substituted isoquinolinyl wherein said optional substituent(s) are selected from alkyl, alkoxy, OH, F, Cl, CN, COOR8, CONR8R9, CF₃ and NR8R9.

5. A compound according to claim 1, as defined by formula (II),

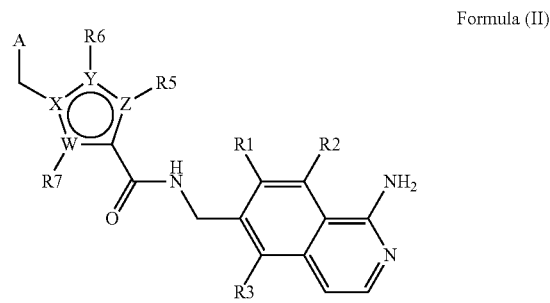

Formula (II)

wherein R1, R2 and R3 are independently selected from H, alkyl, COOR8, CONR8R9, OH, alkoxy, NR8R9, F and Cl.

6. A compound according to claim 5, wherein R1, R2 and R3 are independently selected from H and alkyl.

7. A compound according to claim 1, wherein B is a fused 6,5-heteroaromatic bicyclic ring, containing N and, optionally, one or two additional heteroatoms independently selected from N, O and S, which is optionally mono-, di or tri-substituted with a substituent selected from alkyl, alkoxy, OH, halo, CN, COOR8, CONR8R9, CF₃ and NR8R9.

8. A compound according to claim 7, wherein B is selected from optionally substituted indole, optionally substituted indazole and optionally substituted 1H-pyrrolo[2,3-b]pyridine; wherein said optional substituents are selected from alkyl, alkoxy, OH, F, Cl, CN, COOR8, CONR8R9, CF₃ and NR8R9.

9. A compound according to claim 8, wherein B is selected from optionally mono-, di or tri-substituted 1H-pyrrolo[2,3-b]pyridine, wherein said optional substituent(s) are selected from alkyl, alkoxy, OH, F, Cl, CN, COOR8, CONR8R9, CF₃ and NR8R9.

10. A compound according to claim 1, as defined by formula (III),

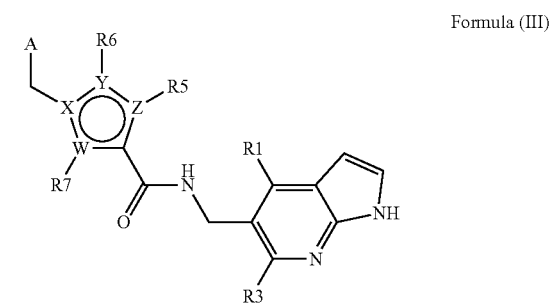

Formula (III)

wherein R1 and R3 are independently selected from H, alkyl, COOR8, CONR8R9, OH, alkoxy, NR8R9, F and Cl.

11. A compound according to claim 10, wherein R1 and R3 are independently selected from H and alkyl.

12. A compound according to claim 1, wherein at least one of R5, R6 and R7 is present and is independently selected from alkyl, halo, OH, aryl, heteroaryl and CF₃.

13. A compound according to claim 1 wherein W, X, Y and Z are independently selected from C and N, wherein the ring containing W, X, Y and Z is a five-membered heterocycle selected from pyrrole, pyrazole, imidazole, 1, 2, 3-triazole and 1, 2, 4-triazole.

14. A compound according to claim 1 wherein A is heteroaryl substituted by methyl, phenyl, morpholinyl, piperidinyl or —NR10R11, wherein said phenyl is optionally substituted with 1, 2 or 3 substituents independently selected from alkyl, alkoxy, methylenedioxy, ethylenedioxy, OH, halo, CN, morpholinyl, piperidinyl, heteroaryl, —(CH$_2$)$_{0-3}$—O-heteroaryl, aryl$^b$, —O-aryl$^b$, —(CH$_2$)$_{1-3}$-aryl$^b$, —(CH$_2$)$_{1-3}$-heteroaryl, —COOR10, —CONR10R11, —(CH$_2$)$_{1-3}$—NR14R15, CF$_3$ and —NR10R11; or A is phenyl substituted by heteroaryl, —(CH$_2$)$_{1-3}$-heteroaryl or —(CH$_2$)$_{1-3}$—NR14R15.

15. A compound according to claim 14 wherein A is selected from:

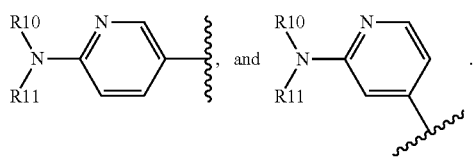

16. A compound according to claim 14 wherein A is:

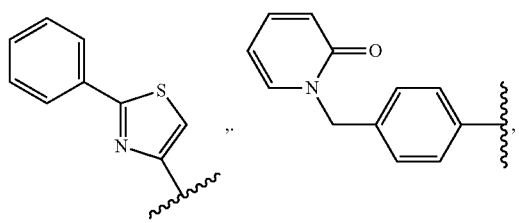

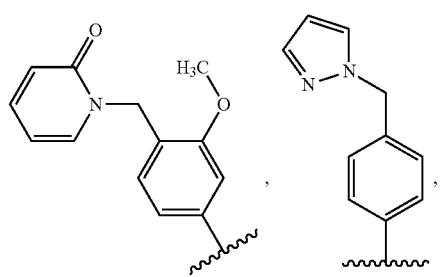

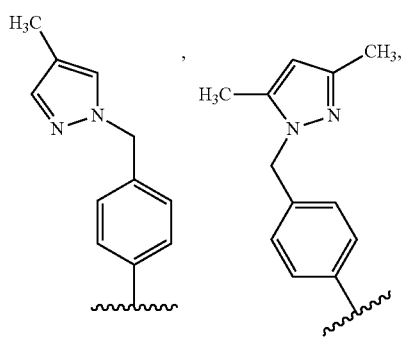

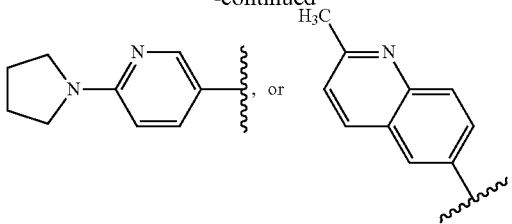

17. A compound according to claim 1, that is:
2,5-Dimethyl-1-(2-phenyl-thiazol-4-ylmethyl)-1H-pyrrole-3-carboxylic acid (1-amino-isoquinolin-6-ylmethyl)-amide;
2,5-Dimethyl-1-[4-(2-oxo-2H-pyridin-1-ylmethyl)-benzyl]-1H-pyrrole-3-carboxylic acid (1-amino-isoquinolin-6-ylmethyl)-amide;
2,5-Dimethyl-1-[4-(4-methyl-pyrazol-1-ylmethyl)-benzyl]-1H-pyrrole-3-carboxylic acid (1-amino-isoquinolin-6-ylmethyl)-amide;
1-Ethyl-4-methyl-5-[4-(4-methyl-pyrazol-1-ylmethyl)-benzyl]-1H-pyrrole-2-carboxylic acid (1-amino-isoquinolin-6-ylmethyl)-amide;
1-Ethyl-4-methyl-5-[4-(2-oxo-2H-pyridin-1-ylmethyl)-benzyl]-1H-pyrrole-2-carboxylic acid (1-amino-isoquinolin-6-ylmethyl)-amide;
3-Methyl-1-[4-(4-methyl-pyrazol-1-ylmethyl)-benzyl]-1H-pyrazole-4-carboxylic acid (1-amino-isoquinolin-6-ylmethyl)-amide;
3-Cyclopropyl-1-[4-(4-methyl-pyrazol-1-ylmethyl)-benzyl]-1H-pyrazole-4-carboxylic acid (1-amino-isoquinolin-6-ylmethyl)-amide;
3-Isopropyl-1-[4-(4-methyl-pyrazol-1-ylmethyl)-benzyl]-1H-pyrazole-4-carboxylic acid (1-amino-isoquinolin-6-ylmethyl)-amide;
3-Cyclobutyl-1-[4-(4-methyl-pyrazol-1-ylmethyl)-benzyl]-1H-pyrazole-4-carboxylic acid (1-amino-isoquinolin-6-ylmethyl)-amide;
3-Hydroxymethyl-1-[4-(4-methyl-pyrazol-1-ylmethyl)-benzyl]-1H-pyrazole-4-carboxylic acid (1-amino-isoquinolin-6-ylmethyl)-amide;
3-Cyano-1-[4-(4-methyl-pyrazol-1-ylmethyl)-benzyl]-1H-pyrazole-4-carboxylic acid (1-amino-isoquinolin-6-ylmethyl)-amide;
4-Methyl-2-[4-(4-methyl-pyrazol-1-ylmethyl)-benzyl]-thiazole-5-carboxylic acid (1-amino-isoquinolin-6-ylmethyl)-amide;
3-(3,5-Dimethyl-isoxazol-4-yl)-1-[4-(4-methyl-pyrazol-1-ylmethyl)-benzyl]-1H-pyrazole-4-carboxylic acid (1-amino-isoquinolin-6-ylmethyl)-amide;
1-[4-(4-Methyl-pyrazol-1-ylmethyl)-benzyl]-3-morpholin-4-yl-1H-pyrazole-4-carboxylic acid (1-amino-isoquinolin-6-ylmethyl)-amide;
5-Amino-1-(4-pyrazol-1-ylmethyl-benzyl)-1H-pyrazole-4-carboxylic acid (1-amino-isoquinolin-6-ylmethyl)-amide;
1-(6-Pyrrolidin-1-yl-pyridin-3-ylmethyl)-3-trifluoromethyl-1H-pyrazole-4-carboxylic acid (1-amino-isoquinolin-6-ylmethyl)-amide;
3-Cyclopropyl-1-(5-methoxy-6-pyrrolidin-1-yl-pyridin-3-ylmethyl)-1H-pyrazole-4-carboxylic acid (1-amino-isoquinolin-6-ylmethyl)-amide;
1-[4-(4-Methyl-pyrazol-1-ylmethyl)-benzyl]-3-phenyl-1H-pyrazole-4-carboxylic acid (1-amino-isoquinolin-6-ylmethyl)-amide;

1-[4-(4-Methyl-pyrazol-1-ylmethyl)-benzyl]-3-trifluoromethyl-1H-pyrazole-4-carboxylic acid (1-amino-isoquinolin-6-ylmethyl)-amide;
3-Amino-1-[4-(4-methyl-pyrazol-1-ylmethyl)-benzyl]-1H-pyrazole-4-carboxylic acid (1-amino-isoquinolin-6-ylmethyl)-amide;
3-Methoxymethyl-1-[4-(4-methyl-pyrazol-1-ylmethyl)-benzyl]-1H-pyrazole-4-carboxylic acid (1-amino-isoquinolin-6-ylmethyl)-amide;
3-Difluoromethyl-1-[4-(4-methyl-pyrazol-1-ylmethyl)-benzyl]-1H-pyrazole-4-carboxylic acid (1-amino-isoquinolin-6-ylmethyl)-amide;
1-[4-(4-Methyl-pyrazol-1-ylmethyl)-benzyl]-3-thiophen-3-yl-1H-pyrazole-4-carboxylic acid (1-amino-isoquinolin-6-ylmethyl)-amide;
5-Amino-1-(4-pyrazol-1-ylmethyl-benzyl)-1H-pyrazole-4-carboxylic acid (1-amino-isoquinolin-6-ylmethyl)-amide;
1-(2-Pyrrolidin-1-yl-pyridin-4-ylmethyl)-3-trifluoromethyl-1H-pyrazole-4-carboxylic acid (1-amino-isoquinolin-6-ylmethyl)-amide;
1-(6-Ethoxy-pyridin-3-ylmethyl)-3-trifluoromethyl-1H-pyrazole-4-carboxylic acid (1-amino-isoquinolin-6-ylmethyl)-amide;
1-[2-(3,3-Difluoro-pyrrolidin-1-yl)-pyridin-4-ylmethyl]-3-trifluoromethyl-1H-pyrazole-4-carboxylic acid (1-amino-isoquinolin-6-ylmethyl)-amide;
1-[6-(3,3-Difluoro-pyrrolidin-1-yl)-pyridin-3-ylmethyl]-3-trifluoromethyl-1H-pyrazole-4-carboxylic acid (1-amino-isoquinolin-6-ylmethyl)-amide;
1-[6-((R)-3-Methyl-pyrrolidin-1-yl)-pyridin-3-ylmethyl]-3-trifluoromethyl-1H-pyrazole-4-carboxylic acid (1-amino-isoquinolin-6-ylmethyl)-amide;
1-[6-((S)-3-Methyl-pyrrolidin-1-yl)-pyridin-3-ylmethyl]-3-trifluoromethyl-1H-pyrazole-4-carboxylic acid (1-amino-isoquinolin-6-ylmethyl)-amide;
1-[6-((S)-3-Fluoro-pyrrolidin-1-yl)-pyridin-3-ylmethyl]-3-trifluoromethyl-1H-pyrazole-4-carboxylic acid (1-amino-isoquinolin-6-ylmethyl)-amide;
1-[6-((R)-3-Fluoro-pyrrolidin-1-yl)-pyridin-3-ylmethyl]-3-trifluoromethyl-1H-pyrazole-4-carboxylic acid (1-amino-isoquinolin-6-ylmethyl)-amide;
1-[6-((S)-2-Methyl-pyrrolidin-1-yl)-pyridin-3-ylmethyl]-3-trifluoromethyl-1H-pyrazole-4-carboxylic acid (1-amino-isoquinolin-6-ylmethyl)-amide;
1-[6-((R)-2-Methyl-pyrrolidin-1-yl)-pyridin-3-ylmethyl]-3-trifluoromethyl-1H-pyrazole-4-carboxylic acid (1-amino-isoquinolin-6-ylmethyl)-amide;
1-(2-Pyrrolidin-1-yl-pyrimidin-5-ylmethyl)-3-trifluoromethyl-1H-pyrazole-4-carboxylic acid (1-amino-isoquinolin-6-ylmethyl)-amide;
1-(5-Pyrrolidin-1-yl-pyrazin-2-ylmethyl)-3-trifluoromethyl-1H-pyrazole-4-carboxylic acid (1-amino-isoquinolin-6-ylmethyl)-amide;
1-[2-((S)-3-Methyl-pyrrolidin-1-yl)-pyridin-4-ylmethyl]-3-trifluoromethyl-1H-pyrazole-4-carboxylic acid (1-amino-isoquinolin-6-ylmethyl)-amide;
1-[6-(3-Hydroxymethyl-pyrrolidin-1-yl)-pyridin-3-ylmethyl]-3-trifluoromethyl-1H-pyrazole-4-carboxylic acid (1-amino-isoquinolin-6-ylmethyl)-amide;
1-[6-((R)-3-Hydroxymethyl-pyrrolidin-1-yl)-pyridin-3-ylmethyl]-3-trifluoromethyl-1H-pyrazole-4-carboxylic acid (1-amino-isoquinolin-6-ylmethyl)-amide;
1-(6-Propoxy-pyridin-3-ylmethyl)-3-trifluoromethyl-1H-pyrazole-4-carboxylic acid (1-amino-isoquinolin-6-ylmethyl)-amide;
1-(5-Fluoro-6-pyrrolidin-1-yl-pyridin-3-ylmethyl)-3-trifluoromethyl-1H-pyrazole-4-carboxylic acid (1-amino-isoquinolin-6-ylmethyl)-amide;
1-(6-Ethoxy-5-fluoro-pyridin-3-ylmethyl)-3-trifluoromethyl-1H-pyrazole-4-carboxylic acid (1-amino-isoquinolin-6-ylmethyl)-amide;
1-(4-Pyrazol-1-ylmethyl-benzyl)-3-trifluoromethyl-1H-pyrazole-4-carboxylic acid (1-amino-isoquinolin-6-ylmethyl)-amide;
1-[4-(4-Cyano-pyrazol-1-ylmethyl)-benzyl]-3-trifluoromethyl-1H-pyrazole-4-carboxylic acid (1-amino-isoquinolin-6-ylmethyl)-amide;
1-[4-(4-Carbamoyl-pyrazol-1-ylmethyl)-benzyl]-3-trifluoromethyl-1H-pyrazole-4-carboxylic acid (1-amino-isoquinolin-6-ylmethyl)-amide;
1-(6-Pyrazol-1-ylmethyl-pyridin-3-ylmethyl)-3-trifluoromethyl-1H-pyrazole-4-carboxylic acid (1-amino-isoquinolin-6-ylmethyl)-amide;
1-(2-Pyrazol-1-ylmethyl-thiazol-4-ylmethyl)-3-trifluoromethyl-1H-pyrazole-4-carboxylic acid (1-amino-isoquinolin-6-ylmethyl)-amide;
1-[2-(4-Methyl-pyrazol-1-ylmethyl)-thiazol-4-ylmethyl]-3-trifluoromethyl-1H-pyrazole-4-carboxylic acid (1-amino-isoquinolin-6-ylmethyl)-amide;
3-Cyclopropyl-1-{6-[(2-methoxy-ethyl)-methyl-amino]-pyridin-3-ylmethyl}-1H-pyrazole-4-carboxylic acid (1-amino-isoquinolin-6-ylmethyl)-amide;
3-Cyclopropyl-1-[6-(3,3-difluoro-pyrrolidin-1-yl)-pyridin-3-ylmethyl]-1H-pyrazole-4-carboxylic acid (1-amino-isoquinolin-6-ylmethyl)-amide;
3-Cyclopropyl-1-(4-methoxy-6-pyrrolidin-1-yl-pyridin-3-ylmethyl)-1H-pyrazole-4-carboxylic acid (1-amino-isoquinolin-6-ylmethyl)-amide;
3-Cyclopropyl-1-(6-pyrrolidin-1-yl-pyridin-3-ylmethyl)-1H-pyrazole-4-carboxylic acid (1-amino-isoquinolin-6-ylmethyl)-amide;
3-Cyclopropyl-1-(4-[1,2,3]triazol-1-ylmethyl-benzyl)-1H-pyrazole-4-carboxylic acid (1-amino-isoquinolin-6-ylmethyl)-amide;
3-Cyclopropyl-1-(6-phenoxy-pyridin-3-ylmethyl)-1H-pyrazole-4-carboxylic acid (1-amino-isoquinolin-6-ylmethyl)-amide;
1-(5-Chloro-6-ethoxy-pyridin-3-ylmethyl)-3-cyclopropyl-1H-pyrazole-4-carboxylic acid (1-amino-isoquinolin-6-ylmethyl)-amide;
3-Cyclopropyl-1-(6-diethylamino-5-fluoro-pyridin-3-ylmethyl)-1H-pyrazole-4-carboxylic acid (1-amino-isoquinolin-6-ylmethyl)-amide;
1-(5-Chloro-6-pyrrolidin-1-yl-pyridin-3-ylmethyl)-3-cyclopropyl-1H-pyrazole-4-carboxylic acid (1-amino-isoquinolin-6-ylmethyl)-amide;
3-Amino-1-(6-ethoxy-pyridin-3-ylmethyl)-1H-pyrazole-4-carboxylic acid (1-amino-isoquinolin-6-ylmethyl)-amide;
3-Amino-1-(6-pyrrolidin-1-yl-pyridin-3-ylmethyl)-1H-pyrazole-4-carboxylic acid (1-amino-isoquinolin-6-ylmethyl)-amide;
or a pharmaceutically acceptable salt or solvate thereof.

18. A compound according to claim 1, selected from that is:

1-[4-(2-Oxo-2H-pyridin-1-ylmethyl)-benzyl]-3-trifluoromethyl-1H-pyrazole-4-carboxylic acid (1H-pyrrolo[2,3-b]pyridin-5-ylmethyl)-amide;
1-[4-(2-Oxo-2H-pyridin-1-ylmethyl)-benzyl]-3-trifluoromethyl-1H-pyrazole-4-carboxylic acid (4,6-dimethyl-1H-pyrrolo[2,3-b]pyridin-5-ylmethyl)-amide;

1-[4-(4-Methyl-pyrazol-1-ylmethyl)-benzyl]-3-trifluoromethyl-1H-pyrazole-4-carboxylic acid (4,6-dimethyl-1H-pyrrolo[2,3-b]pyridin-5-ylmethyl)-amide;

1-[4-(4-Methyl-pyrazol-1-ylmethyl)-benzyl]-3-trifluoromethyl-1H-pyrazole-4-carboxylic acid (1H-pyrrolo[2,3-b]pyridin-5-ylmethyl)-amide;

1-[4-(4-Methyl-pyrazol-1-ylmethyl)-benzyl]-3-trifluoromethyl-1H-pyrazole-4-carboxylic acid (1H-indol-5-ylmethyl)-amide;

3-Amino-1-[4-(2-oxo-2H-pyridin-1-ylmethyl)-benzyl]-1H-pyrazole-4-carboxylic acid (1H-indazol-4-ylmethyl)-amide;

1-[4-(2-Oxo-2H-pyridin-1-ylmethyl)-benzyl]-3-trifluoromethyl-1H-pyrazole-4-carboxylic acid (1H-indazol-4-ylmethyl)-amide;

or a pharmaceutically acceptable salt or solvate thereof.

19. A pharmaceutical composition comprising a compound as claimed in claim 1 and a pharmaceutically acceptable carrier, diluent or excipient.

20. The pharmaceutical composition of claim 19, comprising a compound that is:

2,5-Dimethyl-1-(2-phenyl-thiazol-4-ylmethyl)-1H-pyrrole-3-carboxylic acid (1-amino-isoquinolin-6-ylmethyl)-amide;

2,5-Dimethyl-1-[4-(2-oxo-2H-pyridin-1-ylmethyl)-benzyl]-1H-pyrrole-3-carboxylic acid (1-amino-isoquinolin-6-ylmethyl)-amide;

2,5-Dimethyl-1-[4-(4-methyl-pyrazol-1-ylmethyl)-benzyl]-1H-pyrrole-3-carboxylic acid (1-amino-isoquinolin-6-ylmethyl)-amide;

1-Ethyl-4-methyl-5-[4-(4-methyl-pyrazol-1-ylmethyl)-benzyl]-1H-pyrrole-2-carboxylic acid (1-amino-isoquinolin-6-ylmethyl)-amide;

1-Ethyl-4-methyl-5-[4-(2-oxo-2H-pyridin-1-ylmethyl)-benzyl]-1H-pyrrole-2-carboxylic acid (1-amino-isoquinolin-6-ylmethyl)-amide;

3-Methyl-1-[4-(4-methyl-pyrazol-1-ylmethyl)-benzyl]-1H-pyrazole-4-carboxylic acid (1-amino-isoquinolin-6-ylmethyl)-amide;

3-Cyclopropyl-1-[4-(4-methyl-pyrazol-1-ylmethyl)-benzyl]-1H-pyrazole-4-carboxylic acid (1-amino-isoquinolin-6-ylmethyl)-amide;

3-Isopropyl-1-[4-(4-methyl-pyrazol-1-ylmethyl)-benzyl]-1H-pyrazole-4-carboxylic acid (1-amino-isoquinolin-6-ylmethyl)-amide;

3-Cyclobutyl-1-[4-(4-methyl-pyrazol-1-ylmethyl)-benzyl]-1H-pyrazole-4-carboxylic acid (1-amino-isoquinolin-6-ylmethyl)-amide;

3-Hydroxymethyl-1-[4-(4-methyl-pyrazol-1-ylmethyl)-benzyl]-1H-pyrazole-4-carboxylic acid (1-amino-isoquinolin-6-ylmethyl)-amide;

3-Cyano-1-[4-(4-methyl-pyrazol-1-ylmethyl)-benzyl]-1H-pyrazole-4-carboxylic acid (1-amino-isoquinolin-6-ylmethyl)-amide;

4-Methyl-2-[4-(4-methyl-pyrazol-1-ylmethyl)-benzyl]-thiazole-5-carboxylic acid (1-amino-isoquinolin-6-ylmethyl)-amide;

3-(3,5-Dimethyl-isoxazol-4-yl)-1-[4-(4-methyl-pyrazol-1-ylmethyl)-benzyl]-1H-pyrazole-4-carboxylic acid (1-amino-isoquinolin-6-ylmethyl)-amide;

1-[4-(4-Methyl-pyrazol-1-ylmethyl)-benzyl]-3-morpholin-4-yl-1H-pyrazole-4-carboxylic acid (1-amino-isoquinolin-6-ylmethyl)-amide;

5-Amino-1-(4-pyrazol-1-ylmethyl-benzyl)-1H-pyrazole-4-carboxylic acid (1-amino-isoquinolin-6-ylmethyl)-amide;

1-(6-Pyrrolidin-1-yl-pyridin-3-ylmethyl)-3-trifluoromethyl-1H-pyrazole-4-carboxylic acid (1-amino-isoquinolin-6-ylmethyl)-amide;

3-Cyclopropyl-1-(5-methoxy-6-pyrrolidin-1-yl-pyridin-3-ylmethyl)-1H-pyrazole-4-carboxylic acid (1-amino-isoquinolin-6-ylmethyl)-amide;

1-[4-(4-Methyl-pyrazol-1-ylmethyl)-benzyl]-3-phenyl-1H-pyrazole-4-carboxylic acid (1-amino-isoquinolin-6-ylmethyl)-amide;

1-[4-(4-Methyl-pyrazol-1-ylmethyl)-benzyl]-3-trifluoromethyl-1H-pyrazole-4-carboxylic acid (1-amino-isoquinolin-6-ylmethyl)-amide;

3-Amino-1-[4-(4-methyl-pyrazol-1-ylmethyl)-benzyl]-1H-pyrazole-4-carboxylic acid (1-amino-isoquinolin-6-ylmethyl)-amide;

3-Methoxymethyl-1-[4-(4-methyl-pyrazol-1-ylmethyl)-benzyl]-1H-pyrazole-4-carboxylic acid (1-amino-isoquinolin-6-ylmethyl)-amide;

3-Difluoromethyl-1-[4-(4-methyl-pyrazol-1-ylmethyl)-benzyl]-1H-pyrazole-4-carboxylic acid (1-amino-isoquinolin-6-ylmethyl)-amide;

1-[4-(4-Methyl-pyrazol-1-ylmethyl)-benzyl]-3-thiophen-3-yl-1H-pyrazole-4-carboxylic acid (1-amino-isoquinolin-6-ylmethyl)-amide;

5-Amino-1-(4-pyrazol-1-ylmethyl-benzyl)-1H-pyrazole-4-carboxylic acid (1-amino-isoquinolin-6-ylmethyl)-amide;

1-(2-Pyrrolidin-1-yl-pyridin-4-ylmethyl)-3-trifluoromethyl-1H-pyrazole-4-carboxylic acid (1-amino-isoquinolin-6-ylmethyl)-amide;

1-(6-Ethoxy-pyridin-3-ylmethyl)-3-trifluoromethyl-1H-pyrazole-4-carboxylic acid (1-amino-isoquinolin-6-ylmethyl)-amide;

1-[2-(3,3-Difluoro-pyrrolidin-1-yl)-pyridin-4-ylmethyl]-3-trifluoromethyl-1H-pyrazole-4-carboxylic acid (1-amino-isoquinolin-6-ylmethyl)-amide;

1-[6-(3,3-Difluoro-pyrrolidin-1-yl)-pyridin-3-ylmethyl]-3-trifluoromethyl-1H-pyrazole-4-carboxylic acid (1-amino-isoquinolin-6-ylmethyl)-amide;

1-[6-((R)-3-Methyl-pyrrolidin-1-yl)-pyridin-3-ylmethyl]-3-trifluoromethyl-1H-pyrazole-4-carboxylic acid (1-amino-isoquinolin-6-ylmethyl)-amide;

1-[6-((S)-3-Methyl-pyrrolidin-1-yl)-pyridin-3-ylmethyl]-3-trifluoromethyl-1H-pyrazole-4-carboxylic acid (1-amino-isoquinolin-6-ylmethyl)-amide;

1-[6-((S)-3-Fluoro-pyrrolidin-1-yl)-pyridin-3-ylmethyl]-3-trifluoromethyl-1H-pyrazole-4-carboxylic acid (1-amino-isoquinolin-6-ylmethyl)-amide;

1-[6-((R)-3-Fluoro-pyrrolidin-1-yl)-pyridin-3-ylmethyl]-3-trifluoromethyl-1H-pyrazole-4-carboxylic acid (1-amino-isoquinolin-6-ylmethyl)-amide;

1-[6-((S)-2-Methyl-pyrrolidin-1-yl)-pyridin-3-ylmethyl]-3-trifluoromethyl-1H-pyrazole-4-carboxylic acid (1-amino-isoquinolin-6-ylmethyl)-amide;

1-[6-((R)-2-Methyl-pyrrolidin-1-yl)-pyridin-3-ylmethyl]-3-trifluoromethyl-1H-pyrazole-4-carboxylic acid (1-amino-isoquinolin-6-ylmethyl)-amide;

1-(2-Pyrrolidin-1-yl-pyrimidin-5-ylmethyl)-3-trifluoromethyl-1H-pyrazole-4-carboxylic acid (1-amino-isoquinolin-6-ylmethyl)-amide;

1-(5-Pyrrolidin-1-yl-pyrazin-2-ylmethyl)-3-trifluoromethyl-1H-pyrazole-4-carboxylic acid (1-amino-isoquinolin-6-ylmethyl)-amide;

1-[2-((S)-3-Methyl-pyrrolidin-1-yl)-pyridin-4-ylmethyl]-3-trifluoromethyl-1H-pyrazole-4-carboxylic acid (1-amino-isoquinolin-6-ylmethyl)-amide;

1-[6-(3-Hydroxymethyl-pyrrolidin-1-yl)-pyridin-3-ylmethyl]-3-trifluoromethyl-1H-pyrazole-4-carboxylic acid (1-amino-isoquinolin-6-ylmethyl)-amide;

1-[6-((R)-3-Hydroxymethyl-pyrrolidin-1-yl)-pyridin-3-ylmethyl]-3-trifluoromethyl-1H-pyrazole-4-carboxylic acid (1-amino-isoquinolin-6-ylmethyl)-amide;

1-(6-Propoxy-pyridin-3-ylmethyl)-3-trifluoromethyl-1H-pyrazole-4-carboxylic acid (1-amino-isoquinolin-6-ylmethyl)-amide;

1-(5-Fluoro-6-pyrrolidin-1-yl-pyridin-3-ylmethyl)-3-trifluoromethyl-1H-pyrazole-4-carboxylic acid (1-amino-isoquinolin-6-ylmethyl)-amide;

1-(6-Ethoxy-5-fluoro-pyridin-3-ylmethyl)-3-trifluoromethyl-1H-pyrazole-4-carboxylic acid (1-amino-isoquinolin-6-ylmethyl)-amide;

1-(4-Pyrazol-1-ylmethyl-benzyl)-3-trifluoromethyl-1H-pyrazole-4-carboxylic acid (1-amino-isoquinolin-6-ylmethyl)-amide;

1-[4-(4-Cyano-pyrazol-1-ylmethyl)-benzyl]-3-trifluoromethyl-1H-pyrazole-4-carboxylic acid (1-amino-isoquinolin-6-ylmethyl)-amide;

1-[4-(4-Carbamoyl-pyrazol-1-ylmethyl)-benzyl]-3-trifluoromethyl-1H-pyrazole-4-carboxylic acid (1-amino-isoquinolin-6-ylmethyl)-amide;

1-(6-Pyrazol-1-ylmethyl-pyridin-3-ylmethyl)-3-trifluoromethyl-1H-pyrazole-4-carboxylic acid (1-amino-isoquinolin-6-ylmethyl)-amide;

1-(2-Pyrazol-1-ylmethyl-thiazol-4-ylmethyl)-3-trifluoromethyl-1H-pyrazole-4-carboxylic acid (1-amino-isoquinolin-6-ylmethyl)-amide;

1-[2-(4-Methyl-pyrazol-1-ylmethyl)-thiazol-4-ylmethyl]-3-trifluoromethyl-1H-pyrazole-4-carboxylic acid (1-amino-isoquinolin-6-ylmethyl)-amide;

3-Cyclopropyl-1-[6-[(2-methoxy-ethyl)-methyl-amino]-pyridin-3-ylmethyl]-1H-pyrazole-4-carboxylic acid (1-amino-isoquinolin-6-ylmethyl)-amide;

3-Cyclopropyl-1-[6-(3,3-difluoro-pyrrolidin-1-yl)-pyridin-3-ylmethyl]-1H-pyrazole-4-carboxylic acid (1-amino-isoquinolin-6-ylmethyl)-amide;

3-Cyclopropyl-1-(4-methoxy-6-pyrrolidin-1-yl-pyridin-3-ylmethyl)-1H-pyrazole-4-carboxylic acid (1-amino-isoquinolin-6-ylmethyl)-amide;

3-Cyclopropyl-1-(6-pyrrolidin-1-yl-pyridin-3-ylmethyl)-1H-pyrazole-4-carboxylic acid (1-amino-isoquinolin-6-ylmethyl)-amide;

3-Cyclopropyl-1-(4-[1,2,3]triazol-1-ylmethyl-benzyl)-1H-pyrazole-4-carboxylic acid (1-amino-isoquinolin-6-ylmethyl)-amide;

3-Cyclopropyl-1-(6-phenoxy-pyridin-3-ylmethyl)-1H-pyrazole-4-carboxylic acid (1-amino-isoquinolin-6-ylmethyl)-amide;

1-(5-Chloro-6-ethoxy-pyridin-3-ylmethyl)-3-cyclopropyl-1H-pyrazole-4-carboxylic acid (1-amino-isoquinolin-6-ylmethyl)-amide;

3-Cyclopropyl-1-(6-diethylamino-5-fluoro-pyridin-3-ylmethyl)-1H-pyrazole-4-carboxylic acid (1-amino-isoquinolin-6-ylmethyl)-amide;

1-(5-Chloro-6-pyrrolidin-1-yl-pyridin-3-ylmethyl)-3-cyclopropyl-1H-pyrazole-4-carboxylic acid (1-amino-isoquinolin-6-ylmethyl)-amide;

3-Amino-1-(6-ethoxy-pyridin-3-ylmethyl)-1H-pyrazole-4-carboxylic acid (1-amino-isoquinolin-6-ylmethyl)-amide;

3-Amino-1-(6-pyrrolidin-1-yl-pyridin-3-ylmethyl)-1H-pyrazole-4-carboxylic acid (1-amino-isoquinolin-6-ylmethyl)-amide;

or a pharmaceutically acceptable salt or solvate thereof, and a pharmaceutically acceptable carrier, diluent or excipient.

21. The pharmaceutical composition of claim 19, comprising a compound that is:

1-[4-(2-Oxo-2H-pyridin-1-ylmethyl)-benzyl]-3-trifluoromethyl-1H-pyrazole-4-carboxylic acid (1H-pyrrolo[2,3-b]pyridin-5-ylmethyl)-amide;

1-[4-(2-Oxo-2H-pyridin-1-ylmethyl)-benzyl]-3-trifluoromethyl-1H-pyrazole-4-carboxylic acid (4,6-dimethyl-1H-pyrrolo[2,3-b]pyridin-5-ylmethyl)-amide;

1-[4-(4-Methyl-pyrazol-1-ylmethyl)-benzyl]-3-trifluoromethyl-1H-pyrazole-4-carboxylic acid (4,6-dimethyl-1H-pyrrolo[2,3-b]pyridin-5-ylmethyl)-amide;

1-[4-(4-Methyl-pyrazol-1-ylmethyl)-benzyl]-3-trifluoromethyl-1H-pyrazole-4-carboxylic acid (1H-pyrrolo[2,3-b]pyridin-5-ylmethyl)-amide;

1-[4-(4-Methyl-pyrazol-1-ylmethyl)-benzyl]-3-trifluoromethyl-1H-pyrazole-4-carboxylic acid (1H-indol-5-ylmethyl)-amide;

3-Amino-1-[4-(2-oxo-2H-pyridin-1-ylmethyl)-benzyl]-1H-pyrazole-4-carboxylic acid (1H-indazol-4-ylmethyl)-amide;

1-[4-(2-Oxo-2H-pyridin-1-ylmethyl)-benzyl]-3-trifluoromethyl-1H-pyrazole-4-carboxylic acid (1H-indazol-4-ylmethyl)-amide;

or a pharmaceutically acceptable salt or solvate thereof, and a pharmaceutically acceptable carrier, diluent or excipient.

22. A method of treatment of a disease or condition in which plasma kallikrein activity is implicated wherein the disease or condition in which plasma kallikrein activity is implicated is visual acuity, diabetic retinopathy, diabetic macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery or bleeding from post operative surgery, wherein the method comprises administering to a subject in need thereof a therapeutically effective amount of a compound of claim 1.

23. The method of claim 22, wherein the disease or condition in which plasma kallikrein activity is implicated is retinal vascular permeability associated with diabetic retinopathy and diabetic macular edema.

24. The method of claim 22, comprising administering to a subject in need thereof a therapeutically effective amount of a compound that is:

2,5-Dimethyl-1-(2-phenyl-thiazol-4-ylmethyl)-1H-pyrrole-3-carboxylic acid (1-amino-isoquinolin-6-ylmethyl)-amide;

2,5-Dimethyl-1-[4-(2-oxo-2H-pyridin-1-ylmethyl)-benzyl]-1H-pyrrole-3-carboxylic acid (1-amino-isoquinolin-6-ylmethyl)-amide;

2,5-Dimethyl-1-[4-(4-methyl-pyrazol-1-ylmethyl)-benzyl]-1H-pyrrole-3-carboxylic acid (1-amino-isoquinolin-6-ylmethyl)-amide;

1-Ethyl-4-methyl-5-[4-(4-methyl-pyrazol-1-ylmethyl)-benzyl]-1H-pyrrole-2-carboxylic acid (1-amino-isoquinolin-6-ylmethyl)-amide;

1-Ethyl-4-methyl-5-[4-(2-oxo-2H-pyridin-1-ylmethyl)-benzyl]-1H-pyrrole-2-carboxylic acid (1-amino-isoquinolin-6-ylmethyl)-amide;

3-Methyl-1-[4-(4-methyl-pyrazol-1-ylmethyl)-benzyl]-1H-pyrazole-4-carboxylic acid (1-amino-isoquinolin-6-ylmethyl)-amide;

3-Cyclopropyl-1-[4-(4-methyl-pyrazol-1-ylmethyl)-benzyl]-1H-pyrazole-4-carboxylic acid (1-amino-isoquinolin-6-ylmethyl)-amide;
3-Isopropyl-1-[4-(4-methyl-pyrazol-1-ylmethyl)-benzyl]-1H-pyrazole-4-carboxylic acid (1-amino-isoquinolin-6-ylmethyl)-amide;
3-Cyclobutyl-1-[4-(4-methyl-pyrazol-1-ylmethyl)-benzyl]-1H-pyrazole-4-carboxylic acid (1-amino-isoquinolin-6-ylmethyl)-amide;
3-Hydroxymethyl-1-[4-(4-methyl-pyrazol-1-ylmethyl)-benzyl]-1H-pyrazole-4-carboxylic acid (1-amino-isoquinolin-6-ylmethyl)-amide;
3-Cyano-1-[4-(4-methyl-pyrazol-1-ylmethyl)-benzyl]-1H-pyrazole-4-carboxylic acid (1-amino-isoquinolin-6-ylmethyl)-amide;
4-Methyl-2-[4-(4-methyl-pyrazol-1-ylmethyl)-benzyl]-thiazole-5-carboxylic acid (1-amino-isoquinolin-6-ylmethyl)-amide;
3-(3,5-Dimethyl-isoxazol-4-yl)-1-[4-(4-methyl-pyrazol-1-ylmethyl)-benzyl]-1H-pyrazole-4-carboxylic acid (1-amino-isoquinolin-6-ylmethyl)-amide;
1-[4-(4-Methyl-pyrazol-1-ylmethyl)-benzyl]-3-morpholin-4-yl-1H-pyrazole-4-carboxylic acid (1-amino-isoquinolin-6-ylmethyl)-amide;
5-Amino-1-(4-pyrazol-1-ylmethyl-benzyl)-1H-pyrazole-4-carboxylic acid (1-amino-isoquinolin-6-ylmethyl)-amide;
1-(6-Pyrrolidin-1-yl-pyridin-3-ylmethyl)-3-trifluoromethyl-1H-pyrazole-4-carboxylic acid (1-amino-isoquinolin-6-ylmethyl)-amide;
3-Cyclopropyl-1-(5-methoxy-6-pyrrolidin-1-yl-pyridin-3-ylmethyl)-1H-pyrazole-4-carboxylic acid (1-amino-isoquinolin-6-ylmethyl)-amide;
1-[4-(4-Methyl-pyrazol-1-ylmethyl)-benzyl]-3-phenyl-1H-pyrazole-4-carboxylic acid (1-amino-isoquinolin-6-ylmethyl)-amide;
1-[4-(4-Methyl-pyrazol-1-ylmethyl)-benzyl]-3-trifluoromethyl-1H-pyrazole-4-carboxylic acid (1-amino-isoquinolin-6-ylmethyl)-amide;
3-Amino-1-[4-(4-methyl-pyrazol-1-ylmethyl)-benzyl]-1H-pyrazole-4-carboxylic acid (1-amino-isoquinolin-6-ylmethyl)-amide;
3-Methoxymethyl-1-[4-(4-methyl-pyrazol-1-ylmethyl)-benzyl]-1H-pyrazole-4-carboxylic acid (1-amino-isoquinolin-6-ylmethyl)-amide;
3-Difluoromethyl-1-[4-(4-methyl-pyrazol-1-ylmethyl)-benzyl]-1H-pyrazole-4-carboxylic acid (1-amino-isoquinolin-6-ylmethyl)-amide;
1-[4-(4-Methyl-pyrazol-1-ylmethyl)-benzyl]-3-thiophen-3-yl-1H-pyrazole-4-carboxylic acid (1-amino-isoquinolin-6-ylmethyl)-amide;
5-Amino-1-(4-pyrazol-1-ylmethyl-benzyl)-1H-pyrazole-4-carboxylic acid (1-amino-isoquinolin-6-ylmethyl)-amide;
1-(2-Pyrrolidin-1-yl-pyridin-4-ylmethyl)-3-trifluoromethyl-1H-pyrazole-4-carboxylic acid (1-amino-isoquinolin-6-ylmethyl)-amide;
1-(6-Ethoxy-pyridin-3-ylmethyl)-3-trifluoromethyl-1H-pyrazole-4-carboxylic acid (1-amino-isoquinolin-6-ylmethyl)-amide;
1-[2-(3,3-Difluoro-pyrrolidin-1-yl)-pyridin-4-ylmethyl]-3-trifluoromethyl-1H-pyrazole-4-carboxylic acid (1-amino-isoquinolin-6-ylmethyl)-amide;
1-[6-(3,3-Difluoro-pyrrolidin-1-yl)-pyridin-3-ylmethyl]-3-trifluoromethyl-1H-pyrazole-4-carboxylic acid (1-amino-isoquinolin-6-ylmethyl)-amide;
1-[6-((R)-3-Methyl-pyrrolidin-1-yl)-pyridin-3-ylmethyl]-3-trifluoromethyl-1H-pyrazole-4-carboxylic acid (1-amino-isoquinolin-6-ylmethyl)-amide;
1-[6-((S)-3-Methyl-pyrrolidin-1-yl)-pyridin-3-ylmethyl]-3-trifluoromethyl-1H-pyrazole-4-carboxylic acid (1-amino-isoquinolin-6-ylmethyl)-amide;
1-[6-((S)-3-Fluoro-pyrrolidin-1-yl)-pyridin-3-ylmethyl]-3-trifluoromethyl-1H-pyrazole-4-carboxylic acid (1-amino-isoquinolin-6-ylmethyl)-amide;
1-[6-((R)-3-Fluoro-pyrrolidin-1-yl)-pyridin-3-ylmethyl]-3-trifluoromethyl-1H-pyrazole-4-carboxylic acid (1-amino-isoquinolin-6-ylmethyl)-amide;
1-[6-((S)-2-Methyl-pyrrolidin-1-yl)-pyridin-3-ylmethyl]-3-trifluoromethyl-1H-pyrazole-4-carboxylic acid (1-amino-isoquinolin-6-ylmethyl)-amide;
1-[6-((R)-2-Methyl-pyrrolidin-1-yl)-pyridin-3-ylmethyl]-3-trifluoromethyl-1H-pyrazole-4-carboxylic acid (1-amino-isoquinolin-6-ylmethyl)-amide;
1-(2-Pyrrolidin-1-yl-pyrimidin-5-ylmethyl)-3-trifluoromethyl-1H-pyrazole-4-carboxylic acid (1-amino-isoquinolin-6-ylmethyl)-amide;
1-(5-Pyrrolidin-1-yl-pyrazin-2-ylmethyl)-3-trifluoromethyl-1H-pyrazole-4-carboxylic acid (1-amino-isoquinolin-6-ylmethyl)-amide;
1-[2-((S)-3-Methyl-pyrrolidin-1-yl)-pyridin-4-ylmethyl]-3-trifluoromethyl-1H-pyrazole-4-carboxylic acid (1-amino-isoquinolin-6-ylmethyl)-amide;
1-[6-(3-Hydroxymethyl-pyrrolidin-1-yl)-pyridin-3-ylmethyl]-3-trifluoromethyl-1H-pyrazole-4-carboxylic acid (1-amino-isoquinolin-6-ylmethyl)-amide;
1-[6-((R)-3-Hydroxymethyl-pyrrolidin-1-yl)-pyridin-3-ylmethyl]-3-trifluoromethyl-1H-pyrazole-4-carboxylic acid (1-amino-isoquinolin-6-ylmethyl)-amide;
1-(6-Propoxy-pyridin-3-ylmethyl)-3-trifluoromethyl-1H-pyrazole-4-carboxylic acid (1-amino-isoquinolin-6-ylmethyl)-amide;
1-(5-Fluoro-6-pyrrolidin-1-yl-pyridin-3-ylmethyl)-3-trifluoromethyl-1H-pyrazole-4-carboxylic acid (1-amino-isoquinolin-6-ylmethyl)-amide;
1-(6-Ethoxy-5-fluoro-pyridin-3-ylmethyl)-3-trifluoromethyl-1H-pyrazole-4-carboxylic acid (1-amino-isoquinolin-6-ylmethyl)-amide;
1-(4-Pyrazol-1-ylmethyl-benzyl)-3-trifluoromethyl-1H-pyrazole-4-carboxylic acid (1-amino-isoquinolin-6-ylmethyl)-amide;
1-[4-(4-Cyano-pyrazol-1-ylmethyl)-benzyl]-3-trifluoromethyl-1H-pyrazole-4-carboxylic acid (1-amino-isoquinolin-6-ylmethyl)-amide;
1-[4-(4-Carbamoyl-pyrazol-1-ylmethyl)-benzyl]-3-trifluoromethyl-1H-pyrazole-4-carboxylic acid (1-amino-isoquinolin-6-ylmethyl)-amide;
1-(6-Pyrazol-1-ylmethyl-pyridin-3-ylmethyl)-3-trifluoromethyl-1H-pyrazole-4-carboxylic acid (1-amino-isoquinolin-6-ylmethyl)-amide;
1-(2-Pyrazol-1-ylmethyl-thiazol-4-ylmethyl)-3-trifluoromethyl-1H-pyrazole-4-carboxylic acid (1-amino-isoquinolin-6-ylmethyl)-amide;
1-[2-(4-Methyl-pyrazol-1-ylmethyl)-thiazol-4-ylmethyl]-3-trifluoromethyl-1H-pyrazole-4-carboxylic acid (1-amino-isoquinolin-6-ylmethyl)-amide;
3-Cyclopropyl-1-[6-[(2-methoxy-ethyl)-methyl-amino]-pyridin-3-ylmethyl]-1H-pyrazole-4-carboxylic acid (1-amino-isoquinolin-6-ylmethyl)-amide;
3-Cyclopropyl-1-[6-(3,3-difluoro-pyrrolidin-1-yl)-pyridin-3-ylmethyl]-1H-pyrazole-4-carboxylic acid (1-amino-isoquinolin-6-ylmethyl)-amide;

3-Cyclopropyl-1-(4-methoxy-6-pyrrolidin-1-yl-pyridin-3-ylmethyl)-1H-pyrazole-4-carboxylic acid (1-amino-isoquinolin-6-ylmethyl)-amide;

3-Cyclopropyl-1-(6-pyrrolidin-1-yl-pyridin-3-ylmethyl)-1H-pyrazole-4-carboxylic acid (1-amino-isoquinolin-6-ylmethyl)-amide;

3-Cyclopropyl-1-(4-[1,2,3]triazol-1-ylmethyl-benzyl)-1H-pyrazole-4-carboxylic acid (1-amino-isoquinolin-6-ylmethyl)-amide;

3-Cyclopropyl-1-(6-phenoxy-pyridin-3-ylmethyl)-1H-pyrazole-4-carboxylic acid (1-amino-isoquinolin-6-ylmethyl)-amide;

1-(5-Chloro-6-ethoxy-pyridin-3-ylmethyl)-3-cyclopropyl-1H-pyrazole-4-carboxylic acid (1-amino-isoquinolin-6-ylmethyl)-amide;

3-Cyclopropyl-1-(6-diethylamino-5-fluoro-pyridin-3-ylmethyl)-1H-pyrazole-4-carboxylic acid (1-amino-isoquinolin-6-ylmethyl)-amide;

1-(5-Chloro-6-pyrrolidin-1-yl-pyridin-3-ylmethyl)-3-cyclopropyl-1H-pyrazole-4-carboxylic acid (1-amino-isoquinolin-6-ylmethyl)-amide;

3-Amino-1-(6-ethoxy-pyridin-3-ylmethyl)-1H-pyrazole-4-carboxylic acid (1-amino-isoquinolin-6-ylmethyl)-amide;

3-Amino-1-(6-pyrrolidin-1-yl-pyridin-3-ylmethyl)-1H-pyrazole-4-carboxylic acid (1-amino-isoquinolin-6-ylmethyl)-amide;

or a pharmaceutically acceptable salt or solvate thereof.

25. The method of claim 22, comprising administering to a subject in need thereof a therapeutically effective amount of a compound that is:

1-[4-(2-Oxo-2H-pyridin-1-ylmethyl)-benzyl]-3-trifluoromethyl-1H-pyrazole-4-carboxylic acid (1H-pyrrolo[2,3-b]pyridin-5-ylmethyl)-amide;

1-[4-(2-Oxo-2H-pyridin-1-ylmethyl)-benzyl]-3-trifluoromethyl-1H-pyrazole-4-carboxylic acid (4,6-dimethyl-1H-pyrrolo[2,3-b]pyridin-5-ylmethyl)-amide;

1-[4-(4-Methyl-pyrazol-1-ylmethyl)-benzyl]-3-trifluoromethyl-1H-pyrazole-4-carboxylic acid (4,6-dimethyl-1H-pyrrolo[2,3-b]pyridin-5-ylmethyl)-amide;

1-[4-(4-Methyl-pyrazol-1-ylmethyl)-benzyl]-3-trifluoromethyl-1H-pyrazole-4-carboxylic acid (1H-pyrrolo[2,3-b]pyridin-5-ylmethyl)-amide;

1-[4-(4-Methyl-pyrazol-1-ylmethyl)-benzyl]-3-trifluoromethyl-1H-pyrazole-4-carboxylic acid (1H-indol-5-ylmethyl)-amide;

3-Amino-1-[4-(2-oxo-2H-pyridin-1-ylmethyl)-benzyl]-1H-pyrazole-4-carboxylic acid (1H-indazol-4-ylmethyl)-amide;

1-[4-(2-Oxo-2H-pyridin-1-ylmethyl)-benzyl]-3-trifluoromethyl-1H-pyrazole-4-carboxylic acid (1H-indazol-4-ylmethyl)-amide;

or a pharmaceutically acceptable salt or solvate thereof.

26. The method of claim 24, wherein the disease or condition is retinal vascular permeability associated with diabetic retinopathy or diabetic macular edema.

27. The method of claim 25, wherein the disease or condition is retinal vascular permeability associated with diabetic retinopathy or diabetic macular edema.

\* \* \* \* \*